US011542528B2

(12) United States Patent
Higgins et al.

(10) Patent No.: US 11,542,528 B2
(45) Date of Patent: Jan. 3, 2023

(54) TRANSPOSITION-BASED THERAPIES

(71) Applicant: Saliogen Therapeutics, Inc., Cambridge, MA (US)

(72) Inventors: Joseph J. Higgins, Cambridge, MA (US); Scott McMillan, Cambridge, MA (US); Ray Tabibiazar, Cambridge, MA (US)

(73) Assignee: Saliogen Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/669,939

(22) Filed: Feb. 11, 2022

(65) Prior Publication Data

US 2022/0243227 A1 Aug. 4, 2022

Related U.S. Application Data

(63) Continuation of application No. PCT/US2021/030729, filed on May 4, 2021.

(60) Provisional application No. 63/175,345, filed on Apr. 15, 2021, provisional application No. 63/058,200, filed on Jul. 29, 2020, provisional application No. 63/027,561, filed on May 20, 2020, provisional application No. 63/019,709, filed on May 4, 2020.

(51) Int. Cl.

| | |
|---|---|
| ***C12N 9/12*** | (2006.01) |
| ***C12N 9/22*** | (2006.01) |
| ***C12N 15/90*** | (2006.01) |

(52) U.S. Cl.

CPC ........... *C12N 15/90* (2013.01); *C12N 9/1241* (2013.01); *C12N 9/22* (2013.01); *C07K 2319/80* (2013.01)

(58) Field of Classification Search

CPC .......................... C12N 9/1241; C07K 2319/80

See application file for complete search history.

(56) References Cited

U.S. PATENT DOCUMENTS

| | | | |
|---|---|---|---|
| 8,399,643 | B2 | 3/2013 | Ostertag et al. |
| 8,420,782 | B2 | 4/2013 | Bonas et al. |
| 8,470,973 | B2 | 6/2013 | Bonas et al. |
| 8,586,526 | B2 | 11/2013 | Gregory et al. |
| 8,912,138 | B2 | 12/2014 | Gregory et al. |
| 9,017,967 | B2 | 4/2015 | Bonas et al. |
| 9,200,045 | B2 | 12/2015 | Liu et al. |
| 9,353,378 | B2 | 5/2016 | Bonas et al. |
| 9,388,430 | B2 | 7/2016 | Liu et al. |
| 9,428,767 | B2 | 8/2016 | Minshull et al. |
| 9,453,054 | B2 | 9/2016 | Bonas et al. |
| 9,493,750 | B2 | 11/2016 | Gregory et al. |
| 9,534,234 | B2 | 1/2017 | Minshull et al. |
| 9,574,209 | B2 | 2/2017 | Minshull et al. |
| 9,580,697 | B2 | 2/2017 | Minshull et al. |
| 9,670,503 | B2 | 6/2017 | Craig |
| 9,783,790 | B2 | 10/2017 | Craig |
| 9,809,628 | B2 | 11/2017 | Bonas et al. |
| 10,041,077 | B2 | 8/2018 | Minshull et al. |
| 10,131,885 | B2 | 11/2018 | Ostertag et al. |
| 10,233,454 | B2 | 3/2019 | Minshull et al. |
| 10,287,559 | B2 | 5/2019 | Ostertag et al. |
| 10,344,285 | B2 | 7/2019 | Minshull et al. |
| 10,415,022 | B2 | 9/2019 | Craig |
| 10,435,696 | B2 | 10/2019 | Minshull et al. |
| 10,533,190 | B2 | 1/2020 | Doudna et al. |
| 10,550,407 | B2 | 2/2020 | Doudna et al. |
| 10,793,878 | B1 | 10/2020 | Doudna et al. |
| 10,900,054 | B2 | 1/2021 | Doudna et al. |
| 10,927,384 | B2 | 2/2021 | Minshull et al. |
| 11,060,086 | B2 | 7/2021 | Minshull et al. |
| 11,060,098 | B2 | 7/2021 | Minshull et al. |
| 11,060,109 | B2 | 7/2021 | Minshull et al. |
| 11,162,102 | B2 | 11/2021 | Minshull et al. |
| 2006/0210977 | A1 | 9/2006 | Kaminski |
| 2009/0042297 | A1 | 2/2009 | George, Jr. et al. |
| 2011/0047635 | A1 | 2/2011 | Moisyadi et al. |

FOREIGN PATENT DOCUMENTS

| | | | | |
|---|---|---|---|---|
| WO | WO 2008/100424 A2 | 8/2008 | | |
| WO | WO 2010/085699 A2 | 7/2010 | | |
| WO | WO 2010/099301 A2 | 9/2010 | | |
| WO | WO 2013/012824 A2 | 1/2013 | | |
| WO | WO 2015/157611 A2 | 10/2015 | | |
| WO | WO 2016/172703 A2 | 10/2016 | | |
| WO | WO-2018112415 A1 * | 6/2018 | ............ | A61K 35/17 |
| WO | WO 2019/108932 A1 | 6/2019 | | |
| WO | WO 2020/077357 A1 | 4/2020 | | |

(Continued)

OTHER PUBLICATIONS

Owens et al. Transcription activator like effector (TALE)-directed piggyBac transposition in human cells. Nucleic Acids Research, doi:10.1093/nar/gkt677, printed as pp. 1-11 and pp. 1/18-18/18 of Supplementary Data, Aug. 5, 2013. (Year: 2013).*

(Continued)

*Primary Examiner* — Jennifer Dunston

(74) *Attorney, Agent, or Firm* — Morgan, Lewis & Bockius LLP

(57) ABSTRACT

Gene therapy compositions and methods are provided that make use of transposases and/or chimeric transposases for targeted transposition, including engineered enzymes and nucleic acids encoding the same. The provided compositions and methods are suitable of treating, for example, an inherited or acquired disease in a patient, as well as treating and/or mitigating a variety of diseases.

28 Claims, 82 Drawing Sheets

Specification includes a Sequence Listing.

(56) References Cited

FOREIGN PATENT DOCUMENTS

| | | | |
|---|---|---|---|
| WO | WO 2020/077360 A1 | 4/2020 | |
| WO | WO 2020/163755 A1 | 8/2020 | |
| WO | WO 2021/222653 A1 | 11/2021 | |
| WO | WO 2021/222654 A1 | 11/2021 | |

OTHER PUBLICATIONS

Aboye, et al., "Biological Synthesis of Circular Polypeptides," The Journal of Biological Chemistry, vol. 287, No. 32, pp. 27026-27032, Aug. 2012.
Aguirre, "Concepts and Strategies in Retinal Gene Therapy," IOVS, vol. 58, No. 12, pp. 5399-5411, 2017.
Alexopoulou, et al., "The CMV early enhancer/chicken β actin (CAG) promoter can be used to drive transgene expression during the differentiation of murine embryonic stem cells into vascular progenitors," BMC Cell Biology, 2008, 9:2, 11 pages.
Balasubramanian, et al., "Generation of High Expressing Chinese Hamster Ovary Cell Pools Using the Leap-In Transposon System," Biotechnology Journal, vol. 13, No. 10, doi.org/10.1002/biot.201700748, 2018.
Baldrick, "Pharmaceutical Excipient Development: The Need for Preclinical Guidance," Regulatory Toxicology and Pharmacology, vol. 32, No. 2, pp. 210-218, 2000.
Bejerano, et al., "Ultraconserved Elements in the Human Genome," Science, vol. 304, No. 5675, pp. 1321-1325, 2004.
Boch, et al., "TALEs of genome targeting," Nature Biotechnology, vol. 29, pp. 135-136, 2011.
Bouallègue, et al., "Molecular Evolution of *piggyBac* Superfamily: From Selfishness to Domestication," Genome Biol. Evol., vol. 9, No. 2, pp. 323-339, 2017.
Burnight, et al., "A Hyperactive Transposase Promotes Persistent Gene Transfer of a piggyBac DNA Transposon," Molecular Therapy-Nucleic Acids (2012) 1, e5.
Buskirk, et al., "Directed evolution of ligand dependence: Small-molecule-activated protein splicing," PNAS, vol. 101, No. 29, pp. 10505-10510, Jul. 2004.
Campos-Sánchez, et al., "Genomic Landscape of Human, Bat, and Ex Vivo DNA Transposon Integrations," Mol. Biol. Evol., vol. 31, No. 7, pp. 1816-1832, Apr. 2014.
Charman, "Lipids, Lipophilic Drugs, and Oral Drug Delivery—Some Emerging Concepts," Journal of Pharmaceutical Sciences, vol. 89, No. 8, pp. 967-978, 2000.
Chylinski, et al., "Classification and evolution of type II CRISPR-Cas systems," Nucleic Acid Research, vol. 42, No. 10, pp. 6091-6105, 2014.
De Palmenaer, et al., "IS4family goes genomic," BMC Evolutionary Biology, 8:18, doi: 10.1186/1471-2148-8-18, Jan. 2008.
Di Polo, et al., "Transcriptional activation of the human rod cGMP-phosphodiesterase βsubunit gene is mediated by an upstream AP-1 element," Nucleic Acids Research, vol. 25, No. 19, pp. 3863-3867, 1997.
Dominguez, et al., "Beyond editing: repurposing CRISPR-Cas9 for precision genome regulation and interrogation," Nat Rev Mol Cell Biol., vol. 17, No. 1, pp. 5-15, Jan. 2016.
Fischer, et al., "Regulated transposition of a fish transposon in the mouse germ line," PNAS, vol. 98, No. 12, pp. 6759-6764, Jun. 2001.
Hernandez, et al., "Latent Adeno-Associated Virus Infection Elicits Humoral but Not Cell-Mediated Immune Responses in a Nonhuman Primate Model," Journal of Virology, vol. 73, No. 10, pp. 8549-8558, Oct. 1999.
Hew, et al., "RNA-guided piggyBac transposition in human cells," Synthetic Biology, vol. 4, No. 1, 12 pages, 2019.
Hockemeyer, et al., "Highly efficient gene targeting of expresses and silent genes in human ESCs and iPSCs using zinc finger nucleases," Nat Biotechnol., vol. 27, No. 9, pp. 851-857, Sep. 2009.
Hottentot, et al., "Targeted Locus Amplification and Next-Generation Sequencing," Genotyping, Methods in Molecular Biology, vol. 1492. Humana Press, New York, NY. https://doi.org/10.1007/978-1-4939-6442-0_13.2017.
Ivics, et al., "Molecular Reconstruction of *Sleeping Beauty, a Tc1*-like Transposon from Fish, and Its Transposition in Human Cells," Cell. vol. 91, pp. 501-510, 1997.
Jebb, et al., "Six reference-quality genomes reveal evolution of bat adaptations," Nature, vol. 583, pp. 578-584, 2020.
Jin, et al., "The hyperactive Sleeping Beauty tranposase SB100X improves the genetic modification of T cells to express a chimeric antigen receptor," Gene Therapy, vol. 18, pp. 849-856, 2011.
Jinek, et al., "A Programmable Dual-RNA-Guided DNA Endonuclease in Adaptive Bacterial Immunity," Science, vol. 337, pp. 816-821, Aug. 2012.
Joung, et al., "TALENs: a widely applicable technology for targeted genome editing," Nat Rev Mol Cell Biol., vol. 14, No. 1, pp. 49-55, Jan. 2013.
Kan, et al., "The Evaluation of Novel Photoreceptor Specific Promoters in an EIAV Lentiviral Vector for TargetedGene Expression in the Photoreceptors of the Eye," Molecular Therapy, vol. 15, Suppl. 1, S258, May 1, 2007.
Kay, et al., "Transient immunomodulation with anti-CD40 ligand antibody and CTLA4lg enhances persistence and secondary adenovirus-mediated gene transfer into mouse liver," PNAS, vol. 94, No. 9, pp. 4686-4691, Apr. 1997.
Kettlun, et al., "Manipulating *piggyBac* Transposon Chromosomal Integration Site Selection in Human Cells," Molecular Therapy, vol. 19, No. 9, pp. 1636-1644, 2011.
Khani, et al., "AAV-Mediated Expression Targeting of Rod and Cone Photoreceptors with a Human Rhodopsin Kinase Promoter," IOVS, vol. 48, pp. 3954-3961, 2007.
Klompe, et al., "Transposon-encoded CRISPR-Cas systems direct RNA-guided DNA integration," Nature, vol. 571, pp. 219-225, 2019.
Kosugi, et al., "Six Classes of Nuclear Localization Signals Specific to Different Binding Grooves of Importin α," The Journal of Biological Chemistry, vol. 284, No. 1, pp. 478-485, 2009.
Lestini, et al., "Surface modification of liposomes for selective cell targeting in cardiovascular drug delivery," Journal of Controlled Release, vol. 78, pp. 235-247, Jan. 2002.
Li, et al., "Cone-specific expression using a human red opsin promoter in recombinant AAV," Vision Research, vol. 48, pp. 332-338, 2008.
Lobritz, et al., "HIV-1 Entry, Inhibitors, and Resistance," Viruses 2010, vol. 2, pp. 1069-1105.
Luo, et al., "Comparative analysis of chimeric ZFP-, TALE- and Cas9-piggyBac transposases for integration into a single locus in human cells," Nucleic Acids Research, vol. 45, No. 14, pp. 8411-8422, 2017.
McDougald, et al., "CRISPR Activation Enhances In Vitro Potency of AAV Vectors Driven by Tissue-SpecificPromoters," Mol Ther Methods Clin Dev. vol. 13, pp. 380-389, 2019.
Miller, et al., "A TALE nuclease architecture for efficient genome editing," Nature Biotechnology, vol. 29, pp. 143-148, 2011.
Mitra, et al., "piggyBac can bypass DNA synthesis during cut and paste transposition," The EMBO Journal, vol. 27, No. 7, pp. 1097-1109, 2008.
Mitra, et al., "Functional characterization of *piggyBat* from the bat *Myotis lucifugus* unveils an active mammalianDNA transposon," PNAS, vol. 110, No. 1, pp. 234-239, Jan. 2013.
Moldt, et al., "Cis-acting gene regulatory activities in the terminal regions of sleeping beauty DNA transposon-based vectors," Hum Gene Ther., vol. 18, No. 12, pp. 1193-1204, 2007.
Mootz, et al., "Protein Splicing Triggered by a Small Molecule," J. Am. Chem. Soc., vol. 124, No. 31, pp. 9044-9045, 2002.
Mootz, et al., "Conditional Protein Splicing: A New Tool to Control Protein Structure and Function in Vitro and in Vivo," J. Am. Chern. Soc., vol. 125, No. 35, pp. 10561-10569, 2003.
Nanda, et al., "Inteins in Science: Evolution to Application," Microorganisms, vol. 8, 20 pages, Dec. 2004.
Nathwani, et al., "Self-complementary adeno-associated virus vectors containing a novel liver-specific human factor IX expression

(56) References Cited

OTHER PUBLICATIONS cassette enable highly efficient transduction of murine and nonhuman primate liver," Blood, vol. 107, No. 7, pp. 2653-2661, Apr. 2006.
Owens, et al., "Chimeric piggyBac transposases for genomic targeting in human cells," Nucleic Acids Research, vol. 40, No. 14, pp. 6978-6991, 2012.
Owens, et al., "Transcription activator like effector (TALE)-directed *piggyBac* transposition in human cells," Nucelic Acids Research, vol. 41, No. 19, pp. 9197-9207, 2013.
Owens, et al., "Novel Piggybac Transposase Vectors for Safer Gene Addition Into Mammalian Genomes," Disseration, 177 pages, May 2014.
Papapetrou, et al., "Genomic safe harbors permit high βglobin transgene expression in thalassemia induced pluripotent stem cells," Nat Biotechnol., vol. 29, No. 1, pp. 73-78, Jan. 2011.
Patel, et al., "Lipid nanoparticles for delivery of messenger RNA to the back of the eye," Journal of Controlled Release, vol. 303, pp. 91-100, Jun. 2019.
Peck, et al., "Directed Evolution of a Small-Molecule-Triggered Intein with Improved Splicing Properties in Mammalian Cells," Chemistry & Biology, vol. 18, pp. 619-630, 2011.
Pellenz, et al., "New Human Chromosomal Sites with "Safe Harbor" Potential for Targeted Transgene Insertion," Human Gene Therapy, vol. 30, No. 7, pp. 814-828, Jul. 2019.
Plasterk, et al., "Resident aliens: the Tc1/*mariner* superfamily of transposable elements," Trends in Genetics, vol. 15, No. 8, pp. 326-332, 1999.
Powell, et al., "Compendium of excipients for parenteral formulations," PDA J Pharm Sci Technol. vol. 52, No. 5, pp. 238-311, 1998.
Qi, et al., "Repurposing CRISPR as an RNA-Guided Platform for Sequencespecific Control of Gene Expression," Cell, vol. 152, No. 5, pp. 1173-1183, Feb. 2013.
Ray, et al., "Bats with hATs: Evidence for Recent DNA Transposon Activity in Genus Myotis," Mol Biol Evol, vol. 24, No. 3, pp. 632-639, 2007. DOI: 10.1093/molbev/msl192.
Ray, et al., "Multiple waves of recent DNA transposon activity in the bat, Myotis lucifugus," Genome Research, vol. 18, pp. 717-728, 2008.
Rivel-Gervier, et al., "Kinetics and Epigenetics of Retroviral Silencing in Mouse Embryonic Stem Cells Defined by Deletion of the D4Z4 Element," Molecular Therapy, vol. 21, No. 8, pp. 1536-1550, 2013.
Sarmiento, et al., "Biotechnological applications of protein splicing," Curr Protein Pept Sci., vol. 20, No. 5, pp. 408-424, 2019.
Schwartz, et al., "Post-translational enzyme activation in an animal via optimized conditional protein splicing," Nature Chemical Biology, vol. 3, pp. 50-54, 2007.
Skretas, et al., "Regulation of protein activity with small-molecule-controlled inteins," Protein Science, vol. 14, pp. 523-532, 2005.
Streubel, et al., "TAL effector RVD specificities and efficiencies," Nature Biotechnology, vol. 30, pp. 593-595, 2012.
Tebas, et al., "Gene Editing of *CCR5* in Autologous CD4 T Cells of Persons Infected with HIV," The New England Journal of Medicine, vol. 370, No. 10, pp. 901-910, 2014.
Tipanee, et al., "Moving Forward from Preclinical Studies to Clinical Trials," Human Gene Therapy, vol. 28, No. 11, pp. 1087-1104, 2017.
Truong, et al., "Development of an intein-mediated split-Cas9 system for gene therapy," Nucleic Acids Research, vol. 43, No. 13, pp. 6450-6458, Jun. 2015.
Urschitz, et al., "Helper-independent piggyBac plasmids for gene delivery approaches: Strategies for avoiding potential genotoxic effects," PNAS, vol. 107, No. 8, pp. 8117-8122, 2010.
Voight, et al., "Sleeping Beauty transposase structure allows rational design of hyperactive variants for genetic Engineering," Nature Communications. vol. 7, Article No. 11126, 2016.
Wang, "Lyophilization and development of solid protein pharmaceuticals," International Journal of Pharmaceutics, vol. 203, pp. 1-60, 2000.
Wang, et al., "CRISPR/Cas9 in Genome Editing and Beyond," Annu Rev Biochem., vol. 85, pp. 227-264, Jun. 2016.
Wilber, et al., "RNA as a Source of Transposase for Sleeping Beauty-Mediated Gene Insertion and Expression in Somatic Cells and Tissues," Molecular Therapy, vol. 13, No. 3, pp. 625-630, 2006.
Wood, et al., "Intein Applications: From Protein Purification and Labeling to Metabolic Control Methods," The Journal of Biological Chemistry, vol. 289, No. 21, pp. 14512-14519, May 2014.
Woodard, et al., "*piggyBac*-mg models and new therapeutic strategies," Trends Biotechnol., vol. 33, No. 9, pp. 525-533, 2015.
Ye, et al., "TAL effectors mediate high-efficiency transposition of the *piggyBac* transposon in silkworm *Bombyx mori* L," Scientifice Reports, vol. 5:17172, 10 pages, doi: 10.1038/srep17172, Nov. 2015.
Yusa, et al., "A hyperactive *piggyBac* transposase for mammalian applications," PNAS, vol. 108, No. 4, pp. 1531-1536, Jan. 2011.
International Search Report & Written Opinion PCT Application No. PCT/US21/30729, dated Oct. 22, 2021, 12 pages.

* cited by examiner

FIG. 3

DNA binding codes for human genomic safe harbor in areas of open chromatin

| GSHS | ID | Sequence | TALE (DNA binding code) |
|---|---|---|---|
| AAVS1 | 1 | TGGCCGGCCTGACCACTGG (SEQ ID NO: 23) | NH NH HD HD NH NH HD HD NG NH NI HD HD NI HD NG NH NH |
| AAVS1 | 2 | TGAAGGCCTGGCCGGCCTG (SEQ ID NO: 24) | NH NI NI NH NH HD HD NG NH NH HD HD NH NH HD HD NG NH |
| AAVS1 | 3 | TGAGCACTGAAGGCCTGGC (SEQ ID NO: 25) | NH NI NH HD NI HD NG NH NI NI NH NH HD HD NG NH NH HD |
| AAVS1 | 4 | TCCACTGAGCACTGAAGGC (SEQ ID NO: 26) | HD HD NI HD NG NH NI NH HD NI HD NG NH NI NI NH NH HD |
| AAVS1 | 5 | TGGTTTCCACTGAGCACTG (SEQ ID NO: 27) | NH NH NG NG NG HD HD NI HD NG NH NI NH HD NI HD NG NH |
| AAVS1 | 6 | TGGGGAAAATGACCCAACA (SEQ ID NO: 28) | NH NH NH NH NI NI NI NI NG NH NI HD HD HD NI NI HD NI |
| AAVS1 | 7 | TAGGACAGTGGGGAAAATG (SEQ ID NO: 29) | NI NH NH NI HD NI NH NG NH NH NH NH NI NI NI NI NG NH |
| AAVS1 | 8 | TCCAGGGACACGGTGCTAG (SEQ ID NO: 30) | HD HD NI NH NH NH NI HD NI HD NH NH NG NH HD NG NI NH |
| AAVS1 | 9 | TCAGAGCCAGGAGTCCTGG (SEQ ID NO: 31) | HD NI NH NI NH HD HD NI NH NH NI NH NG HD HD NG NH NH |
| AAVS1 | 10 | TCCTTCAGAGCCAGGAGTC (SEQ ID NO: 32) | HD HD NG NG HD NI NH NI NH HD HD NI NH NH NI NH NG HD |
| AAVS1 | 11 | TCCTCCTTCAGAGCCAGGA (SEQ ID NO: 33) | HD HD NG HD HD NG NG HD NI NH NI NH HD HD NI NH NH NI |
| AAVS1 | 12 | TCCAGCCCCTCCTCCTTCA (SEQ ID NO: 34) | HD HD NI NH HD HD HD HD NG HD HD NG HD HD NG NG HD NI |
| AAVS1 | 13 | TCCGAGCTTGACCCTTGGA (SEQ ID NO: 35) | HD HD NH NI NH HD NG NG NH NI HD HD HD NG NG NH NH NI |
| AAVS1 | 14 | TGGTTTCCGAGCTTGACCC (SEQ ID NO: 36) | NH NH NG NG NG HD HD NH NI NH HD NG NG NH NI HD HD HD |
| AAVS1 | 15 | TGGGGTGGTTTCCGAGCTT (SEQ ID NO: 37) | NH NH NH NH NG NH NH NG NG NG HD HD NH NI NH HD NG NG |
| AAVS1 | 16 | TCTGCTGGGGTGGTTTCCG (SEQ ID NO: 38) | HD NG NH HD NG NH NH NH NH NG NH NH NG NG NG HD HD NH |
| AAVS1 | 17 | TGCAGAGTATCTGCTGGGG (SEQ ID NO: 39) | NH HD NI NH NI NH NG NI NG HD NG NH HD NG NH NH NH NH |
| AAVS1 | AVS1 | CCAATCCCCTCAGT (SEQ ID NO: 40) | HD HD NI NI NG HD HD HD HD NG HD NI NH NG |
| AAVS1 | AVS2 | CAGTGCTCAGTGGAA (SEQ ID NO: 41) | HD NI NH NG NH HD NG HD NI NH NG NH NH NI NI |
| AAVS1 | AVS3 | GAAACATCCGGCGACTCA (SEQ ID NO: 42) | NH NI NI NI HD NI NG HD HD NH NH HD NH NI HD NG HD NI |
| hROSA26 | 1F | TCGCCCCTCAAATCTTACA (SEQ ID NO: 43) | HD NH HD HD HD HD NG HD NI NI NI NG HD NG NG NI HD NI |
| hROSA26 | 2F | TCAAATCTTACAGCTGCTC (SEQ ID NO: 44) | HD NI NI NI NG HD NG NG NI HD NI NH HD NG NH HD NG HD |
| hROSA26 | 3F | TCTTACAGCTGCTCACTCC (SEQ ID NO: 45) | HD NG NG NI HD NI NH HD NG NH HD NG HD NI HD NG HD HD |

FIG. 3 (Cont.)

| | | | |
|---|---|---|---|
| hROSA26 | 4F | TACAGCTGCTCACTCCCCT (SEQ ID NO: 46) | NI HD NI NH HD NG NH HD NG HD NI HD NG HD HD HD HD NG |
| hROSA26 | 5F | TGCTCACTCCCCTGCAGGG (SEQ ID NO: 47) | NH HD NG HD NI HD NG HD HD HD HD NG NH HD NI NH NH NH |
| hROSA26 | 6F | TCCCCTGCAGGGCAACGCC (SEQ ID NO: 48) | HD HD HD HD NG NH HD NI NH NH NH HD NI NI HD NH HD HD |
| hROSA26 | 7F | TGCAGGGCAACGCCCAGGG (SEQ ID NO: 49) | NH HD NI NH NH NH HD NI NI HD NH HD HD HD NI NH NH NH |
| hROSA26 | 8R | TCTCGATTATGGGCGGGAT (SEQ ID NO: 50) | HD NG HD NH NI NG NG NI NG NH NH NH HD NH NH NH NI NG |
| hROSA26 | 9R | TCGCTTCTCGATTATGGGC (SEQ ID NO: 51) | HD NH HD NG NG HD NG HD NH NI NG NG NI NG NH NH NH HD |
| hROSA26 | 10R | TGTCGAGTCGCTTCTCGAT (SEQ ID NO: 52) | NH NG HD NH NI NH NG HD NH HD NG NG HD NG HD NH NI NG |
| hROSA26 | 11R | TCCATGTCGAGTCGCTTCT (SEQ ID NO: 53) | HD HD NI NG NH NG HD NH NI NH NG HD NH HD NG NG HD NG |
| hROSA26 | 12R | TCGCCTCCATGTCGAGTCG (SEQ ID NO: 54) | HD NH HD HD NG HD HD NI NG NH NG HD NH NI NH NG HD NH |
| hROSA26 | 13R | TCGTCATCGCCTCCATGTC (SEQ ID NO: 55) | HD NH NG HD NI NG HD NH HD HD NG HD HD NI NG NH NG HD |
| hROSA26 | 14R | TGATCTCGTCATCGCCTCC (SEQ ID NO: 56) | NH NI NG HD NG HD NH NG HD NI NG HD NH HD HD NG HD HD |
| hROSA26 | ROSA1 | GCTTCAGCTTCCTA (SEQ ID NO: 57) | NH HD NG NG HD NI NH HD NG NG HD HD NG NI |
| hROSA26 | ROSA2 | CTGTGATCATGCCA (SEQ ID NO: 58) | HD NG NK NG NH NI NG HD NI NG NH HD HD NI |
| hROSA26 | TALER2 | ACAGTGGTACACACCT (SEQ ID NO: 59) | NI HD NI NN NG NN NN NG NI HD NI HD NI HD HD NG |
| hROSA26 | TALER3 | CCACCCCCCACTAAG (SEQ ID NO: 60) | HD HD NI HD HD HD HD HD HD NI HD NG NI NI NN |
| hROSA26 | TALER4 | CATTGGCCGGGCAC (SEQ ID NO: 61) | HD NI NG NG NN NN HD HD NN NN NN HD NI HD |
| hROSA26 | TALER5 | GCTTGAACCCAGGAGA (SEQ ID NO: 62) | NN HD NG NG NN NI NI HD HD HD NI NN NN NI NN NI |
| CCR5 | TALC3 | ACACCCGATCCACTGGG (SEQ ID NO: 63) | NI HD NI HD HD HD NN NI NG HD HD NI HD NG NN NN NN |
| CCR5 | TALC4 | GCTGCATCAACCCC (SEQ ID NO: 64) | NN HD NG NN HD NI NG HD NI NI HD HD HD HD |
| CCR5 | TALC5 | GCCACAAACAGAAATA (SEQ ID NO: 65) | NN NN HD NI HD NN NI NI NI HD NI HD HD HD NG HD HD |
| CCR5 | TALC7 | GGTGGCTCATGCCTG (SEQ ID NO: 66) | NN NN NG NN NN HD NG HD NI NG NN HD HD NG NN |
| CCR5 | TALC8 | GATTTGCACAGCTCAT (SEQ ID NO: 67) | NN NI NG NG NG NN HD NI HD NI NN HD NG HD NI NG |
| Chr 2 | SHCHR2-1 | AAGCTCTGAGGAGCA (SEQ ID NO: 68) | NI NI NH HD NG HD NG NH NI NH NH NI NH HD |
| Chr 2 | SHCHR2-2 | CCCTAGCTGTCCC (SEQ ID NO: 69) | HD HD HD NG NI NK HD NG NH NG HD HD HD HD |

FIG. 3 (Cont.)

| | | | |
|---|---|---|---|
| Chr 2 | SHCHR2-3 | GCCTAGCATGCTAG (SEQ ID NO: 70) | NH HD HD NG NI NH HD NI NG NH HD NG NI NH |
| Chr 2 | SHCHR2-4 | ATGGGCTTCACGGAT (SEQ ID NO: 71) | NI NG NH NH NH HD NG NG HD NI HD NH NH NI NG |
| Chr 4 | SHCHR4-1 | GAAACTATGCCTGC (SEQ ID NO: 72) | NH NI NI NI HD NG NI NG NH HD HD NG NH HD |
| Chr 4 | SHCHR4-2 | GCACCATTGCTCCC (SEQ ID NO: 73) | NH HD NI HD HD NI NG NG NH HD NG HD HD HD |
| Chr 4 | SHCHR4-3 | GACATGCAACTCAG (SEQ ID NO: 74) | NH NI HD NI NG NH HD NI NI HD NG HD NI NH |
| Chr 6 | SHCHR6-1 | ACACCACTAGGGGT (SEQ ID NO: 75) | NI HD NI HD HD NI HD NG NI NH NH NH NH NG |
| Chr 6 | SHCHR6-2 | GTCTGCTAGACAGG (SEQ ID NO: 76) | NH NG HD NG NH HD NG NI NH NI HD NI NH NH |
| Chr 6 | SHCHR6-3 | GGCCTAGACAGGCTG (SEQ ID NO: 77) | NH NH HD HD NG NI NH NI HD NI NH NH HD NG NH |
| Chr 6 | SHCHR6-4 | GAGGCATTCTTATCG (SEQ ID NO: 78) | NH NI NH NH HD NI NG NG HD NG NG NI NG HD NH |
| Chr 10 | SHCHR10-1 | GCCTGGAAACGTTCC (SEQ ID NO: 79) | NN HD HD NG NN NN NI NI NI HD NN NG NG HD HD |
| Chr 10 | SHCHR10-2 | GTGCTCTGACAATA (SEQ ID NO: 80) | NN NG NN HD NG HD NG NN NI HD NI NI NG NI |
| Chr 10 | SHCHR10-3 | GTTTTGCAGCCTCC (SEQ ID NO: 81) | NN NG NG NG NG NN HD NI NN HD HD NG HD HD |
| Chr 10 | SHCHR10-4 | ACAGCTGTGGAACGT (SEQ ID NO: 82) | NI HD NI NN HD NG NN NG NN NN NI NI HD NN NG |
| Chr 10 | SHCHR10-5 | GGCTCTCTTCCTCCT (SEQ ID NO: 83) | HD NI NI NN NI HD HD NN NI NN HD NI HD NG NN HD NG NN |
| Chr 11 | SHCHR11-1 | CTATCCCAAAACTCT (SEQ ID NO: 84) | HD NG NI NG HD HD HD NI NI NI NI HD NG HD NG |
| Chr 11 | SHCHR11-2 | GAAAAACTATGTAT (SEQ ID NO: 85) | NH NI NI NI NI NI HD NG NI NG NH NG NI NG |
| Chr 11 | SHCHR11-3 | AGGCAGGCTGGTTGA (SEQ ID NO: 86) | NI NH NH HD NI NH NH HD NG NH NH NG NG NH NI |
| Chr 17 | SHCHR17-1 | CAATACAACCACGC (SEQ ID NO: 87) | HD NI NI NG NI HD NI NI HD HD NI HD NN HD |
| Chr 17 | SHCHR17-2 | ATGACGGACTCAACT (SEQ ID NO: 88) | NI NG NN NI HD NN NN NI HD NG HD NI NI HD NG |
| Chr 17 | SHCHR17-3 | CACAACATTTGTAA (SEQ ID NO: 89) | HD NI HD NI NI HD NI NG NG NG NN NG NI NI |
| Chr 17 | SHCHR17-4 | ATTTCCAGTGCACA (SEQ ID NO: 90) | NI NG NG NG HD HD NI NN NG NN HD NI HD NI |

FIG. 3 (Cont.)

Code:

| RVD | Nucleotide | RVD | Nucleotide |
|---|---|---|---|
| HD | C | NI | A |
| NH | G | NN | G, A |
| NK | G | NS | G, C, A |
| NG | T, mC | | |

FIG. 4

Guide RNAs to target human genomic safe harbor sites using dCas in areas of open chromatin

| GSHS | Identifier | Sequence |
|---|---|---|
| AAVS1 | 14F | CACCGGGAGCCACGAAAACAGATCC (SEQ ID NO: 99) |
| AAVS1 | 15F | CACCGCGAAAACAGATCCAGGGACA (SEQ ID NO: 100) |
| AAVS1 | 16F | CACCGAGATCCAGGGACACGGTGCT (SEQ ID NO: 101) |
| AAVS1 | 17F | CACCGGACACGGTGCTAGGACAGTG (SEQ ID NO: 102) |
| AAVS1 | 18F | CACCGGAAAATGACCCAACAGCCTC (SEQ ID NO: 103) |
| AAVS1 | 19F | CACCGGCCTGGCCGGCCTGACCACT (SEQ ID NO: 104) |
| AAVS1 | 20F | CACCGCTGAGCACTGAAGGCCTGGC (SEQ ID NO: 105) |
| AAVS1 | 21F | CACCGTGGTTTCCACTGAGCACTGA (SEQ ID NO: 106) |
| AAVS1 | 22F | CACCGGATAGCCAGGAGTCCTTTCG (SEQ ID NO: 107) |
| AAVS1 | 23F | CACCGGCGCTTCCAGTGCTCAGACT (SEQ ID NO: 108) |
| AAVS1 | 24F | CACCGCAGTGCTCAGACTAGGGAAG (SEQ ID NO: 109) |
| AAVS1 | 25F | CACCGGCCCCTCCTCCTTCAGAGCC (SEQ ID NO: 110) |
| AAVS1 | 26F | CACCGTCCTTCAGAGCCAGGAGTCC (SEQ ID NO: 111) |
| AAVS1 | 27F | CACCGTGGTTTCCGAGCTTGACCCT (SEQ ID NO: 112) |
| AAVS1 | 28F | CACCGCTGCAGAGTATCTGCTGGGG (SEQ ID NO: 113) |
| AAVS1 | 29F | CACCGCGTTCCTGCAGAGTATCTGC (SEQ ID NO: 114) |
| AAVS1 | 14R | AAACGGATCTGTTTTCGTGGCTCCC (SEQ ID NO: 115) |
| AAVS1 | 15R | AAACTGTCCCTGGATCTGTTTTCGC (SEQ ID NO: 116) |
| AAVS1 | 16R | AAACAGCACCGTGTCCCTGGATCTC (SEQ ID NO: 117) |
| AAVS1 | 17R | AAACCACTGTCCTAGCACCGTGTCC (SEQ ID NO: 118) |
| AAVS1 | 18R | AAACGAGGCTGTTGGGTCATTTTCC (SEQ ID NO: 119) |
| AAVS1 | 19R | AAACAGTGGTCAGGCCGGCCAGGCC (SEQ ID NO: 120) |
| AAVS1 | 20R | AAACGCCAGGCCTTCAGTGCTCAGC (SEQ ID NO: 121) |

FIG. 4 (Cont.)

| | | |
|---|---|---|
| AAVS1 | 21R | AAACTCAGTGCTCAGTGGAAACCAC (SEQ ID NO: 122) |
| AAVS1 | 22R | AAACCGAAAGGACTCCTGGCTATCC (SEQ ID NO: 123) |
| AAVS1 | 23R | AAACAGTCTGAGCACTGGAAGCGCC (SEQ ID NO: 124) |
| AAVS1 | 24R | AAACCTTCCCTAGTCTGAGCACTGC (SEQ ID NO: 125) |
| AAVS1 | 25R | AAACGGCTCTGAAGGAGGAGGGGCC (SEQ ID NO: 126) |
| AAVS1 | 26R | AAACGGACTCCTGGCTCTGAAGGAC (SEQ ID NO: 127) |
| AAVS1 | 27R | AAACAGGGTCAAGCTCGGAAACCAC (SEQ ID NO: 128) |
| AAVS1 | 28R | AAACCCCCAGCAGATACTCTGCAGC (SEQ ID NO: 129) |
| AAVS1 | 29R | AAACGCAGATACTCTGCAGGAACGC (SEQ ID NO: 130) |
| AAVS1 | AAVS1 | TCCCCTCCCAGAAAGACCTG (SEQ ID NO: 131) |
| AAVS1 | gAAVS2 | TGGGCTCCAAGCAATCCTGG (SEQ ID NO: 132) |
| AAVS1 | gAAVS3 | GTGGCTCAGGAGGTACCTGG (SEQ ID NO: 133) |
| AAVS1 | gAAVS4 | GAGCCACGAAAACAGATCCA (SEQ ID NO: 134) |
| | | |
| AAVS1 | gAAVS5 | AAGTGAACGGGGAAGGGAGG (SEQ ID NO: 135) |
| AAVS1 | gAAVS6 | GACAAAAGCCGAAGTCCAGG (SEQ ID NO: 136) |
| AAVS1 | gAAVS7 | GTGGTTGATAAACCCACGTG (SEQ ID NO: 137) |
| AAVS1 | gAAVS8 | TGGGAACAGCCACAGCAGGG (SEQ ID NO: 138) |
| AAVS1 | gAAVS9 | GCAGGGGAACGGGGATGCAG (SEQ ID NO: 139) |
| AAVS1 | gAAVS10 | GAGATGGTGGACGAGGAAGG (SEQ ID NO: 140) |
| AAVS1 | gAAVS11 | GAGATGGCTCCAGGAAATGG (SEQ ID NO: 141) |
| AAVS1 | gAAVS12 | TAAGGAATCTGCCTAACAGG (SEQ ID NO: 142) |

FIG. 4 (Cont.)

| | | |
|---|---|---|
| AAVS1 | gAAVS13 | TCAGGAGACTAGGAAGGAGG (SEQ ID NO: 143) |
| AAVS1 | gAAVS14 | TATAAGGTGGTCCCAGCTCG (SEQ ID NO: 144) |
| AAVS1 | gAAVS15 | CTGGAAGATGCCATGACAGG (SEQ ID NO: 145) |
| AAVS1 | gAAVS16 | GCACAGACTAGAGAGGTAAG (SEQ ID NO: 146) |
| AAVS1 | gAAVS17 | ACAGACTAGAGAGGTAAGGG (SEQ ID NO: 147) |
| AAVS1 | gAAVS18 | GAGAGGTGACCCGAATCCAC (SEQ ID NO: 148) |
| AAVS1 | gAAVS19 | GCACAGGCCCCAGAAGGAGA (SEQ ID NO: 149) |
| AAVS1 | gAAVS20 | CCGGAGAGGACCCAGACACG (SEQ ID NO: 150) |
| AAVS1 | gAAVS21 | GAGAGGACCCAGACACGGGG (SEQ ID NO: 151) |
| AAVS1 | gAAVS22 | GCAACACAGCAGAGAGCAAG (SEQ ID NO: 152) |
| AAVS1 | gAAVS23 | GAAGAGGGAGTGGAGGAAGA (SEQ ID NO: 153) |
| AAVS1 | gAAVS24 | AAGACGGAACCTGAAGGAGG (SEQ ID NO: 154) |
| AAVS1 | gAAVS25 | AGAAAGCGGCACAGGCCCAG (SEQ ID NO: 155) |
| AAVS1 | gAAVS26 | GGGAAACAGTGGGCCAGAGG (SEQ ID NO: 156) |
| AAVS1 | gAAVS27 | GTCCGGACTCAGGAGAGAGA (SEQ ID NO: 157) |
| AAVS1 | gAAVS28 | GGCACAGCAAGGGCACTCGG (SEQ ID NO: 158) |
| AAVS1 | gAAVS29 | GAAGAGGGGAAGTCGAGGGA (SEQ ID NO: 159) |
| AAVS1 | gAAVS30 | GGGAATGGTAAGGAGGCCTG (SEQ ID NO: 160) |
| AAVS1 | gAAVS31 | GCAGAGTGGTCAGCACAGAG (SEQ ID NO: 161) |
| AAVS1 | gAAVS32 | GCACAGAGTGGCTAAGCCCA (SEQ ID NO: 162) |
| AAVS1 | gAAVS33 | GACGGGGTGTCAGCATAGGG (SEQ ID NO: 163) |
| AAVS1 | gAAVS34 | GCCCAGGGCCAGGAACGACG (SEQ ID NO: 164) |
| AAVS1 | gAAVS35 | GGTGGAGTCCAGCACGGCGC (SEQ ID NO: 165) |
| AAVS1 | gAAVS36 | ACAGGCCGCCAGGAACTCGG (SEQ ID NO: 166) |

FIG. 4 (Cont.)

| | | |
|---|---|---|
| AAVS1 | gAAVS37 | ACTAGGAAGTGTGTAGCACC (SEQ ID NO: 167) |
| AAVS1 | gAAVS38 | ATGAATAGCAGACTGCCCCG (SEQ ID NO: 168) |
| AAVS1 | gAAVS39 | ACACCCCTAAAAGCACAGTG (SEQ ID NO: 169) |
| AAVS1 | gAAVS40 | CAAGGAGTTCCAGCAGGTGG (SEQ ID NO: 170) |
| AAVS1 | gAAVS41 | AAGGAGTTCCAGCAGGTGGG (SEQ ID NO: 171) |
| AAVS1 | gAAVS42 | TGGAAAGAGGAGGGAAGAGG (SEQ ID NO: 172) |
| AAVS1 | gAAVS43 | TCGAATTCCTAACTGCCCCG (SEQ ID NO: 173) |
| | | |
| AAVS1 | gAAVS44 | GACCTGCCCAGCACACCCTG (SEQ ID NO: 174) |
| AAVS1 | gAAVS45 | GGAGCAGCTGCGGCAGTGGG (SEQ ID NO: 175) |
| AAVS1 | gAAVS46 | GGGAGGGAGAGCTTGGCAGG (SEQ ID NO: 176) |
| AAVS1 | gAAVS47 | GTTACGTGGCCAAGAAGCAG (SEQ ID NO: 177) |
| AAVS1 | gAAVS48 | GCTGAACAGAGAAGAGCTGG (SEQ ID NO: 178) |
| AAVS1 | gAAVS49 | TCTGAGGGTGGAGGGACTGG (SEQ ID NO: 179) |
| AAVS1 | gAAVS50 | GGAGAGGTGAGGGACTTGGG (SEQ ID NO: 180) |
| AAVS1 | gAAVS51 | GTGAACCAGGCAGACAACGA (SEQ ID NO: 181) |
| AAVS1 | gAAVS52 | CAGGTACCTCCTGAGCCACG (SEQ ID NO: 182) |
| AAVS1 | gAAVS53 | GGGGGAGTAGGGGCATGCAG (SEQ ID NO: 183) |
| hROSA26 | gHROSA26-1 | GCAAATGGCCAGCAAGGGTG (SEQ ID NO: 184) |
| hROSA26 | gHROSA26-2 | CAAATGGCCAGCAAGGGTGG (SEQ ID NO: 309) |
| hROSA26 | gHROSA26-3 | GCAGAACCTGAGGATATGGA (SEQ ID NO: 310) |
| hROSA26 | gHROSA26-3 | AATACACAGAATGAAAATAG (SEQ ID NO: 311) |
| hROSA26 | gHROSA26-4 | CTGGTGACTAGAATAGGCAG (SEQ ID NO: 312) |
| hROSA26 | gHROSA26-5 | TGGTGACTAGAATAGGCAGT (SEQ ID NO: 313) |
| hROSA26 | gHROSA26-6 | TAAAAGAATGTGAAAAGATG (SEQ ID NO: 314) |
| hROSA26 | gHROSA26-7 | TCAGGAGTTCAAGACCACCC (SEQ ID NO: 315) |

FIG. 4 (Cont.)

| | | |
|---|---|---|
| hROSA26 | gHROSA26-8 | TGTAGTCCCAGTTATGCAGG (SEQ ID NO: 316) |
| hROSA26 | gHROSA26-9 | GGGTTCACACCACAAATGCA (SEQ ID NO: 317) |
| hROSA26 | gHROSA26-10 | GGCAAATGGCCAGCAAGGGT (SEQ ID NO: 318) |
| hROSA26 | gHROSA26-11 | AGAAACCAATCCCAAAGCAA (SEQ ID NO: 319) |
| hROSA26 | gHROSA26-12 | GCCAAGGACACCAAAACCCA (SEQ ID NO: 320) |
| hROSA26 | gHROSA26-13 | AGTGGTGATAAGGCAACAGT (SEQ ID NO: 321) |
| hROSA26 | gHROSA26-14 | CCTGAGACAGAAGTATTAAG (SEQ ID NO: 322) |
| hROSA26 | gHROSA26-15 | AAGGTCACACAATGAATAGG (SEQ ID NO: 323) |
| hROSA26 | gHROSA26-16 | CACCATACTAGGGAAGAAGA (SEQ ID NO: 324) |
| hROSA26 | gHROSA26-17 | CAATACCCTGCCCTTAGTGG (SEQ ID NO: 327) |
| hROSA26 | gHROSA26-18 | AATACCCTGCCCTTAGTGGG (SEQ ID NO: 325) |
| hROSA26 | gHROSA26-19 | TTAGTGGGGGGTGGAGTGGG (SEQ ID NO: 326) |
| hROSA26 | gHROSA26-20 | GTGGGGGGTGGAGTGGGGGG (SEQ ID NO: 328) |
| hROSA26 | gHROSA26-21 | GGGGGGTGGAGTGGGGGGTG (SEQ ID NO: 329) |
| hROSA26 | gHROSA26-22 | GGGGTGGAGTGGGGGGTGGG (SEQ ID NO: 330) |
| hROSA26 | gHROSA26-23 | GGGTGGAGTGGGGGGTGGGG (SEQ ID NO: 331) |
| hROSA26 | gHROSA26-24 | GGGGGTGGGGAAAGACATCG (SEQ ID NO: 332) |
| hROSA26 | gHROSA26-25 | GCAAATGGCCAGCAAGGGTG (SEQ ID NO: 184) |
| hROSA26 | gHROSA26-26 | CAAATGGCCAGCAAGGGTGG (SEQ ID NO: 309) |
| hROSA26 | gHROSA26-27 | GCAGAACCTGAGGATATGGA (SEQ ID NO: 310) |
| hROSA26 | gHROSA26-28 | AATACACAGAATGAAAATAG (SEQ ID NO: 311) |
| | | |
| hROSA26 | gHROSA26-29 | CTGGTGACTAGAATAGGCAG (SEQ ID NO: 312) |
| hROSA26 | gHROSA26-30 | TGGTGACTAGAATAGGCAGT (SEQ ID NO: 313) |

FIG. 4 (Cont.)

| | | |
|---|---|---|
| hROSA26 | gHROSA26-31 | TAAAAGAATGTGAAAAGATG (SEQ ID NO: 314) |
| hROSA26 | gHROSA26-32 | TCAGGAGTTCAAGACCACCC (SEQ ID NO: 315) |
| hROSA26 | gHROSA26-33 | TGTAGTCCCAGTTATGCAGG (SEQ ID NO: 316) |
| hROSA26 | gHROSA26-34 | GGGTTCACACCACAAATGCA (SEQ ID NO: 317) |
| hROSA26 | gHROSA26-35 | GGCAAATGGCCAGCAAGGGT (SEQ ID NO: 318) |
| hROSA26 | gHROSA26-36 | AGAAACCAATCCCAAAGCAA (SEQ ID NO: 319) |
| hROSA26 | gHROSA26-37 | GCCAAGGACACCAAAACCCA (SEQ ID NO: 320) |
| hROSA26 | gHROSA26-38 | AGTGGTGATAAGGCAACAGT (SEQ ID NO: 321) |
| hROSA26 | gHROSA26-39 | CCTGAGACAGAAGTATTAAG (SEQ ID NO: 322) |
| hROSA26 | gHROSA26-40 | AAGGTCACACAATGAATAGG (SEQ ID NO: 323) |
| hROSA26 | gHROSA26-41 | CACCATACTAGGGAAGAAGA (SEQ ID NO: 324) |
| hROSA26 | gHROSA26-42 | CAATACCCTGCCCTTAGTGG (SEQ ID NO: 327) |
| hROSA26 | gHROSA26-43 | AATACCCTGCCCTTAGTGGG (SEQ ID NO: 325) |
| hROSA26 | gHROSA26-44 | TTAGTGGGGGGTGGAGTGGG (SEQ ID NO: 326) |
| hROSA26 | gHROSA26-45 | GTGGGGGGTGGAGTGGGGGG (SEQ ID NO: 328) |
| hROSA26 | gHROSA26-46 | GGGGGGTGGAGTGGGGGGTG (SEQ ID NO: 329) |
| hROSA26 | gHROSA26-47 | GGGGTGGAGTGGGGGGTGGG (SEQ ID NO: 330) |
| hROSA26 | gHROSA26-48 | GGGTGGAGTGGGGGGTGGGG (SEQ ID NO: 331) |
| hROSA26 | gHROSA26-49 | GGGGGTGGGGAAAGACATCG (SEQ ID NO: 332) |
| hROSA26 | gHROSA26-50 | GCAGCTGTGAATTCTGATAG (SEQ ID NO: 333) |
| hROSA26 | gHROSA26-51 | GAGATCAGAGAAACCAGATG (SEQ ID NO: 334) |
| hROSA26 | gHROSA26-52 | TCTATACTGATTGCAGCCAG (SEQ ID NO: 335) |
| hROSA26 | gHROSA26-1 | GCAAATGGCCAGCAAGGGTG (SEQ ID NO: 184) |
| hROSA26 | 44F | CACCGAATCGAGAAGCGACTCGACA (SEQ ID NO: 185) |
| hROSA26 | 45F | CACCGGTCCCTGGGCGTTGCCCTGC (SEQ ID NO: 186) |
| hROSA26 | 46F | CACCGCCCTGGGCGTTGCCCTGCAG (SEQ ID NO: 187) |

FIG. 4 (Cont.)

| | | |
|---|---|---|
| hROSA26 | 1nF | CACCGCCGTGGGAAGATAAACTAAT (SEQ ID NO: 188) |
| hROSA26 | 2nF | CACCGTCCCCTGCAGGGCAACGCCC (SEQ ID NO: 189) |
| hROSA26 | 3nF | CACCGGTCGAGTCGCTTCTCGATTA (SEQ ID NO: 190) |
| hROSA26 | 4nF | CACCGCTGCTGCCTCCCGTCTTGTA (SEQ ID NO: 191) |
| hROSA26 | 5nF | CACCGGAGTGCCGCAATACCTTTAT (SEQ ID NO: 192) |
| hROSA26 | 6nF | CACCGACACTTTGGTGGTGCAGCAA (SEQ ID NO: 193) |
| hROSA26 | 7nF | CACCGTCTCAAATGGTATAAAACTC (SEQ ID NO: 194) |
| hROSA26 | 8nF | CACCGCCGTGGGAAGATAAACTAAT (SEQ ID NO: 188) |
| hROSA26 | 9F | CACCGAATCCCGCCCATAATCGAGA (SEQ ID NO: 195) |
| hROSA26 | 10F | CACCGTCCCGCCCATAATCGAGAAG (SEQ ID NO: 196) |
| hROSA26 | 11F | CACCGCCCATAATCGAGAAGCGACT (SEQ ID NO: 197) |
| | | |
| hROSA26 | 12F | CACCGGAGAAGCGACTCGACATGGA (SEQ ID NO: 198) |
| hROSA26 | 13F | CACCGGAAGCGACTCGACATGGAGG (SEQ ID NO: 199) |
| hROSA26 | 14F | CACCGGCGACTCGACATGGAGGCGA (SEQ ID NO: 200) |
| hROSA26 | 44F | AAACTGTCGAGTCGCTTCTCGATTC (SEQ ID NO: 201) |
| hROSA26 | 45F | AAACGCAGGGCAACGCCCAGGGACC (SEQ ID NO: 202) |
| hROSA26 | 46F | AAACCTGCAGGGCAACGCCCAGGGC (SEQ ID NO: 203) |
| hROSA26 | 1nR | AAACATTAGTTTATCTTCCCACGGC (SEQ ID NO: 204) |
| hROSA26 | 2nR | AAACGGGCGTTGCCCTGCAGGGGAC (SEQ ID NO: 205) |
| hROSA26 | 3nR | AAACTAATCGAGAAGCGACTCGACC (SEQ ID NO: 206) |
| hROSA26 | 4nR | AAACTACAAGACGGGAGGCAGCAGC (SEQ ID NO: 207) |
| hROSA26 | 5nR | AAACATAAAGGTATTGCGGCACTCC (SEQ ID NO: 208) |

FIG. 4 (Cont.)

| | | |
|---|---|---|
| hROSA26 | 6nR | AAACTTGCTGCACCACCAAAGTGTC (SEQ ID NO: 209) |
| hROSA26 | 7nR | AAACGAGTTTTATACCATTTGAGAC (SEQ ID NO: 210) |
| hROSA26 | 8nR | AAACATTAGTTTATCTTCCCACGGC (SEQ ID NO: 204) |
| hROSA26 | 9R | AAACTCTCGATTATGGGCGGGATTC (SEQ ID NO: 211) |
| hROSA26 | 10R | AAACCTTCTCGATTATGGGCGGGAC (SEQ ID NO: 212) |
| hROSA26 | 11R | AAACAGTCGCTTCTCGATTATGGGC (SEQ ID NO: 213) |
| hROSA26 | 12R | AAACTCCATGTCGAGTCGCTTCTCC (SEQ ID NO: 214) |
| hROSA26 | 13R | AAACCCTCCATGTCGAGTCGCTTCC (SEQ ID NO: 215) |
| hROSA26 | 14R | AAACTCGCCTCCATGTCGAGTCGCC (SEQ ID NO: 216) |
| CCR5 | 1F | CACCGACAGGGTTAATGTGAAGTCC (SEQ ID NO: 217) |
| CCR5 | 2F | CACCGTCCCCCTCTACATTTAAAGT (SEQ ID NO: 218) |
| CCR5 | 3F | CACCGCATTTAAAGTTGGTTTAAGT (SEQ ID NO: 219) |
| CCR5 | 4F | CACCGTTAGAAAATATAAAGAATAA (SEQ ID NO: 220) |
| CCR5 | 5 | CACCGTAAATGCTTACTGGTTTGAA (SEQ ID NO: 221) |
| CCR5 | 6F | CACCGTCCTGGGTCCAGAAAAAGAT (SEQ ID NO: 222) |
| CCR5 | 7F | CACCGTTGGGTGGTGAGCATCTGTG (SEQ ID NO: 223) |
| CCR5 | 8F | CACCGCGGGGAGAGTGGAGAAAAAG (SEQ ID NO: 224) |
| CCR5 | 9F | CACCGGTTAAAACTCTTTAGACAAC (SEQ ID NO: 225) |
| CCR5 | 10F | CACCGGAAAATCCCCACTAAGATCC (SEQ ID NO: 226) |
| CCR5 | 1R | AAACGGACTTCACATTAACCCTGTC (SEQ ID NO: 227) |
| CCR5 | 2R | AAACACTTTAAATGTAGAGGGGGAC (SEQ ID NO: 228) |
| CCR5 | 3R | AAACACTTAAACCAACTTTAAATGC (SEQ ID NO: 229) |
| CCR5 | 4R | AAACTTATTCTTTATATTTTCTAAC (SEQ ID NO: 230) |
| CCR5 | 5R | AAACTTCAAACCAGTAAGCATTTAC (SEQ ID NO: 231) |
| CCR5 | 6R | AAACATCTTTTTCTGGACCCAGGAC (SEQ ID NO: 232) |
| CCR5 | 7R | AAACCACAGATGCTCACCACCCAAC (SEQ ID NO: 233) |

FIG. 4 (Cont.)

| | | |
|---|---|---|
| CCR5 | 8R | AAACCTTTTTCTCCACTCTCCCCGC (SEQ ID NO: 234) |
| | | |
| CCR5 | 9R | AAACGTTGTCTAAAGAGTTTTAACC (SEQ ID NO: 235) |
| CCR5 | 10R | AAACGGATCTTAGTGGGGATTTTCC (SEQ ID NO: 236) |
| CCR5 | gCCR5-1 | AGTAGCAGTAATGAAGCTGG (SEQ ID NO: 237) |
| CCR5 | gCCR5-2 | ATACCCAGACGAGAAAGCTG (SEQ ID NO: 238) |
| CCR5 | gCCR5-3 | TACCCAGACGAGAAAGCTGA (SEQ ID NO: 239) |
| CCR5 | gCCR5-4 | GGTGGTGAGCATCTGTGTGG (SEQ ID NO: 240) |
| CCR5 | gCCR5-5 | AAATGAGAAGAAGAGGCACA (SEQ ID NO: 241) |
| CCR5 | gCCR5-6 | CTTGTGGCCTGGGAGAGCTG (SEQ ID NO: 242) |
| CCR5 | gCCR5-7 | GCTGTAGAAGGAGACAGAGC (SEQ ID NO: 243) |
| CCR5 | gCCR5-8 | GAGCTGGTTGGGAAGACATG (SEQ ID NO: 244) |
| CCR5 | gCCR5-9 | CTGGTTGGGAAGACATGGGG (SEQ ID NO: 245) |
| CCR5 | gCCR5-10 | CGTGAGGATGGGAAGGAGGG (SEQ ID NO: 246) |
| CCR5 | gCCR5-11 | ATGCAGAGTCAGCAGAACTG (SEQ ID NO: 247) |
| CCR5 | gCCR5-12 | AAGACATCAAGCACAGAAGG (SEQ ID NO: 248) |
| CCR5 | gCCR5-13 | TCAAGCACAGAAGGAGGAGG (SEQ ID NO: 249) |
| CCR5 | gCCR5-14 | AACCGTCAATAGGCAAAGGG (SEQ ID NO: 250) |
| CCR5 | gCCR5-15 | CCGTATTTCAGACTGAATGG (SEQ ID NO: 251) |
| CCR5 | gCCR5-16 | GAGAGGACAGGTGCTACAGG (SEQ ID NO: 252) |
| CCR5 | gCCR5-17 | AACCAAGGAAGGGCAGGAGG (SEQ ID NO: 253) |
| CCR5 | gCCR5-18 | GACCTCTGGGTGGAGACAGA (SEQ ID NO: 254) |
| CCR5 | gCCR5-19 | CAGATGACCATGACAAGCAG (SEQ ID NO: 255) |
| CCR5 | gCCR5-20 | AACACCAGTGAGTAGAGCGG (SEQ ID NO: 256) |

FIG. 4 (Cont.)

| | | |
|---|---|---|
| CCR5 | gCCR5-21 | AGGACCTTGAAGCACAGAGA (SEQ ID NO: 257) |
| CCR5 | gCCR5-22 | TACAGAGGCAGACTAACCCA (SEQ ID NO: 258) |
| CCR5 | gCCR5-23 | ACAGAGGCAGACTAACCCAG (SEQ ID NO: 259) |
| CCR5 | gCCR5-24 | TAAATGACGTGCTAGACCTG (SEQ ID NO: 260) |
| CCR5 | gCCR5-25 | AGTAACCACTCAGGACAGGG (SEQ ID NO: 261) |
| chr2 | gchr2-1 | ACCACAAAACAGAAACACCA (SEQ ID NO: 262) |
| chr2 | gchr2-2 | GTTTGAAGACAAGCCTGAGG (SEQ ID NO: 263) |
| chr4 | gchr4-1 | GCTGAACCCCAAAAGACAGG (SEQ ID NO: 264) |
| chr4 | gchr4-2 | GCAGCTGAGACACACACCAG (SEQ ID NO: 265) |
| chr4 | gchr4-3 | AGGACACCCCAAAGAAGCTG (SEQ ID NO: 266) |
| chr4 | gchr4-4 | GGACACCCCAAAGAAGCTGA (SEQ ID NO: 267) |
| chr6 | gchr6-1 | CCAGTGCAATGGACAGAAGA (SEQ ID NO: 268) |
| chr6 | gchr6-2 | AGAAGAGGGAGCCTGCAAGT (SEQ ID NO: 269) |
| chr6 | gchr6-3 | GTGTTTGGGCCCTAGAGCGA (SEQ ID NO: 270) |
| chr6 | gchr6-4 | CATGTGCCTGGTGCAATGCA (SEQ ID NO: 271) |
| chr6 | gchr6-5 | TACAAAGAGGAAGATAAGTG (SEQ ID NO: 272) |
| chr6 | gchr6-6 | GTCACAGAATACACCACTAG (SEQ ID NO: 273) |
| | | |
| chr6 | gchr6-7 | GGGTTACCCTGGACATGGAA (SEQ ID NO: 274) |
| chr6 | gchr6-8 | CATGGAAGGGTATTCACTCG (SEQ ID NO: 275) |
| chr6 | gchr6-9 | AGAGTGGCCTAGACAGGCTG (SEQ ID NO: 276) |
| chr6 | gchr6-10 | CATGCTGGACAGCTCGGCAG (SEQ ID NO: 277) |
| chr6 | gchr6-11 | AGTGAAAGAAGAGAAAATTC (SEQ ID NO: 278) |
| chr6 | gchr6-12 | TGGTAAGTCTAAGAAACCTA (SEQ ID NO: 279) |
| chr6 | gchr6-13 | CCCACAGCCTAACCACCCTA (SEQ ID NO: 280) |
| chr6 | gchr6-14 | AATATTTCAAAGCCCTAGGG (SEQ ID NO: 281) |

FIG. 4 (Cont.)

| | | |
|---|---|---|
| chr6 | gchr6-15 | GCACTCGGAACAGGGTCTGG (SEQ ID NO: 282) |
| chr6 | gchr6-16 | AGATAGGAGCTCCAACAGTG (SEQ ID NO: 283) |
| chr6 | gchr6-17 | AAGTTAGAGCAGCCAGGAAA (SEQ ID NO: 284) |
| chr6 | gchr6-18 | TAGAGCAGCCAGGAAAGGGA (SEQ ID NO: 285) |
| chr6 | gchr6-19 | TGAATACCCTTCCATGTCCA (SEQ ID NO: 286) |
| chr6 | gchr6-20 | CCTGCATTGCACCAGGCACA (SEQ ID NO: 287) |
| chr6 | gchr6-21 | TCTAGGGCCCAAACACACCT (SEQ ID NO: 288) |
| chr6 | gchr6-22 | TCCCTCCATCTATCAAAAGG (SEQ ID NO: 289) |
| chr10 | gchr10-1 | AGCCCTGAGACAGAAGCAGG (SEQ ID NO: 290) |
| chr10 | gchr10-2 | GCCCTGAGACAGAAGCAGGT (SEQ ID NO: 291) |
| chr10 | gchr10-3 | AGGAGATGCAGTGATACGCA (SEQ ID NO: 292) |
| chr10 | gchr10-4 | ACAATACCAAGGGTATCCGG (SEQ ID NO: 293) |
| chr10 | gchr10-5 | TGATAAAGAAAACAAAGTGA (SEQ ID NO: 294) |
| chr10 | gchr10-6 | AAAGAAAACAAAGTGAGGGA (SEQ ID NO: 295) |
| chr10 | gchr10-7 | GTGGCAAGTGGAGAAATTGA (SEQ ID NO: 296) |
| chr10 | gchr10-8 | CAAGTGGAGAAATTGAGGGA (SEQ ID NO: 297) |
| chr10 | gchr10-9 | GTGGTGATGATTGCAGCTGG (SEQ ID NO: 298) |
| chr11 | gchr11-1 | CTATGTGCCTGACACACAGG (SEQ ID NO: 299) |
| chr11 | gchr11-2 | GGGTTGGACCAGGAAAGAGG (SEQ ID NO: 300) |
| chr17 | gchr17-1 | GATGCCTGGAAAAGGAAAGA (SEQ ID NO: 301) |
| chr17 | gchr17-2 | TAGTATGCACCTGCAAGAGG (SEQ ID NO: 302) |
| chr17 | gchr17-3 | TATGCACCTGCAAGAGGCGG (SEQ ID NO: 303) |
| chr17 | gchr17-4 | AGGGGAAGAAGAGAAGCAGA (SEQ ID NO: 304) |
| chr17 | gchr17-5 | GCTGAATCAAGAGACAAGCG (SEQ ID NO: 305) |
| chr17 | gchr17-6 | AAGCAAATAAATCTCCTGGG (SEQ ID NO: 306) |
| chr17 | gchr17-7 | AGATGAGTGCTAGAGACTGG (SEQ ID NO: 307) |
| chr17 | gchr17-8 | CTGATGGTTGAGCACAGCAG (SEQ ID NO: 308) |

FIG. 5A

Hyperactive MLT mutants from transposase DNA and transposase protein

| **Nucleotide change** | Amino Acid Change |
| --- | --- |
| T13C | S5P |
| T22C | S8P |
| T22C/T37C | S8P/C13R |
| A26G | D9G |
| A29G | D10G |
| A32G | E11G |
| T37C | C13R |
| C41T | A14V |
| A106G | S36G |
| G161A | S54N |
| T375G | N125K |
| A389C | K130T |
| G715A | G239S |
| A880G | T294A |
| A898G | T300A |
| A1033G | I345V |
| G1280A | R427H |
| A1424G | D475G |
| A1441G | M481V |
| C1472A | P491Q |
| G1558A | A520T |
| G1681A | A561T |

FIG. 5B

Excision positive and Integration deficient MLT mutants from transposase DNA and transposase protein

| MLT Backbone | MLT Mutant 1 | MLT Mutant 2 | MLT Mutant 3 |
|---|---|---|---|
| S8P/C13R | R164N | 0 | 0 |
| S8P/C13R | W168V | 0 | 0 |
| S8P/C13R | W168V | K369A | 0 |
| S8P/C13R | M278A | 0 | 0 |
| S8P/C13R | K286A | 0 | 0 |
| S8P/C13R | R287A | 0 | 0 |
| S8P/C13R | R333A | 0 | 0 |
| S8P/C13R | R333A | E284A | 0 |
| S8P/C13R | R333A | E284A | R336A |
| S8P/C13R | K334A | 0 | 0 |
| S8P/C13R | N335A | 0 | 0 |
| S8P/C13R | K349A | 0 | 0 |
| S8P/C13R | K350A | 0 | 0 |
| S8P/C13R | K368A | 0 | 0 |
| S8P/C13R | K369A | 0 | 0 |
| S8P/C13R | D416N | 0 | 0 |
| S8P/C13R | D416N | K286A | 0 |
| S8P/C13R | D416N | R287A | 0 |
| S8P/C13R | D416N | R333A | 0 |
| S8P/C13R | D416N | K334A | 0 |
| S8P/C13R | D416N | R336A | 0 |
| S8P/C13R | D416N | K349A | 0 |
| S8P/C13R | D416N | K350A | 0 |

FIG. 5B (Cont.)

| | | | |
|---|---|---|---|
| S8P/C13R | D416N | K368A | 0 |
| S8P/C13R | D416N | K369A | 0 |
| S8P/C13R | D416N | N310A | 0 |

Three Dimensional Model of MLT Using Phyre$^2$ Showing DNA Binding Domains

Secondary structure prediction for MLT, generated using Phyre2

Consensus
1. Trichnolpulsia ni
2. Myotis lucifugus
3. Myotis myotis 2a
4. Myotis myotis 1
5. Pteropus vampyrus 1
6. Myotis lucifugus 2
7. Myotis myotis 2
8. Myotis myotis 2b

FIG. 10

Nucleotide sequence alignment of engineered MLT (SEQ ID NO: 337, human codon-optimized, "MLT") and published sequence by Mitra et al. (SEQ ID NO: 336, Identity 77.67%, Gaps 1.44%)

```
MLT            78   ATGGCCCAGCACAGCGACTACCCCGACGACGAGTTCAGAGCCGATAAGCT
Mitra et al. 1    ATGGCGCAACACTCAGATTACTCCGACGATGAATTTTGTGCTGACAAACT

MLT            128  GAGTAACTA--CAGCTGCGACAGCGACCTGGAAAACGCCAGCACATCCGA
Mitra et al. 51   GTCCAATTATTCA--TGCGATAGCGACCTCGAAAACGCTTCCACGTCTGA

MLT            176  CGAGGACAGCTCTGACGACGAGGTGATGGTGCGGCCCAGAACCCTGAGAC
Mitra et al. 99   TGAAGATAGCAGCGATGATGAAGTAATGGTGAGGCCTCGCACCCTCCGCC

MLT            226  GGAGAAGAATCAGC------AGCTCTAGCAGCGACTCTGAATCCGACATC
Mitra et al. 149  GTCGCCGCATCAGCTCTTCGAGCTCT------GATTCTGAATCCGATATT

MLT            270  GAGGGCGGCCGGGAAGAGTGGAGCCACGTGGACAACCCTCCTGTTCTGGA
Mitra et al. 193  GAGGGTGGCCGCGAGGAGTGGTCCCACGTAGACAATCCGCCGGTGCTGGA

MLT            320  AGATTTTCTGGGCCATCAGGGCCTGAACACCGACGCCGTGATCAACAACA
Mitra et al. 243  GGACTTCCTAGGCCACCAAGGTCTGAACACTGACGCAGTAATCAACAATA
```

FIG. 10 (cont.)

```
MLT            370  TCGAGGATGCCGTGAAGCTGTTCATAGGAGATGATTTCTTTGAGTTCCTG
Mitra et al. 293  TCGAAGATGCAGTTAAACTGTTTATCGGTGACGATTTCTTCGAGTTTCTG

MLT            420  GTCGAGGAATCCAACCGCTATTACAACCAGAATAGAAACAACTTCAAGCT
Mitra et al. 343  GTGGAGGAATCTAACCGGTACTATAACCAGAATCGTAATAACTTCAAGCT

MLT            470  GAGCAAGAAAAG--CCTGAAGTGGAAGGACATCACCCCTCAGGAGATGAA
Mitra et al. 393  CTCTA--AAAAGTCTCTGAAGTGGAAGGACATCACCCCTCAGGAGATGAA

MLT            518  AAAGTTCCTGGGACTGATCGTTCTGATGGGACAGGTGCGGAAGGACAGAA
Mitra et al. 441  AAAGTTCCTCGGTCTGATCGTTCTGATGGGCCAAGTTCGCAAGGATCGTC

MLT            568  GGGATGATTACTGGACAACCGAACCTTGGACCGAGACCCCTTACTTTGGC
Mitra et al. 491  GTGACGACTATTGGACTACCGAACCGTGGACGGAAACTCCATACTTTGGC

MLT            618  AAGACCATGACCAGAGACAGATTCAGACAGATCTGGAAAGCCTGGCACTT
Mitra et al. 541  AAGACCATGACTCGTGACCGTTTCCGTCAGATCTGGAAGGCCTGGCACTT

MLT            668  CAACAACAATGCTGATATCGTGAACGAGTCTGATAGACTGTGTAAAGTGC
Mitra et al. 591  CAATAACAACGCTGACATTGTCAACGAGTCTGATCGTCTGTGTAAGGTTC

MLT            718  GGCCAGTGTTGGATTACTTCGTGCCTAAGTTCATCAACATCTATAAGCCT
Mitra et al. 641  GCCCTGTGCTGGATTACTTCGTTCCAAAATTCATTAACATTTACAAACCA
```

FIG. 10 (cont.)

```
MLT            768  CACCAGCAGCTGAGCCTGGATGAAGGCATCGTGCCCTGGCGGGGCAGACT
Mitra et al.   691  CATCAGCAGCTGTCCCTGGATGAGGGCATCGTGCCGTGGCGCGGCCGCCT

MLT            818  GTTCTTCAGAGTGTACAATGCTGGCAAGATCGTCAAATACGGCATCCTGG
Mitra et al.   741  GTTCTTCCGTGTCTATAATGCTGGCAAGATTGTGAAGTACGGTATCCTGG

MLT            868  TGCGCCTTCTGTGCGAGAGCGATACAGGCTACATCTGTAATATGGAAATC
Mitra et al.   791  TTCGCCTGCTGTGCGAAAGCGACACTGGCTACATCTGTAACATGGAGATC

MLT            918  TACTGCGGCGAGGGCAAAAGACTGCTGGAAACCATCCAGACCGTCGTTTC
Mitra et al.   841  TACTGCGGCGAGGGCAAACGTCTCCTCGAAACTATCCAGACCGTCGTGTC

MLT            968  CCCTTATACCGACAGCTGGTACCACATCTACATGGACAACTACTACAATT
Mitra et al.   891  TCCATACACGGATTCCTGGTATCATATTTACATGGATAACTATTATAACA

MLT           1018  CTGTGGCCAACTGCGAGGCCCTGATGAAGAACAAGTTTAGAATCTGCGGC
Mitra et al.   941  GCGTGGCTAACTGTGAAGCTCTGATGAAAAATAAGTTCCGTATTTGCGGT

MLT           1068  ACAATCAGAAAAAACAGAGGCATCCCTAAGGACTTCCAGACCATCTCTCT
Mitra et al.   991  ACTATCCGTAAGAATCGTGGAATTCCGAAAGATTTCCAGACCATCTCCCT

MLT           1118  GAAGAAGGGCGAAACCAAGTTCATCAGAAAGAACGACATCCTGCTCCAAG
Mitra et al.  1041  GAAAAAGGGTGAAACTAAGTTCATTCGCAAAAACGACATCCTCCTGCAAG
```

FIG. 10 (cont.)

```
MLT             1168 TGTGGCAGTCCAAGAAACCCGTGTACCTGATCAGCAGC-ATCCATAGCGC
Mitra et al.    1091 TCTGGCAGTCTAAAAAGCCTGTATATCTGATC-TCATCTATTCACAGCGC

MLT             1217 CGAGATGGAAGAAAGCCAGAACATCGACAGAACAAGCAAGAAGAAGATCG
Mitra et al.    1140 TGAAATGGAAGAATCTCAGAACATTGATCGCACCTCCAAGAAAAAGATCG

MLT             1267 TGAAGCCCAATGCTCTGATCGACTACAACAAGCACATGAAAGGCGTGGAC
Mitra et al.    1190 TCAAACCGAATGCATTGATTGATTACAACAAGCACATGAAGGGCGTTGAT

MLT             1317 CGGGCCGACCAGTACCTGTCTTATTACTCTATCCTGAGAAGAACAGTGAA
Mitra et al.    1240 CGTGCTGACCAGTACCTGTCTTATTACTCTATCCTGCGCCGTACTGTGAA

MLT             1367 ATGGACCAAGAGACTGGCCATGTACATGATCAATTGCGCCCTGTTCAACA
Mitra et al.    1290 GTGGACTAAACGTCTCGCTATGTACATGATTAATTGTGCGCTGTTCAATT

MLT             1417 GCTACGCCGTGTACAAGTCCGTGCGACAAAGAAAAATGGGATTCAAGATG
Mitra et al.    1340 CTTACGCTGTGTATAAAGCGTGCGTCAGCGCAAAATGGGCTTTAAAATG

MLT             1467 TTCCTGAAGCAGACAGCCATCCACTGGCTGACAGACGACATTCCTGAGGA
Mitra et al.    1390 TTCCTGAAGCAGACGGCTATTCACTGGCTGACCGACGATATTCCGGAAGA

MLT             1517 CATGGACATTGTGCCAGATCTGCAACCTGTGCCCAGCACCTCTGGTATGA
Mitra et al.    1440 TATGGACATTGTCCCGGATCTCCAGCCGGTACCGAGCACCAGCGGTATGC
```

FIG. 10 (cont.)

```
MLT             1567 GAGCTAAGCCTCCCACCAGCGATCCTCCATGTAGACTGAGCATGGACATG
Mitra et al. 1490 GTGCTAAACCTCCGACTAGTGATCCGCCTTGCCGTCTGTCTATGGATATG

MLT             1617 CGGAAGCACACCCTGCAGGCCATCGTCGGCAGCGGCAAGAAGAAGAACAT
Mitra et al. 1540 CGTAAGCATACCCTGCAGGCAATTGTGGGCTCTGGCAAAAAGAAAAATAT

MLT             1667 CCTTAGACGGTGCAGGGTGTGCAGCGTGCACAAGCTGCGGAGCGAGACTC
Mitra et al. 1590 CCTGCGTCGTTGCCGCGTATGCTCTGTACACAAACTGCGTTCTGAGACTC

MLT             1717 GGTACATGTGCAAGTTTTGCAACATTCCCCTGCACAAGGGAGCCTGCTTC
Mitra et al. 1640 GTTATATGTGTAAATTTTGCAATATTCCACTCCACAAGGGTGCGTGCTTC

MLT             1767 GAGAAGTACCACACCCTGAAGAATTA-CTAG--
Mitra et al. 1690 GAGAAGTACCATACGCTGAAGAACTATCTCGAG
```

FIG. 11

Nucleotide alignment of engineered MLT ("MLT", SEQ ID NO: 338) and the sequence from WO2010085699 (SEQ ID NO: 339, Identity 73.68%, Gaps 1.16%)

```
MLT             1    ATGGCCCAGCA--CAGCGACTACCCCGACGACGAGTTCAGAGCCGATAAGCTGAGTAACTACAGCTGCGACAGCGACCTG
WO 2010085699   1    ATGTCGCAGCATTCA--GACTATACTCATGATGAGTTTTGTGCAGACAAGTTGTCCAATTATTCTTGTGATAGCGATCTT

MLT             79   GAAAACGCCAGCACATCCGACGAGGA---CAGCTCTGACGACGAGGTGATGGTGCGGCCCAGAACCCTGAGACGGAGAAG
WO 2010085699   79   GAAAATGCGAGTACAAGTGATGAAGATTCTAG---TGATGATGAAGTAATGGTGCGTCCCAGGACATTGAGGCGACGAAG

MLT             156  AATCAGCAGCTCTAGCAGCGACTCTGAATCCGACATCGAGGGCGGCCGGGAAGAGTGGAGCCACGTGGACAACCCTCCTG
WO 2010085699   156  AATTTCGAGCTCCAGCTCTGACTCAGAGTCAGATATAGAAGGCGGGAGAGAAGAATGGTCGCATGTTGATAATCCACCGG

MLT             236  TTCTGGAAGATTTTCTGGGCCATCAGGGCCTGAACACCGACGCCGTGATCAACAACATCGAGGATGCCGTGAAGCTGTTC
WO 2010085699   236  TCTTAGAAGATTTTTTAGGGCATCAAGGATTAAACACAGATGCTGTTATAAATAATATAGAAGATGCCGTGAAATTATTT

MLT             316  ATAGGAGATGATTTCTTTGAGTTCCTGGTCGAGGAATCCAACCGCTATTACAACCAGAATAGAAACAACTTCAAGCTGAG
WO 2010085699   316  ATCGGAGATGATTTTTTTGAATTTCTTGTAGAGGAGTCAAACAGGTATTATAATCAAAATAGGAATAATTTCAAACTTTC

MLT             396  CAAGAAAAGCCTGAAGTGGAAGGACATCACCCCTCAGGAGATGAAAAAGTTCCTGGGACTGATCGTTCTGATGGGACAGG
WO 2010085699   396  AAAAAAAAGCCTAAAGTGGAAAGATATAACCCCTCAAGAGATGAAGAAGTTTTTAGGGTTAATTGTTCTCATGGGACAGG

MLT             476  TGCGGAAGGACAGAAGGGATGATTACTGGACAACCGAACCTTGGACCGAGACCCCTTACTTTGGCAAGACCATGACCAGA
WO 2010085699   476  TGCGCAAAGATAGAAGAGATGACTATTGGACCACGGAGCCATGGACGGAGACGCCATATTTTGGTAAAACGATGACGAGA

MLT             556  GACAGATTCAGACAGATCTGGAAAGCCTGGCACTTCAACAACAATGCTGATATCGTGAACGAGTCTGATAGACTGTGTAA
WO 2010085699   556  GACAGGTTCCGACAGATATGGAAAGCTTGGCACTTCAATAATAATGCGGATATCGTAAATGAATCAGATAGACTTTGCAA
```

FIG. 11 (cont.)

```
MLT            636  AGTGCGGCCAGTGTTGGATTACTTCGTGCCTAAGTTCATCAACATCTATAAGCCTCACCAGCAGCTGAGC-CTGGATGAA
WO 2010085699  636  AGTGAGACCAGTACTAGATTATTTTGTGCCTAAATTTATAAATATTTACAAACCTCATCAGCA-ATTATCACTAGATGAA

MLT            715  GGCATCGTGCCCTGGCGGGGCAGACTGTTCTTCAGAGTGTACAATGCTGGCAAGATCGTCAAATACGGCATCCTGGTGCG
WO 2010085699  715  GGGATCGTACCTTGGAGGGGAAGATTATTCTTTAGGGTATATAATGCTGGCAAGATCGTTAAATATGGAATATTGGTTCG

MLT            795  CCTTCTGTGCGAGAGCGATACAGGCTACATCTGTAATATGGAAATCTACTGCGGCGAGGGCAAAAGACTGCTGGAAACCA
WO 2010085699  795  TTTGTTGTGCGAAAGTGATACAGGATATATCTGTAACATGGAAATTTATTGCGGCGAAGGAAAGCGATTATTGGAAACGA

MLT            875  TCCAGACCGTCGTTTCCCCTTATACCGACAGCTGGTACCACATCTACATGGACAACTACTACAATTCTGTGGCCAACTGC
WO 2010085699  875  TACAAACAGTAGTGTCTCCATACACTGATTCGTGGTACCATATATATATGGACAATTATTATAATAGCGTCGCAAATTGT

MLT            955  GAGGCCCTGATGAAGAACAAGTTTAGAATCTGCGGCACAATCAGAAAAAACAGAGGCATCCCTAAGGACTTCCAGACCAT
WO 2010085699  955  GAAGCACTTATGAAAAACAAATTCAGAATATGTGGAACAATCCGGAAAAATCGAGGTATACCTAAAGATTTTCAAACAAT

MLT            1035 CTCTCTGAAGAAGGGCGAAACCAAGTTCATCAGAAAGAACGACATCCTGCTCCAAGTGTGGCAGTCCAAGAAACCCGTGT
WO 2010085699  1035 TTCTTTGAAAAAAGGTGAAACAAAATTTATAAGGAAAAATGATATATTGTTACAAGTGTGGCAATCAAAAAAGCCTGTAT

MLT            1115 ACCTGA--TCAGCAGCATCCATAGCGCCGAGATGGAAGAAAGCCAGAACATCGACAGAACAAGCAAGAAGAAGATCGTGA
WO 2010085699  1115 ACCTGATTTCTTC--GATTCATTCTGCGGAGATGGAAGAAAGTCAGAATATTGACAGAACATCAAAAAAGAAAATTGTCA

MLT            1193 AGCCCAATGCTCTGATCGACTACAACAAGCACATGAAAGGCGTGGACCGGGCCGACCAGTACCTGTCTTATTACTCTATC
WO 2010085699  1193 AACCGAATGCACTCATTGACTACAATAAACATATGAAAGGTGTTGACCGGGCCGACCAATACCTTTCATATTATTCGATA
```

FIG. 11 (cont.)

```
MLT            1273 CTGAGAAGAACAGTGAAATGGACCAAGAGACTGGCCATGTACATGATCAATTGCGCCCTGTTCAACAGCTACGCCGTGTA
WO 2010085699  1273 TTGCGGAGGACGGTCAAATGGACAAAAAGGTTGGCAATGTATATGATAAATTGCGCATTATTTAATTCTTATGCAGTTTA

MLT            1353 CAAGTCCGTGCGACAAAGAAAAATGGGATTCAAGATGTTCCTGAAGCAGACAGCCATCCACTGGCTGACAGACGACATTC
WO 2010085699  1353 CAAATCAGTGAGGCAAAGAAAAATGGGTTTTAAAATGTTTTTGAAACAAACAGCTATCCACTGGTTGACGGATGATATTC

MLT            1433 CTGAGGACATGGACATTGTGCCAGATCTGCAACCTGTGCCCAGCACCTCTGGTATGAGAGCTAAGCCTCCCACCAGC-GA
WO 2010085699  1433 CAGAGGACATGGACATTGTTCCAGACCTTCAACCAGTACCGTCTACTTCTGGAATGCGGGCTAAACCACCTA-CATCTGA

MLT            1512 TCCTCCATGTAGACTGAGC-ATGGACATGCGGAAGCACACCCTGCAGGCCATCGTCGGCAGCGGCAAGAAGAAGAACATC
WO 2010085699  1512 TCCACCATGCAGGCT-ATCGATGGACATGAGAAAGCATACGTTACAGGCAATTGTCGGAAGTGGAAAAAAGAAAAACATT

MLT            1591 CTTAGACGGTGCAGGGTGTGCAGCGTGCACAAGCTGCGGAGCGAGACTCGGTACATGTGCAAGTTTTGCAACATTCCCCT
WO 2010085699  1591 TTGAGAAGGTGTCGCGTATGTTCCGTTCATAAATTGCGCAGTGAGACACGCTACATGTGCAAATTTTGCAATATACCTCT

MLT            1671 GCACAAGGGAGCCTGCTTCGAGAAGTACCACACCCTGAAGAATTACTAG
WO 2010085699  1671 ACATAAAGGGGCGTGTTTTGAAAAATATCATACGCTAAAAAACTAT---
```

FIG. 12

Amino acid alignment of engineered MLT (SEQ ID NO: 340, L573del/E574del/S2A, with S8P, C13R, and N125K mutations, "MLT") and a published sequence by Mitra et al. (SEQ ID NO: 341, Mitra contained 2 extra amino acids on C-terminus)

```
MLT             MAQHSDYPDDEFRADKLSNYSCDSDLENASTSDEDSSDDEVMVRPRTLRRRRISSSSSDS   60
                MAQHSDY DDEF ADKLSNYSCDSDLENASTSDEDSSDDEVMVRPRTLRRRRISSSSSDS
Mitra et al.    MAQHSDYSDDEFCADKLSNYSCDSDLENASTSDEDSSDDEVMVRPRTLRRRRISSSSSDS   60

MLT             ESDIEGGREEWSHVDNPPVLEDFLGHQGLNTDAVINNIEDAVKLFIGDDFFEFLVEESNR   120
                ESDIEGGREEWSHVDNPPVLEDFLGHQGLNTDAVINNIEDAVKLFIGDDFFEFLVEESNR
Mitra et al.    ESDIEGGREEWSHVDNPPVLEDFLGHQGLNTDAVINNIEDAVKLFIGDDFFEFLVEESNR   120

MLT             YYNQKRNNFKLSKKSLKWKDITPQEMKKFLGLIVLMGQVRKDRRDDYWTTEPWTETPYFG   180
                YYNQNRNNFKLSKKSLKWKDITPQEMKKFLGLIVLMGQVRKDRRDDYWTTEPWTETPYFG
Mitra et al.    YYNQNRNNFKLSKKSLKWKDITPQEMKKFLGLIVLMGQVRKDRRDDYWTTEPWTETPYFG   180

MLT             KTMTRDRFRQIWKAWHFNNNADIVNESDRLCKVRPVLDYFVPKFINIYKPHQQLSLDEGI   240
                KTMTRDRFRQIWKAWHFNNNADIVNESDRLCKVRPVLDYFVPKFINIYKPHQQLSLDEGI
Mitra et al.    KTMTRDRFRQIWKAWHFNNNADIVNESDRLCKVRPVLDYFVPKFINIYKPHQQLSLDEGI   240

MLT             VPWRGRLFFRVYNAGKIVKYGILVRLLCESDTGYICNMEIYCGEGKRLLETIQTVVSPYT   300
                VPWRGRLFFRVYNAGKIVKYGILVRLLCESDTGYICNMEIYCGEGKRLLETIQTVVSPYT
Mitra et al.    VPWRGRLFFRVYNAGKIVKYGILVRLLCESDTGYICNMEIYCGEGKRLLETIQTVVSPYT   300
```

FIG. 12 (cont.)

```
MLT             DSWYHIYMDNYYNSVANCEALMKNKFRICGTIRKNRGIPKDFQTISLKKGETKFIRKNDI   360
                DSWYHIYMDNYYNSVANCEALMKNKFRICGTIRKNRGIPKDFQTISLKKGETKFIRKNDI
Mitra et al.    DSWYHIYMDNYYNSVANCEALMKNKFRICGTIRKNRGIPKDFQTISLKKGETKFIRKNDI   360

MLT             LLQVWQSKKPVYLISSIHSAEMEESQNIDRTSKKKIVKPNALIDYNKHMKGVDRADQYLS   420
                LLQVWQSKKPVYLISSIHSAEMEESQNIDRTSKKKIVKPNALIDYNKHMKGVDRADQYLS
Mitra et al.    LLQVWQSKKPVYLISSIHSAEMEESQNIDRTSKKKIVKPNALIDYNKHMKGVDRADQYLS   420

MLT             YYSILRRTVKWTKRLAMYMINCALFNSYAVYKSVRQRKMGFKMFLKQTAIHWLTDDIPED   480
                YYSILRRTVKWTKRLAMYMINCALFNSYAVYKSVRQRKMGFKMFLKQTAIHWLTDDIPED
Mitra et al.    YYSILRRTVKWTKRLAMYMINCALFNSYAVYKSVRQRKMGFKMFLKQTAIHWLTDDIPED   480

MLT             MDIVPDLQPVPSTSGMRAKPPTSDPPCRLSMDMRKHTLQAIVGSGKKKNILRRCRVCSVH   540
                MDIVPDLQPVPSTSGMRAKPPTSDPPCRLSMDMRKHTLQAIVGSGKKKNILRRCRVCSVH
Mitra et al.    MDIVPDLQPVPSTSGMRAKPPTSDPPCRLSMDMRKHTLQAIVGSGKKKNILRRCRVCSVH   540

MLT             KLRSETRYMCKFCNIPLHKGACFEKYHTLKNY*   572
                KLRSETRYMCKFCNIPLHKGACFEKYHTLKNY
Mitra et al.    KLRSETRYMCKFCNIPLHKGACFEKYHTLKNY LE 574
```

FIG. 13

Comparison of an amino acid of engineered MLT (SEQ ID NO: 9, L573del/E574del/S2A, with S8P and C13R mutations, "MLT") and the sequence from WO2010085699 (SEQ ID NO: 343)

```
MLT            MAQHSDYPDDEFRADKLSNYSCDSDLENASTSDEDSSDDEVMVRPRTLRRRRISSSSSDS   60
               M+QHSDY DDEF ADKLSNYSCDSDLENASTSDEDSSDDEVMVRPRTLRRRRISSSSSDS
WO 2010085699  MSQHSDYSDDEFCADKLSNYSCDSDLENASTSDEDSSDDEVMVRPRTLRRRRISSSSSDS   60

MLT            ESDIEGGREEWSHVDNPPVLEDFLGHQGLNTDAVINNIEDAVKLFIGDDFFEFLVEESNR  120
               ESDIEGGREEWSHVDNPPVLEDFLGHQGLNTDAVINNIEDAVKLFIGDDFFEFLVEESNR
WO 2010085699  ESDIEGGREEWSHVDNPPVLEDFLGHQGLNTDAVINNIEDAVKLFIGDDFFEFLVEESNR  120

MLT            YYNQNRNNFKLSKKSLKWKDITPQEMKKFLGLIVLMGQVRKDRRDDYWTTEPWTETPYFG  180
               YYNQNRNNFKLSKKSLKWKDITPQEMKKFLGLIVLMGQVRKDRRDDYWTTEPWTETPYFG
WO 2010085699  YYNQNRNNFKLSKKSLKWKDITPQEMKKFLGLIVLMGQVRKDRRDDYWTTEPWTETPYFG  180

MLT            KTMTRDRFRQIWKAWHFNNNADIVNESDRLCKVRPVLDYFVPKFINIYKPHQQLSLDEGI  240
               KTMTRDRFRQIWKAWHFNNNADIVNESDRLCKVRPVLDYFVPKFINIYKPHQQLSLDEGI
WO 2010085699  KTMTRDRFRQIWKAWHFNNNADIVNESDRLCKVRPVLDYFVPKFINIYKPHQQLSLDEGI  240
```

FIG. 13 (cont.)

```
MLT             VPWRGRLFFRVYNAGKIVKYGILVRLLCESDTGYICNMEIYCGEGKRLLETIQTVVSPYT  300
                VPWRGRLFFRVYNAGKIVKYGILVRLLCESDTGYICNMEIYCGEGKRLLETIQT  SPYT
WO 2010085699   VPWRGRLFFRVYNAGKIVKYGILVRLLCESDTGYICNMEIYCGEGKRLLETIQT-WSPYT  299

MLT             DSWYHIYMDNYYNSVANCEALMKNKFRICGTIRKNRGIPKDFQTISLKKGETKFIRKNDI  360
                DSWYHIYMDNYYNSVANCEALMKNKFRICGTIRKNRGIPKDFQTISLKKGETKFIRKNDI
WO 2010085699   DSWYHIYMDNYYNSVANCEALMKNKFRICGTIRKNRGIPKDFQTISLKKGETKFIRKNDI  359

MLT             LLQVWQSKKPVYLISSIHSAEMEESQNIDRTSKKKIVKPNALIDYNKHMKGVDRADQYLS  420
                LLQVWQSKKPVYLISS HSAEMEESQNIDRTSKKKIVKPNALIDYNKHMKGVDRADQYLS
WO 2010085699   LLQVWQSKKPVYLISS-HSAEMEESQNIDRTSKKKIVKPNALIDYNKHMKGVDRADQYLS  418
```

FIG. 13 (cont.)

```
MLT             YYSILRRTVKWTKRLAMYMINCALFNSYAVYKSVRQRKMGFKMFLKQTAIHWLTDDIPED 480
                YYSILRR  KWTKRLAMYMINCALFNSYAVYKSVRQRKMGFKMFLKQTA HWLTDDIPED
WO 2010085699   YYSILRRW-KWTKRLAMYMINCALFNSYAVYKSVRQRKMGFKMFLKQTA-HWLTDDIPED 476

MLT             MDIVPDLQPVPSTSGMRAKPPTSDPPCRLSMDMRKHTLQAIVGSGKKKNILRRCRVCSVH 540
                MDIVPDLQPVPSTSGMRAKPPTSDPPCRLSMDMRKHTLQAIVGSGKKKNILRRCRVCSVH
WO 2010085699   MDIVPDLQPVPSTSGMRAKPPTSDPPCRLSMDMRKHTLQAIVGSGKKKNILRRCRVCSVH 536

MLT             KLRSETRYMCKFCNIPLHKGACFEKYHTLKNY*   572
                KLRSETRYMCKFCNIPLHKGACFEKYHTLKN
WO 2010085699   KLRSETRYMCKFCNIPLHKGACFEKYHTLKN-    567
```

FIG. 14

**Comparison of a terminal left end of MLT to a published sequence (Ray *et al.*, *piggyBac1_ML*)**

```
LEFT END (RAY ET AL.)   1    TTAACACTTGGATTGCGGGAAACGAGTTAAGTCGGCTCGCGTGAATTGCGCGTACTCCGC
MLT Left End            1    TTAACACTTGGATTGCGGGAAACGAGTTAAGTCGGCTCGCGTGAATTGCGCGTACTCCGC

LEFT END (RAY ET AL.)   61   GGGAGCCGTCTTAACTCGGTTCATATAGATTTGCGGTGGAGTGCGGGAAACGTGTAAACT
MLT Left End            61   GGGAGCCGTCTTAACTCGGTTCATATAGATTTGCGGTGGAGTGCGGGAAACGTGTAAACT

LEFT END (RAY ET AL.)   121  CGGGCCGATTGTAACTGCGTATTACCAAATATTTGTT  SEQ ID NO: 430
MLT Left End            121  CGGGCCGATTGTAACTGCGTATTACCAAATATTTGTT  SEQ ID NO: 431
```

FIG. 15

**Comparison of a terminal right end of MLT to a published sequence (Ray *et al. piggyBac1_ML*)**

| | | | |
|---|---|---|---|
| RIGHT END (RAY ET AL.) | 2423 | AATTATTTATGTACTGAATAGATAAAAAAATGTCTGTGATTGAATAAATTTTCATTTTTT | |
| MLT Right End | 1 | AATTATTTATGTACTGAATAGATaaaaaaaTGTCTGTGATTGAATAAATTTTCATTTTTT | |
| RIGHT END (RAY ET AL.) | 2483 | ACACAAGAAACCGAAAATTTCATTTCAATCGAACCCATACTTCAAAAGATATAGGCATTT | |
| MLT Right End | 61 | ACACAAGAAACCGAAAATTTCATTTCAATCGAACCCATACTTCAAAAGATATAGGCATTT | |
| RIGHT END (RAY ET AL.) | 2453 | TAAACTAACTCTGATTTTGCGCGGGAAACCTAAATAATTGCCCGCGCCATCTTATATTTT | |
| MLT Right End | 121 | TAAACTAACTCTGATTTTGCGCGGGAAACCTAAATAATTGCCCGCGCCATCTTATATTTT | |
| RIGHT END (RAY ET AL.) | 2603 | GGCGGGAAATTCACCCGACACCGTAGTGTTAA | SEQ ID NO: 432 |
| MLT Right End | 181 | GGCGGGAAATTCACCCGACACCGTAGTGTTAA | SEQ ID NO: 433 |

No piggyBac
piggyBac
S8P/C13R

No MLT
MLT
S8P
C13R
N125K hRosa26 genomic PRC 1.0% agarose gel

SEQUENCE LISTING

<160> NUMBER OF SEQ ID NOS: 435

<210> SEQ ID NO 1
<211> LENGTH: 4
<212> TYPE: DNA
<213> ORGANISM: Artificial Sequence
<220> FEATURE:
<223> OTHER INFORMATION: Synthetic Sequence

<400> SEQUENCE: 1

```
ttaa                                                                    4
```

<210> SEQ ID NO 2
<211> LENGTH: 572
<212> TYPE: PRT
<213> ORGANISM: Artificial Sequence
<220> FEATURE:
<223> OTHER INFORMATION: Synthetic Sequence

<400> SEQUENCE: 2

```
Met Ala Gln His Ser Asp Tyr Ser Asp Asp Glu Phe Cys Ala Asp Lys
1               5                   10                  15

Leu Ser Asn Tyr Ser Cys Asp Ser Asp Leu Glu Asn Ala Ser Thr Ser
            20                  25                  30

Asp Glu Asp Ser Ser Asp Asp Glu Val Met Val Arg Pro Arg Thr Leu
        35                  40                  45

Arg Arg Arg Arg Ile Ser Ser Ser Ser Ser Asp Ser Glu Ser Asp Ile
    50                  55                  60

Glu Gly Gly Arg Glu Glu Trp Ser His Val Asp Asn Pro Pro Val Leu
65                  70                  75                  80

Glu Asp Phe Leu Gly His Gln Gly Leu Asn Thr Asp Ala Val Ile Asn
                85                  90                  95

Asn Ile Glu Asp Ala Val Lys Leu Phe Ile Gly Asp Asp Phe Phe Glu
            100                 105                 110

Phe Leu Val Glu Glu Ser Asn Arg Tyr Tyr Asn Gln Asn Arg Asn Asn
        115                 120                 125

Phe Lys Leu Ser Lys Lys Ser Leu Lys Trp Lys Asp Ile Thr Pro Gln
    130                 135                 140

Glu Met Lys Lys Phe Leu Gly Leu Ile Val Leu Met Gly Gln Val Arg
145                 150                 155                 160

Lys Asp Arg Arg Asp Asp Tyr Trp Thr Thr Glu Pro Trp Thr Glu Thr
                165                 170                 175

Pro Tyr Phe Gly Lys Thr Met Thr Arg Asp Arg Phe Arg Gln Ile Trp
            180                 185                 190

Lys Ala Trp His Phe Asn Asn Asn Ala Asp Ile Val Asn Glu Ser Asp
        195                 200                 205

Arg Leu Cys Lys Val Arg Pro Val Leu Asp Tyr Phe Val Pro Lys Phe
    210                 215                 220

Ile Asn Ile Tyr Lys Pro His Gln Gln Leu Ser Leu Asp Glu Gly Ile
225                 230                 235                 240

Val Pro Trp Arg Gly Arg Leu Phe Phe Arg Val Tyr Asn Ala Gly Lys
                245                 250                 255

Ile Val Lys Tyr Gly Ile Leu Val Arg Leu Leu Cys Glu Ser Asp Thr
            260                 265                 270

Gly Tyr Ile Cys Asn Met Glu Ile Tyr Cys Gly Glu Gly Lys Arg Leu
        275                 280                 285
```

```
Leu Glu Thr Ile Gln Thr Val Val Ser Pro Tyr Thr Asp Ser Trp Tyr
    290                 295                 300

His Ile Tyr Met Asp Asn Tyr Tyr Asn Ser Val Ala Asn Cys Glu Ala
305                 310                 315                 320

Leu Met Lys Asn Lys Phe Arg Ile Cys Gly Thr Ile Arg Lys Asn Arg
                325                 330                 335

Gly Ile Pro Lys Asp Phe Gln Thr Ile Ser Leu Lys Lys Gly Glu Thr
            340                 345                 350

Lys Phe Ile Arg Lys Asn Asp Ile Leu Leu Gln Val Trp Gln Ser Lys
        355                 360                 365

Lys Pro Val Tyr Leu Ile Ser Ser Ile His Ser Ala Glu Met Glu Glu
    370                 375                 380

Ser Gln Asn Ile Asp Arg Thr Ser Lys Lys Lys Ile Val Lys Pro Asn
385                 390                 395                 400

Ala Leu Ile Asp Tyr Asn Lys His Met Lys Gly Val Asp Arg Ala Asp
                405                 410                 415

Gln Tyr Leu Ser Tyr Tyr Ser Ile Leu Arg Arg Thr Val Lys Trp Thr
            420                 425                 430

Lys Arg Leu Ala Met Tyr Met Ile Asn Cys Ala Leu Phe Asn Ser Tyr
        435                 440                 445

Ala Val Tyr Lys Ser Val Arg Gln Arg Lys Met Gly Phe Lys Met Phe
    450                 455                 460

Leu Lys Gln Thr Ala Ile His Trp Leu Thr Asp Asp Ile Pro Glu Asp
465                 470                 475                 480

Met Asp Ile Val Pro Asp Leu Gln Pro Val Pro Ser Thr Ser Gly Met
                485                 490                 495

Arg Ala Lys Pro Pro Thr Ser Asp Pro Pro Cys Arg Leu Ser Met Asp
            500                 505                 510

Met Arg Lys His Thr Leu Gln Ala Ile Val Gly Ser Gly Lys Lys Lys
        515                 520                 525

Asn Ile Leu Arg Arg Cys Arg Val Cys Ser Val His Lys Leu Arg Ser
    530                 535                 540

Glu Thr Arg Tyr Met Cys Lys Phe Cys Asn Ile Pro Leu His Lys Gly
545                 550                 555                 560

Ala Cys Phe Glu Lys Tyr His Thr Leu Lys Asn Tyr
                565                 570


<210> SEQ ID NO 3
<211> LENGTH: 1719
<212> TYPE: DNA
<213> ORGANISM: Artificial Sequence
<220> FEATURE:
<223> OTHER INFORMATION: Synthetic Sequence

<400> SEQUENCE: 3

atggcccagc acagcgacta cagcgacgac gagttctgtg ccgataagct gagtaactac      60

agctgcgaca gcgacctgga aaacgccagc acatccgacg aggacagctc tgacgacgag     120

gtgatggtgc ggcccagaac cctgagacgg agaagaatca gcagctctag cagcgactct     180

gaatccgaca tcgagggcgg ccgggaagag tggagccacg tggacaaccc tcctgttctg     240

gaagattttc tgggccatca gggcctgaac accgacgccg tgatcaacaa catcgaggat     300

gccgtgaagc tgttcatagg agatgatttc tttgagttcc tggtcgagga atccaaccgc     360

tattacaacc agaatagaaa caacttcaag ctgagcaaga aaagcctgaa gtggaaggac     420
```

```
atcacccctc aggagatgaa aaagttcctg ggactgatcg ttctgatggg acaggtgcgg    480

aaggacagaa gggatgatta ctggacaacc gaaccttgga ccgagacccc ttactttggc    540

aagaccatga ccagagacag attcagacag atctggaaag cctggcactt caacaacaat    600

gctgatatcg tgaacgagtc tgatagactg tgtaaagtgc ggccagtgtt ggattacttc    660

gtgcctaagt tcatcaacat ctataagcct caccagcagc tgagcctgga tgaaggcatc    720

gtgccctggc ggggcagact gttcttcaga gtgtacaatg ctggcaagat cgtcaaatac    780

ggcatcctgg tgcgccttct gtgcgagagc gatacaggct acatctgtaa tatggaaatc    840

tactgcggcg agggcaaaag actgctggaa accatccaga ccgtcgtttc cccttatacc    900

gacagctggt accacatcta catggacaac tactacaatt ctgtggccaa ctgcgaggcc    960

ctgatgaaga acaagtttag aatctgcggc acaatcagaa aaaacagagg catccctaag   1020

gacttccaga ccatctctct gaagaagggc gaaaccaagt tcatcagaaa gaacgacatc   1080

ctgctccaag tgtggcagtc caagaaaccc gtgtacctga tcagcagcat ccatagcgcc   1140

gagatggaag aaagccagaa catcgacaga acaagcaaga agaagatcgt gaagcccaat   1200

gctctgatcg actacaacaa gcacatgaaa ggcgtggacc gggccgacca gtacctgtct   1260

tattactcta tcctgagaag aacagtgaaa tggaccaaga gactggccat gtacatgatc   1320

aattgcgccc tgttcaacag ctacgccgtg tacaagtccg tgcgacaaag aaaaatggga   1380

ttcaagatgt tcctgaagca gacagccatc cactggctga cagacgacat tcctgaggac   1440

atggacattg tgccagatct gcaacctgtg cccagcacct ctggtatgag agctaagcct   1500

cccaccagcg atcctccatg tagactgagc atggacatgc ggaagcacac cctgcaggcc   1560

atcgtcggca gcggcaagaa gaagaacatc cttagacggt gcagggtgtg cagcgtgcac   1620

aagctgcgga gcgagactcg gtacatgtgc aagttttgca acattcccct gcacaaggga   1680

gcctgcttcg agaagtacca caccctgaag aattactag                          1719
```

<210> SEQ ID NO 4
<211> LENGTH: 568
<212> TYPE: PRT
<213> ORGANISM: Artificial Sequence
<220> FEATURE:
<223> OTHER INFORMATION: Synthetic Sequence

<400> SEQUENCE: 4

```
Met Ser Gln His Ser Asp Tyr Ser Asp Asp Glu Phe Cys Ala Asp Lys
1               5                   10                  15

Leu Ser Asn Tyr Ser Cys Asp Ser Asp Leu Glu Asn Ala Ser Thr Ser
            20                  25                  30

Asp Glu Asp Ser Ser Asp Asp Glu Val Met Val Arg Pro Arg Thr Leu
        35                  40                  45

Arg Arg Arg Arg Ile Ser Ser Ser Ser Ser Asp Ser Glu Ser Asp Ile
    50                  55                  60

Glu Gly Gly Arg Glu Glu Trp Ser His Val Asp Asn Pro Pro Val Leu
65                  70                  75                  80

Glu Asp Phe Leu Gly His Gln Gly Leu Asn Thr Asp Ala Val Ile Asn
                85                  90                  95

Asn Ile Glu Asp Ala Val Lys Leu Phe Ile Gly Asp Asp Phe Phe Glu
            100                 105                 110

Phe Leu Val Glu Glu Ser Asn Arg Tyr Tyr Asn Gln Asn Arg Asn Asn
        115                 120                 125
```

-continued

```
Phe Lys Leu Ser Lys Lys Ser Leu Lys Trp Lys Asp Ile Thr Pro Gln
    130                 135                 140

Glu Met Lys Lys Phe Leu Gly Leu Ile Val Leu Met Gly Gln Val Arg
145                 150                 155                 160

Lys Asp Arg Arg Asp Asp Tyr Trp Thr Thr Glu Pro Trp Thr Glu Thr
                165                 170                 175

Pro Tyr Phe Gly Lys Thr Met Thr Arg Asp Arg Phe Arg Gln Ile Trp
            180                 185                 190

Lys Ala Trp His Phe Asn Asn Asn Ala Asp Ile Val Asn Glu Ser Asp
        195                 200                 205

Arg Leu Cys Lys Val Arg Pro Val Leu Asp Tyr Phe Val Pro Lys Phe
    210                 215                 220

Ile Asn Ile Tyr Lys Pro His Gln Gln Leu Ser Leu Asp Glu Gly Ile
225                 230                 235                 240

Val Pro Trp Arg Gly Arg Leu Phe Phe Arg Val Tyr Asn Ala Gly Lys
                245                 250                 255

Ile Val Lys Tyr Gly Ile Leu Val Arg Leu Leu Cys Glu Ser Asp Thr
            260                 265                 270

Gly Tyr Ile Cys Asn Met Glu Ile Tyr Cys Gly Glu Gly Lys Arg Leu
        275                 280                 285

Leu Glu Thr Ile Gln Thr Trp Ser Pro Tyr Thr Asp Ser Trp Tyr His
    290                 295                 300

Ile Tyr Met Asp Asn Tyr Tyr Asn Ser Val Ala Asn Cys Glu Ala Leu
305                 310                 315                 320

Met Lys Asn Lys Phe Arg Ile Cys Gly Thr Ile Arg Lys Asn Arg Gly
                325                 330                 335

Ile Pro Lys Asp Phe Gln Thr Ile Ser Leu Lys Lys Gly Glu Thr Lys
            340                 345                 350

Phe Ile Arg Lys Asn Asp Ile Leu Leu Gln Val Trp Gln Ser Lys Lys
        355                 360                 365

Pro Val Tyr Leu Ile Ser Ser His Ser Ala Glu Met Glu Glu Ser Gln
    370                 375                 380

Asn Ile Asp Arg Thr Ser Lys Lys Lys Ile Val Lys Pro Asn Ala Leu
385                 390                 395                 400

Ile Asp Tyr Asn Lys His Met Lys Gly Val Asp Arg Ala Asp Gln Tyr
                405                 410                 415

Leu Ser Tyr Tyr Ser Ile Leu Arg Arg Trp Lys Trp Thr Lys Arg Leu
            420                 425                 430

Ala Met Tyr Met Ile Asn Cys Ala Leu Phe Asn Ser Tyr Ala Val Tyr
        435                 440                 445

Lys Ser Val Arg Gln Arg Lys Met Gly Phe Lys Met Phe Leu Lys Gln
    450                 455                 460

Thr Ala His Trp Leu Thr Asp Asp Ile Pro Glu Asp Met Asp Ile Val
465                 470                 475                 480

Pro Asp Leu Gln Pro Val Pro Ser Thr Ser Gly Met Arg Ala Lys Pro
                485                 490                 495

Pro Thr Ser Asp Pro Pro Cys Arg Leu Ser Met Asp Met Arg Lys His
            500                 505                 510

Thr Leu Gln Ala Ile Val Gly Ser Gly Lys Lys Lys Asn Ile Leu Arg
        515                 520                 525

Arg Cys Arg Val Cys Ser Val His Lys Leu Arg Ser Glu Thr Arg Tyr
    530                 535                 540
```

-continued

```
Met Cys Lys Phe Cys Asn Ile Pro Leu His Lys Gly Ala Cys Phe Glu
545                 550                 555                 560

Lys Tyr His Thr Leu Lys Asn Tyr
                565
```

<210> SEQ ID NO 5
<211> LENGTH: 1716
<212> TYPE: DNA
<213> ORGANISM: Artificial Sequence
<220> FEATURE:
<223> OTHER INFORMATION: Synthetic Sequence

<400> SEQUENCE: 5

```
atgtcgcagc attcagacta ttctcatgat gagttttgtg cagacaagtt gtccaattat     60

tcttgtgata gcgatcttga aaatgcgagt acaagtgatg aagattctag tgatgatgaa    120

gtaatggtgc gtcccaggac attgaggcga cgaagaattt cgagctccag ctctgactca    180

gagtcagata tagaaggcgg gagagaagaa tggtcgcatg ttgataatcc accggtctta    240

gaagattttt tagggcatca aggattaaac acagatgctg ttataaataa tatagaagat    300

gccgtgaaat tatttatcgg agatgatttt tttgaatttc ttgtagagga gtcaaacagg    360

tattataatc aaaataggaa taatttcaaa ctttcaaaaa aaagcctaaa gtggaaagat    420

ataacccctc aagagatgaa gaagtttttta gggttaattg ttctcatggg acaggtgcgc    480

aaagatagaa gagatgacta ttggaccacg gagccatgga cggagacgcc atattttggt    540

aaaacgatga cgagagacag gttccgacag atatggaaag cttggcactt caataataat    600

gcggatatcg taaatgaatc agatagactt tgcaaagtga gaccagtact agattatttt    660

gtgcctaaat ttataaatat ttacaaacct catcagcaat tatcactaga tgaagggatc    720

gtaccttgga ggggaagatt attctttagg gtatataatg ctggcaagat cgttaaatat    780

ggaatattgg ttcgtttgtt gtgcgaaagt gatacaggat atatctgtaa catggaaatt    840

tattgcggcg aaggaaagcg attattggaa acgatacaaa cagtagtgtc tccatacact    900

gattcgtggt accatatata tatggacaat tattataata gcgtcgcaaa ttgtgaagca    960

cttatgaaaa acaaattcag aatatgtgga acaatccgga aaaatcgagg tatacctaaa   1020

gattttcaaa caatttcttt gaaaaaaggt gaaacaaaat ttataaggaa aaatgatata   1080

ttgttacaag tgtggcaatc aaaaaagcct gtatacctga tttcttcgat tcattctgcg   1140

gagatggaag aaagtcagaa tattgacaga acatcaaaaa agaaaattgt caaaccgaat   1200

gcactcattg actacaataa acatatgaaa ggtgttgacc gggccgacca ataccttca    1260

tattattcga tattgcggag gacggtcaaa tggacaaaaa ggttggcaat gtatatgata   1320

aattgcgcat tatttaattc ttatgcagtt tacaaatcag tgaggcaaag aaaaatgggt   1380

tttaaaatgt tttgaaaca aacagctatc cactggttga cggatgatat tccagaggac   1440

atggacattg ttccagacct tcaaccagta ccgtctactt ctggaatgcg ggctaaacca   1500

cctacatctg atccaccatg caggctatcg atggacatga gaaagcatac gttacaggca   1560

attgtcggaa gtggaaaaaa gaaaaacatt ttgagaaggt gtcgcgtatg ttccgttcat   1620

aaattgcgca gtgagacacg ctacatgtgc aaattttgca atatacctct acataaaggg   1680

gcgtgttttg aaaaatatca tacgctaaaa aactat                             1716
```

<210> SEQ ID NO 6
<211> LENGTH: 1719
<212> TYPE: DNA
<213> ORGANISM: Artificial Sequence
<220> FEATURE:
<223> OTHER INFORMATION: Synthetic Sequence

<400> SEQUENCE: 6
atggcccagc acagcgacta cagcgacgac gagttctgtg ccgataagct gagtaactac 60
agctgcgaca gcgacctgga aaacgccagc acatccgacg aggacagctc tgacgacgag 120
gtgatggtgc ggcccagaac cctgagacgg agaagaatca gcagctctag cagcgactct 180
gaatccgaca tcgagggcgg ccgggaagag tggagccacg tggacaaccc tcctgttctg 240
gaagattttc tgggccatca gggcctgaac accgacgccg tgatcaacaa catcgaggat 300
gccgtgaagc tgttcatagg agatgatttc tttgagttcc tggtcgagga atccaaccgc 360
tattacaacc agaagagaaa caacttcaag ctgagcaaga aaagcctgaa gtggaaggac 420
atcacccctc aggagatgaa aaagttcctg ggactgatcg ttctgatggg acaggtgcgg 480
aaggacagaa gggatgatta ctggacaacc gaaccttgga ccgagacccc ttactttggc 540
aagaccatga ccagagacag attcagacag atctggaaag cctggcactt caacaacaat 600
gctgatatcg tgaacgagtc tgatagactg tgtaaagtgc ggccagtgtt ggattacttc 660
gtgcctaagt tcatcaacat ctataagcct caccagcagc tgagcctgga tgaaggcatc 720
gtgccctggc ggggcagact gttcttcaga gtgtacaatg ctggcaagat cgtcaaatac 780
ggcatcctgg tgcgccttct gtgcgagagc gatacaggct acatctgtaa tatggaaatc 840
tactgcggcg agggcaaaag actgctggaa accatccaga ccgtcgtttc cccttatacc 900
gacagctggt accacatcta catggacaac tactacaatt ctgtggccaa ctgcgaggcc 960
ctgatgaaga acaagtttag aatctgcggc acaatcagaa aaaacagagg catccctaag 1020
gacttccaga ccatctctct gaagaagggc gaaaccaagt tcatcagaaa gaacgacatc 1080
ctgctccaag tgtggcagtc caagaaaccc gtgtacctga tcagcagcat ccatagcgcc 1140
gagatggaag aaagccagaa catcgacaga acaagcaaga agaagatcgt gaagcccaat 1200
gctctgatcg actacaacaa gcacatgaaa ggcgtggacc gggccgacca gtacctgtct 1260
tattactcta tcctgagaag aacagtgaaa tggaccaaga gactggccat gtacatgatc 1320
aattgcgccc tgttcaacag ctacgccgtg tacaagtccg tgcgacaaag aaaaatggga 1380
ttcaagatgt tcctgaagca gacagccatc cactggctga cagacgacat tcctgaggac 1440
atggacattg tgccagatct gcaacctgtg cccagcacct ctggtatgag agctaagcct 1500
cccaccagcg atcctccatg tagactgagc atggacatgc ggaagcacac cctgcaggcc 1560
atcgtcggca gcggcaagaa gaagaacatc cttagacggt gcagggtgtg cagcgtgcac 1620
aagctgcgga gcgagactcg gtacatgtgc aagttttgca acattcccct gcacaaggga 1680
gcctgcttcg agaagtacca caccctgaag aattactag 1719

<210> SEQ ID NO 7
<211> LENGTH: 572
<212> TYPE: PRT
<213> ORGANISM: Artificial Sequence
<220> FEATURE:
<223> OTHER INFORMATION: Synthetic Sequence

<400> SEQUENCE: 7

Met Ala Gln His Ser Asp Tyr Ser Asp Asp Glu Phe Cys Ala Asp Lys
1 5 10 15

Leu Ser Asn Tyr Ser Cys Asp Ser Asp Leu Glu Asn Ala Ser Thr Ser
20 25 30

-continued

```
Asp Glu Asp Ser Ser Asp Asp Glu Val Met Val Arg Pro Arg Thr Leu
        35                  40                  45

Arg Arg Arg Arg Ile Ser Ser Ser Ser Ser Asp Ser Glu Ser Asp Ile
    50                  55                  60

Glu Gly Gly Arg Glu Glu Trp Ser His Val Asp Asn Pro Pro Val Leu
65                  70                  75                  80

Glu Asp Phe Leu Gly His Gln Gly Leu Asn Thr Asp Ala Val Ile Asn
                85                  90                  95

Asn Ile Glu Asp Ala Val Lys Leu Phe Ile Gly Asp Asp Phe Phe Glu
            100                 105                 110

Phe Leu Val Glu Glu Ser Asn Arg Tyr Tyr Asn Gln Lys Arg Asn Asn
        115                 120                 125

Phe Lys Leu Ser Lys Lys Ser Leu Lys Trp Lys Asp Ile Thr Pro Gln
    130                 135                 140

Glu Met Lys Lys Phe Leu Gly Leu Ile Val Leu Met Gly Gln Val Arg
145                 150                 155                 160

Lys Asp Arg Arg Asp Asp Tyr Trp Thr Thr Glu Pro Trp Thr Glu Thr
                165                 170                 175

Pro Tyr Phe Gly Lys Thr Met Thr Arg Asp Arg Phe Arg Gln Ile Trp
            180                 185                 190

Lys Ala Trp His Phe Asn Asn Asn Ala Asp Ile Val Asn Glu Ser Asp
        195                 200                 205

Arg Leu Cys Lys Val Arg Pro Val Leu Asp Tyr Phe Val Pro Lys Phe
    210                 215                 220

Ile Asn Ile Tyr Lys Pro His Gln Gln Leu Ser Leu Asp Glu Gly Ile
225                 230                 235                 240

Val Pro Trp Arg Gly Arg Leu Phe Phe Arg Val Tyr Asn Ala Gly Lys
                245                 250                 255

Ile Val Lys Tyr Gly Ile Leu Val Arg Leu Leu Cys Glu Ser Asp Thr
            260                 265                 270

Gly Tyr Ile Cys Asn Met Glu Ile Tyr Cys Gly Glu Gly Lys Arg Leu
        275                 280                 285

Leu Glu Thr Ile Gln Thr Val Val Ser Pro Tyr Thr Asp Ser Trp Tyr
    290                 295                 300

His Ile Tyr Met Asp Asn Tyr Tyr Asn Ser Val Ala Asn Cys Glu Ala
305                 310                 315                 320

Leu Met Lys Asn Lys Phe Arg Ile Cys Gly Thr Ile Arg Lys Asn Arg
                325                 330                 335

Gly Ile Pro Lys Asp Phe Gln Thr Ile Ser Leu Lys Lys Gly Glu Thr
            340                 345                 350

Lys Phe Ile Arg Lys Asn Asp Ile Leu Leu Gln Val Trp Gln Ser Lys
        355                 360                 365

Lys Pro Val Tyr Leu Ile Ser Ser Ile His Ser Ala Glu Met Glu Glu
    370                 375                 380

Ser Gln Asn Ile Asp Arg Thr Ser Lys Lys Lys Ile Val Lys Pro Asn
385                 390                 395                 400

Ala Leu Ile Asp Tyr Asn Lys His Met Lys Gly Val Asp Arg Ala Asp
                405                 410                 415

Gln Tyr Leu Ser Tyr Tyr Ser Ile Leu Arg Arg Thr Val Lys Trp Thr
            420                 425                 430

Lys Arg Leu Ala Met Tyr Met Ile Asn Cys Ala Leu Phe Asn Ser Tyr
        435                 440                 445
```

```
Ala Val Tyr Lys Ser Val Arg Gln Arg Lys Met Gly Phe Lys Met Phe
    450                 455                 460

Leu Lys Gln Thr Ala Ile His Trp Leu Thr Asp Asp Ile Pro Glu Asp
465                 470                 475                 480

Met Asp Ile Val Pro Asp Leu Gln Pro Val Pro Ser Thr Ser Gly Met
                485                 490                 495

Arg Ala Lys Pro Pro Thr Ser Asp Pro Pro Cys Arg Leu Ser Met Asp
            500                 505                 510

Met Arg Lys His Thr Leu Gln Ala Ile Val Gly Ser Gly Lys Lys Lys
        515                 520                 525

Asn Ile Leu Arg Arg Cys Arg Val Cys Ser Val His Lys Leu Arg Ser
    530                 535                 540

Glu Thr Arg Tyr Met Cys Lys Phe Cys Asn Ile Pro Leu His Lys Gly
545                 550                 555                 560

Ala Cys Phe Glu Lys Tyr His Thr Leu Lys Asn Tyr
                565                 570
```

<210> SEQ ID NO 8
<211> LENGTH: 1719
<212> TYPE: DNA
<213> ORGANISM: Artificial Sequence
<220> FEATURE:
<223> OTHER INFORMATION: Synthetic Sequence

<400> SEQUENCE: 8

```
atggcccagc acagcgacta ccccgacgac gagttcagag ccgataagct gagtaactac     60

agctgcgaca gcgacctgga aaacgccagc acatccgacg aggacagctc tgacgacgag    120

gtgatggtgc ggcccagaac cctgagacgg agaagaatca gcagctctag cagcgactct    180

gaatccgaca tcgagggcgg ccgggaagag tggagccacg tggacaaccc tcctgttctg    240

gaagattttc tgggccatca gggcctgaac accgacgccg tgatcaacaa catcgaggat    300

gccgtgaagc tgttcatagg agatgatttc tttgagttcc tggtcgagga atccaaccgc    360

tattacaacc agaatagaaa caacttcaag ctgagcaaga aaagcctgaa gtggaaggac    420

atcacccctc aggagatgaa aaagttcctg ggactgatcg ttctgatggg acaggtgcgg    480

aaggacagaa gggatgatta ctggacaacc gaaccttgga ccgagacccc ttactttggc    540

aagaccatga ccagagacag attcagacag atctggaaag cctggcactt caacaacaat    600

gctgatatcg tgaacgagtc tgatagactg tgtaaagtgc ggccagtgtt ggattacttc    660

gtgcctaagt tcatcaacat ctataagcct caccagcagc tgagcctgga tgaaggcatc    720

gtgccctggc ggggcagact gttcttcaga gtgtacaatg ctggcaagat cgtcaaatac    780

ggcatcctgg tgcgccttct gtgcgagagc gatacaggct acatctgtaa tatggaaatc    840

tactgcggcg agggcaaaag actgctggaa accatccaga ccgtcgtttc cccttatacc    900

gacagctggt accacatcta catggacaac tactacaatt ctgtggccaa ctgcgaggcc    960

ctgatgaaga acaagtttag aatctgcggc acaatcagaa aaaacagagg catccctaag   1020

gacttccaga ccatctctct gaagaagggc gaaaccaagt tcatcagaaa gaacgacatc   1080

ctgctccaag tgtggcagtc caagaaaccc gtgtacctga tcagcagcat ccatagcgcc   1140

gagatggaag aaagccagaa catcgacaga acaagcaaga agaagatcgt gaagcccaat   1200

gctctgatcg actacaacaa gcacatgaaa ggcgtggacc gggccgacca gtacctgtct   1260

tattactcta tcctgagaag aacagtgaaa tggaccaaga gactggccat gtacatgatc   1320
```

```
aattgcgccc tgttcaacag ctacgccgtg tacaagtccg tgcgacaaag aaaaatggga   1380

ttcaagatgt tcctgaagca gacagccatc cactggctga cagacgacat tcctgaggac   1440

atggacattg tgccagatct gcaacctgtg cccagcacct ctggtatgag agctaagcct   1500

cccaccagcg atcctccatg tagactgagc atggacatgc ggaagcacac cctgcaggcc   1560

atcgtcggca gcggcaagaa gaagaacatc cttagacggt gcagggtgtg cagcgtgcac   1620

aagctgcgga gcgagactcg gtacatgtgc aagttttgca acattcccct gcacaaggga   1680

gcctgcttcg agaagtacca caccctgaag aattactag                           1719
```

<210> SEQ ID NO 9
<211> LENGTH: 572
<212> TYPE: PRT
<213> ORGANISM: Artificial Sequence
<220> FEATURE:
<223> OTHER INFORMATION: Synthetic Sequence

<400> SEQUENCE: 9

```
Met Ala Gln His Ser Asp Tyr Pro Asp Asp Glu Phe Arg Ala Asp Lys
1               5                   10                  15

Leu Ser Asn Tyr Ser Cys Asp Ser Asp Leu Glu Asn Ala Ser Thr Ser
            20                  25                  30

Asp Glu Asp Ser Ser Asp Asp Glu Val Met Val Arg Pro Arg Thr Leu
        35                  40                  45

Arg Arg Arg Arg Ile Ser Ser Ser Ser Ser Asp Ser Glu Ser Asp Ile
    50                  55                  60

Glu Gly Gly Arg Glu Glu Trp Ser His Val Asp Asn Pro Pro Val Leu
65                  70                  75                  80

Glu Asp Phe Leu Gly His Gln Gly Leu Asn Thr Asp Ala Val Ile Asn
                85                  90                  95

Asn Ile Glu Asp Ala Val Lys Leu Phe Ile Gly Asp Asp Phe Phe Glu
            100                 105                 110

Phe Leu Val Glu Glu Ser Asn Arg Tyr Tyr Asn Gln Asn Arg Asn Asn
        115                 120                 125

Phe Lys Leu Ser Lys Lys Ser Leu Lys Trp Lys Asp Ile Thr Pro Gln
    130                 135                 140

Glu Met Lys Lys Phe Leu Gly Leu Ile Val Leu Met Gly Gln Val Arg
145                 150                 155                 160

Lys Asp Arg Arg Asp Asp Tyr Trp Thr Thr Glu Pro Trp Thr Glu Thr
                165                 170                 175

Pro Tyr Phe Gly Lys Thr Met Thr Arg Asp Arg Phe Arg Gln Ile Trp
            180                 185                 190

Lys Ala Trp His Phe Asn Asn Asn Ala Asp Ile Val Asn Glu Ser Asp
        195                 200                 205

Arg Leu Cys Lys Val Arg Pro Val Leu Asp Tyr Phe Val Pro Lys Phe
    210                 215                 220

Ile Asn Ile Tyr Lys Pro His Gln Gln Leu Ser Leu Asp Glu Gly Ile
225                 230                 235                 240

Val Pro Trp Arg Gly Arg Leu Phe Phe Arg Val Tyr Asn Ala Gly Lys
                245                 250                 255

Ile Val Lys Tyr Gly Ile Leu Val Arg Leu Leu Cys Glu Ser Asp Thr
            260                 265                 270

Gly Tyr Ile Cys Asn Met Glu Ile Tyr Cys Gly Glu Gly Lys Arg Leu
        275                 280                 285
```

```
Leu Glu Thr Ile Gln Thr Val Val Ser Pro Tyr Thr Asp Ser Trp Tyr
    290                 295                 300

His Ile Tyr Met Asp Asn Tyr Tyr Asn Ser Val Ala Asn Cys Glu Ala
305                 310                 315                 320

Leu Met Lys Asn Lys Phe Arg Ile Cys Gly Thr Ile Arg Lys Asn Arg
                325                 330                 335

Gly Ile Pro Lys Asp Phe Gln Thr Ile Ser Leu Lys Lys Gly Glu Thr
            340                 345                 350

Lys Phe Ile Arg Lys Asn Asp Ile Leu Leu Gln Val Trp Gln Ser Lys
        355                 360                 365

Lys Pro Val Tyr Leu Ile Ser Ser Ile His Ser Ala Glu Met Glu Glu
    370                 375                 380

Ser Gln Asn Ile Asp Arg Thr Ser Lys Lys Lys Ile Val Lys Pro Asn
385                 390                 395                 400

Ala Leu Ile Asp Tyr Asn Lys His Met Lys Gly Val Asp Arg Ala Asp
                405                 410                 415

Gln Tyr Leu Ser Tyr Tyr Ser Ile Leu Arg Arg Thr Val Lys Trp Thr
            420                 425                 430

Lys Arg Leu Ala Met Tyr Met Ile Asn Cys Ala Leu Phe Asn Ser Tyr
        435                 440                 445

Ala Val Tyr Lys Ser Val Arg Gln Arg Lys Met Gly Phe Lys Met Phe
    450                 455                 460

Leu Lys Gln Thr Ala Ile His Trp Leu Thr Asp Asp Ile Pro Glu Asp
465                 470                 475                 480

Met Asp Ile Val Pro Asp Leu Gln Pro Val Pro Ser Thr Ser Gly Met
                485                 490                 495

Arg Ala Lys Pro Pro Thr Ser Asp Pro Pro Cys Arg Leu Ser Met Asp
            500                 505                 510

Met Arg Lys His Thr Leu Gln Ala Ile Val Gly Ser Gly Lys Lys Lys
        515                 520                 525

Asn Ile Leu Arg Arg Cys Arg Val Cys Ser Val His Lys Leu Arg Ser
    530                 535                 540

Glu Thr Arg Tyr Met Cys Lys Phe Cys Asn Ile Pro Leu His Lys Gly
545                 550                 555                 560

Ala Cys Phe Glu Lys Tyr His Thr Leu Lys Asn Tyr
                565                 570


<210> SEQ ID NO 10
<211> LENGTH: 594
<212> TYPE: PRT
<213> ORGANISM: Artificial Sequence
<220> FEATURE:
<223> OTHER INFORMATION: Synthetic Sequence

<400> SEQUENCE: 10

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80
```

-continued

```
Lys Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

Arg Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495
```

```
Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Thr Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe


<210> SEQ ID NO 11
<211> LENGTH: 280
<212> TYPE: PRT
<213> ORGANISM: Artificial Sequence
<220> FEATURE:
<223> OTHER INFORMATION: Synthetic Sequence

<400> SEQUENCE: 11

Met Ser Asn Pro Arg Lys Arg Ser Ile Pro Thr Cys Asp Val Asn Phe
1               5                   10                  15

Val Leu Glu Gln Leu Leu Ala Glu Asp Ser Phe Asp Glu Ser Asp Phe
            20                  25                  30

Ser Glu Ile Asp Asp Ser Asp Asp Phe Ser Asp Ser Ala Ser Glu Asp
        35                  40                  45

Tyr Thr Val Arg Pro Pro Ser Asp Ser Glu Ser Asp Gly Asn Ser Pro
    50                  55                  60

Thr Ser Ala Asp Ser Gly Arg Ala Leu Lys Trp Ser Thr Arg Val Met
65                  70                  75                  80

Ile Pro Arg Gln Arg Tyr Asp Phe Thr Gly Thr Pro Gly Arg Lys Val
                85                  90                  95

Asp Val Ser Asp Thr Thr Asp Pro Leu Gln Tyr Phe Glu Leu Phe Phe
            100                 105                 110

Thr Glu Glu Leu Val Ser Lys Ile Thr Ser Glu Met Asn Ala Gln Ala
        115                 120                 125

Ala Leu Leu Ala Ser Lys Pro Pro Gly Pro Lys Gly Phe Ser Arg Met
    130                 135                 140

Asp Lys Trp Lys Asp Thr Asp Asn Asp Glu Leu Lys Val Phe Phe Ala
145                 150                 155                 160

Val Met Leu Leu Gln Gly Ile Val Gln Lys Pro Glu Leu Glu Met Phe
                165                 170                 175

Trp Ser Thr Arg Pro Leu Leu Asp Ile Pro Tyr Leu Arg Gln Ile Met
            180                 185                 190

Thr Gly Glu Arg Phe Leu Leu Leu Leu Arg Cys Leu His Phe Val Asn
        195                 200                 205

Asn Ser Ser Ile Ser Ala Gly Gln Ser Lys Ala Gln Ile Ser Leu Gln
    210                 215                 220

Lys Ile Lys Pro Val Phe Asp Phe Leu Val Asn Lys Phe Ser Thr Val
225                 230                 235                 240

Tyr Thr Pro Asn Arg Asn Ile Ala Val Asp Glu Ser Leu Met Leu Phe
                245                 250                 255
```

```
Lys Gly Arg Leu Ala Met Lys Gln Tyr Ile Pro Thr Lys Met Asn Leu
            260                 265                 270

Lys Asp Ser Ala Asp Gly Leu Lys
        275                 280


<210> SEQ ID NO 12
<211> LENGTH: 252
<212> TYPE: PRT
<213> ORGANISM: Artificial Sequence
<220> FEATURE:
<223> OTHER INFORMATION: Synthetic Sequence

<400> SEQUENCE: 12

Met Asp Leu Arg Cys Gln His Thr Val Leu Ser Ile Arg Glu Ser Arg
1               5                   10                  15

Gly Leu Leu Pro Asn Leu Lys Met Lys Thr Ser Arg Met Lys Lys Gly
            20                  25                  30

Asp Ile Ile Phe Ser Arg Lys Gly Asp Ile Leu Leu Leu Ala Trp Lys
        35                  40                  45

Asp Lys Arg Val Val Arg Met Ile Ser Ile His Asp Thr Ser Val Ser
    50                  55                  60

Thr Thr Gly Lys Lys Asn Arg Lys Thr Gly Glu Asn Ile Val Lys Pro
65                  70                  75                  80

Ala Cys Ile Lys Glu Tyr Asn Ala His Met Lys Gly Val Asp Arg Ala
                85                  90                  95

Asp Gln Phe Leu Ser Cys Cys Ser Ile Leu Arg Lys Met Met Lys Trp
            100                 105                 110

Thr Lys Lys Val Val Leu Tyr Leu Ile Asn Cys Gly Leu Phe Asn Ser
        115                 120                 125

Phe Arg Val Tyr Asn Val Leu Asn Pro Gln Ala Lys Met Lys Tyr Lys
    130                 135                 140

Gln Phe Leu Leu Ser Val Ala Arg Asp Trp Ile Met Asp Asp Asn Asn
145                 150                 155                 160

Glu Gly Ser Pro Glu Pro Glu Thr Asn Leu Ser Ser Pro Ser Pro Gly
                165                 170                 175

Gly Ala Arg Arg Ala Pro Arg Lys Asp Pro Pro Lys Arg Leu Ser Gly
            180                 185                 190

Asp Met Lys Gln His Glu Pro Thr Cys Ile Pro Ala Ser Gly Lys Lys
        195                 200                 205

Lys Phe Pro Thr Arg Ala Cys Arg Val Cys Ala His Gly Lys Arg Ser
    210                 215                 220

Glu Ser Arg Tyr Leu Cys Lys Phe Cys Leu Val Pro Leu His Arg Gly
225                 230                 235                 240

Lys Cys Phe Thr Gln Tyr His Thr Leu Lys Lys Tyr
                245                 250


<210> SEQ ID NO 13
<211> LENGTH: 432
<212> TYPE: PRT
<213> ORGANISM: Artificial Sequence
<220> FEATURE:
<223> OTHER INFORMATION: Synthetic Sequence

<400> SEQUENCE: 13

Met Lys Ala Phe Leu Gly Val Ile Leu Asn Met Gly Val Leu Asn His
1               5                   10                  15
```

```
Pro Asn Leu Gln Ser Tyr Trp Ser Met Asp Phe Glu Ser His Ile Pro
            20                  25                  30

Phe Phe Arg Ser Val Phe Lys Arg Glu Arg Phe Leu Gln Ile Phe Trp
        35                  40                  45

Met Leu His Leu Lys Asn Asp Gln Lys Ser Ser Lys Asp Leu Arg Thr
    50                  55                  60

Arg Thr Glu Lys Val Asn Cys Phe Leu Ser Tyr Leu Glu Met Lys Phe
65                  70                  75                  80

Arg Glu Arg Phe Cys Pro Gly Arg Glu Ile Ala Val Asp Glu Ala Val
                85                  90                  95

Val Gly Phe Lys Gly Lys Ile His Phe Ile Thr Tyr Asn Pro Lys Lys
            100                 105                 110

Pro Thr Lys Trp Gly Ile Arg Leu Tyr Val Leu Ser Asp Ser Lys Cys
        115                 120                 125

Gly Tyr Val His Ser Phe Val Pro Tyr Tyr Gly Gly Ile Thr Ser Glu
    130                 135                 140

Thr Leu Val Arg Pro Asp Leu Pro Phe Thr Ser Arg Ile Val Leu Glu
145                 150                 155                 160

Leu His Glu Arg Leu Lys Asn Ser Val Pro Gly Ser Gln Gly Tyr His
                165                 170                 175

Phe Phe Thr Asp Arg Tyr Tyr Thr Ser Val Thr Leu Ala Lys Glu Leu
            180                 185                 190

Phe Lys Glu Lys Thr His Leu Thr Gly Thr Ile Met Pro Asn Arg Lys
        195                 200                 205

Asp Asn Pro Pro Val Ile Lys His Gln Lys Leu Lys Lys Gly Glu Ile
    210                 215                 220

Val Ala Phe Arg Asp Glu Asn Val Met Leu Leu Ala Trp Lys Asp Lys
225                 230                 235                 240

Arg Ile Val Thr Leu Ser Thr Trp Asp Ser Glu Thr Glu Ser Val Glu
                245                 250                 255

Arg Arg Val Gly Gly Gly Lys Glu Ile Val Leu Lys Pro Lys Val Val
            260                 265                 270

Thr Asn Tyr Thr Lys Phe Met Gly Gly Val Asp Ile Ala Asp Tyr Thr
        275                 280                 285

Ser Thr Tyr Cys Phe Met Arg Lys Thr Leu Lys Trp Trp Arg Thr Leu
    290                 295                 300

Phe Phe Trp Gly Leu Glu Val Ser Val Val Asn Ser Tyr Ile Leu Tyr
305                 310                 315                 320

Lys Glu Cys Gln Lys Arg Lys Asn Glu Lys Pro Ile Thr His Val Lys
                325                 330                 335

Phe Ile Arg Lys Leu Val His Asp Leu Val Gly Glu Phe Arg Asp Gly
            340                 345                 350

Thr Leu Thr Ser Arg Gly Arg Leu Leu Ser Thr Asn Leu Glu Gln Arg
        355                 360                 365

Leu Asp Gly Lys Leu His Ile Ile Thr Pro His Pro Asn Lys Lys His
    370                 375                 380

Lys Asp Cys Val Val Cys Ser Asn Arg Lys Ile Lys Gly Gly Arg Arg
385                 390                 395                 400

Glu Thr Ile Tyr Ile Cys Glu Thr Cys Glu Cys Lys Pro Gly Leu His
                405                 410                 415

Val Gly Glu Cys Phe Lys Lys Tyr His Thr Met Lys Asn Tyr Arg Asp
            420                 425                 430
```

<210> SEQ ID NO 14
<211> LENGTH: 662
<212> TYPE: PRT
<213> ORGANISM: Artificial Sequence
<220> FEATURE:
<223> OTHER INFORMATION: Synthetic Sequence

<400> SEQUENCE: 14

```
Met Pro Ser Leu Arg Lys Arg Lys Glu Thr Asn Glu Thr Asp Thr Leu
1               5                   10                  15

Pro Glu Val Phe Asn Asp Asn Leu Ser Asp Ile Pro Ser Glu Ile Glu
            20                  25                  30

Asp Ala Asp Asp Cys Phe Asp Asp Ser Gly Asp Asp Ser Thr Asp Ser
        35                  40                  45

Thr Asp Ser Glu Ile Ile Arg Pro Val Arg Lys Arg Lys Val Ala Val
    50                  55                  60

Leu Ser Ser Asp Ser Asp Thr Asp Glu Ala Thr Asp Asn Cys Trp Ser
65                  70                  75                  80

Glu Ile Asp Thr Pro Pro Arg Leu Gln Met Phe Glu Gly His Ala Gly
                85                  90                  95

Val Thr Thr Phe Pro Ser Gln Cys Asp Ser Val Pro Ser Val Thr Asn
            100                 105                 110

Leu Phe Phe Gly Asp Glu Leu Phe Glu Met Leu Cys Lys Glu Leu Ser
        115                 120                 125

Asn Tyr His Asp Gln Thr Ala Met Lys Arg Lys Thr Pro Ser Arg Thr
    130                 135                 140

Leu Lys Trp Ser Pro Val Thr Gln Lys Asp Ile Lys Lys Phe Leu Gly
145                 150                 155                 160

Leu Ile Ile Leu Met Gly Gln Thr Arg Lys Asp Ser Leu Lys Asp Tyr
                165                 170                 175

Trp Ser Thr Asp Pro Leu Ile Cys Thr Pro Ile Phe Pro Gln Thr Met
            180                 185                 190

Ser Arg His Arg Phe Glu Gln Ile Trp Thr Phe Trp His Phe Asn Asp
        195                 200                 205

Asn Ala Lys Met Asp Ser Arg Ser Gly Arg Leu Phe Lys Ile Gln Pro
    210                 215                 220

Val Leu Asp Tyr Phe Leu His Lys Phe Arg Thr Ile Tyr Lys Pro Lys
225                 230                 235                 240

Gln Gln Leu Ser Leu Asp Glu Gly Met Ile Pro Trp Arg Gly Arg Phe
                245                 250                 255

Lys Phe Arg Thr Tyr Asn Pro Ala Lys Ile Thr Lys Tyr Gly Leu Leu
            260                 265                 270

Val Arg Met Val Cys Glu Ser Asp Thr Gly Tyr Ile Cys Ser Met Glu
        275                 280                 285

Ile Tyr Thr Ala Glu Gly Arg Lys Leu Gln Glu Thr Val Leu Ser Val
    290                 295                 300

Leu Gly Pro Tyr Leu Gly Ile Trp His His Ile Tyr Gln Asp Asn Tyr
305                 310                 315                 320

Tyr Asn Ala Thr Ser Thr Ala Glu Leu Leu Leu Gln Asn Lys Thr Arg
                325                 330                 335

Val Cys Gly Thr Ile Arg Glu Ser Arg Gly Leu Pro Pro Asn Leu Glu
            340                 345                 350

Met Lys Thr Ser Arg Met Lys Lys Gly Asp Ile Ile Phe Ser Arg Lys
        355                 360                 365
```

-continued

```
Gly Asp Ile Leu Leu Leu Ala Trp Lys Asp Lys Arg Val Val Arg Met
    370                 375                 380

Ile Ser Thr Ile His Asp Thr Ser Val Ser Thr Thr Gly Lys Lys Asn
385                 390                 395                 400

Arg Lys Thr Gly Glu Asn Ile Val Lys Pro Thr Cys Ile Lys Glu Tyr
                405                 410                 415

Asn Ala His Met Lys Gly Val Asp Arg Ala Asp Gln Phe Leu Ser Cys
            420                 425                 430

Cys Ser Ile Leu Arg Lys Thr Met Lys Trp Thr Lys Lys Val Val Leu
        435                 440                 445

Tyr Leu Ile Asn Cys Gly Leu Phe Asn Ser Phe Arg Val Tyr Asn Val
    450                 455                 460

Leu Asn Pro Gln Ala Lys Met Lys Tyr Lys Gln Phe Leu Leu Ser Val
465                 470                 475                 480

Ala Arg Asp Trp Ile Thr Asp Asp Asn Asn Glu Gly Ser Pro Glu Pro
                485                 490                 495

Glu Thr Asn Leu Ser Ser Pro Ser Pro Gly Gly Ala Arg Arg Ala Pro
            500                 505                 510

Arg Lys Asp Pro Pro Lys Arg Leu Ser Gly Asp Met Lys Gln His Glu
        515                 520                 525

Pro Thr Cys Ile Pro Ala Ser Gly Lys Lys Lys Phe Pro Thr Arg Ala
    530                 535                 540

Cys Arg Val Cys Ala Ala His Gly Lys Arg Ser Glu Ser Arg Tyr Leu
545                 550                 555                 560

Cys Lys Phe Cys Leu Val Pro Leu His Arg Gly Lys Cys Phe Thr Gln
                565                 570                 575

Tyr His Thr Leu Lys Lys Tyr Met Asp Leu Arg Cys Gln His Thr Val
            580                 585                 590

Leu Ser Thr Val Gly Arg Gly Tyr Ser Val Leu Ala Arg Phe Lys Pro
        595                 600                 605

Arg Thr Asn Glu Arg Thr Gly Ser Ser His Cys His Val Gln Val Pro
    610                 615                 620

Ala Gly Gly Gln Gly Pro Pro Ser Thr Ile Ile Ala Asn Gly Cys Gly
625                 630                 635                 640

Cys Lys Leu Glu Pro Met Val Arg Thr Arg Ser Pro Thr Cys Leu Val
                645                 650                 655

Ile Glu Phe Gly Cys Met
            660


<210> SEQ ID NO 15
<211> LENGTH: 673
<212> TYPE: PRT
<213> ORGANISM: Artificial Sequence
<220> FEATURE:
<223> OTHER INFORMATION: Synthetic Sequence

<400> SEQUENCE: 15

Met Pro Ser Leu Arg Lys Arg Lys Glu Thr Asn Glu Thr Asp Thr Leu
1               5                   10                  15

Pro Glu Val Phe Asn Asp Asn Leu Ser Asp Ile Pro Ser Glu Ile Glu
            20                  25                  30

Asp Ala Asp Asp Cys Phe Asp Asp Ser Gly Asp Asp Ser Thr Asp Ser
        35                  40                  45

Thr Glu Ser Glu Ile Ile Arg Pro Val Arg Lys Arg Lys Val Ala Val
    50                  55                  60
```

```
Leu Ser Ser Asp Ser Asn Thr Asp Glu Ala Thr Asp Asn Cys Trp Ser
65                  70                  75                  80

Glu Ile Asp Thr Pro Pro Arg Leu Gln Met Phe Glu Gly His Ala Gly
                85                  90                  95

Val Thr Thr Phe Pro Ser Gln Cys Asp Ser Val Pro Ser Val Thr Asn
            100                 105                 110

Leu Phe Phe Gly Asp Glu Leu Phe Glu Met Leu Cys Lys Glu Leu Ser
        115                 120                 125

Asn Tyr His Asp Gln Thr Ala Met Lys Arg Lys Thr Pro Ser Arg Thr
    130                 135                 140

Leu Lys Trp Ser Pro Val Thr Gln Lys Asp Ile Lys Lys Phe Leu Gly
145                 150                 155                 160

Leu Ile Ile Leu Met Gly Gln Thr Arg Lys Asp Ser Trp Lys Asp Tyr
                165                 170                 175

Trp Ser Thr Asp Pro Leu Ile Cys Thr Pro Ile Phe Pro Gln Thr Met
            180                 185                 190

Ser Arg His Arg Phe Glu Gln Ile Trp Thr Phe Trp His Phe Asn Asp
        195                 200                 205

Asn Ala Lys Met Asp Ser Cys Ser Gly Arg Leu Phe Lys Ile Gln Pro
    210                 215                 220

Val Leu Asp Tyr Phe Leu His Lys Phe Arg Thr Ile Tyr Lys Pro Lys
225                 230                 235                 240

Gln Gln Leu Ser Leu Asp Glu Gly Met Ile Pro Trp Arg Gly Arg Leu
                245                 250                 255

Lys Phe Thr Tyr Asn Pro Ala Ile Thr Lys Tyr Gly Leu Leu Val Arg
            260                 265                 270

Met Val Cys Glu Ser Asp Thr Gly Tyr Ile Cys Asn Met Glu Ile Tyr
        275                 280                 285

Thr Ala Glu Arg Lys Lys Leu Gln Glu Thr Val Leu Ser Val Leu Gly
    290                 295                 300

Pro Tyr Leu Gly Ile Trp His His Ile Tyr Gln Asp Asn Tyr Tyr Asn
305                 310                 315                 320

Ala Thr Ser Thr Ala Glu Leu Leu Leu Gln Asn Lys Thr Arg Val Cys
                325                 330                 335

Gly Thr Ile Arg Glu Ser Arg Gly Leu Pro Pro Asn Leu Lys Met Lys
            340                 345                 350

Thr Ser Arg Met Lys Lys Gly Asp Ile Ile Phe Ser Arg Lys Gly Asp
        355                 360                 365

Ile Leu Leu Leu Ala Trp Lys Asp Lys Arg Val Val Arg Met Ile Ser
    370                 375                 380

Thr Ile His Asp Thr Ser Val Ser Thr Thr Gly Lys Lys Asn Arg Lys
385                 390                 395                 400

Thr Gly Glu Asn Ile Val Lys Pro Thr Cys Ile Lys Glu Tyr Asn Ala
                405                 410                 415

His Met Lys Gly Val Asp Arg Ala Asp Gln Phe Leu Ser Cys Cys Ser
            420                 425                 430

Ile Leu Arg Lys Thr Thr Lys Trp Thr Lys Lys Val Val Leu Tyr Leu
        435                 440                 445

Ile Asn Cys Gly Leu Phe Asn Ser Phe Arg Val Tyr Asn Ile Leu Asn
    450                 455                 460

Pro Gln Ala Lys Met Lys Tyr Lys Gln Phe Leu Leu Ser Val Ala Arg
465                 470                 475                 480
```

Asp Trp Ile Thr Asp Asp Asn Asn Glu Gly Ser Pro Glu Pro Glu Thr
485 490 495

Asn Leu Ser Ser Pro Ser Ser Gly Gly Ala Arg Arg Ala Pro Arg Lys
500 505 510

Asp Gln Pro Lys Arg Leu Ser Gly Asp Met Lys Gln His Glu Pro Thr
515 520 525

Cys Ile Pro Ala Ser Gly Lys Lys Lys Phe Pro Thr Ala Cys Arg Val
530 535 540

Cys Ala Ala His Gly Lys Arg Ser Glu Ser Arg Tyr Leu Arg Lys Phe
545 550 555 560

Cys Phe Val Pro Leu Arg Gly Lys Cys Phe Met Tyr His Thr Leu Lys
565 570 575

Lys Tyr Ser Glu Leu Phe Ser Leu Ile Val Val Ser Lys Ile Gln Asn
580 585 590

Val Ile Ile Tyr Lys Thr Thr Lys Val Tyr Met Arg Tyr Val Met Arg
595 600 605

Ser His Cys Pro Leu Ser Phe Leu Val Phe Ala Pro Ser Val Lys Asp
610 615 620

Arg Ser Arg Val Phe Ser Phe Phe Thr Arg His Leu Leu Trp Thr Leu
625 630 635 640

Asp Val Asn Thr Leu Ser Cys Pro His Arg Met Lys Arg Ser His Trp
645 650 655

Trp Lys Pro Cys Arg Ser Ile Tyr Glu Lys Leu Tyr Asn Cys Thr Asn
660 665 670

Pro

<210> SEQ ID NO 16
<211> LENGTH: 254
<212> TYPE: PRT
<213> ORGANISM: Artificial Sequence
<220> FEATURE:
<223> OTHER INFORMATION: Synthetic Sequence

<400> SEQUENCE: 16

Met Asp Leu Arg Cys Gln His Thr Val Leu Ser Ile Arg Glu Ser Arg
1 5 10 15

Gly Leu Pro Pro Asn Leu Lys Met Lys Thr Ser Arg Met Lys Lys Gly
20 25 30

Asp Ile Ile Phe Ser Arg Lys Gly Asp Ile Leu Leu Leu Ala Trp Lys
35 40 45

Asp Lys Arg Val Val Arg Met Ile Ser Thr Ile His Asp Thr Ser Val
50 55 60

Ser Thr Thr Gly Lys Lys Asn Arg Lys Thr Gly Glu Asn Ile Val Lys
65 70 75 80

Pro Ala Cys Ile Lys Glu Tyr Asn Ala His Met Lys Gly Val Asp Arg
85 90 95

Ala Asp Gln Phe Leu Ser Cys Cys Ser Ile Leu Arg Lys Thr Met Lys
100 105 110

Trp Thr Lys Lys Val Val Leu Tyr Leu Ile Asn Cys Gly Leu Phe Asn
115 120 125

Ser Phe Arg Val Tyr Asn Val Leu Asn Pro Gln Ala Lys Met Lys Tyr
130 135 140

Lys Gln Phe Leu Leu Ser Val Ala Arg Asp Trp Ile Thr Asp Asp Asn
145 150 155 160

-continued

```
Asn Glu Gly Ser Pro Glu Pro Glu Thr Asn Leu Ser Ser Pro Ser Pro
                165                 170                 175

Gly Gly Ala Arg Arg Ala Pro Arg Lys Asp Pro Pro Lys Arg Leu Ser
            180                 185                 190

Gly Asp Met Lys Gln His Glu Pro Thr Cys Ile Pro Ala Ser Gly Lys
        195                 200                 205

Lys Lys Phe Pro Thr Arg Ala Cys Arg Val Cys Ala Ala His Gly Lys
    210                 215                 220

Arg Ser Glu Ser Arg Tyr Leu Cys Lys Phe Cys Leu Val Pro Leu His
225                 230                 235                 240

Arg Gly Lys Cys Phe Thr Gln Tyr His Thr Leu Lys Lys Tyr
                245                 250
```

<210> SEQ ID NO 17
<211> LENGTH: 594
<212> TYPE: PRT
<213> ORGANISM: Artificial Sequence
<220> FEATURE:
<223> OTHER INFORMATION: Synthetic Sequence

<400> SEQUENCE: 17

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Pro Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270
```

-continued

```
Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Gly Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Lys Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Ser Ala Ser Cys Lys Lys
                565                 570                 575

Cys Lys Lys Val Ile Cys Arg Glu His Asn Ile Asp Met Cys Gln Ser
            580                 585                 590

Cys Phe


<210> SEQ ID NO 18
<211> LENGTH: 1782
<212> TYPE: DNA
<213> ORGANISM: Artificial Sequence
<220> FEATURE:
<223> OTHER INFORMATION: Synthetic Sequence

<400> SEQUENCE: 18

atgggcagca gcctggacga cgagcacatc ctgagcgccc tgctgcagag cgacgacgag      60

ctggtcggcg aggacagcga cagcgaggtg agcgaccacg tgagcgagga cgacgtgcag     120

tccgacaccg aggaggcctt catcgacgag gtgcacgagg tgcagcctac cagcagcggc     180

tccgagatcc tggacgagca gaacgtgatc gagcagcccg gcagctccct ggccagcaac     240
```

```
aggatcctga ccctgcccca gaggaccatc aggggcaaga acaagcactg ctggtccacc    300

tccaagccca ccaggcggag cagggtgtcc gccctgaaca tcgtgagaag ccagaggggc    360

cccaccagga tgtgcaggaa catctacgac cccctgctgt gcttcaagct gttcttcacc    420

gacgagatca tcagcgagat cgtgaagtgg accaacgccg agatcagcct gaagaggcgg    480

gagagcatga cctccgccac cttcagggac accaacgagg acgagatcta cgccttcttc    540

ggcatcctgg tgatgaccgc cgtgaggaag gacaaccaca tgagcaccga cgacctgttc    600

gacagatccc tgagcatggt gtacgtgagc gtgatgagca gggacagatt cgacttcctg    660

atcagatgcc tgaggatgga cgacaagagc atcaggccca ccctgcggga gaacgacgtg    720

ttcacccccg tgagaaagat ctgggacctg ttcatccacc agtgcatcca gaactacacc    780

cctggcgccc acctgaccat cgacgagcag ctgctgggct tcaggggcag gtgcccccttc    840

agggtctata tccccaacaa gcccagcaag tacggcatca agatcctgat gatgtgcgac    900

agcggcacca agtacatgat caacggcatg ccctacctgg gcaggggcac ccagaccaac    960

ggcgtgcccc tgggcgagta ctacgtgaag gagctgtcca agcccgtcca cggcagctgc   1020

agaaacatca cctgcgacaa ctggttcacc agcatccccc tggccaagaa cctgctgcag   1080

gagccctaca agctgaccat cgtgggcacc gtgagaagca acaagagaga gatccccgag   1140

gtcctgaaga acagcaggtc caggcccgtg ggcaccagca tgttctgctt cgacggcccc   1200

ctgaccctgg tgtcctacaa gcccaagccc gccaagatgg tgtacctgct gtccagctgc   1260

gacgaggacg ccagcatcaa cgagagcacc ggcaagcccc agatggtgat gtactacaac   1320

cagaccaagg gcggcgtgga caccctggac cagatgtgca gcgtgatgac ctgcagcaga   1380

aagaccaaca ggtggcccat ggccctgctg tacggcatga tcaacatcgc ctgcatcaac   1440

agcttcatca tctacagcca caacgtgagc agcaagggcg agaaggtgca gagccggaaa   1500

aagttcatgc ggaacctgta catgggcctg acctccagct tcatgaggaa gaggctggag   1560

gcccccaccc tgaagagata cctgagggac aacatcagca acatcctgcc caaagaggtg   1620

cccggcacca gcgacgacag caccgaggag cccgtgatga agaagaggac ctactgcacc   1680

tactgtccca gcaagatcag aagaaaggcc agcgccagct gcaagaagtg taagaaggtc   1740

atctgccggg agcacaacat cgacatgtgc cagagctgtt tc                      1782
```

<210> SEQ ID NO 19
<211> LENGTH: 205
<212> TYPE: DNA
<213> ORGANISM: Artificial Sequence
<220> FEATURE:
<223> OTHER INFORMATION: Synthetic Sequence

<400> SEQUENCE: 19

```
ttaaccctag aaagataatc atattgtgac gtacgttaaa gataatcatg cgtaaaattg     60

acgcatgtgt tttatcggtc tgtatatcga ggtttattta ttaatttgaa tagatattaa    120

gttttattat atttacactt acatactaat aataaattca acaaacaatt tatttatgtt    180

tatttattta ttaaaaaaaa acaaa                                          205
```

<210> SEQ ID NO 20
<211> LENGTH: 310
<212> TYPE: DNA
<213> ORGANISM: Artificial Sequence
<220> FEATURE:
<223> OTHER INFORMATION: Synthetic Sequence

<400> SEQUENCE: 20
atctataaca agaaaatata tatataataa gttatcacgt aagtagaaca tgaaataaca 60
atataattat cgtatgagtt aaatcttaaa agtcacgtaa aagataatca tgcgtcattt 120
tgactcacgc ggtcgttata gttcaaaatc agtgacactt accgcattga caagcacgcc 180
tcacgggagc tccaagcggc gactgagatg tcctaaatgc acagcgacgg attcgcgcta 240
tttagaaaga gagagcaata tttcaagaat gcatgcgtca attttacgca gactatcttt 300
ctagggttaa 310

<210> SEQ ID NO 21
<211> LENGTH: 157
<212> TYPE: DNA
<213> ORGANISM: Artificial Sequence
<220> FEATURE:
<223> OTHER INFORMATION: Synthetic Sequence

<400> SEQUENCE: 21
ttaacacttg gattgcggga aacgagttaa gtcggctcgc gtgaattgcg cgtactccgc 60
gggagccgtc ttaactcggt tcatatagat ttgcggtgga gtgcgggaaa cgtgtaaact 120
cgggccgatt gtaactgcgt attaccaaat atttgtt 157

<210> SEQ ID NO 22
<211> LENGTH: 212
<212> TYPE: DNA
<213> ORGANISM: Artificial Sequence
<220> FEATURE:
<223> OTHER INFORMATION: Synthetic Sequence

<400> SEQUENCE: 22
aattatttat gtactgaata gataaaaaaa tgtctgtgat tgaataaatt ttcatttttt 60
acacaagaaa ccgaaaattt catttcaatc gaacccatac ttcaaaagat ataggcattt 120
taaactaact ctgattttgc gcgggaaacc taaataattg cccgcgccat cttatatttt 180
ggcgggaaat tcacccgaca ccgtagtgtt aa 212

<210> SEQ ID NO 23
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 23
tggccggcct gaccactgg 19

<210> SEQ ID NO 24
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 24
tgaaggcctg gccggcctg 19

<210> SEQ ID NO 25
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 25
tgagcactga aggcctggc 19

<210> SEQ ID NO 26
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 26
tccactgagc actgaaggc 19

<210> SEQ ID NO 27
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 27
tggtttccac tgagcactg 19

<210> SEQ ID NO 28
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 28
tggggaaaat gacccaaca 19

<210> SEQ ID NO 29
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 29
taggacagtg gggaaaatg 19

<210> SEQ ID NO 30
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 30
tccagggaca cggtgctag 19

<210> SEQ ID NO 31
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 31
tcagagccag gagtcctgg 19

<210> SEQ ID NO 32

<211> LENGTH: 19
<212> TYPE: DNA
<213> ORGANISM: Artificial Sequence
<220> FEATURE:
<223> OTHER INFORMATION: Synthetic Sequence

<400> SEQUENCE: 32
tccttcagag ccaggagtc 19

<210> SEQ ID NO 33
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 33
tcctccttca gagccagga 19

<210> SEQ ID NO 34
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 34
tccagcccct cctccttca 19

<210> SEQ ID NO 35
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 35
tccgagcttg acccttgga 19

<210> SEQ ID NO 36
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 36
tggtttccga gcttgaccc 19

<210> SEQ ID NO 37
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 37
tggggtggtt tccgagcttt ggggtggttt ccgagctt 38

<210> SEQ ID NO 38
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 38
tctgctgggg tggtttccg 19

<210> SEQ ID NO 39
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 39
tgcagagtat ctgctggggt gcagagtatc tgctgggg 38

<210> SEQ ID NO 40
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 40
ccaatcccct cagt 14

<210> SEQ ID NO 41
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 41
cagtgctcag tggaa 15

<210> SEQ ID NO 42
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 42
gaaacatccg gcgactca 18

<210> SEQ ID NO 43
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 43
tcgcccctca aatcttaca 19

<210> SEQ ID NO 44
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 44
tcaaatctta cagctgctc 19

<210> SEQ ID NO 45

<211> LENGTH: 19
<212> TYPE: DNA
<213> ORGANISM: Artificial Sequence
<220> FEATURE:
<223> OTHER INFORMATION: Synthetic Sequence

<400> SEQUENCE: 45
tcttacagct gctcactcc 19

<210> SEQ ID NO 46
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 46
tacagctgct cactcccct 19

<210> SEQ ID NO 47
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 47
tgctcactcc cctgcaggg 19

<210> SEQ ID NO 48
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 48
tcccctgcag ggcaacgcc 19

<210> SEQ ID NO 49
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 49
tgcagggcaa cgcccaggg 19

<210> SEQ ID NO 50
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 50
tctcgattat gggcgggat 19

<210> SEQ ID NO 51
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 51
tcgcttctcg attatgggc 19

<210> SEQ ID NO 52
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 52
tgtcgagtcg cttctcgat 19

<210> SEQ ID NO 53
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 53
tccatgtcga gtcgcttct 19

<210> SEQ ID NO 54
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 54
tcgcctccat gtcgagtcg 19

<210> SEQ ID NO 55
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 55
tcgtcatcgc ctccatgtc 19

<210> SEQ ID NO 56
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 56
tgatctcgtc atcgcctcc 19

<210> SEQ ID NO 57
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 57
gcttcagctt ccta 14

<210> SEQ ID NO 58

-continued

<211> LENGTH: 14
<212> TYPE: DNA
<213> ORGANISM: Artificial Sequence
<220> FEATURE:
<223> OTHER INFORMATION: Synthetic Sequence

<400> SEQUENCE: 58
ctgtgatcat gcca 14

<210> SEQ ID NO 59
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 59
acagtggtac acacct 16

<210> SEQ ID NO 60
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 60
ccacccccca ctaag 15

<210> SEQ ID NO 61
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 61
cattggccgg gcac 14

<210> SEQ ID NO 62
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 62
gcttgaaccc aggaga 16

<210> SEQ ID NO 63
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 63
acacccgatc cactggg 17

<210> SEQ ID NO 64
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 64
gctgcatcaa cccc 14

<210> SEQ ID NO 65
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 65
gccacaaaca gaaata 16

<210> SEQ ID NO 66
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 66
ggtggctcat gcctg 15

<210> SEQ ID NO 67
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 67
gatttgcaca gctcat 16

<210> SEQ ID NO 68
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 68
aagctctgag gagca 15

<210> SEQ ID NO 69
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 69
ccctagctgt ccc 13

<210> SEQ ID NO 70
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 70
gcctagcatg ctag 14

<210> SEQ ID NO 71

<211> LENGTH: 15
<212> TYPE: DNA
<213> ORGANISM: Artificial Sequence
<220> FEATURE:
<223> OTHER INFORMATION: Synthetic Sequence

<400> SEQUENCE: 71
atgggcttca cggat 15

<210> SEQ ID NO 72
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 72
gaaactatgc ctgc 14

<210> SEQ ID NO 73
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 73
gcaccattgc tccc 14

<210> SEQ ID NO 74
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 74
gacatgcaac tcag 14

<210> SEQ ID NO 75
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 75
acaccactag gggt 14

<210> SEQ ID NO 76
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 76
gtctgctaga cagg 14

<210> SEQ ID NO 77
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 77
ggcctagaca ggctg 15

<210> SEQ ID NO 78
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 78
gaggcattct tatcg 15

<210> SEQ ID NO 79
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 79
gcctggaaac gttcc 15

<210> SEQ ID NO 80
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 80
gtgctctgac aata 14

<210> SEQ ID NO 81
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 81
gttttgcagc ctcc 14

<210> SEQ ID NO 82
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 82
acagctgtgg aacgt 15

<210> SEQ ID NO 83
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 83
ggctctcttc ctcct 15

<210> SEQ ID NO 84

<211> LENGTH: 15
<212> TYPE: DNA
<213> ORGANISM: Artificial Sequence
<220> FEATURE:
<223> OTHER INFORMATION: Synthetic Sequence

<400> SEQUENCE: 84
ctatcccaaa actct 15

<210> SEQ ID NO 85
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 85
gaaaaactat gtat 14

<210> SEQ ID NO 86
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 86
aggcaggctg gttga 15

<210> SEQ ID NO 87
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 87
caatacaacc acgc 14

<210> SEQ ID NO 88
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 88
atgacggact caact 15

<210> SEQ ID NO 89
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 89
cacaacattt gtaa 14

<210> SEQ ID NO 90
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 90
atttccagtg caca 14

<210> SEQ ID NO 91
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 91
gtttagctca cccgtgagcc 20

<210> SEQ ID NO 92
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 92
cccaatatta ttgttctctg 20

<210> SEQ ID NO 93
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 93
ggggtgggat aggggatacg 20

<210> SEQ ID NO 94
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 94
ggatccccct ctacatttaa 20

<210> SEQ ID NO 95
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 95
gtgatcttgt acaaatcatt 20

<210> SEQ ID NO 96
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 96
ctacacagaa tctgttagaa 20

<210> SEQ ID NO 97

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 97
taagctagag aatagatctc 20

<210> SEQ ID NO 98
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 98
tcaatacact taatgattta 20

<210> SEQ ID NO 99
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 99
caccgggagc cacgaaaaca gatcc 25

<210> SEQ ID NO 100
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 100
caccgcgaaa acagatccag ggaca 25

<210> SEQ ID NO 101
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 101
caccgagatc cagggacacg gtgct 25

<210> SEQ ID NO 102
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 102
caccggacac ggtgctagga cagtg 25

<210> SEQ ID NO 103
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 103
caccggaaaa tgacccaaca gcctc 25

<210> SEQ ID NO 104
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 104
caccggcctg gccggcctga ccact 25

<210> SEQ ID NO 105
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 105
caccgctgag cactgaaggc ctggc 25

<210> SEQ ID NO 106
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 106
caccgtggtt tccactgagc actga 25

<210> SEQ ID NO 107
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 107
caccggatag ccaggagtcc tttcg 25

<210> SEQ ID NO 108
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 108
caccggcgct tccagtgctc agact 25

<210> SEQ ID NO 109
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 109
caccgcagtg ctcagactag ggaag 25

<210> SEQ ID NO 110

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 110
caccggcccc tcctccttca gagcc 25

<210> SEQ ID NO 111
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 111
caccgtcctt cagagccagg agtcc 25

<210> SEQ ID NO 112
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 112
caccgtggtt tccgagcttg accct 25

<210> SEQ ID NO 113
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 113
caccgctgca gagtatctgc tgggg 25

<210> SEQ ID NO 114
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 114
caccgcgttc ctgcagagta tctgc 25

<210> SEQ ID NO 115
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 115
aaacggatct gttttcgtgg ctccc 25

<210> SEQ ID NO 116
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 116
aaactgtccc tggatctgtt ttcgc 25

<210> SEQ ID NO 117
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 117
aaacagcacc gtgtccctgg atctc 25

<210> SEQ ID NO 118
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 118
aaaccactgt cctagcaccg tgtcc 25

<210> SEQ ID NO 119
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 119
aaacgaggct gttgggtcat tttcc 25

<210> SEQ ID NO 120
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 120
aaacagtggt caggccggcc aggcc 25

<210> SEQ ID NO 121
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 121
aaacgccagg ccttcagtgc tcagc 25

<210> SEQ ID NO 122
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 122
aaactcagtg ctcagtggaa accac 25

<210> SEQ ID NO 123

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 123
aaaccgaaag gactcctggc tatcc 25

<210> SEQ ID NO 124
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 124
aaacagtctg agcactggaa gcgcc 25

<210> SEQ ID NO 125
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 125
aaaccttccc tagtctgagc actgc 25

<210> SEQ ID NO 126
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 126
aaacggctct gaaggaggag gggcc 25

<210> SEQ ID NO 127
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 127
aaacggactc ctggctctga aggac 25

<210> SEQ ID NO 128
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 128
aaacagggtc aagctcggaa accac 25

<210> SEQ ID NO 129
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 129
aaacccccag cagatactct gcagc 25

<210> SEQ ID NO 130
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 130
aaacgcagat actctgcagg aacgc 25

<210> SEQ ID NO 131
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 131
tcccctccca gaaagacctg 20

<210> SEQ ID NO 132
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 132
tgggctccaa gcaatcctgg 20

<210> SEQ ID NO 133
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 133
gtggctcagg aggtacctgg 20

<210> SEQ ID NO 134
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 134
gagccacgaa aacagatcca 20

<210> SEQ ID NO 135
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 135
aagtgaacgg ggaagggagg 20

<210> SEQ ID NO 136

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 136
gacaaaagcc gaagtccagg 20

<210> SEQ ID NO 137
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 137
gtggttgata aacccacgtg 20

<210> SEQ ID NO 138
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 138
tgggaacagc cacagcaggg 20

<210> SEQ ID NO 139
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 139
gcaggggaac ggggatgcag 20

<210> SEQ ID NO 140
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 140
gagatggtgg acgaggaagg 20

<210> SEQ ID NO 141
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 141
gagatggctc caggaaatgg 20

<210> SEQ ID NO 142
<211> LENGTH: 20
<212> TYPE: DNA
<213> ORGANISM: Artificial Sequence
<220> FEATURE:
<223> OTHER INFORMATION: Synthetic Sequence -continued

<400> SEQUENCE: 142
taaggaatct gcctaacagg 20

<210> SEQ ID NO 143
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 143
tcaggagact aggaaggagg 20

<210> SEQ ID NO 144
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 144
tataaggtgg tcccagctcg 20

<210> SEQ ID NO 145
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 145
ctggaagatg ccatgacagg 20

<210> SEQ ID NO 146
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 146
gcacagacta gagaggtaag 20

<210> SEQ ID NO 147
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 147
acagactaga gaggtaaggg 20

<210> SEQ ID NO 148
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 148
gagaggtgac ccgaatccac 20

<210> SEQ ID NO 149

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 149
gcacaggccc cagaaggaga 20

<210> SEQ ID NO 150
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 150
ccggagagga cccagacacg 20

<210> SEQ ID NO 151
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 151
gagaggaccc agacacgggg 20

<210> SEQ ID NO 152
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 152
gcaacacagc agagagcaag 20

<210> SEQ ID NO 153
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 153
gaagagggag tggaggaaga 20

<210> SEQ ID NO 154
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 154
aagacggaac ctgaaggagg 20

<210> SEQ ID NO 155
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 155
agaaagcggc acaggcccag 20

<210> SEQ ID NO 156
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 156
gggaaacagt gggccagagg 20

<210> SEQ ID NO 157
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 157
gtccggactc aggagagaga 20

<210> SEQ ID NO 158
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 158
ggcacagcaa gggcactcgg 20

<210> SEQ ID NO 159
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 159
gaagagggga agtcgaggga 20

<210> SEQ ID NO 160
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 160
gggaatggta aggaggcctg 20

<210> SEQ ID NO 161
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 161
gcagagtggt cagcacagag 20

<210> SEQ ID NO 162

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 162
gcacagagtg gctaagccca 20

<210> SEQ ID NO 163
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 163
gacggggtgt cagcataggg 20

<210> SEQ ID NO 164
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 164
gcccagggcc aggaacgacg 20

<210> SEQ ID NO 165
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 165
ggtggagtcc agcacggcgc 20

<210> SEQ ID NO 166
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 166
acaggccgcc aggaactcgg 20

<210> SEQ ID NO 167
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 167
actaggaagt gtgtagcacc 20

<210> SEQ ID NO 168
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 168
atgaatagca gactgccccg 20

<210> SEQ ID NO 169
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 169
acacccctaa aagcacagtg 20

<210> SEQ ID NO 170
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 170
caaggagttc cagcaggtgg 20

<210> SEQ ID NO 171
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 171
aaggagttcc agcaggtggg 20

<210> SEQ ID NO 172
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 172
tggaaagagg agggaagagg 20

<210> SEQ ID NO 173
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 173
tcgaattcct aactgccccg 20

<210> SEQ ID NO 174
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 174
gacctgccca gcacaccctg 20

<210> SEQ ID NO 175

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 175
ggagcagctg cggcagtggg 20

<210> SEQ ID NO 176
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 176
gggagggaga gcttggcagg 20

<210> SEQ ID NO 177
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 177
gttacgtggc caagaagcag 20

<210> SEQ ID NO 178
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 178
gctgaacaga gaagagctgg 20

<210> SEQ ID NO 179
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 179
tctgagggtg gagggactgg 20

<210> SEQ ID NO 180
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 180
ggagaggtga gggacttggg 20

<210> SEQ ID NO 181
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 181
gtgaaccagg cagacaacga 20

<210> SEQ ID NO 182
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 182
caggtacctc ctgagccacg 20

<210> SEQ ID NO 183
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 183
gggggagtag gggcatgcag 20

<210> SEQ ID NO 184
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 184
gcaaatggcc agcaagggtg 20

<210> SEQ ID NO 185
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 185
caccgaatcg agaagcgact cgaca 25

<210> SEQ ID NO 186
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 186
caccggtccc tgggcgttgc cctgc 25

<210> SEQ ID NO 187
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 187
caccgccctg ggcgttgccc tgcag 25

<210> SEQ ID NO 188

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 188
caccgccgtg ggaagataaa ctaat 25

<210> SEQ ID NO 189
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 189
caccgtcccc tgcagggcaa cgccc 25

<210> SEQ ID NO 190
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 190
caccggtcga gtcgcttctc gatta 25

<210> SEQ ID NO 191
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 191
caccgctgct gcctcccgtc ttgta 25

<210> SEQ ID NO 192
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 192
caccggagtg ccgcaatacc tttat 25

<210> SEQ ID NO 193
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 193
caccgacact ttggtggtgc agcaa 25

<210> SEQ ID NO 194
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 194
caccgtctca aatggtataa aactc 25

<210> SEQ ID NO 195
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 195
caccgaatcc cgcccataat cgaga 25

<210> SEQ ID NO 196
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 196
caccgtcccg cccataatcg agaag 25

<210> SEQ ID NO 197
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 197
caccgcccat aatcgagaag cgact 25

<210> SEQ ID NO 198
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 198
caccggagaa gcgactcgac atgga 25

<210> SEQ ID NO 199
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 199
caccggaagc gactcgacat ggagg 25

<210> SEQ ID NO 200
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 200
caccggcgac tcgacatgga ggcga 25

<210> SEQ ID NO 201

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 201
aaactgtcga gtcgcttctc gattc 25

<210> SEQ ID NO 202
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 202
aaacgcaggg caacgcccag ggacc 25

<210> SEQ ID NO 203
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 203
aaacctgcag ggcaacgccc agggc 25

<210> SEQ ID NO 204
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 204
aaacattagt ttatcttccc acggc 25

<210> SEQ ID NO 205
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 205
aaacgggcgt tgccctgcag gggac 25

<210> SEQ ID NO 206
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 206
aaactaatcg agaagcgact cgacc 25

<210> SEQ ID NO 207
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 207
aaactacaag acgggaggca gcagc 25

<210> SEQ ID NO 208
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 208
aaacataaag gtattgcggc actcc 25

<210> SEQ ID NO 209
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 209
aaacttgctg caccaccaaa gtgtc 25

<210> SEQ ID NO 210
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 210
aaacgagttt tataccattt gagac 25

<210> SEQ ID NO 211
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 211
aaactctcga ttatgggcgg gattc 25

<210> SEQ ID NO 212
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 212
aaaccttctc gattatgggc gggac 25

<210> SEQ ID NO 213
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 213
aaacagtcgc ttctcgatta tgggc 25

<210> SEQ ID NO 214

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 214
aaactccatg tcgagtcgct tctcc 25

<210> SEQ ID NO 215
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 215
aaaccctcca tgtcgagtcg cttcc 25

<210> SEQ ID NO 216
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 216
aaactcgcct ccatgtcgag tcgcc 25

<210> SEQ ID NO 217
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 217
caccgacagg gttaatgtga agtcc 25

<210> SEQ ID NO 218
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 218
caccgtcccc ctctacattt aaagt 25

<210> SEQ ID NO 219
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 219
caccgcattt aaagttggtt taagt 25

<210> SEQ ID NO 220
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 220
caccgttaga aaatataaag aataa 25

<210> SEQ ID NO 221
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 221
caccgtaaat gcttactggt ttgaa 25

<210> SEQ ID NO 222
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 222
caccgtcctg ggtccagaaa aagat 25

<210> SEQ ID NO 223
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 223
caccgttggg tggtgagcat ctgtg 25

<210> SEQ ID NO 224
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 224
caccgcgggg agagtggaga aaaag 25

<210> SEQ ID NO 225
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 225
caccggttaa aactctttag acaac 25

<210> SEQ ID NO 226
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 226
caccggaaaa tccccactaa gatcc 25

<210> SEQ ID NO 227

<211> LENGTH: 25
<212> TYPE: DNA
<213> ORGANISM: Artificial Sequence
<220> FEATURE:
<223> OTHER INFORMATION: Synthetic Sequence

<400> SEQUENCE: 227
aaacggactt cacattaacc ctgtc 25

<210> SEQ ID NO 228
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 228
aaacacttta aatgtagagg gggac 25

<210> SEQ ID NO 229
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 229
aaacacttaa accaacttta aatgc 25

<210> SEQ ID NO 230
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 230
aaacttattc tttatatttt ctaac 25

<210> SEQ ID NO 231
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 231
aaacttcaaa ccagtaagca tttac 25

<210> SEQ ID NO 232
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 232
aaacatcttt ttctggaccc aggac 25

<210> SEQ ID NO 233
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 233
aaaccacaga tgctcaccac ccaac                                    25

<210> SEQ ID NO 234
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 234
aaaccttttt ctccactctc cccgc                                    25

<210> SEQ ID NO 235
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 235
aaacgttgtc taaagagttt taacc                                    25

<210> SEQ ID NO 236
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 236
aaacggatct tagtggggat tttcc                                    25

<210> SEQ ID NO 237
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 237
agtagcagta atgaagctgg                                          20

<210> SEQ ID NO 238
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 238
atacccagac gagaaagctg                                          20

<210> SEQ ID NO 239
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 239
tacccagacg agaaagctga                                          20

<210> SEQ ID NO 240

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 240
ggtggtgagc atctgtgtgg 20

<210> SEQ ID NO 241
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 241
aaatgagaag aagaggcaca 20

<210> SEQ ID NO 242
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 242
cttgtggcct gggagagctg 20

<210> SEQ ID NO 243
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 243
gctgtagaag gagacagagc 20

<210> SEQ ID NO 244
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 244
gagctggttg ggaagacatg 20

<210> SEQ ID NO 245
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 245
ctggttggga agacatgggg 20

<210> SEQ ID NO 246
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 246
cgtgaggatg ggaaggaggg 20

<210> SEQ ID NO 247
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 247
atgcagagtc agcagaactg 20

<210> SEQ ID NO 248
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 248
aagacatcaa gcacagaagg 20

<210> SEQ ID NO 249
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 249
tcaagcacag aaggaggagg 20

<210> SEQ ID NO 250
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 250
aaccgtcaat aggcaaaggg 20

<210> SEQ ID NO 251
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 251
ccgtatttca gactgaatgg 20

<210> SEQ ID NO 252
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 252
gagaggacag gtgctacagg 20

<210> SEQ ID NO 253

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 253
aaccaaggaa gggcaggagg 20

<210> SEQ ID NO 254
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 254
gacctctggg tggagacaga 20

<210> SEQ ID NO 255
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 255
cagatgacca tgacaagcag 20

<210> SEQ ID NO 256
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 256
aacaccagtg agtagagcgg 20

<210> SEQ ID NO 257
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 257
aggaccttga agcacagaga 20

<210> SEQ ID NO 258
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 258
tacagaggca gactaaccca 20

<210> SEQ ID NO 259
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 259
acagaggcag actaacccag 20

<210> SEQ ID NO 260
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 260
taaatgacgt gctagacctg 20

<210> SEQ ID NO 261
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 261
agtaaccact caggacaggg 20

<210> SEQ ID NO 262
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 262
accacaaaac agaaacacca 20

<210> SEQ ID NO 263
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 263
gtttgaagac aagcctgagg 20

<210> SEQ ID NO 264
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 264
gctgaacccc aaaagacagg 20

<210> SEQ ID NO 265
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 265
gcagctgaga cacacaccag 20

<210> SEQ ID NO 266

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 266
aggacacccc aaagaagctg 20

<210> SEQ ID NO 267
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 267
ggacacccca aagaagctga 20

<210> SEQ ID NO 268
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 268
ccagtgcaat ggacagaaga 20

<210> SEQ ID NO 269
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 269
agaagaggga gcctgcaagt 20

<210> SEQ ID NO 270
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 270
gtgtttgggc cctagagcga 20

<210> SEQ ID NO 271
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 271
catgtgcctg gtgcaatgca 20

<210> SEQ ID NO 272
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 272
tacaaagagg aagataagtg 20

<210> SEQ ID NO 273
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 273
gtcacagaat acaccactag 20

<210> SEQ ID NO 274
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 274
gggttaccct ggacatggaa 20

<210> SEQ ID NO 275
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 275
catggaaggg tattcactcg 20

<210> SEQ ID NO 276
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 276
agagtggcct agacaggctg 20

<210> SEQ ID NO 277
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 277
catgctggac agctcggcag 20

<210> SEQ ID NO 278
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 278
agtgaaagaa gagaaaattc 20

<210> SEQ ID NO 279

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 279
tggtaagtct aagaaaccta 20

<210> SEQ ID NO 280
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 280
cccacagcct aaccacccta 20

<210> SEQ ID NO 281
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 281
aatatttcaa agccctaggg 20

<210> SEQ ID NO 282
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 282
gcactcggaa cagggtctgg 20

<210> SEQ ID NO 283
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 283
agataggagc tccaacagtg 20

<210> SEQ ID NO 284
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 284
aagttagagc agccaggaaa 20

<210> SEQ ID NO 285
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 285
tagagcagcc aggaaaggga 20

<210> SEQ ID NO 286
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 286
tgaataccct tccatgtcca 20

<210> SEQ ID NO 287
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 287
cctgcattgc accaggcaca 20

<210> SEQ ID NO 288
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 288
tctagggccc aaacacacct 20

<210> SEQ ID NO 289
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 289
tccctccatc tatcaaaagg 20

<210> SEQ ID NO 290
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 290
agccctgaga cagaagcagg 20

<210> SEQ ID NO 291
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 291
gccctgagac agaagcaggt 20

<210> SEQ ID NO 292

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 292
aggagatgca gtgatacgca 20

<210> SEQ ID NO 293
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 293
acaataccaa gggtatccgg 20

<210> SEQ ID NO 294
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 294
tgataaagaa aacaaagtga 20

<210> SEQ ID NO 295
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 295
aaagaaaaca aagtgaggga 20

<210> SEQ ID NO 296
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 296
gtggcaagtg gagaaattga 20

<210> SEQ ID NO 297
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 297
caagtggaga aattgaggga 20

<210> SEQ ID NO 298
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 298
gtggtgatga ttgcagctgg 20

<210> SEQ ID NO 299
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 299
ctatgtgcct gacacacagg 20

<210> SEQ ID NO 300
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 300
gggttggacc aggaaagagg 20

<210> SEQ ID NO 301
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 301
gatgcctgga aaaggaaaga 20

<210> SEQ ID NO 302
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 302
tagtatgcac ctgcaagagg 20

<210> SEQ ID NO 303
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 303
tatgcacctg caagaggcgg 20

<210> SEQ ID NO 304
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 304
aggggaagaa gagaagcaga 20

<210> SEQ ID NO 305

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 305
gctgaatcaa gagacaagcg 20

<210> SEQ ID NO 306
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 306
aagcaaataa atctcctggg 20

<210> SEQ ID NO 307
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 307
agatgagtgc tagagactgg 20

<210> SEQ ID NO 308
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 308
ctgatggttg agcacagcag 20

<210> SEQ ID NO 309
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 309
caaatggcca gcaagggtgg 20

<210> SEQ ID NO 310
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 310
gcagaacctg aggatatgga 20

<210> SEQ ID NO 311
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 311
aatacacaga atgaaaatag 20

<210> SEQ ID NO 312
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 312
ctggtgacta gaataggcag 20

<210> SEQ ID NO 313
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 313
tggtgactag aataggcagt 20

<210> SEQ ID NO 314
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 314
taaaagaatg tgaaaagatg 20

<210> SEQ ID NO 315
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 315
tcaggagttc aagaccaccc 20

<210> SEQ ID NO 316
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 316
tgtagtccca gttatgcagg 20

<210> SEQ ID NO 317
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 317
gggttcacac cacaaatgca 20

<210> SEQ ID NO 318

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 318
ggcaaatggc cagcaagggt 20

<210> SEQ ID NO 319
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 319
agaaaccaat cccaaagcaa 20

<210> SEQ ID NO 320
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 320
gccaaggaca ccaaaaccca 20

<210> SEQ ID NO 321
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 321
agtggtgata aggcaacagt 20

<210> SEQ ID NO 322
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 322
cctgagacag aagtattaag 20

<210> SEQ ID NO 323
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 323
aaggtcacac aatgaatagg 20

<210> SEQ ID NO 324
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 324
caccatacta gggaagaaga 20

<210> SEQ ID NO 325
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 325
aataccctgc ccttagtggg 20

<210> SEQ ID NO 326
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 326
ttagtggggg gtggagtggg 20

<210> SEQ ID NO 327
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 327
caataccctg cccttagtgg 20

<210> SEQ ID NO 328
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 328
gtggggggtg gagtgggggg 20

<210> SEQ ID NO 329
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 329
ggggggtgga gtggggggtg 20

<210> SEQ ID NO 330
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 330
ggggtggagt ggggggtggg 20

<210> SEQ ID NO 331

<211> LENGTH: 20
<212> TYPE: DNA
<213> ORGANISM: Artificial Sequence
<220> FEATURE:
<223> OTHER INFORMATION: Synthetic Sequence

<400> SEQUENCE: 331
gggtggagtg gggggtgggg 20

<210> SEQ ID NO 332
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 332
gggggtgggg aaagacatcg 20

<210> SEQ ID NO 333
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 333
gcagctgtga attctgatag 20

<210> SEQ ID NO 334
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 334
gagatcagag aaaccagatg 20

<210> SEQ ID NO 335
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 335
tctatactga ttgcagccag 20

<210> SEQ ID NO 336
<211> LENGTH: 1722
<212> TYPE: DNA
<213> ORGANISM: Artificial Sequence
<220> FEATURE:
<223> OTHER INFORMATION: Synthetic Sequence

<400> SEQUENCE: 336
atggcgcaac actcagatta ctccgacgat gaattttgtg ctgacaaact gtccaattat 60
tcatgcgata gcgacctcga aaacgcttcc acgtctgatg aagatagcag cgatgatgaa 120
gtaatggtga ggcctcgcac cctccgccgt cgccgcatca gctcttcgag ctctgattct 180
gaatccgata ttgagggtgg ccgcgaggag tggtcccacg tagacaatcc gccggtgctg 240
gaggacttcc taggccacca aggtctgaac actgacgcag taatcaacaa tatcgaagat 300
gcagttaaac tgtttatcgg tgacgatttc ttcgagtttc tggtggagga atctaaccgg 360

```
tactataacc agaatcgtaa taacttcaag ctctctaaaa agtctctgaa gtggaaggac    420
atcacccctc aggagatgaa aaagttcctc ggtctgatcg ttctgatggg ccaagttcgc    480
aaggatcgtc gtgacgacta ttggactacc gaaccgtgga cggaaactcc atactttggc    540
aagaccatga ctcgtgaccg tttccgtcag atctggaagg cctggcactt caataacaac    600
gctgacattg tcaacgagtc tgatcgtctg tgtaaggttc gccctgtgct ggattacttc    660
gttccaaaat tcattaacat ttacaaacca catcagcagc tgtccctgga tgagggcatc    720
gtgccgtggc gcggccgcct gttcttccgt gtctataatg ctggcaagat tgtgaagtac    780
ggtatcctgg ttcgcctgct gtgcgaaagc gacactggct acatctgtaa catggagatc    840
tactgcggcg agggcaaacg tctcctcgaa actatccaga ccgtcgtgtc tccatacacg    900
gattcctggt atcatattta catggataac tattataaca gcgtggctaa ctgtgaagct    960
ctgatgaaaa ataagttccg tatttgcggt actatccgta agaatcgtgg aattccgaaa   1020
gatttccaga ccatctccct gaaaaagggt gaaactaagt tcattcgcaa aaacgacatc   1080
ctcctgcaag tctggcagtc taaaaagcct gtatatctga tctcatctat tcacagcgct   1140
gaaatggaag aatctcagaa cattgatcgc acctccaaga aaaagatcgt caaaccgaat   1200
gcattgattg attacaacaa gcacatgaag ggcgttgatc gtgctgacca gtacctgtct   1260
tattactcta tcctgcgccg tactgtgaag tggactaaac gtctcgctat gtacatgatt   1320
aattgtgcgc tgttcaattc ttacgctgtg tataaaagcg tgcgtcagcg caaaatgggc   1380
tttaaaatgt tcctgaagca gacggctatt cactggctga ccgacgatat tccggaagat   1440
atggacattg tcccggatct ccagccggta ccgagcacca gcggtatgcg tgctaaacct   1500
ccgactagtg atccgccttg ccgtctgtct atggatatgc gtaagcatac cctgcaggca   1560
attgtgggct ctggcaaaaa gaaaaatatc ctgcgtcgtt gccgcgtatg ctctgtacac   1620
aaactgcgtt ctgagactcg ttatatgtgt aaattttgca atattccact ccacaagggt   1680
gcgtgcttcg agaagtacca tacgctgaag aactatctcg ag                      1722
```

<210> SEQ ID NO 337
<211> LENGTH: 1719
<212> TYPE: DNA
<213> ORGANISM: Artificial Sequence
<220> FEATURE:
<223> OTHER INFORMATION: Synthetic Sequence

<400> SEQUENCE: 337

```
atggcccagc acagcgacta ccccgacgac gagttcagag ccgataagct gagtaactac     60
agctgcgaca gcgacctgga aaacgccagc acatccgacg aggacagctc tgacgacgag    120
gtgatggtgc ggcccagaac cctgagacgg agaagaatca gcagctctag cagcgactct    180
gaatccgaca tcgagggcgg ccgggaagag tggagccacg tggacaaccc tcctgttctg    240
gaagattttc tgggccatca gggcctgaac accgacgccg tgatcaacaa catcgaggat    300
gccgtgaagc tgttcatagg agatgatttc tttgagttcc tggtcgagga atccaaccgc    360
tattacaacc agaatagaaa caacttcaag ctgagcaaga aaagcctgaa gtggaaggac    420
atcacccctc aggagatgaa aaagttcctg ggactgatcg ttctgatggg acaggtgcgg    480
aaggacagaa gggatgatta ctggacaacc gaaccttgga ccgagacccc ttactttggc    540
aagaccatga ccagagacag attcagacag atctggaaag cctggcactt caacaacaat    600
gctgatatcg tgaacgagtc tgatagactg tgtaaagtgc ggccagtgtt ggattacttc    660
```

-continued

```
gtgcctaagt tcatcaacat ctataagcct caccagcagc tgagcctgga tgaaggcatc     720

gtgccctggc ggggcagact gttcttcaga gtgtacaatg ctggcaagat cgtcaaatac     780

ggcatcctgg tgcgccttct gtgcgagagc gatacaggct acatctgtaa tatggaaatc     840

tactgcggcg agggcaaaag actgctggaa accatccaga ccgtcgtttc cccttatacc     900

gacagctggt accacatcta catggacaac tactacaatt ctgtggccaa ctgcgaggcc     960

ctgatgaaga acaagtttag aatctgcggc acaatcagaa aaaacagagg catccctaag    1020

gacttccaga ccatctctct gaagaagggc gaaaccaagt tcatcagaaa gaacgacatc    1080

ctgctccaag tgtggcagtc caagaaaccc gtgtacctga tcagcagcat ccatagcgcc    1140

gagatggaag aaagccagaa catcgacaga acaagcaaga agaagatcgt gaagcccaat    1200

gctctgatcg actacaacaa gcacatgaaa ggcgtggacc gggccgacca gtacctgtct    1260

tattactcta tcctgagaag aacagtgaaa tggaccaaga gactggccat gtacatgatc    1320

aattgcgccc tgttcaacag ctacgccgtg tacaagtccg tgcgacaaag aaaaatggga    1380

ttcaagatgt tcctgaagca gacagccatc cactggctga cagacgacat tcctgaggac    1440

atggacattg tgccagatct gcaacctgtg cccagcacct ctggtatgag agctaagcct    1500

cccaccagcg atcctccatg tagactgagc atggacatgc ggaagcacac cctgcaggcc    1560

atcgtcggca gcggcaagaa gaagaacatc cttagacggt gcagggtgtg cagcgtgcac    1620

aagctgcgga gcgagactcg gtacatgtgc aagttttgca acattcccct gcacaaggga    1680

gcctgcttcg agaagtacca caccctgaag aattactag                           1719
```

<210> SEQ ID NO 338
<211> LENGTH: 1719
<212> TYPE: DNA
<213> ORGANISM: Artificial Sequence
<220> FEATURE:
<223> OTHER INFORMATION: Synthetic Sequence

<400> SEQUENCE: 338

```
atggcccagc acagcgacta ccccgacgac gagttcagag ccgataagct gagtaactac      60

agctgcgaca gcgacctgga aaacgccagc acatccgacg aggacagctc tgacgacgag     120

gtgatggtgc ggcccagaac cctgagacgg agaagaatca gcagctctag cagcgactct     180

gaatccgaca tcgagggcgg ccgggaagag tggagccacg tggacaaccc tcctgttctg     240

gaagattttc tgggccatca gggcctgaac accgacgccg tgatcaacaa catcgaggat     300

gccgtgaagc tgttcatagg agatgatttc tttgagttcc tggtcgagga atccaaccgc     360

tattacaacc agaatagaaa caacttcaag ctgagcaaga aaagcctgaa gtggaaggac     420

atcacccctc aggagatgaa aaagttcctg ggactgatcg ttctgatggg acaggtgcgg     480

aaggacagaa gggatgatta ctggacaacc gaaccttgga ccgagacccc ttactttggc     540

aagaccatga ccagagacag attcagacag atctggaaag cctggcactt caacaacaat     600

gctgatatcg tgaacgagtc tgatagactg tgtaaagtgc ggccagtgtt ggattacttc     660

gtgcctaagt tcatcaacat ctataagcct caccagcagc tgagcctgga tgaaggcatc     720

gtgccctggc ggggcagact gttcttcaga gtgtacaatg ctggcaagat cgtcaaatac     780

ggcatcctgg tgcgccttct gtgcgagagc gatacaggct acatctgtaa tatggaaatc     840

tactgcggcg agggcaaaag actgctggaa accatccaga ccgtcgtttc cccttatacc     900

gacagctggt accacatcta catggacaac tactacaatt ctgtggccaa ctgcgaggcc     960

ctgatgaaga acaagtttag aatctgcggc acaatcagaa aaaacagagg catccctaag    1020
```

```
gacttccaga ccatctctct gaagaagggc gaaaccaagt tcatcagaaa gaacgacatc   1080
ctgctccaag tgtggcagtc caagaaaccc gtgtacctga tcagcagcat ccatagcgcc   1140
gagatggaag aaagccagaa catcgacaga acaagcaaga agaagatcgt gaagcccaat   1200
gctctgatcg actacaacaa gcacatgaaa ggcgtggacc gggccgacca gtacctgtct   1260
tattactcta tcctgagaag aacagtgaaa tggaccaaga gactggccat gtacatgatc   1320
aattgcgccc tgttcaacag ctacgccgtg tacaagtccg tgcgacaaag aaaaatggga   1380
ttcaagatgt tcctgaagca gacagccatc cactggctga cagacgacat tcctgaggac   1440
atggacattg tgccagatct gcaacctgtg cccagcacct ctggtatgag agctaagcct   1500
cccaccagcg atcctccatg tagactgagc atggacatgc ggaagcacac cctgcaggcc   1560
atcgtcggca gcggcaagaa gaagaacatc cttagacggt gcagggtgtg cagcgtgcac   1620
aagctgcgga gcgagactcg gtacatgtgc aagttttgca acattcccct gcacaaggga   1680
gcctgcttcg agaagtacca caccctgaag aattactag                          1719
```

<210> SEQ ID NO 339
<211> LENGTH: 1716
<212> TYPE: DNA
<213> ORGANISM: Artificial Sequence
<220> FEATURE:
<223> OTHER INFORMATION: Synthetic Sequence

<400> SEQUENCE: 339

```
atgtcgcagc attcagacta tactcatgat gagttttgtg cagacaagtt gtccaattat     60
tcttgtgata gcgatcttga aaatgcgagt acaagtgatg aagattctag tgatgatgaa    120
gtaatggtgc gtcccaggac attgaggcga cgaagaattt cgagctccag ctctgactca    180
gagtcagata tagaaggcgg gagagaagaa tggtcgcatg ttgataatcc accggtctta    240
gaagattttt tagggcatca aggattaaac acagatgctg ttataaataa tatagaagat    300
gccgtgaaat tatttatcgg agatgatttt tttgaatttc ttgtagagga gtcaaacagg    360
tattataatc aaaataggaa taatttcaaa ctttcaaaaa aaagcctaaa gtggaaagat    420
ataacccctc aagagatgaa gaagttttta gggttaattg ttctcatggg acaggtgcgc    480
aaagatagaa gagatgacta ttggaccacg gagccatgga cggagacgcc atattttggt    540
aaaacgatga cgagagacag gttccgacag atatggaaag cttggcactt caataataat    600
gcggatatcg taaatgaatc agatagactt tgcaaagtga gaccagtact agattatttt    660
gtgcctaaat ttataaatat ttacaaacct catcagcaat tatcactaga tgaagggatc    720
gtaccttgga ggggaagatt attctttagg gtatataatg ctggcaagat cgttaaatat    780
ggaatattgg ttcgtttgtt gtgcgaaagt gatacaggat atatctgtaa catggaaatt    840
tattgcggcg aaggaaagcg attattggaa acgatacaaa cagtagtgtc tccatacact    900
gattcgtggt accatatata tatggacaat tattataata gcgtcgcaaa ttgtgaagca    960
cttatgaaaa acaaattcag aatatgtgga acaatccgga aaaatcgagg tatacctaaa   1020
gattttcaaa caatttcttt gaaaaaaggt gaaacaaaat ttataaggaa aaatgatata   1080
ttgttacaag tgtggcaatc aaaaaagcct gtatacctga tttcttcgat tcattctgcg   1140
gagatggaag aaagtcagaa tattgacaga acatcaaaaa agaaaattgt caaaccgaat   1200
gcactcattg actacaataa acatatgaaa ggtgttgacc gggccgacca ataccttca    1260
tattattcga tattgcggag gacggtcaaa tggacaaaaa ggttggcaat gtatatgata   1320
```

-continued aattgcgcat tatttaattc ttatgcagtt tacaaatcag tgaggcaaag aaaaatgggt 1380
tttaaaatgt ttttgaaaca aacagctatc cactggttga cggatgatat tccagaggac 1440
atggacattg ttccagacct tcaaccagta ccgtctactt ctggaatgcg ggctaaacca 1500
cctacatctg atccaccatg caggctatcg atggacatga gaaagcatac gttacaggca 1560
attgtcggaa gtggaaaaaa gaaaaacatt ttgagaaggt gtcgcgtatg ttccgttcat 1620
aaattgcgca gtgagacacg ctacatgtgc aaattttgca atatacctct acataaaggg 1680
gcgtgttttg aaaaatatca tacgctaaaa aactat 1716

<210> SEQ ID NO 340
<211> LENGTH: 572
<212> TYPE: PRT
<213> ORGANISM: Artificial Sequence
<220> FEATURE:
<223> OTHER INFORMATION: Synthetic Sequence

<400> SEQUENCE: 340

Met Ala Gln His Ser Asp Tyr Pro Asp Asp Glu Phe Arg Ala Asp Lys
1 5 10 15

Leu Ser Asn Tyr Ser Cys Asp Ser Asp Leu Glu Asn Ala Ser Thr Ser
20 25 30

Asp Glu Asp Ser Ser Asp Asp Glu Val Met Val Arg Pro Arg Thr Leu
35 40 45

Arg Arg Arg Arg Ile Ser Ser Ser Ser Ser Asp Ser Glu Ser Asp Ile
50 55 60

Glu Gly Gly Arg Glu Glu Trp Ser His Val Asp Asn Pro Pro Val Leu
65 70 75 80

Glu Asp Phe Leu Gly His Gln Gly Leu Asn Thr Asp Ala Val Ile Asn
85 90 95

Asn Ile Glu Asp Ala Val Lys Leu Phe Ile Gly Asp Asp Phe Phe Glu
100 105 110

Phe Leu Val Glu Glu Ser Asn Arg Tyr Tyr Asn Gln Lys Arg Asn Asn
115 120 125

Phe Lys Leu Ser Lys Lys Ser Leu Lys Trp Lys Asp Ile Thr Pro Gln
130 135 140

Glu Met Lys Lys Phe Leu Gly Leu Ile Val Leu Met Gly Gln Val Arg
145 150 155 160

Lys Asp Arg Arg Asp Asp Tyr Trp Thr Thr Glu Pro Trp Thr Glu Thr
165 170 175

Pro Tyr Phe Gly Lys Thr Met Thr Arg Asp Arg Phe Arg Gln Ile Trp
180 185 190

Lys Ala Trp His Phe Asn Asn Asn Ala Asp Ile Val Asn Glu Ser Asp
195 200 205

Arg Leu Cys Lys Val Arg Pro Val Leu Asp Tyr Phe Val Pro Lys Phe
210 215 220

Ile Asn Ile Tyr Lys Pro His Gln Gln Leu Ser Leu Asp Glu Gly Ile
225 230 235 240

Val Pro Trp Arg Gly Arg Leu Phe Phe Arg Val Tyr Asn Ala Gly Lys
245 250 255

Ile Val Lys Tyr Gly Ile Leu Val Arg Leu Leu Cys Glu Ser Asp Thr
260 265 270

Gly Tyr Ile Cys Asn Met Glu Ile Tyr Cys Gly Glu Gly Lys Arg Leu
275 280 285

Leu Glu Thr Ile Gln Thr Val Val Ser Pro Tyr Thr Asp Ser Trp Tyr
290 295 300

His Ile Tyr Met Asp Asn Tyr Tyr Asn Ser Val Ala Asn Cys Glu Ala
305 310 315 320

Leu Met Lys Asn Lys Phe Arg Ile Cys Gly Thr Ile Arg Lys Asn Arg
325 330 335

Gly Ile Pro Lys Asp Phe Gln Thr Ile Ser Leu Lys Lys Gly Glu Thr
340 345 350

Lys Phe Ile Arg Lys Asn Asp Ile Leu Leu Gln Val Trp Gln Ser Lys
355 360 365

Lys Pro Val Tyr Leu Ile Ser Ser Ile His Ser Ala Glu Met Glu Glu
370 375 380

Ser Gln Asn Ile Asp Arg Thr Ser Lys Lys Lys Ile Val Lys Pro Asn
385 390 395 400

Ala Leu Ile Asp Tyr Asn Lys His Met Lys Gly Val Asp Arg Ala Asp
405 410 415

Gln Tyr Leu Ser Tyr Tyr Ser Ile Leu Arg Arg Thr Val Lys Trp Thr
420 425 430

Lys Arg Leu Ala Met Tyr Met Ile Asn Cys Ala Leu Phe Asn Ser Tyr
435 440 445

Ala Val Tyr Lys Ser Val Arg Gln Arg Lys Met Gly Phe Lys Met Phe
450 455 460

Leu Lys Gln Thr Ala Ile His Trp Leu Thr Asp Asp Ile Pro Glu Asp
465 470 475 480

Met Asp Ile Val Pro Asp Leu Gln Pro Val Pro Ser Thr Ser Gly Met
485 490 495

Arg Ala Lys Pro Pro Thr Ser Asp Pro Pro Cys Arg Leu Ser Met Asp
500 505 510

Met Arg Lys His Thr Leu Gln Ala Ile Val Gly Ser Gly Lys Lys Lys
515 520 525

Asn Ile Leu Arg Arg Cys Arg Val Cys Ser Val His Lys Leu Arg Ser
530 535 540

Glu Thr Arg Tyr Met Cys Lys Phe Cys Asn Ile Pro Leu His Lys Gly
545 550 555 560

Ala Cys Phe Glu Lys Tyr His Thr Leu Lys Asn Tyr
565 570

<210> SEQ ID NO 341
<211> LENGTH: 574
<212> TYPE: PRT
<213> ORGANISM: Artificial Sequence
<220> FEATURE:
<223> OTHER INFORMATION: Synthetic Sequence

<400> SEQUENCE: 341

Met Ala Gln His Ser Asp Tyr Ser Asp Asp Glu Phe Cys Ala Asp Lys
1 5 10 15

Leu Ser Asn Tyr Ser Cys Asp Ser Asp Leu Glu Asn Ala Ser Thr Ser
20 25 30

Asp Glu Asp Ser Ser Asp Asp Glu Val Met Val Arg Pro Arg Thr Leu
35 40 45

Arg Arg Arg Arg Ile Ser Ser Ser Ser Ser Asp Ser Glu Ser Asp Ile
50 55 60

Glu Gly Gly Arg Glu Glu Trp Ser His Val Asp Asn Pro Pro Val Leu
65 70 75 80

```
Glu Asp Phe Leu Gly His Gln Gly Leu Asn Thr Asp Ala Val Ile Asn
                85                  90                  95

Asn Ile Glu Asp Ala Val Lys Leu Phe Ile Gly Asp Asp Phe Phe Glu
            100                 105                 110

Phe Leu Val Glu Glu Ser Asn Arg Tyr Tyr Asn Gln Asn Arg Asn Asn
        115                 120                 125

Phe Lys Leu Ser Lys Lys Ser Leu Lys Trp Lys Asp Ile Thr Pro Gln
    130                 135                 140

Glu Met Lys Lys Phe Leu Gly Leu Ile Val Leu Met Gly Gln Val Arg
145                 150                 155                 160

Lys Asp Arg Arg Asp Asp Tyr Trp Thr Thr Glu Pro Trp Thr Glu Thr
                165                 170                 175

Pro Tyr Phe Gly Lys Thr Met Thr Arg Asp Arg Phe Arg Gln Ile Trp
            180                 185                 190

Lys Ala Trp His Phe Asn Asn Asn Ala Asp Ile Val Asn Glu Ser Asp
        195                 200                 205

Arg Leu Cys Lys Val Arg Pro Val Leu Asp Tyr Phe Val Pro Lys Phe
    210                 215                 220

Ile Asn Ile Tyr Lys Pro His Gln Gln Leu Ser Leu Asp Glu Gly Ile
225                 230                 235                 240

Val Pro Trp Arg Gly Arg Leu Phe Phe Arg Val Tyr Asn Ala Gly Lys
                245                 250                 255

Ile Val Lys Tyr Gly Ile Leu Val Arg Leu Leu Cys Glu Ser Asp Thr
            260                 265                 270

Gly Tyr Ile Cys Asn Met Glu Ile Tyr Cys Gly Glu Gly Lys Arg Leu
        275                 280                 285

Leu Glu Thr Ile Gln Thr Val Val Ser Pro Tyr Thr Asp Ser Trp Tyr
    290                 295                 300

His Ile Tyr Met Asp Asn Tyr Tyr Asn Ser Val Ala Asn Cys Glu Ala
305                 310                 315                 320

Leu Met Lys Asn Lys Phe Arg Ile Cys Gly Thr Ile Arg Lys Asn Arg
                325                 330                 335

Gly Ile Pro Lys Asp Phe Gln Thr Ile Ser Leu Lys Lys Gly Glu Thr
            340                 345                 350

Lys Phe Ile Arg Lys Asn Asp Ile Leu Leu Gln Val Trp Gln Ser Lys
        355                 360                 365

Lys Pro Val Tyr Leu Ile Ser Ser Ile His Ser Ala Glu Met Glu Glu
    370                 375                 380

Ser Gln Asn Ile Asp Arg Thr Ser Lys Lys Lys Ile Val Lys Pro Asn
385                 390                 395                 400

Ala Leu Ile Asp Tyr Asn Lys His Met Lys Gly Val Asp Arg Ala Asp
                405                 410                 415

Gln Tyr Leu Ser Tyr Tyr Ser Ile Leu Arg Arg Thr Val Lys Trp Thr
            420                 425                 430

Lys Arg Leu Ala Met Tyr Met Ile Asn Cys Ala Leu Phe Asn Ser Tyr
        435                 440                 445

Ala Val Tyr Lys Ser Val Arg Gln Arg Lys Met Gly Phe Lys Met Phe
    450                 455                 460

Leu Lys Gln Thr Ala Ile His Trp Leu Thr Asp Asp Ile Pro Glu Asp
465                 470                 475                 480

Met Asp Ile Val Pro Asp Leu Gln Pro Val Pro Ser Thr Ser Gly Met
                485                 490                 495
```

```
Arg Ala Lys Pro Pro Thr Ser Asp Pro Pro Cys Arg Leu Ser Met Asp
            500                 505                 510

Met Arg Lys His Thr Leu Gln Ala Ile Val Gly Ser Gly Lys Lys Lys
        515                 520                 525

Asn Ile Leu Arg Arg Cys Arg Val Cys Ser Val His Lys Leu Arg Ser
    530                 535                 540

Glu Thr Arg Tyr Met Cys Lys Phe Cys Asn Ile Pro Leu His Lys Gly
545                 550                 555                 560

Ala Cys Phe Glu Lys Tyr His Thr Leu Lys Asn Tyr Leu Glu
                565                 570


<210> SEQ ID NO 342

<400> SEQUENCE: 342

000


<210> SEQ ID NO 343
<211> LENGTH: 507
<212> TYPE: PRT
<213> ORGANISM: Artificial Sequence
<220> FEATURE:
<223> OTHER INFORMATION: Synthetic Sequence

<400> SEQUENCE: 343

Met Ser Gln His Ser Asp Tyr Ser Asp Asp Glu Phe Cys Ala Asp Lys
1               5                   10                  15

Leu Ser Asn Tyr Ser Cys Asp Ser Asp Leu Glu Asn Ala Ser Thr Ser
            20                  25                  30

Asp Glu Asp Ser Ser Asp Asp Glu Val Met Val Arg Pro Arg Thr Leu
        35                  40                  45

Arg Arg Arg Arg Ile Ser Ser Ser Ser Ser Asp Ser Glu Ser Asp Ile
    50                  55                  60

Glu Gly Gly Arg Glu Glu Trp Ser His Val Asp Asn Pro Pro Val Leu
65                  70                  75                  80

Glu Asp Phe Leu Gly His Gln Gly Leu Asn Thr Asp Ala Val Ile Asn
                85                  90                  95

Asn Ile Glu Asp Ala Val Lys Leu Phe Ile Gly Asp Asp Phe Phe Glu
            100                 105                 110

Phe Leu Val Glu Glu Ser Asn Arg Lys Thr Met Thr Arg Asp Arg Phe
        115                 120                 125

Arg Gln Ile Trp Lys Ala Trp His Phe Asn Asn Asn Ala Asp Ile Val
    130                 135                 140

Asn Glu Ser Asp Arg Leu Cys Lys Val Arg Pro Val Leu Asp Tyr Phe
145                 150                 155                 160

Val Pro Lys Phe Ile Asn Ile Tyr Lys Pro His Gln Gln Leu Ser Leu
                165                 170                 175

Asp Glu Gly Ile Val Pro Trp Arg Gly Arg Leu Phe Phe Arg Val Tyr
            180                 185                 190

Asn Ala Gly Lys Ile Val Lys Tyr Gly Ile Leu Val Arg Leu Leu Cys
        195                 200                 205

Glu Ser Asp Thr Gly Tyr Ile Cys Asn Met Glu Ile Tyr Cys Gly Glu
    210                 215                 220

Gly Lys Arg Leu Leu Glu Thr Ile Gln Thr Trp Ser Pro Tyr Thr Asp
225                 230                 235                 240

Ser Trp Tyr His Ile Tyr Met Asp Asn Tyr Tyr Asn Ser Val Ala Asn
                245                 250                 255
```

-continued

```
Cys Glu Ala Leu Met Lys Asn Lys Phe Arg Ile Cys Gly Thr Ile Arg
            260                 265                 270

Lys Asn Arg Gly Ile Pro Lys Asp Phe Gln Thr Ile Ser Leu Lys Lys
        275                 280                 285

Gly Glu Thr Lys Phe Ile Arg Lys Asn Asp Ile Leu Leu Gln Val Trp
    290                 295                 300

Gln Ser Lys Lys Pro Val Tyr Leu Ile Ser Ser His Ser Ala Glu Met
305                 310                 315                 320

Glu Glu Ser Gln Asn Ile Asp Arg Thr Ser Lys Lys Lys Ile Val Lys
                325                 330                 335

Pro Asn Ala Leu Ile Asp Tyr Asn Lys His Met Lys Gly Val Asp Arg
            340                 345                 350

Ala Asp Gln Tyr Leu Ser Tyr Tyr Ser Ile Leu Arg Arg Trp Lys Trp
        355                 360                 365

Thr Lys Arg Leu Ala Met Tyr Met Ile Asn Cys Ala Leu Phe Asn Ser
    370                 375                 380

Tyr Ala Val Tyr Lys Ser Val Arg Gln Arg Lys Met Gly Phe Lys Met
385                 390                 395                 400

Phe Leu Lys Gln Thr Ala His Trp Leu Thr Asp Asp Ile Pro Glu Asp
                405                 410                 415

Met Asp Ile Val Pro Asp Leu Gln Pro Val Pro Ser Thr Ser Gly Met
            420                 425                 430

Arg Ala Lys Pro Pro Thr Ser Asp Pro Pro Cys Arg Leu Ser Met Asp
        435                 440                 445

Met Arg Lys His Thr Leu Gln Ala Ile Val Gly Ser Gly Lys Lys Lys
    450                 455                 460

Asn Ile Leu Arg Arg Cys Arg Val Cys Ser Val His Lys Leu Arg Ser
465                 470                 475                 480

Glu Thr Arg Tyr Met Cys Lys Phe Cys Asn Ile Pro Leu His Lys Gly
                485                 490                 495

Ala Cys Phe Glu Lys Tyr His Thr Leu Lys Asn
            500                 505
```

<210> SEQ ID NO 344
<211> LENGTH: 153
<212> TYPE: DNA
<213> ORGANISM: Artificial Sequence
<220> FEATURE:
<223> OTHER INFORMATION: Synthetic Sequence

<400> SEQUENCE: 344

```
cacttggatt gcgggaaacg agttaagtcg gctcgcgtga attgcgcgta ctccgcggga      60

gccgtcttaa ctcggttcat atagatttgc ggtggagtgc gggaaacgtg taaactcggg     120

ccgattgtaa ctgcgtatta ccaaatattt gtt                                  153
```

<210> SEQ ID NO 345
<211> LENGTH: 158
<212> TYPE: DNA
<213> ORGANISM: Artificial Sequence
<220> FEATURE:
<223> OTHER INFORMATION: Synthetic Sequence

<400> SEQUENCE: 345
cacttgggtt gcgggaaacg agttaagtcg gctcgcgtga attgcgcgta ctccgcggga 60
gccgtcttaa actcggttca tatagatttg cggtggagtg cgggaaacgt tgtaaactcg 120
ggccgattgt aactgcgtat taccaaatat ttcatttc 158

<210> SEQ ID NO 346
<211> LENGTH: 181
<212> TYPE: DNA
<213> ORGANISM: Artificial Sequence
<220> FEATURE:
<223> OTHER INFORMATION: Synthetic Sequence

<400> SEQUENCE: 346
aaatgtctgt gattgaataa attttcattt tttacacaag aaaccgaaaa tttcatttca 60
atcgaaccca tacttcaaaa gatataggca ttttaaacta actctgattt tgcgcgggaa 120
acctaaataa ttgcccgcgc catcttatat tttggcggga aattcacccg acaccgtagt 180
g 181

<210> SEQ ID NO 347
<211> LENGTH: 136
<212> TYPE: DNA
<213> ORGANISM: Artificial Sequence
<220> FEATURE:
<223> OTHER INFORMATION: Synthetic Sequence

<400> SEQUENCE: 347
aaacgttgta aactcgggcc gattgtaact gcgtattacc aaatatttca tttcaatcga 60
acccatactt aaaagatata ggcattttaa cgcgccatct tatattttgg cgggaaattc 120
acccgacacc gtagtg 136

<210> SEQ ID NO 348
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(6)
<223> OTHER INFORMATION: Xaa can be any naturally occurring amino acid;
SEQ ID NO: 348 corresponds to the sequence K(K/R)X(K/R)

<400> SEQUENCE: 348

Lys Lys Arg Xaa Lys Arg
1 5

<210> SEQ ID NO 349
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(7)
<223> OTHER INFORMATION: Xaa can be any naturally occurring amino acid;
SEQ ID NO: 349 corresponds to the sequence (K/R)(K/R)X10-
12(K/R)3/5

<400> SEQUENCE: 349

Lys Arg Lys Arg Xaa Lys Arg
1 5

<210> SEQ ID NO 350
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 350

Pro Ala Ala Lys Arg Val Lys Leu Asp
1 5

<210> SEQ ID NO 351
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 351

Lys Arg Pro Ala Ala Thr Lys Lys Ala Gly Gln Ala Lys Lys Lys Lys
1 5 10 15

<210> SEQ ID NO 352
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 352

Pro Lys Lys Lys Arg Lys Val
1 5

<210> SEQ ID NO 353
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 353

Asp Pro Lys Lys Lys Arg Lys Val Asp Pro Lys Lys Lys Arg Lys Val
1 5 10 15

Asp Pro Lys Lys Lys Arg Lys Val
20

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423
<211> LENGTH: 333
<212> TYPE: DNA
<213> ORGANISM: Artificial Sequence
<220> FEATURE:
<223> OTHER INFORMATION: Synthetic Sequence

<400> SEQUENCE: 423
ggcggatctg gcggtagtgc tgagtattgt ctgagttacg aaacggaaat actcacggtt 60
gagtatgggc ttcttccaat tggcaaaatc gttgaaaagc gcatagagtg tacggtgtat 120
tccgtcgata acaacggtaa tatctacacc cagccggtag ctcagtggca cgaccgaggc 180
gaacaggaag tgttcgagta ttgcttggaa gatggctccc ttatccgcgc cactaaagac 240
cataagttta tgacggttga cgggcagatg ctgcctatag acgaaatatt tgagagagag 300
ctggacttga tgagagtcga taatctgcca aat 333

<210> SEQ ID NO 424
<211> LENGTH: 180
<212> TYPE: DNA
<213> ORGANISM: Artificial Sequence
<220> FEATURE:
<223> OTHER INFORMATION: Synthetic Sequence

<400> SEQUENCE: 424
ggcggatctg gcggtagtgg gggttccgga tccataaaga tagctactag gaaatatctt 60
ggcaaacaaa acgtctatga cataggagtt gagcgagatc acaattttgc tttgaagaat 120
gggttcatcg cgtctaattg cttcaacgct agcggcgggt caggaggctc tggtggaagc 180

<210> SEQ ID NO 425
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 425
aatcgagaag cgactcgaca 20

<210> SEQ ID NO 426
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 426
tgccctgcag gggagtgagc 20

<210> SEQ ID NO 427
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 427
gaagcgactc gacatggagg 20

<210> SEQ ID NO 428
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 428
cctgcagggg agtgagcagc 20

<210> SEQ ID NO 429
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 429

Leu Thr Pro Glu Gln Val Val Ala Ile Ala Ser Asn Gly Gly Gly Lys
1 5 10 15

Gln Ala Leu Glu Thr Val Gln Arg Leu Leu Pro Val Leu Cys Gln Ala
20 25 30

His Gly

<210> SEQ ID NO 430
<211> LENGTH: 157
<212> TYPE: DNA
<213> ORGANISM: Artificial Sequence
<220> FEATURE:
<223> OTHER INFORMATION: Synthetic Sequence

<400> SEQUENCE: 430
ttaacacttg gattgcggga aacgagttaa gtcggctcgc gtgaattgcg cgtactccgc 60
gggagccgtc ttaactcggt tcatatagat ttgcggtgga gtgcgggaaa cgtgtaaact 120
cgggccgatt gtaactgcgt attaccaaat atttgtt 157

<210> SEQ ID NO 431
<211> LENGTH: 157
<212> TYPE: DNA
<213> ORGANISM: Artificial Sequence
<220> FEATURE:
<223> OTHER INFORMATION: Synthetic Sequence

<400> SEQUENCE: 431
ttaacacttg gattgcggga aacgagttaa gtcggctcgc gtgaattgcg cgtactccgc 60
gggagccgtc ttaactcggt tcatatagat ttgcggtgga gtgcgggaaa cgtgtaaact 120
cgggccgatt gtaactgcgt attaccaaat atttgtt 157

<210> SEQ ID NO 432
<211> LENGTH: 212
<212> TYPE: DNA
<213> ORGANISM: Artificial Sequence
<220> FEATURE:
<223> OTHER INFORMATION: Synthetic Sequence

<400> SEQUENCE: 432

```
aattatttat gtactgaata gataaaaaaa tgtctgtgat tgaataaatt ttcatttttt     60

acacaagaaa ccgaaaattt catttcaatc gaacccatac ttcaaaagat ataggcattt    120

taaactaact ctgattttgc gcgggaaacc taaataattg cccgcgccat cttatatttt    180

ggcgggaaat tcacccgaca ccgtagtgtt aa                                  212
```

<210> SEQ ID NO 433
<211> LENGTH: 212
<212> TYPE: DNA
<213> ORGANISM: Artificial Sequence
<220> FEATURE:
<223> OTHER INFORMATION: Synthetic Sequence

<400> SEQUENCE: 433

```
aattatttat gtactgaata gataaaaaaa tgtctgtgat tgaataaatt ttcatttttt     60

acacaagaaa ccgaaaattt catttcaatc gaacccatac ttcaaaagat ataggcattt    120

taaactaact ctgattttgc gcgggaaacc taaataattg cccgcgccat cttatatttt    180

ggcgggaaat tcacccgaca ccgtagtgtt aa                                  212
```

<210> SEQ ID NO 434
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 434

```
tcccgcaatc caagtgttaa gcctaggcaa aag                                  33
```

<210> SEQ ID NO 435
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(5)
<220> FEATURE:
<221> NAME/KEY: MISC_FEATURE
<222> LOCATION: (1)..(5)
<223> OTHER INFORMATION: This sequence refers to (Gly4Ser)n in the
      Specification, where n is from about 1 to about 12. For example,
      see the Specification at page 7 and lines 22-26.
<220> FEATURE:
<221> NAME/KEY: misc_feature
<222> LOCATION: (6)..(6)
<223> OTHER INFORMATION: Xaa can be any naturally occurring amino acid

<400> SEQUENCE: 435

```
Gly Gly Gly Gly Ser Xaa
1               5
```

TRANSPOSITION-BASED THERAPIES

PRIORITY

This Application is a continuation of International Application No. PCT/US21/30729, filed May 4, 2021, which claims the benefit of, and priority to, US Application Nos. 63/175,345, filed Apr. 15, 2021, 63/058,200, filed Jul. 29, 2020, 63/027,561, filed May 20, 2020 and 63/019,709, filed May 4, 2020, each of which is hereby incorporated by reference in its entirety.

The present invention relates, in part, to a dual system using enzymes capable of transposition (e.g., engineered transposases and/or chimeric transposases) and transposons for targeting human genomic safe harbor sites (GSHS).

DESCRIPTION OF THE TEXT FILE SUBMITTED ELECTRONICALLY

This application contains a Sequence Listing in ASCII format submitted electronically herewith via EFS-Web. The ASCII copy, created on Oct. 17, 2022, is named SAL-003C1_ST25.txt and is 161,098 bytes in size. The Sequence Listing is incorporated herein by reference in its entirety.

BACKGROUND

Human gene therapy is a promising approach that delivers genes for treating and mitigating various diseases and conditions, including inherited and acquired diseases. Gene therapy involves replacing or complementing a mutated gene (which causes a disease) with a healthy copy of the gene, inactivating or silencing a mutated gene that is functioning improperly (or any other gene), or introducing a new gene into chromosomes. The ability to safely and efficiently integrate genes into a host genome is essential for successful gene therapy in humans.

Currently, the most commonly used vectors for permanent or transient transfer of genes in gene therapy trials are virus-based. Although it is possible to achieve stable genomic integration with high-efficiency using viral vectors, multiple studies have shown serious disadvantages and safety concerns. Thus, adenoviruses and adeno-associated viruses (AAV) have been shown to evoke host human responses that limit administration or re-administration, while retroviruses/lentiviruses preferentially integrate transgenes into euchromatin thereby increasing the risk of insertional mutagenesis or oncogenesis. Viral systems are also limited in cargo size, restricting the size and number of transgenes and their regulatory elements. Viral vector-host interaction can include immunogenicity, and integration of a viral vector DNA in a host genome may have genotoxic effects. Also, because the AAV genome mainly persists in an episomal form in the nucleus of the infected cells, it can be lost in conditions of cell proliferation (such as, e.g. liver growth or other organ growth), limiting therapeutic efficacy. Accordingly, limitations of viral vectors such as pathogenicity, expensive production, and systemic instability have proved to be major obstacles to the use of viral-based systems. In fact, re-administration of viral-based vectors can promote immune responses that can result in life threatening systemic effects and limit gene-transfer efficacy. See Kay et al. *Proc Natl Acad Sci* USA 1997; 94:4686-91; Hernandez et al., *J Virol* 1999; 73:8549-58.

Non-viral vectors (i.e., lipid-based, polymer-based, lipid-polymer based, and poly-lysine) are synthetic tools for encapsulating transgenic DNA or RNA until it reaches the cellular target. Compared to viral vectors, non-viral vectors are generally safer to prepare, and the risk of pathogenic and immunologic complications is diminished.

Non-viral vectors have been designed by modifying the surface of a non-viral vector for targeted therapy. See, e.g., Lestini et al., *J Control Release* 2002; 78:235-47.

Nucleases are also being evaluated for use in non-viral human gene therapy. Clustered regularly interspaced short palindromic repeats (CRISPR)/CRISPR associated (Cas9) and transcription activator-like effector (TALE) nuclease (TALEN) systems induce double-stranded DNA breaks (DSBs). The DSBs enhance homologous recombination to insert transgenes at specific sequences but off-target DNA cleavages at unknown remote sites cause inadvertent mutations that require complex genotoxicity screens for detection. The CRISPR system uses Cas9 complexed with a user-defined guide RNA (gRNA) to recognize and cut complementary sequences. TALEN and CRISPR both use host homology-directed repair to introduce a co-delivered donor template at the desired sequence. The TALEN and CRISPR approaches demonstrate efficient gene transfer, but concerns about their cyto- and genotoxic effects remain significant obstacles for clinical applications. Furthermore, gene addition using homology-directed repair requires replication, thus limiting nuclease technology to dividing tissues (i.e. not effective in non-diving tissue such as the central nervous system). Other gene editing techniques, such as prime editing and base pair editing, are limited to correcting base pairs or small nucleotide stretches. These features limit the in vivo and ex vivo application of this technology to diseases with a single common pathogenic nucleotide variant. However, most genetic disorders have hundreds or even thousands of pathogenic nucleotide variants in one or more genes.

A recombinase recognizes and binds specific sequences at the ends of a transposon, mediates synaptic interactions between the ends to bring them together, interacts with the target DNA, and executes the DNA breakage and joining reactions that underlie recombination. An integrase is a recombinase enzyme that is capable of integrating DNA (e.g., of a virus), into another piece of DNA, usually the host chromosome.

DNA transposons are mobile elements that use a "cut-and-paste" mechanism. DNA is excised by double strand cleavage from the donor molecule and integrated into the acceptor molecule. Transposons move from one position on DNA to a second position on DNA in the presence of a transposase, an enzyme that binds to the end of a transposon and catalyzes its movement to a specific genomic location in a host.

A main concern in transposase-based gene therapy is insertional mutagenesis due to random integration, albeit mostly at known sequences (e.g. TTAA (SEQ ID NO: 1) sequences), near or within loci that activate oncogenes, interrupt tumor-suppressor genes, or disrupt the transcription of normal genes. Thus, while non-viral, transposon gene therapy approaches have great promise for treating individuals with genetic disorders, the challenge is to reduce the risk of random insertion.

Accordingly, there is a clinical need to improve the safety of enzymes capable of transposition, such as, e.g., transposases, to reduce the risk of insertional mutagenesis and oncogenesis.

SUMMARY OF THE INVENTION

Therefore, the present invention provides, in part, novel transposase compositions that have particular use in therapies yet avoid limitations of existing transposases.

In aspects, there is provided a mammalian transposase which is suitable for use in gene therapy, and advantageously gene therapy with large payloads (e.g. a transposon) which is durable. In aspects, the mammalian transposase is an engineered version of an *Myotis lucifugus* transposase (MLT transposase) that has been designed to have an N-terminal amino acid substitution and C-terminal amino acid deletions. In embodiments, the MLT transposase has an amino acid sequence of SEQ ID NO: 2, or a variant thereof. In embodiments, the MLT transposase is further engineered to have amino acid substitutions to improve activity, e.g. at positions corresponding to positions S8, C13, and/or N125 of SEQ ID NO: 2.

In aspects, a composition is provided comprising a transposase enzyme (e.g., an MLT transposase) or nucleic acid encoding the transposase enzyme, wherein the transposase enzyme comprises an amino acid sequence having at least about 80% sequence identity to SEQ ID NO: 2, wherein the transposase enzyme comprises an amino acid substitution at the position corresponding to position S2 of SEQ ID NO: 2.

The present invention provides a gene transfer system or construct comprising a monomer or a head-to-tail dimer enzyme capable of genomic integration by transposition and a DNA binding domain (DBD), such as a transcription activator-like effector protein (TALE) DBD or inactive (dCas9) programmed by a guide RNA (gRNA) (referred to as a dCas9/gRNA complex) as shown in FIGS. 1A-D or in FIG. 2. These chimeric systems, having a DBD fused to an enzyme capable of transposition (e.g., a recombinase, an integrase, or a transposase), direct binding of the enzyme to a specific sequence [e.g. TALE repeat variable di-residues (RVD) or gRNA] near a transposase recognition site such that the transposase is prevented from binding to random recognition sites. In some embodiments, an enzyme (e.g., transposase) of the gene transfer system binds to human genomic safe harbor sites (GSHS). TALEs described herein can physically sequester the enzyme to GSHS and promote transposition to nearby TTAA (SEQ ID NO: 1) sequences in close proximity to the RVD TALE nucleotide sequences. GSHSs in open chromatin sites are specifically targeted based on the predilection for transposases to insert into open chromatin. In addition, dCas9 (i.e. deficient for nuclease activity) is programmed with gRNAs directed to bind at a desired sequence of DNA in GSHS.

In some aspects, a composition is provided that comprises an enzyme capable of transposition comprising (a) a TALE DBD or a dCas9/gRNA DBD; (b) an enzyme capable of targeted genomic integration by transposition, the enzyme being capable of inserting a transposon at a TA dinucleotide site or a TTAA (SEQ ID NO: 1) tetranucleotide site in a GSHS sequence in a nucleic acid molecule; and (c) a linker that connects the TALE or Cas/gRNA DBD and the enzyme.

In some embodiments, the enzyme, e.g., a transposase or a transposase enzyme, is in a dimeric form (e.g. a head to tail dimer). In some embodiments, the enzyme is in a tetrameric form or in another multimeric form. In some embodiments, the enzyme is in a monomeric form.

In some embodiments, the composition is suitable for causing insertion of the transposon in the GSHS when contacted with a biological cell. The TALE DBD or dCas/gRNA complex can be suitable for directing the transposase enzyme to the GSHS sequence. In embodiments, the composition comprises a dCas/gRNA complex.

In some embodiments, a composition is provided that comprises an enzyme capable of transposition comprising (a) a dCas9/gRNA complex; (b) an enzyme capable of targeted genomic integration by transposition, the enzyme being capable of inserting a transposon at a TA dinucleotide site or a TTAA (SEQ ID NO: 1) tetranucleotide site in a GSHS sequence in a nucleic acid molecule; and (c) a linker that connects the dCas/gRNA complex and the enzyme.

In embodiments, the GSHS is in an open chromatin location in a chromosome. In some embodiments, the GSHS is selected from adeno-associated virus site 1 (AAVS1), chemokine (C-C motif) receptor 5 (CCR5) gene, HIV-1 coreceptor, and human Rosa26 locus. In some embodiments, the GSHS is located on human chromosome 2, 4, 6, 10, 11, or 17.

In some embodiments, the GSHS is selected from sites listed in FIG. 3 and FIG. 4, or a variant thereof (e.g. having about 1, or about 2, or about 3, or about 4, or about 5 mutations, independently selected from an insertion, substitution or deletion). In some embodiments, the TALE DBD comprises a sequence of FIG. 3 or a variant thereof (e.g. having about 1, or about 2, or about 3, or about 4, or about 5 mutations, independently selected from an insertion, substitution or deletion). In some embodiments, the dCas/gRNA DBD comprises a sequence of FIG. 4, or a variant thereof (e.g. having about 1, or about 2, or about 3, or about 4, or about 5 mutations, independently selected from insertion, substitution or deletion).

In some embodiments, the GSHS is within about 25, or about 50, or about 100, or about 150, or about 200, or about 300, or about 500 nucleotides of the TA dinucleotide site or TTAA (SEQ ID NO: 1) tetranucleotide site. In some embodiments, the GSHS is greater than 500 nucleotides from the TA dinucleotide site or TTAA (SEQ ID NO: 1) tetranucleotide site.

In embodiments, the TALE DBD comprises one or more repeat sequences. In some embodiments, the TALE DBD or repeat variable di-residue (RVD) comprises about 14, or about 15, or about, 16, or about 17, or about 18, or about 18.5 amino acid repeat sequences. In some embodiments, the RVD is included within TALE amino acid repeat sequences comprising 33 or 34 amino acids.

In some embodiments, the one or more of the TALE DBD repeat sequences comprise an RVD at residue 12 or 13 of the 33 or 34 amino acids. The RVD can recognize certain base pair(s) or residue(s) of the target DNA. In some embodiments, the RVD recognizes one base pair in the nucleic acid molecule. In some embodiments, the RVD recognizes a "C" residue in the nucleic acid molecule and the RVD is selected from HD, N(gap), HA, ND, and HI. In some embodiments, the RVD recognizes a "G" residue in the nucleic acid molecule and the RVD is selected from NN, NH, NK, HN, and NA. In some embodiments, the RVD recognizes an "A" residue in the nucleic acid molecule and the RVD is selected from NI and NS. In some embodiments, the RVD recognizes a "T" residue in the nucleic acid molecule and the RVD is selected from NG, HG, H(gap), and IG. In embodiments, the enzyme (e.g., without limitation, a transposase enzyme) is capable of inserting a transposon at a TA dinucleotide site. In some embodiments, the enzyme is capable of inserting a transposon at a TTAA (SEQ ID NO: 1) tetranucleotide site.

In embodiments, a nucleic acid encoding the enzyme capable of targeted genomic integration by transposition comprises an intein. In embodiments, the nucleic acid encodes the enzyme in the form of first and second portions with the intein encoded between the first and second portions, such that the first and second portions are fused into a functional enzyme upon post-translational excision of the intein from the enzyme.

In embodiments, the enzyme is a recombinase or an integrase. In embodiments, the recombinase is an integrase. In embodiments, the integrase is a transposase or the recombinase is a transposase.

In embodiments, the transposase has one or more mutations that confer hyperactivity. In embodiments, the transposase is a mammal-derived transposase, optionally encoded by a helper RNA.

In embodiments, the enzyme is derived from *Bombyx mori, Xenopus tropicalis, Trichoplusia ni*, or *Myotis lucifugus*. In embodiments, the enzyme is an engineered version, including but not limited to an enzyme that is a monomer, dimer, tetramer (or another multimer), hyperactive, or has a reduced interaction with non-TTAA (SEQ ID NO: 1) recognitions sites (Int−), derived from *Bombyx mori, Xenopus tropicalis, Trichoplusia ni*, or *Myotis lucifugus*. In some embodiments, the transposase enzyme is a *Myotis lucifugus* transposase (referred to herein as MLT or an MLT transposase), which can be either the wild type, monomer, dimer, tetramer (or another multimer), hyperactive, an Int-mutant, or any other variant.

In embodiments, a hyperactive form or Int-form of an MLT transposase has one or more mutations selected from L573X, E574X, and S2X, wherein X is any amino acid or no amino acid, optionally X is A, G, or a deletion, optionally the mutations are L573del, E574del, and S2A.

In embodiments, an MLT transposase, referred to herein as a corrected, engineered MLT transposase, has L573del, E574del, and S2A mutations. Such MLT transposase comprises an amino acid sequence of SEQ ID NO: 2, or a variant having at least about 90%, or at least about 93%, or at least about 95%, or at least about 97%, or at least about 98%, or at least about 99% identity thereto. In embodiments, the MLT transposase is encoded by a nucleotide sequence of SEQ ID NO: 3, or a variant having at least about 90%, or at least about 93%, or at least about 95%, or at least about 97%, or at least about 98%, or at least about 99% identity thereto.

In embodiments, an MLT transposase has the amino acid of SEQ ID NO: 4, or an amino acid sequence having at least about 90%, or at least about 93%, or at least about 95%, or at least about 97%, or at least about 98%, or at least about 99% identity thereto. In some embodiments, the MLT transposase is encoded by the nucleotide sequence of SEQ ID NO: 5, or a nucleotide acid sequence having at least about 90%, or at least about 93%, or at least about 95%, or at least about 97%, or at least about 98%, or at least about 99% identity thereto.

In embodiments, a hyperactive, Int−, or other forms of an MLT transposase include a mutation from FIGS. 5A and 5B, e.g. without limitation, about 1, or about 2, or about 3, or about 4, or about 5 mutations. In embodiments, the transposase can include any of the mutations depicted in FIGS. 5A and 5B, or equivalents thereof.

In embodiments, an MLT transposase in accordance with embodiments of the present disclosure comprises one or more hyperactive mutations that confer hyperactivity upon the MLT transposase. In embodiments, hyperactive mutants comprise one or more substitutions at S8, C13, and N125. In embodiments, hyperactive mutations comprise one or more of S8P, C13R, and N125K mutations.

In embodiments, an MLT transposase has an amino acid sequence having hyperactive mutations at positions which correspond to at least one of S8P, C13R, and N125K mutations relative to the amino acid sequence of SEQ ID NO: 2. In embodiments, an MLT transposase has an amino acid sequence of SEQ ID NO: 7, which has a mutation at a position which corresponds to hyperactive N125K mutation relative to the amino acid sequence of SEQ ID NO: 2.

In embodiments, an MLT transposase has an amino acid sequence of SEQ ID NO: 9, which comprises mutations at positions which correspond to hyperactive S8P and C13R mutations relative to the amino acid sequence of SEQ ID NO: 2.

In embodiments, an MLT transposase has an amino acid sequence having hyperactive mutations at positions which correspond to at least one of S8P, C13R, and N125K mutations relative to the amino acid sequence of SEQ ID NO: 2. It should be appreciated that the MLT transposase having the amino acid sequence of SEQ ID NO: 2 can have two hyperactive mutations (S8P and C13R), without the N125K mutation, or the MLT transposase having the amino acid sequence of SEQ ID NO: 2 can have any other mutation(s) (e.g., any one or more of mutations in FIGS. 5A and 5B). In embodiments, an MLT transposase has an amino acid sequence of SEQ ID NO: 340, which comprises hyperactive mutations at positions which correspond to S8P, C13R, and N125K mutations relative to the amino acid sequence of SEQ ID NO: 2.

In embodiments, the transposase enzyme is derived from *Bombyx mori, Xenopus tropicalis, Trichoplusia ni, Myotis lucifugus, Rhinolophus ferrumequinum, Rousettus aegyptiacus, Phyllostomus discolor, Myotis myotis, Pteropus vampyrus, Pipistrellus kuhlii, troglodytes, Molossus molossus*, or *Homo sapiens*. In embodiments, the transposase enzyme is derived from any of *Trichoplusia ni, Myotis lucifugus, Myotis myotis*, Pan *troglodytes*, or *Pteropus vampyrus* (see FIG. 7). The transposases can have one or more hyperactive and/or integration deficient mutations selected from FIGS. 5A and 5B, or equivalents thereof. One skilled in the art can correspond such mutants to transposases from any of *Trichoplusia ni, Myotis lucifugus, Myotis myotis*, or *Pteropus vampyrus*, with reference to FIG. 7. Also, one skilled in the art can correspond such mutants to transposases from *Bombyx mori, Xenopus tropicalis, Trichoplusia ni, Myotis lucifugus, Rhinolophus ferrumequinum, Rousettus aegyptiacus, Phyllostomus discolor, Myotis myotis, Pteropus vampyrus, Pipistrellus kuhlii, troglodytes, Molossus molossus*, or *Homo sapiens*.

In some embodiments, the enzyme (e.g., without limitation, a transposase) has a nucleotide sequence having at least about 90%, or at least about 93%, or at least about 95%, or at least about 97%, or at least about 98%, or at least about 99% identity to a nucleotide sequence of any of *Rhinolophus ferrumequinum, Rousettus aegyptiacus, Phyllostomus discolor, Myotis myotis, Pteropus vampyrus, Pipistrellus kuhlii*, and *Molossus molossus*. In some embodiments, the transposase enzyme can have an amino acid sequence having at least about 90%, or at least about 93%, or at least about 95%, or at least about 97%, or at least about 98%, or at least about 99% identity to an amino acid sequence of any of *Rhinolophus ferrumequinum, Rousettus aegyptiacus, Phyllostomus discolor, Myotis myotis, Pteropus vampyrus, Pipistrellus kuhlii*, and *Molossus molossus*.

In embodiments, the enzyme (e.g., without limitation, a transposase) is an engineered version, including but not limited to a transposase enzyme that is a monomer, dimer, tetramer, hyperactive, or has a reduced interaction with non-TTAA (SEQ ID NO: 1) recognitions sites (Int−), derived from any of *Bombyx mori, Xenopus tropicalis, Trichoplusia ni, Myotis lucifugus, Rhinolophus ferrumequinum, Rousettus aegyptiacus, Phyllostomus discolor, Myotis myotis, Pteropus vampyrus, Pipistrellus kuhlii*, Pan *troglodytes, Molossus molossus*, and *Homo sapiens*. The transposase enzyme can be either the wild type, monomer, dimer, tetramer or another multimer, hyperactive, or an Int-mutant.

In some embodiments, the linker that connects the TALE DBD and the enzyme capable of targeted genomic integration by transposition is a flexible linker. In some embodiments, the flexible linker is substantially comprised of glycine and serine residues, optionally wherein the flexible linker comprises $(Gly_4Ser)_n$ (SEQ ID NO: 435), where n is from about 1 to about 12. The flexible linker can be of about 20, or about 30, or about 40, or about 50, or about 60 amino acid residues.

A composition comprising an enzyme capable of transposition in accordance with embodiments of the present disclosure can include one or more non-viral vectors. Also, the enzyme (e.g., a chimeric transposase) can be disposed on the same (cis) or different vector (trans) than a transposon with a transgene. Accordingly, in some embodiments, the chimeric transposase and the transposon encompassing a transgene are in cis configuration such that they are included in the same vector. In some embodiments, the chimeric transposase and the transposon encompassing a transgene are in trans configuration such that they are included in different vectors. The vector is any non-viral vector in accordance with the present disclosure.

In some aspects, a nucleic acid encoding an enzyme capable of targeted genomic integration by transposition (e.g., a chimeric transposase) in accordance with embodiments of the present disclosure is provided. The nucleic acid can be DNA or RNA. In some embodiments, the nucleic acid encoding the enzyme is DNA. In some embodiments, the nucleic acid encoding the enzyme capable of targeted genomic integration by transposition (e.g., a chimeric transposase) is RNA such as, e.g., helper RNA. In embodiments, the chimeric transposase is incorporated into a vector. In some embodiments, the vector is a non-viral vector.

In embodiments, a nucleic acid encoding a transposon is a DNA, referred to as a "donor DNA." In embodiments, a nucleic acid encoding an enzyme capable of targeted genomic integration by transposition (e.g., a chimeric transposase) is helper RNA. In embodiments, the donor DNA is incorporated into a plasmid. In embodiments, the donor DNA is a plasmid. In some aspects, a host cell comprising the nucleic acid in accordance with embodiments of the present disclosure is provided.

In some embodiments, a composition or a nucleic acid in accordance with embodiments of the present disclosure is provided wherein the composition is in the form of a lipid nanoparticle (LNP).

In embodiments, a nucleic acid encoding the enzyme and a nucleic acid encoding the transposon are contained within the same lipid nanoparticle (LNP). In some embodiments, the nucleic acid encoding the enzyme and the nucleic acid encoding the transposon are a mixture incorporated into or associated with the same LNP. In some embodiments, the nucleic acid encoding the enzyme and the nucleic acid encoding the transposon are in the form of a co-formulation incorporated into or associated with the same LNP.

In embodiments, the LNP is selected from 1,2-dioleoyl-3-trimethylammonium propane (DOTAP), a cationic cholesterol derivative mixed with dimethylaminoethane-carbamoyl (DC-Chol), phosphatidylcholine (PC), triolein (glyceryl trioleate), and 1,2-distearoyl-sn-glycero-3-phosphoethanolamine-N-[carboxy(polyethylene glycol)-2000] (DSPE-PEG), 1,2-dimyristoyl-rac-glycero-3-methoxypolyethyleneglycol-2000 (DMG-PEG 2K), and 1,2 distearol-sn-glycerol-3phosphocholine (DSPC) and/or comprising of one or more molecules selected from polyethylenimine (PEI) and poly(lactic-co-glycolic acid) (PLGA), and N-Acetylgalactosamine (GalNAc).

In some embodiments, an LNP can be as described, e.g. in Patel et al., *J Control Release* 2019; 303:91-100. The LNP can comprise one or more of a structural lipid (e.g. DSPC), a PEG-conjugated lipid (CDM-PEG), a cationic lipid (MC3), cholesterol, and a targeting ligand (e.g. GalNAc).

In some aspects, a method for inserting a gene into the genome of a cell is provided that comprises contacting a cell with an enzyme (e.g., without limitation, a chimeric transposase) in accordance with embodiments of the present disclosure. The method can be in vivo or ex vivo method.

In some embodiments, the cell is contacted with a nucleic acid encoding the enzyme (e.g., without limitation, a chimeric transposase). In some embodiments, the cell is contacted with an RNA encoding the chimeric transposase, and/or with a construct comprising a transposon with flanking insulators such as, e.g. HS4 and D4Z4. In some embodiments, the cell is contacted with a DNA encoding the chimeric transposase.

In some embodiments, the transposon is flanked by one or more inverted terminal ends. The transposon can be under control of a tissue-specific promoter. In some embodiments, the transposon is an ATP Binding Cassette Subfamily A Member 4 gene (ABC) transporter gene (ABCA4), or functional fragment thereof. As another example, in some embodiments, the transposon is a very low-density lipoprotein receptor gene (VLDLR) or a low-density lipoprotein receptor gene (LDLR), or a functional fragment thereof.

In embodiments, the enzyme is a transposase such as a chimeric transposase, and the method provides reduced insertional mutagenesis or oncogenesis as compared to a method with a non-chimeric transposase.

In embodiments, the method is used to treat an inherited or acquired disease in a patient in need thereof.

For example, in some embodiments, the method is used for treating and/or mitigating a class of Inherited Macular Degeneration (IMDs) (also referred to as Macular dystrophies (MDs), including Stargardt disease (STGD), Best disease, X-linked retinoschisis, pattern dystrophy, Sorsby fundus dystrophy and autosomal dominant drusen. The STGD can be STGD Type 1 (STGD1). In some embodiments, the STGD can be STGD Type 3 (STGD3) or STGD Type 4 (STGD4) disease. The IMD can be characterized by one or more mutations in one or more of ABCA4, ELOVL4, PROM1, BEST1, and PRPH2. The gene therapy can be performed using transposon-based vector systems, with the assistance by chimeric transposases in accordance with the present disclosure, which are provided on the same vector as the gene to be transferred (cis) or on a different vector (trans) or as RNA. The transposon can comprise an ATP binding cassette subfamily A member 4 (ABCA4), or functional fragment thereof, and the transposon-based vector systems can operate under the control of a retina-specific promoter.

In some embodiments, the method is used for treating and/or mitigating familial hypercholesterolemia (FH), such as homozygous FH (HoFH) or heterozygous FH (HeFH) or disorders associated with elevated levels of low-density lipoprotein cholesterol (LDL-C). The gene therapy can be performed using transposon-based vector systems, with the assistance by enzymes (e.g., without limitation, chimeric transposases) in accordance with the present disclosure, which are provided on the same vector (cis) as the gene to be transferred or on a different vector (trans, e.g., a donor DNA/helper RNA system). The transposon can comprise a very low-density lipoprotein receptor gene (VLDLR) or a low-density lipoprotein receptor gene (LDLR), or a functional fragment thereof. The transposon-based vector systems can operate under control of a liver-specific promoter. In some embodiments, the liver-specific promoter is an LP1 promoter. The LP1 promoter can be a human LP1 promoter, which can be constructed as described, e.g., in Nathwani et al. *Blood* vol. 107(7) (2006):2653-61.

It should be appreciated that any other inherited or acquired diseases can be treated and/or mitigated using the method in accordance with the present disclosure.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF DRAWINGS

FIG. 1A. TALEs include nuclear localization signals (NLS) and an activation domain (AD) to function as transcriptional activators. The DNA binding domain has approximately 16.5 repeats of 33-34 amino acids with a residual variable di-residue (RVD) at position 12-13. FIG. 1B. RVDs are shown that have specificity for one or several nucleotides. Only bases of the DNA leading strand are shown. FIG. 1C. A chimeric transposase construct comprising a TALE DNA-binding protein fused thereto by a linker that is greater than 23 amino acids in length (top) and a chimeric transposase construct comprising dCas9 linked to one or more guide RNAs (bottom). FIG. 1D. A schematic diagram showing that chimeric transposases form dimers or tetramers at open chromatin to insert donor DNA at TTAA (SEQ ID NO: 1) recognition sites near DNA binding regions targeted by TALEs or dCas9/gRNA. Binding of the TALE or dCas9/gRNA to GSHS physically sequesters the transposase as a monomer or dimer to the same location and promotes transposition to the nearby TTAA (SEQ ID NO: 1) sequences (FIG. 3 and FIG. 4) near repeat variable di-residues (RVD) nucleotide sequences. All RVDs are preceded by a thymine (T) to bind to the NTR shown in FIG. 1A).

FIGS. 3 and 4 depict DNA binding codes for human genomic safe harbor sites in areas of open chromatin (FIG. 3) and guide RNAs to target human genomic safe harbor sites using dCas in areas of open chromatin (FIG. 4). Genomic locations for chromosomes 2, 4, 6, and 11 are adapted from Pellenz et al. (*Hum Gene Ther* 2019; 30:814-28) and chromosomes 10 and 17 from Papapetrou et al. (*Nat Biotechnol* 2011; 29:73-8). Sequences were downloaded from the UCSC Genome browser using hg18 or hg19 and evaluated with E-TALEN, a software tool to design and evaluate TALE DBD and WU-CRISPR, a software tool to design guide RNAs.

FIG. 5A depicts hyperactive MLT mutants.

FIG. 5B depicts excision positive and integration deficient (Int−) MLT mutants.

FIG. 8A depicts a plasmid construct template that transcribes transposase RNA that is later processed with a 5'-m7G cap1 and pseudouridine substitution. FIG. 8B depicts a generic MLT donor DNA construct template for use with any transgene.

FIG. 10 depicts a nucleotide sequence alignment of MLT (human codon-optimized for RNA) and a published sequence by Mitra et al. (*Proc Natl Acad Sci USA.* 2013 Jan. 2; 110(1):234-9) (Identity 77.67%, Gaps 1.44%).

FIG. 11 depicts a nucleotide sequence alignment of MLT and a sequence from WO2010085699 (Identity 73.68%, Gaps 1.16%).

FIG. 12 depicts an amino acid sequence alignment of MLT (L573del/E574del/S2A, with S8P, C13R, and N125K mutations) and published sequence by Mitra et al. (Mitra contained 2 extra amino acids on C-terminus).

FIG. 13 depicts comparison of an amino acid of an engineered MLT (L573del/E574del/S2A, with S8P and C13R mutations, "MLT") and the sequence from WO2010085699.

FIG. 14 depicts comparison of a terminal left end of MLT to a published sequence (Ray et al., piggyBac1_ML).

FIG. 15 depicts comparison of a terminal right end of MLT to a published sequence (Ray et al. piggyBac1_ML).

FIG. 17A shows that mammalian transposon (Ts) variants S8P, C13R, N125K and S8P/C13R have higher excision frequency that the native enzyme. FIG. 17B shows functional transgene expression in HeLa cells transfected with a donor neomycin transgene, 1:20 serial dilutions. The mammalian MLT transposase variant S8P/C13R showed comparable relative integration to the insect piggyBac in HeLa cells.

FIG. 19A shows analysis of purified MBP-MLT transposase fusion protein by an amylose-resin column. A major protein band of 100+kDa was identified by SDS-PAGE after purification of the expressed protein (MBP-MLT transposase) from the supernatant of the sonicated bacteria on a column of amylose resin. In FIG. 19B, shows a 67.5 kDa MLT transposase-specific band was shown after overnight cleavage of the MBP tag by TEV protease and heparin elution.

FIG. 22A shows % of integration activity for no MLT, MLT-dCas9, MLT-dCas12j, hyperacive piggyBac-dCas12j, hyperacive piggyBac-dCas9, hyperacive piggyBac, and MLT. FIG. 22B shows % of excision activity for no MLT, MLT-Intein-N-terminus, MLT1, and MLT2. FIG. 22C shows % of integration activity for no MLT, MLT-Intein-N-terminus, MLT1, and MLT2. FIG. 22D shows % of excision activity for no MLT, MLT-dCas12j, MLT-dCas9, MLT-Intein-N-terminus dCas9, MLT-Intein-N-terminus, MLT-Intein-N-terminus TALE, MLT-TALE10, and MLT. MLT-TALE10 in 27 bp and 49 bp from TTAA (SEQ ID NO: 1) sites in hROSA29.

Figure 29A:
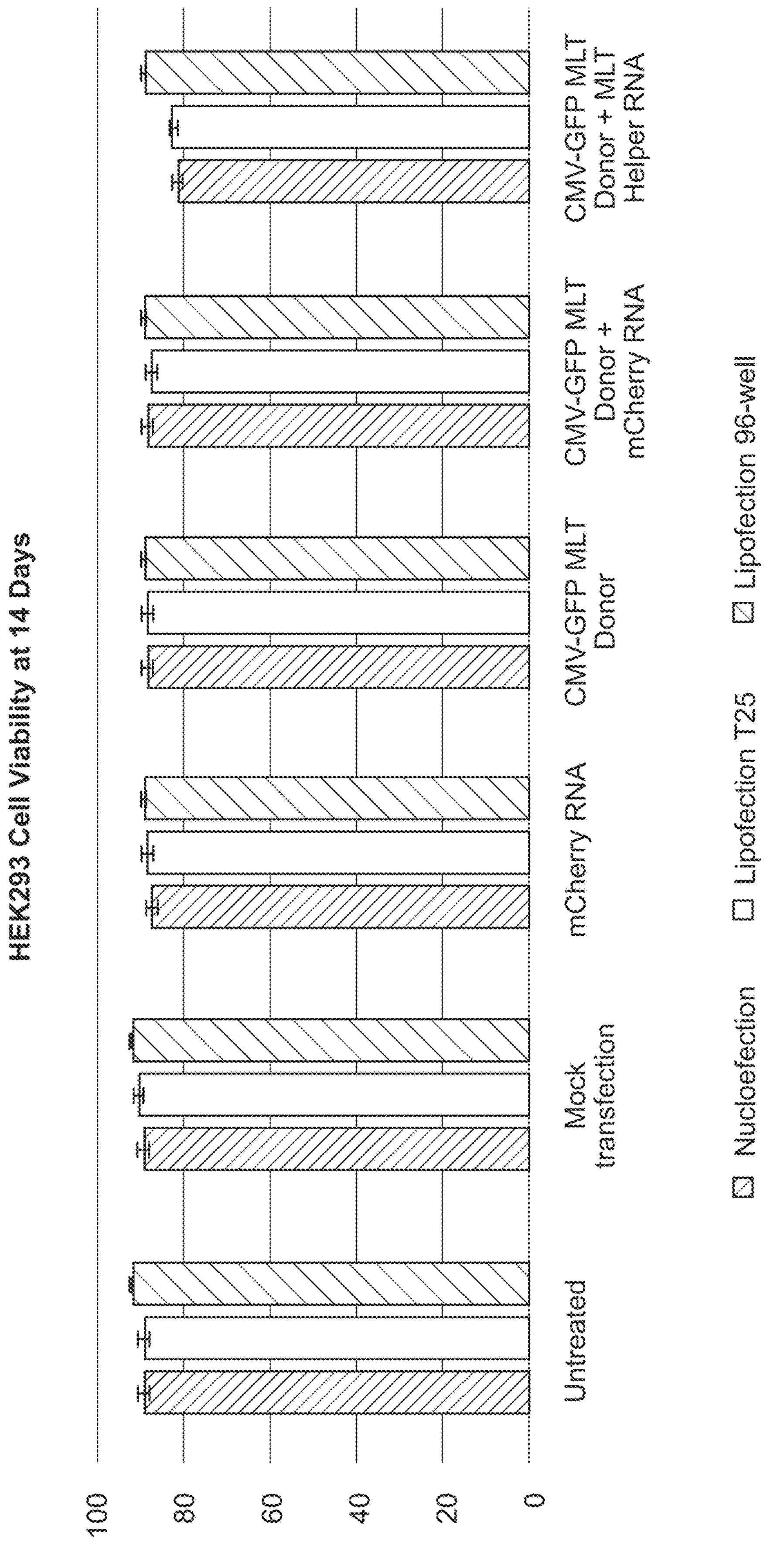
FIGS. 29A and 29B show the viability of HEK293 cells after nucleofection in 96-well plates, lipofection in T25 flasks, and lipofection in 96-well plates, 14 days after transfection (FIG. 29A) and 21 days after transfection (FIG. 29B). Cell viability is slightly better in 96-well plates at 14 days and 21 days after transfection. There are no significant differences in cell viability between the untreated cells and treated cells.
Figure 29B:
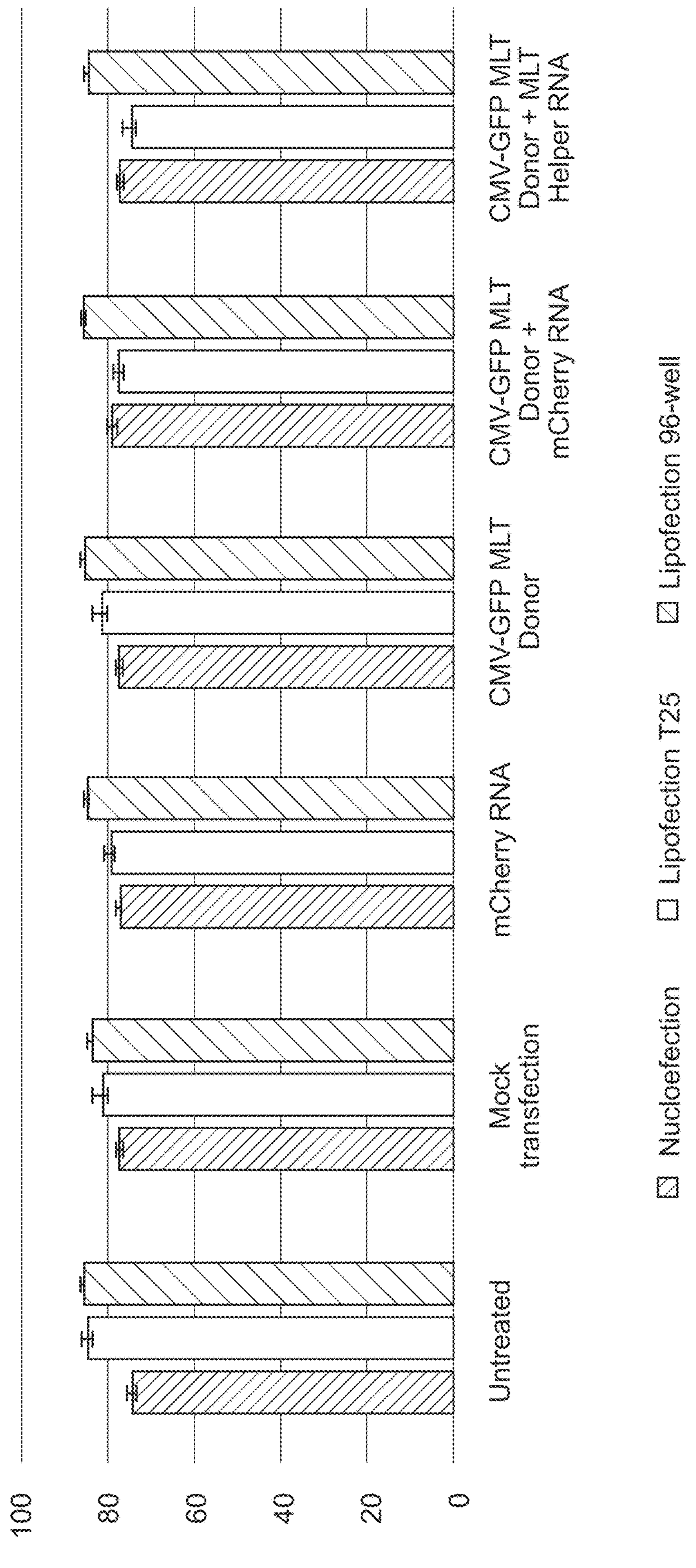
Figure 29C:
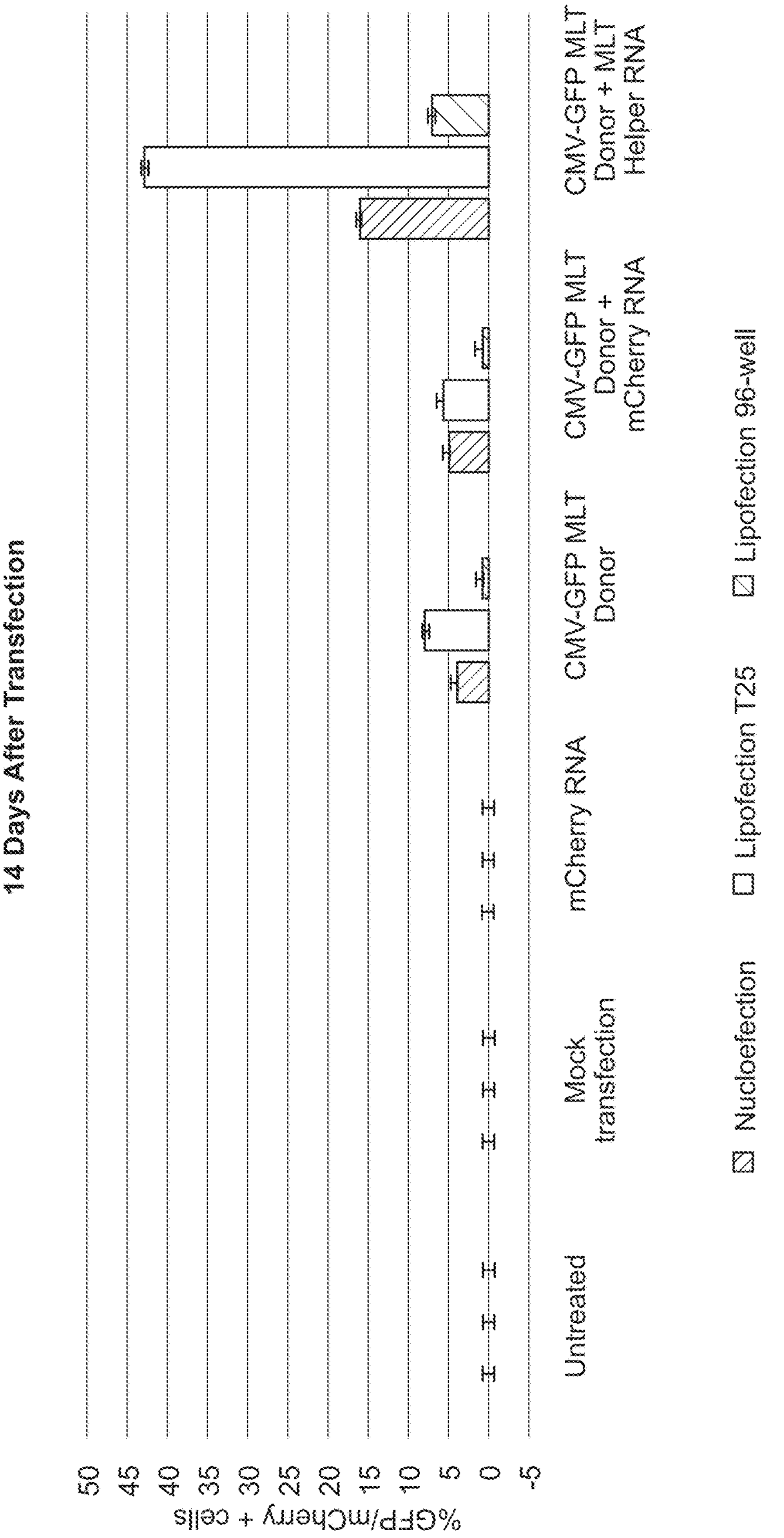
Figure 29D:
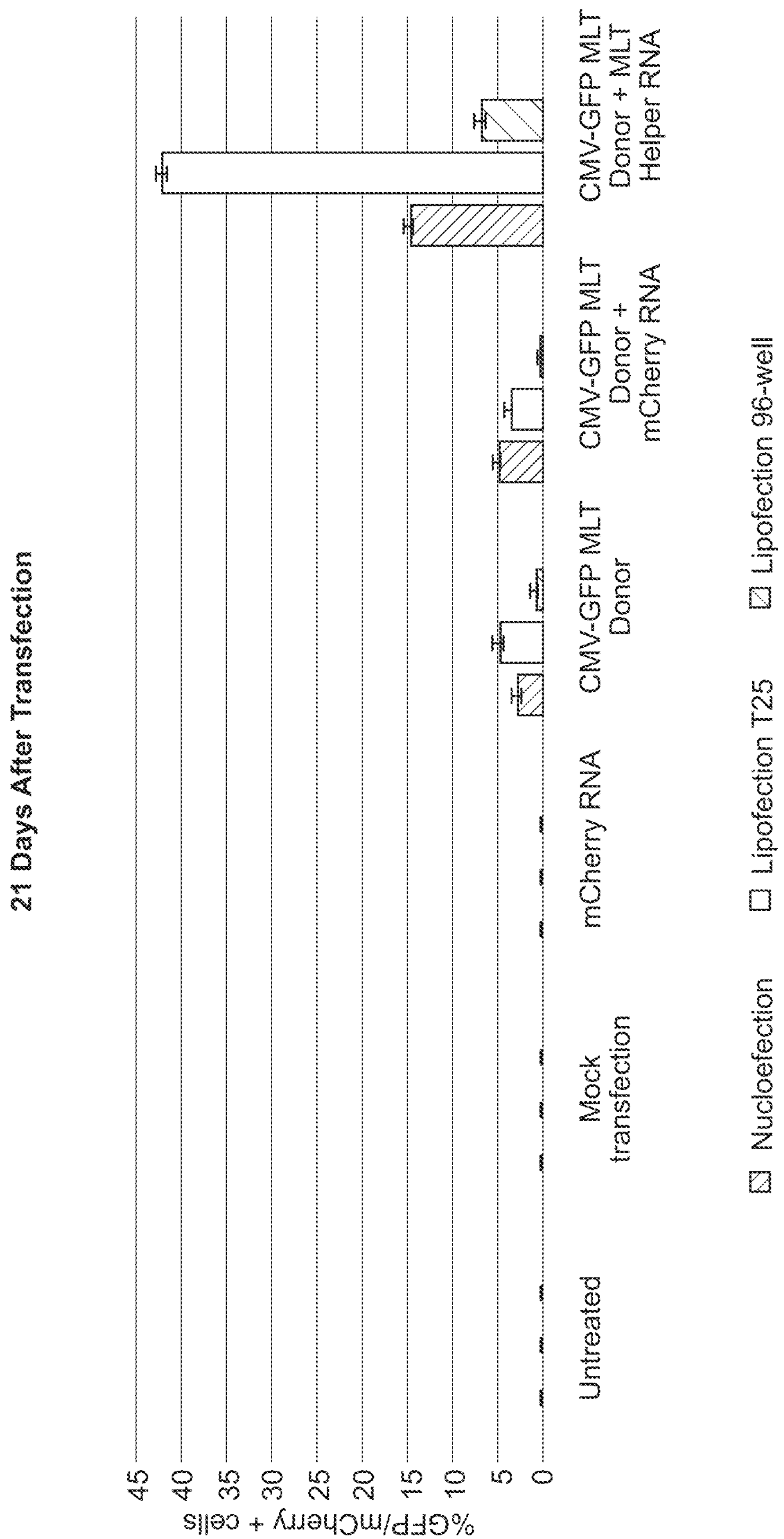

FIGS. 29C and 29D show the percentage of GFP/mCherry positive HEK293 cells after nucleofection in 96-well plates, lipofection in T25 flasks, and lipofection in 96-well plates, 14 days after transfection (FIG. 29C) and 21 days after transfection (FIG. 29D). A FACs gating strategy was applied to samples within each experiment. Selection of GFP-positive and mCherry-positive cell population was obtained. mCherry RNA expression was undetectable at Day 14. The highest % GFP positive cells was observed in the lipofectamine T25 format. The integration efficiency was 35% at 14 days, and 37% at 21 days.

Figure 29E:
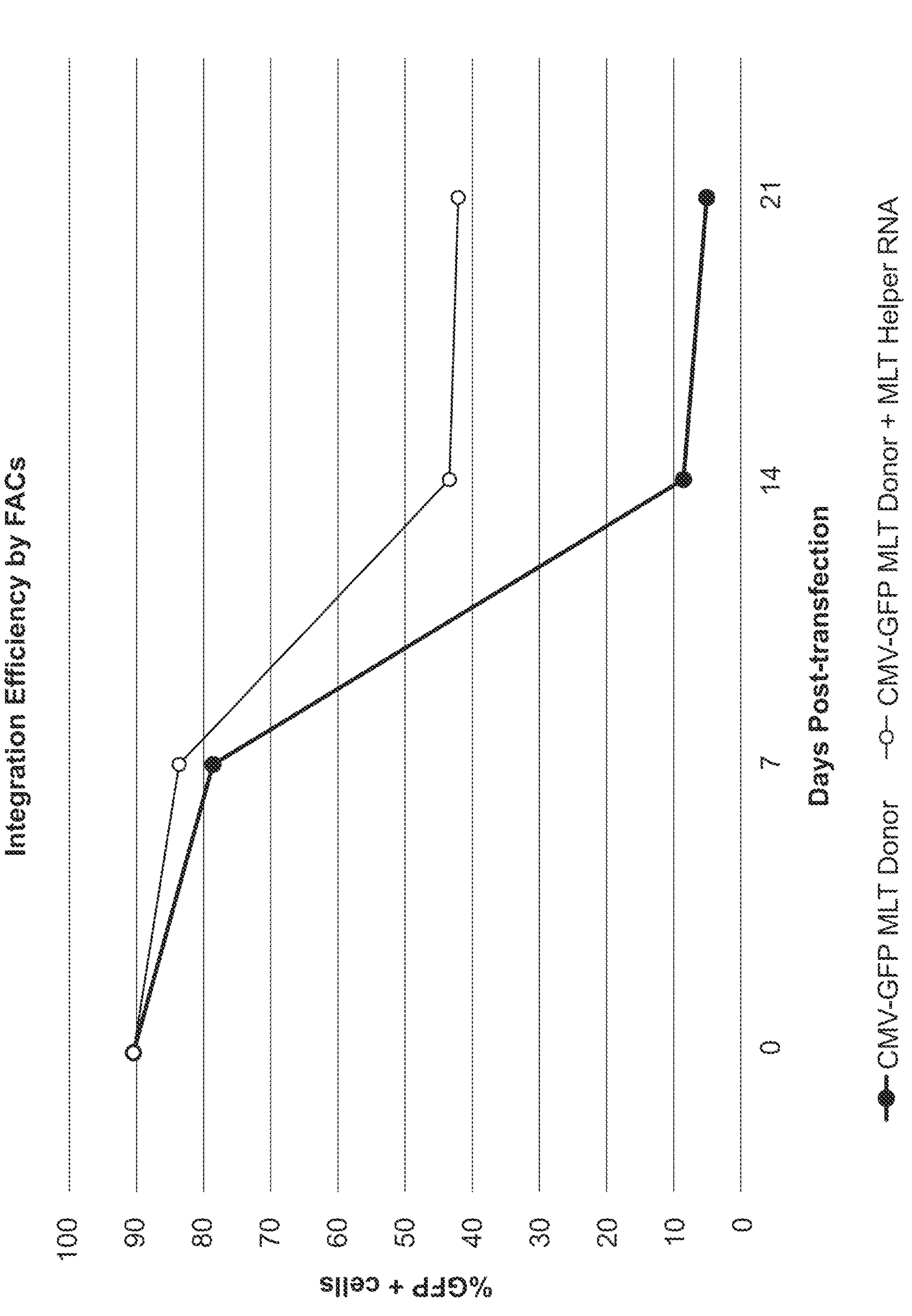

FIG. 29E shows the percentage of GFP positive HEK293 cells after nucleofection lipofection in T25 flasks. The % GFP positive cells was the same in CMV-GFP MLT Donor alone compared to CMV-GFP MLT Donor plus MLT Helper RNA. The % GFP positivity declined rapidly in HEK293 cells transfected with CMV-GFP MLT Donor alone and reached 5% at Day 21. The % GFP positivity stabilized in HEK293 cells transfected with CMV-GFP MLT Donor plus MLT Helper RNA and reached 42% at Day 21. The integration efficiency was calculated at 37%. The top curve is "CMV-GFP Donor".

Figures 30A, 30B, 30C:
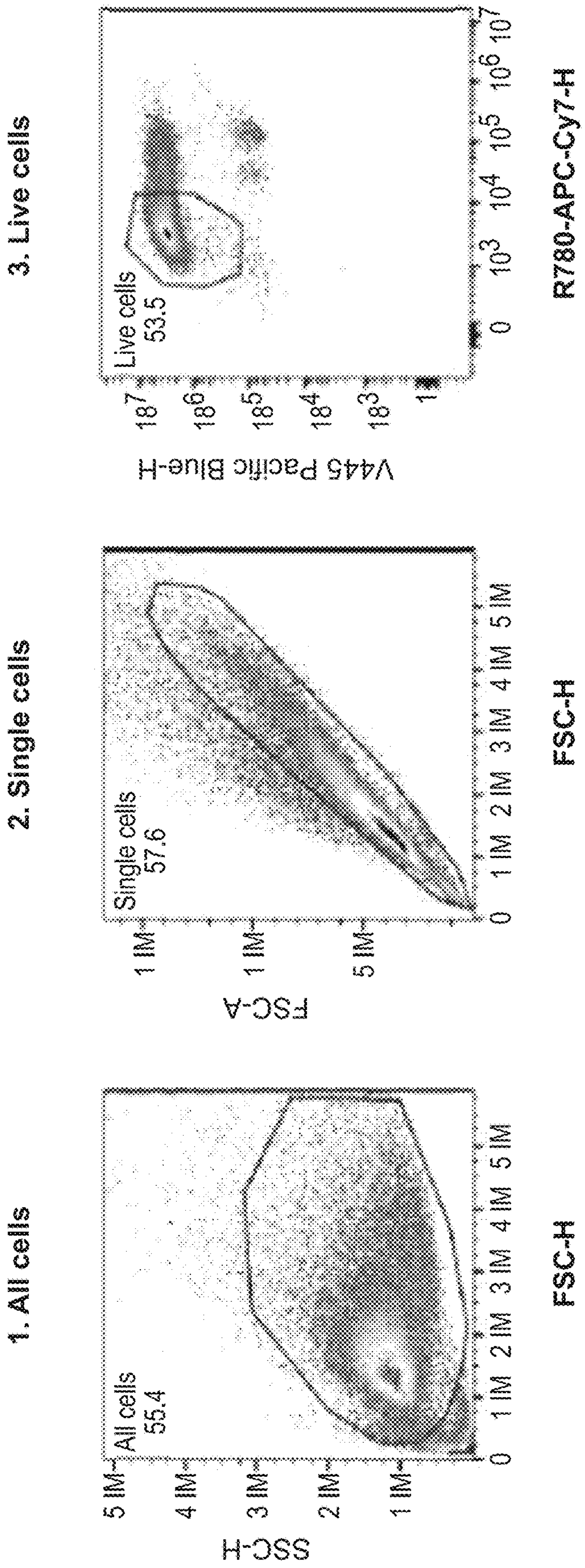
Figure 30D:
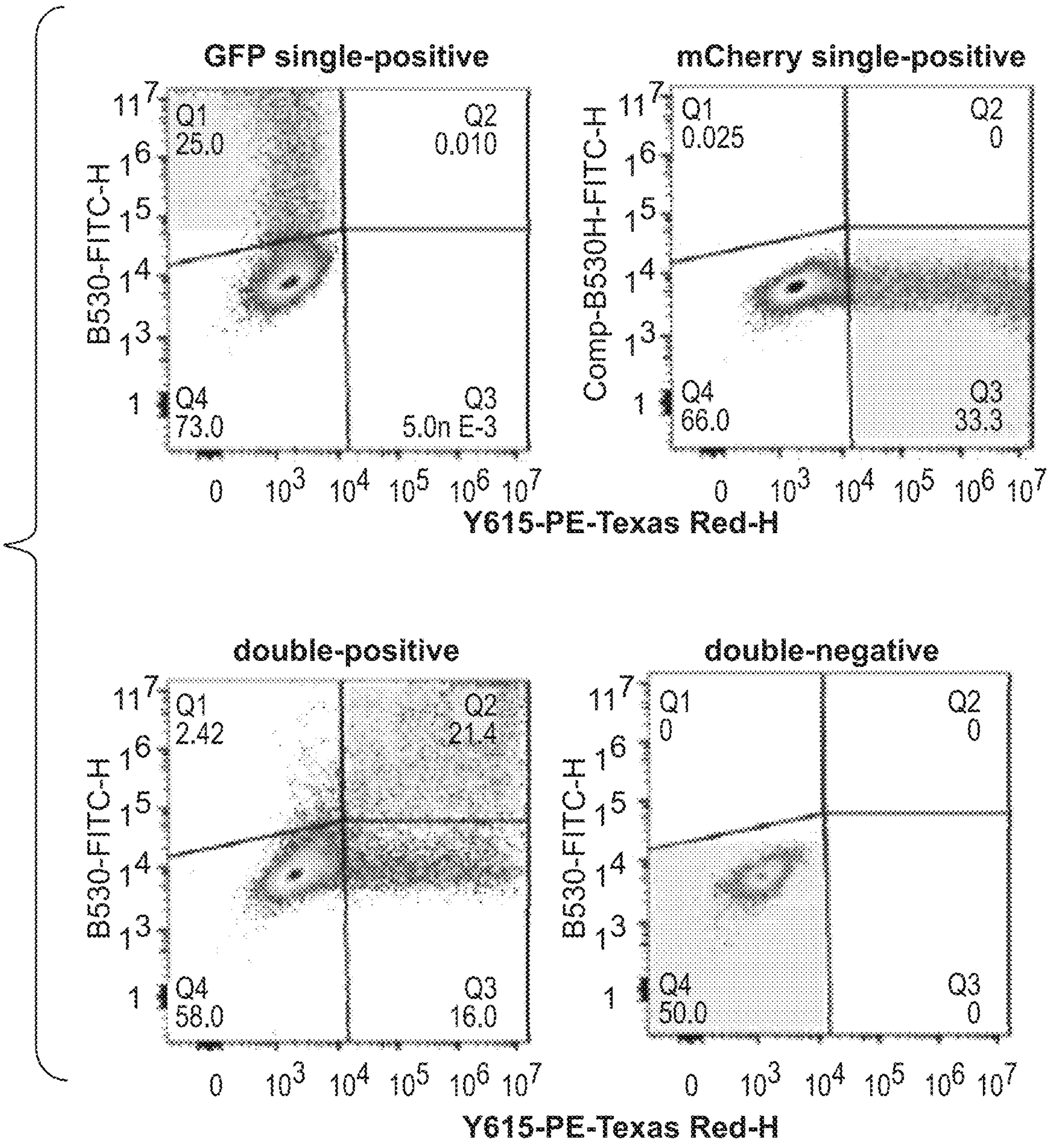

FIGS. 30A, 30B, 30C, and 30D show the FACS gating strategy that determined that neither RNA or DNA affected the viability of HEK293 cells (FIGS. 29A and 29B), RNA expression decreased rapidly after transfection and was undetectable by Day 14 (FIGS. 29C and 29D), and the DNA MLT Donor/MLT RNA Helper system has a high integration efficiency (FIG. 29E). FIG. 30A shows all cells, FIG. 30B shows single cells, and FIG. 30C shows live cells. FIG. 30D shows GFP single-positive cells, mCherry single-positive cells, double-positive cells, and double-negative cells.

Figure 31:
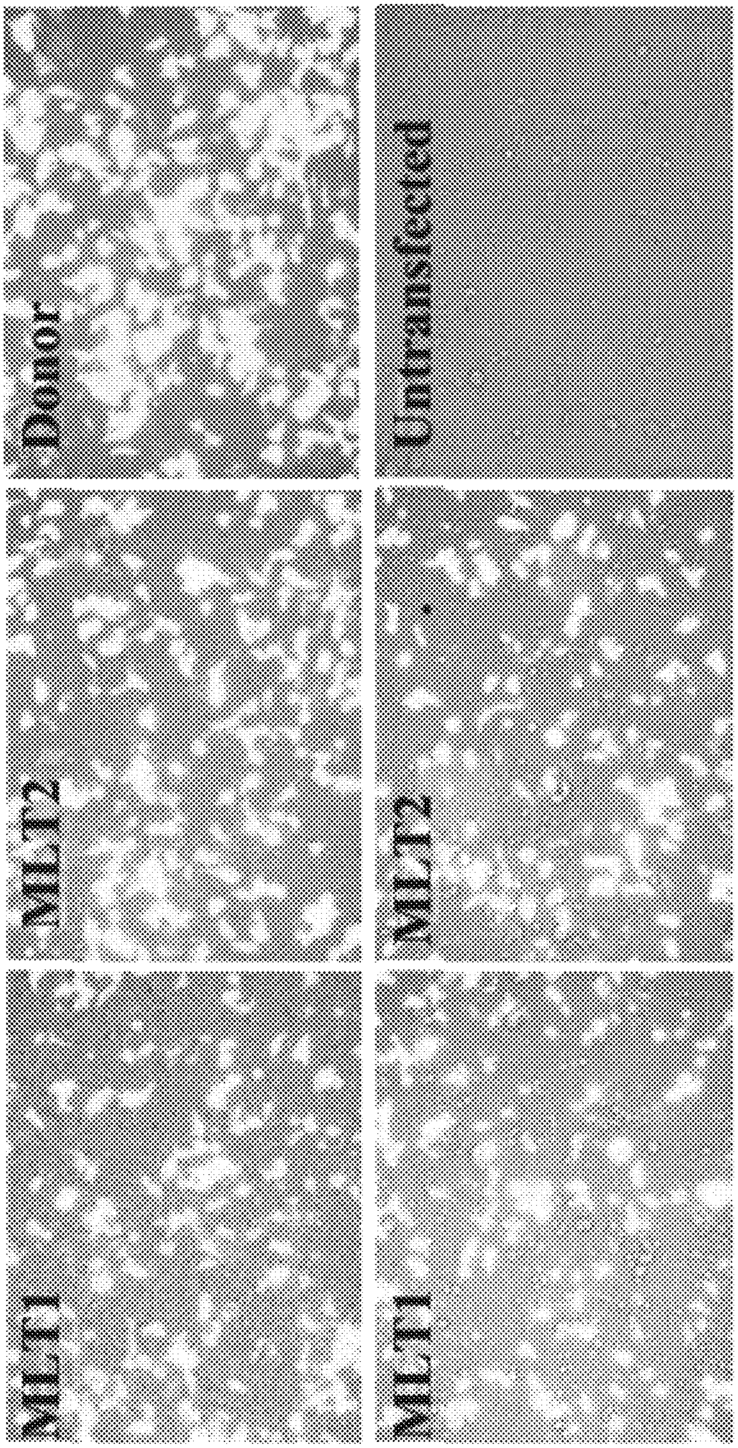

FIG. 31 shows transfection of CMV-GFP MLT Donor plus MLT Helper DNA 24 hours post transfection of HT1080 cells. The results at 24 hours are similar to the DNA MLT Donor/MLT RNA Helper system.

Figure 32:
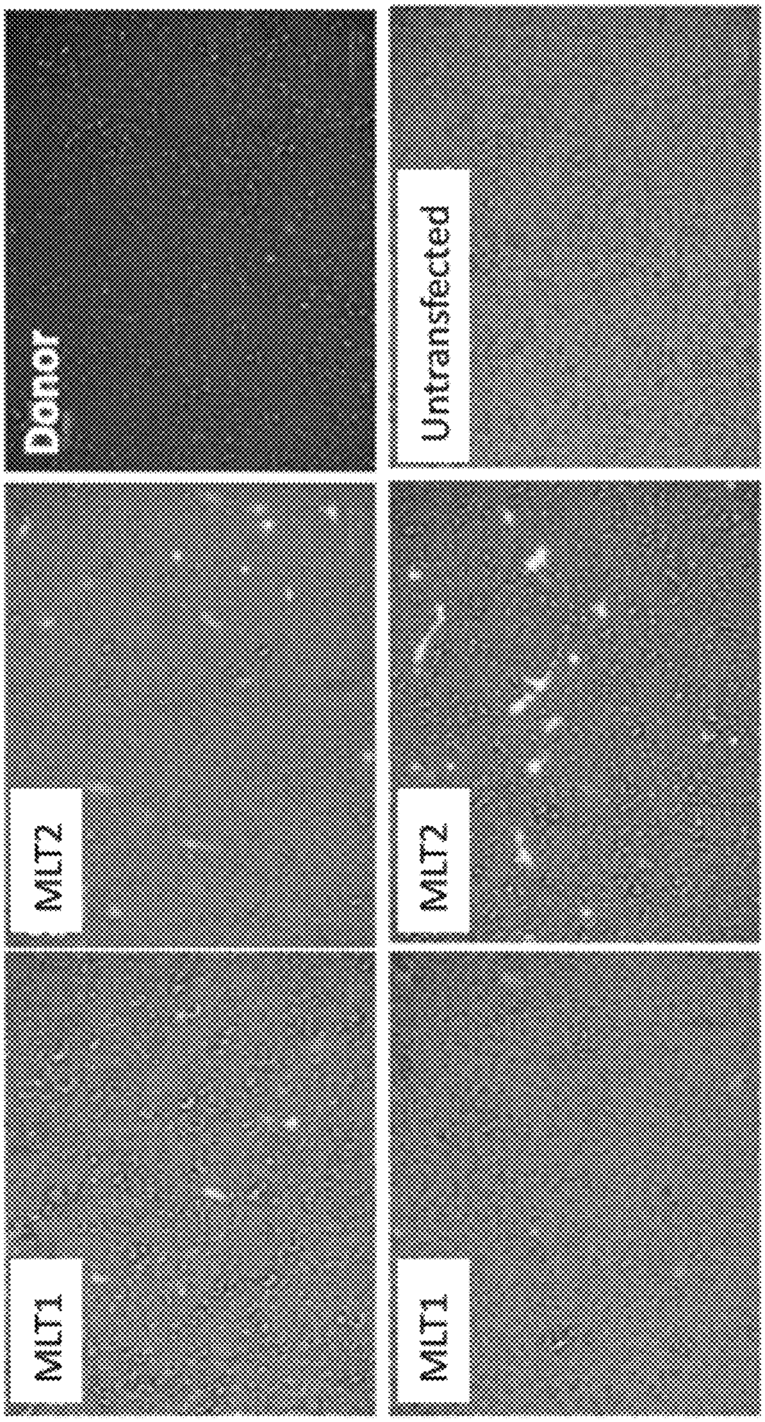

FIG. 32 shows transfection of CMV-GFP MLT Donor plus MLT Helper DNA 2 weeks post transfection of HT1080 cells. The results suggest that DNA MLT Donor/MLT DNA Helper system (~20% GFP+ cells) has less integration efficiency compared to DNA MLT Donor/MLT DNA Helper system.

DETAILED DESCRIPTION OF THE INVENTION

The present invention is based, in part, on the discovery of an engineered transposase enzyme capable of gene insertion that finds use, e.g., in therapy. In aspects, there is provided an engineered MLT enzyme (occasionally referred to as "engineered", "corrected," "the present MLT", "MLT1" or "MLT2").

The present invention is based, in part, on the discovery that an enzyme capable of targeted genomic integration by transposition (e.g., a recombinase, an integrase, or a transposase enzyme), as a monomer or a dimer, can be fused with a transcription activator-like effector proteins (TALE) DNA binding domain (DBD) or a dCas9/gRNA to thereby create a chimeric enzyme capable of a site- or locus-specific transposition. The enzyme (e.g., without limitation, a chimeric transposase) utilizes the specificity of TALE DBD to certain sites within a host genome, which allows using DBDs to target any desired location in the genome. In this way, the chimeric transposase in accordance with the present disclosure allows achieving targeted integration of a transgene.

In embodiments, the enzyme capable of targeted genomic integration by transposition is a recombinase or an integrase. In embodiments, the recombinase is an integrase. In embodiments, the integrase is a transposase or the recombinase is a transposase.

In embodiments, the transposase has one or more mutations that confer hyperactivity. In embodiments, the transposase is a mammal-derived transposase, optionally a helper RNA transposase. Thus, the present compositions and methods for gene transfer utilize a dual transposon/transposase system. Transposable elements are non-viral gene delivery vehicles found ubiquitously in nature. Transposon-based vectors have the capacity of stable genomic integration and long-lasting expression of transgene constructs in cells. Generally speaking, dual transposon and transposase systems work via a cut-and-paste mechanism whereby transposon DNA containing a transgene(s) of interest is integrated into chromosomal DNA by a transposase enzyme at a repetitive sequence site. Dual transposon/transposase (or "donor/helper") plasmid systems insert a transgene flanked by inverted terminal ends ("ends"), such as TTAA (SEQ ID NO: 1) tetranucleotide sites, without leaving a DNA footprint in the human genome. The transposase enzyme is transiently expressed (on the same or a different vector from a vector encoding the transposon) and it catalyzes the insertion events from the donor plasmid to the host genome. Genomic insertions primarily target introns but may target other TTAA (SEQ ID NO: 1) sites and integrate into approximately 50% of human genes.

Selection of a transposon system for gene therapy depends on the system's integration site preference. For example, piggyBac (PB) transposon has preference for transcription units, with insertions primarily targeting introns. Some transposases require certain sites in the host DNA for catalytic activity even if the DNA-enzyme complex is brought into the vicinity of the host-DNA. For example, Tcl/mariner transposon integrates into a TA dinucleotide (Fischer et al., *Proc Natl Acad Sci USA* 2001; 98:6759-64), and piggyBac (PB) transposon integrates into a TTAA (SEQ ID NO: 1) tetranucleotide (Mitra et al., *EMBO J* 2008; 27:1097-109). A benefit of using transposase-based genomic targeting over nuclease-based techniques is that integration via the cut-and-paste mechanism is readily identified by assaying the copy number of transposon insertions (e.g. (nr)LAM-PCR). Therefore, a single insertion clone is not expected to have additional DNA modifications. In comparison, targetable nucleases are capable of mutating genome without introducing an identifiable insert. Therefore, it may be challenging to confirm the DNA integrity of modified cells. Genomic screens to identify off-target nuclease mutations are complex and limited in sequence coverage.

As discussed above, viral (e.g. AAV, lentivirus, etc.) and nuclease-based (e.g. CRISPR/Cas, prime editing base editing) gene therapies are typically limited by mutagenesis risk, and also have drawbacks such as immunogenicity, manufacturing costs, cargo size, and reversibility. Transposons are less likely to activate a proto-oncogene than lentivirus or other retroviruses but cause insertional mutagenesis when a transgene is inserted in one or more locations in a host genome other than the intended locations. In particular, the genomic sites recognized by transposases, such as a TA dinucleotide site or a TTAA (SEQ ID NO: 1) tetranucleotide site, can be found in multiple locations in a genome such that a transgene can be inserted in unintended locations within the genome and have disruptive, often severe effects on the host. For example, the insertional mutagenesis can affect a function of a metabolic gene. Accordingly, to improve the function of a dual transposon/transposase system as a safe and efficient gene therapy tool, it is desired to increase and control the specificity of a transposase's binding and insertion.

Accordingly, in some aspects, a composition is provided that comprises an enzyme capable of transposition, comprising (a) a TALE DBD or a dCas9/gRNA complex; (b) an enzyme capable of targeted genomic integration by transposition, the enzyme being capable of inserting a transposon at a TA dinucleotide site or a TTAA (SEQ ID NO: 1) tetranucleotide site in a GSHS in a nucleic acid molecule; and (c) a linker that connects the TALE DBD or the dCas9/gRNA complex and the enzyme. In embodiments, the enzyme (e.g., a transposase enzyme) is a head to tail dimer. In some embodiments, the enzyme is a tetramer. In some embodiments, the enzyme is a monomer.

In embodiments, TALE or dCas9/gRNA DBDs cause the enzyme capable of transposition (e.g., without limitation, a chimeric transposase) to bind specifically to human GSHS. In embodiments, the TALEs or dCas9/gRNA DBD sequester the transposase to GSHS and promote transposition to nearby TA dinucleotide or TTAA (SEQ ID NO: 1) tetranucleotide sites which can be located in proximity to the repeat variable di-residues (RVD) TALE or gRNA nucleotide sequences. The GSHS regions are located in open chromatin sites that are susceptible to transposase activity. Accordingly, the transposase does not only operate based on its ability to recognize TA or TTAA (SEQ ID NO: 1) sites, but it also directs a transposon (having a transgene) to specific locations in proximity to a TALE or dCas9/gRNA DBD. The chimeric transposase in accordance with embodiments of the present disclosure has negligible risk of genotoxicity and exhibits superior features as compared to existing gene therapies.

In embodiments, the gRNA, e.g. to be associated with dCas9 is AATCGAGAAGCGACTCGACA (SEQ ID NO: 425) and/or TGCCCTGCAGGGGAGTGAGC (SEQ ID NO: 426). In embodiments, the gRNA, e.g. to be associated with dCas9 is GAAGCGACTCGACATGGAGG (SEQ ID NO: 427) and/or CCTGCAGGGGAGTGAGCAGC (SEQ ID NO: 428).

In some embodiments, a chimeric transposase is mutated to be characterized by reduced or inhibited binding of off-target sequences and consequently reliant on a DBD fused thereto, such as a TALE or dCas9/gRNA DBD, for transposition.

The described compositions and methods allow reducing random vector and transgene insertion, which increase a mutagenic risk. The described compositions and methods make use of a transposome system that reduces genotoxicity compared to viral- and nuclease-mediated gene therapies. The dual system is designed to avoid the persistence of an active transposase and efficiently transfect human cell lines without significant cytotoxicity.

In some embodiments, the composition is suitable for causing insertion of the transposon in the GSHS when contacted with a cell comprising a GSHS.

In some embodiments, the TALE or dCas9/gRNA DBD can be suitable for directing the transposase enzyme to the GSHS sequence.

In embodiments, TALE or dCas9/gRNA DBDs are customizable, such as a TALE or dCas9/gRNA DBD can be selected for targeting a specific genomic location. In some embodiments, the genomic location is in proximity to a TA dinucleotide site or a TTAA (SEQ ID NO: 1) tetranucleotide site.

In embodiments, CRISPR (Clustered Regularly Interspaced Short Palindromic Repeat) associated protein 9 (Cas9), or a variant thereof, targets the enzyme to a locus of interest. Cas9 is a generic nuclease, and a guide RNA (gRNA) confers sequence specificity on Cas9 by carrying an identical complementary sequence to a genomic region of interest. Jinek et al. (2012) *Science* 337:816-821. A CRISPR/Cas9 tool only requires Cas9 nuclease for DNA cleavage and a single-guide RNA (sgRNA) for target specificity. See Jinek et al. (2012); Chylinski et al. (2014) *Nucleic Acids Res* 42, 6091-6105. The inactivated form of Cas9, which is a nuclease-deficient (or inactive, or "catalytically dead") Cas9, is typically denoted as "dCas9" and has no substantial nuclease activity. Qi, L. S. et al. (2013). *Cell* 152, 1173-1183. CRISPR/dCas9 binds precisely to specific genomic sequences through targeting of guide RNA (gRNA) sequences. See Dominguez et al., *Nat Rev Mol Cell Biol.* 2016; 17:5-15; Wang et al., *Annu Rev Biochem.* 2016; 85:227-64. dCas9 is utilized to edit gene expression when applied to the transcription binding site of a desired site and/or locus in a genome. When the dCas9 protein is coupled to guide RNA (gRNA) to create dCas9 guide RNA complex, dCas9 prevents the proliferation of repeating codons and DNA sequences that might be harmful to an organism's genome. Essentially, when multiple repeat codons are produced, it elicits a response, or recruits an abundance of dCas9 to combat the overproduction of those codons and results in the shut-down of transcription. Thus, dCas9 works synergistically with gRNA and directly affects the DNA polymerase II from continuing transcription.

In embodiments, the gene-editing system comprises a nuclease-deficient Cas enzyme guide RNA complex. In some embodiments, the gene-editing system comprises a nuclease-deficient (or inactive, or "catalytically dead" Cas9, typically denoted as "dCas9") guide RNA complex.

In embodiments, the dCas9/gRNA complex comprises a guide RNA selected from: GTTTAGCTCACCCGTGAGCC (SEQ ID NO: 91), CCCAATATTATTGTTCTCTG (SEQ ID NO: 92), GGGGTGGGATAGGGGATACG (SEQ ID NO: 93), GGATCCCCCTCTACATTTAA (SEQ ID NO: 94), GTGATCTTGTACAAATCATT (SEQ ID NO: 95), CTACACAGAATCTGTTAGAA (SEQ ID NO: 96), TAAGCTAGAGAATAGATCTC (SEQ ID NO: 97), and TCAATACACTTAATGATTTA (SEQ ID NO: 98), wherein the guide RNA directs the enzyme to a chemokine (C-C motif) receptor 5 (CCR5) gene.

In embodiments, the dCas9/gRNA complex comprises a guide RNA selected from:

(SEQ ID NO: 99)
CACCGGGAGCCACGAAAACAGATCC;

(SEQ ID NO: 100)
CACCGCGAAAACAGATCCAGGGACA;

(SEQ ID NO: 101)
CACCGAGATCCAGGGACACGGTGCT;

(SEQ ID NO: 102)
CACCGGACACGGTGCTAGGACAGTG;

-continued (SEQ ID NO: 103)
CACCGGAAAATGACCCAACAGCCTC;

(SEQ ID NO: 104)
CACCGGCCTGGCCGGCCTGACCACT;

(SEQ ID NO: 105)
CACCGCTGAGCACTGAAGGCCTGGC;

(SEQ ID NO: 106)
CACCGTGGTTTCCACTGAGCACTGA;

(SEQ ID NO: 107)
CACCGGATAGCCAGGAGTCCTTTCG;

(SEQ ID NO: 108)
CACCGGCGCTTCCAGTGCTCAGACT;

(SEQ ID NO: 109)
CACCGCAGTGCTCAGACTAGGGAAG;

(SEQ ID NO: 110)
CACCGGCCCCTCCTCCTTCAGAGCC;

(SEQ ID NO: 111)
CACCGTCCTTCAGAGCCAGGAGTCC;

(SEQ ID NO: 112)
CACCGTGGTTTCCGAGCTTGACCCT;

(SEQ ID NO: 113)
CACCGCTGCAGAGTATCTGCTGGGG;

(SEQ ID NO: 114)
CACCGCGTTCCTGCAGAGTATCTGC;

(SEQ ID NO: 115)
AAACGGATCTGTTTTCGTGGCTCCC;

(SEQ ID NO: 116)
AAACTGTCCCTGGATCTGTTTTCGC;

(SEQ ID NO: 117)
AAACAGCACCGTGTCCCTGGATCTC;

(SEQ ID NO: 118)
AAACCACTGTCCTAGCACCGTGTCC;

(SEQ ID NO: 119)
AAACGAGGCTGTTGGGTCATTTTCC;

(SEQ ID NO: 120)
AAACAGTGGTCAGGCCGGCCAGGCC;

(SEQ ID NO: 121)
AAACGCCAGGCCTTCAGTGCTCAGC;

(SEQ ID NO: 122)
AAACTCAGTGCTCAGTGGAAACCAC;

(SEQ ID NO: 123)
AAACCGAAAGGACTCCTGGCTATCC;

(SEQ ID NO: 124)
AAACAGTCTGAGCACTGGAAGCGCC;

(SEQ ID NO: 125)
AAACCTTCCCTAGTCTGAGCACTGC;

(SEQ ID NO: 126)
AAACGGCTCTGAAGGAGGAGGGGCC;

(SEQ ID NO: 127)
AAACGGACTCCTGGCTCTGAAGGAC;

(SEQ ID NO: 128)
AAACAGGGTCAAGCTCGGAAACCAC;

(SEQ ID NO: 129)
AAACCCCCAGCAGATACTCTGCAGC;

-continued (SEQ ID NO: 130)
AAACGCAGATACTCTGCAGGAACGC;

(SEQ ID NO: 131)
TCCCCTCCCAGAAAGACCTG;

(SEQ ID NO: 132)
TGGGCTCCAAGCAATCCTGG;

(SEQ ID NO: 133)
GTGGCTCAGGAGGTACCTGG;

(SEQ ID NO: 134)
GAGCCACGAAAACAGATCCA;

(SEQ ID NO: 135)
AAGTGAACGGGGAAGGGAGG;

(SEQ ID NO: 136)
GACAAAAGCCGAAGTCCAGG;

(SEQ ID NO: 137)
GTGGTTGATAAACCCACGTG;

(SEQ ID NO: 138)
TGGGAACAGCCACAGCAGGG;

(SEQ ID NO: 139)
GCAGGGGAACGGGGATGCAG;

(SEQ ID NO: 140)
GAGATGGTGGACGAGGAAGG;

(SEQ ID NO: 141)
GAGATGGCTCCAGGAAATGG;

(SEQ ID NO: 142)
TAAGGAATCTGCCTAACAGG;

(SEQ ID NO: 143)
TCAGGAGACTAGGAAGGAGG;

(SEQ ID NO: 144)
TATAAGGTGGTCCCAGCTCG;

(SEQ ID NO: 145)
CTGGAAGATGCCATGACAGG;

(SEQ ID NO: 146)
GCACAGACTAGAGAGGTAAG;

(SEQ ID NO: 147)
ACAGACTAGAGAGGTAAGGG;

(SEQ ID NO: 148)
GAGAGGTGACCCGAATCCAC;

(SEQ ID NO: 149)
GCACAGGCCCCAGAAGGAGA;

(SEQ ID NO: 150)
CCGGAGAGGACCCAGACACG;

(SEQ ID NO: 151)
GAGAGGACCCAGACACGGGG;

(SEQ ID NO: 152)
GCAACACAGCAGAGAGCAAG;

(SEQ ID NO: 153)
GAAGAGGGAGTGGAGGAAGA;

(SEQ ID NO: 154)
AAGACGGAACCTGAAGGAGG;

(SEQ ID NO: 155)
AGAAAGCGGCACAGGCCCAG;

(SEQ ID NO: 156)
GGGAAACAGTGGGCCAGAGG;

-continued (SEQ ID NO: 157) GTCCGGACTCAGGAGAGAGA;

(SEQ ID NO: 158) GGCACAGCAAGGGCACTCGG;

(SEQ ID NO: 159) GAAGAGGGGAAGTCGAGGGA;

(SEQ ID NO: 160) GGGAATGGTAAGGAGGCCTG;

(SEQ ID NO: 161) GCAGAGTGGTCAGCACAGAG;

(SEQ ID NO: 162) GCACAGAGTGGCTAAGCCCA;

(SEQ ID NO: 163) GACGGGGTGTCAGCATAGGG;

(SEQ ID NO: 164) GCCCAGGGCCAGGAACGACG;

(SEQ ID NO: 165) GGTGGAGTCCAGCACGGCGC;

(SEQ ID NO: 166) ACAGGCCGCCAGGAACTCGG;

(SEQ ID NO: 167) ACTAGGAAGTGTGTAGCACC;

(SEQ ID NO: 168) ATGAATAGCAGACTGCCCCG;

(SEQ ID NO: 169) ACACCCCTAAAAGCACAGTG;

(SEQ ID NO: 170) CAAGGAGTTCCAGCAGGTGG;

(SEQ ID NO: 171) AAGGAGTTCCAGCAGGTGGG;

(SEQ ID NO: 172) TGGAAAGAGGAGGGAAGAGG;

(SEQ ID NO: 173) TCGAATTCCTAACTGCCCCG;

(SEQ ID NO: 174) GACCTGCCCAGCACACCCTG;

(SEQ ID NO: 175) GGAGCAGCTGCGGCAGTGGG;

(SEQ ID NO: 176) GGGAGGGAGAGCTTGGCAGG;

(SEQ ID NO: 177) GTTACGTGGCCAAGAAGCAG;

(SEQ ID NO: 178) GCTGAACAGAGAAGAGCTGG;

(SEQ ID NO: 179) TCTGAGGGTGGAGGGACTGG;

(SEQ ID NO: 180) GGAGAGGTGAGGGACTTGGG;

(SEQ ID NO: 181) GTGAACCAGGCAGACAACGA;

(SEQ ID NO: 182) CAGGTACCTCCTGAGCCACG;

(SEQ ID NO: 183) GGGGGAGTAGGGGCATGCAG;

-continued (SEQ ID NO: 184) GCAAATGGCCAGCAAGGGTG;

(SEQ ID NO: 309) CAAATGGCCAGCAAGGGTGG;

(SEQ ID NO: 310) GCAGAACCTGAGGATATGGA;

(SEQ ID NO: 311) AATACACAGAATGAAAATAG;

(SEQ ID NO: 312) CTGGTGACTAGAATAGGCAG;

(SEQ ID NO: 313) TGGTGACTAGAATAGGCAGT;

(SEQ ID NO: 314) TAAAAGAATGTGAAAAGATG;

(SEQ ID NO: 315) TCAGGAGTTCAAGACCACCC;

(SEQ ID NO: 316) TGTAGTCCCAGTTATGCAGG;

(SEQ ID NO: 317) GGGTTCACACCACAAATGCA;

(SEQ ID NO: 318) GGCAAATGGCCAGCAAGGGT;

(SEQ ID NO: 319) AGAAACCAATCCCAAAGCAA;

(SEQ ID NO: 320) GCCAAGGACACCAAAACCCA;

(SEQ ID NO: 321) AGTGGTGATAAGGCAACAGT;

(SEQ ID NO: 322) CCTGAGACAGAAGTATTAAG;

(SEQ ID NO: 323) AAGGTCACACAATGAATAGG;

(SEQ ID NO: 324) CACCATACTAGGGAAGAAGA;

(SEQ ID NO: 327) CAATACCCTGCCCTTAGTGG;

(SEQ ID NO: 325) AATACCCTGCCCTTAGTGGG;

(SEQ ID NO: 326) TTAGTGGGGGGTGGAGTGGG;

(SEQ ID NO: 328) GTGGGGGGTGGAGTGGGGGG;

(SEQ ID NO: 329) GGGGGGTGGAGTGGGGGGTG;

(SEQ ID NO: 330) GGGGTGGAGTGGGGGGTGGG;

(SEQ ID NO: 331) GGGTGGAGTGGGGGGTGGGG;

(SEQ ID NO: 332) GGGGGTGGGGAAAGACATCG;

(SEQ ID NO: 333) GCAGCTGTGAATTCTGATAG;

(SEQ ID NO: 334) GAGATCAGAGAAACCAGATG;

-continued (SEQ ID NO: 335)
TCTATACTGATTGCAGCCAG;

(SEQ ID NO: 185)
CACCGAATCGAGAAGCGACTCGACA;

(SEQ ID NO: 186)
CACCGGTCCCTGGGCGTTGCCCTGC;

(SEQ ID NO: 187)
CACCGCCCTGGGCGTTGCCCTGCAG;

(SEQ ID NO: 188)
CACCGCCGTGGGAAGATAAACTAAT;

(SEQ ID NO: 189)
CACCGTCCCCTGCAGGGCAACGCCC;

(SEQ ID NO: 190)
CACCGGTCGAGTCGCTTCTCGATTA;

(SEQ ID NO: 191)
CACCGCTGCTGCCTCCCGTCTTGTA;

(SEQ ID NO: 192)
CACCGGAGTGCCGCAATACCTTTAT;

(SEQ ID NO: 193)
CACCGACACTTTGGTGGTGCAGCAA;

(SEQ ID NO: 194)
CACCGTCTCAAATGGTATAAAACTC;

(SEQ ID NO: 195)
CACCGAATCCCGCCCATAATCGAGA;

(SEQ ID NO: 196)
CACCGTCCCGCCCATAATCGAGAAG;

(SEQ ID NO: 197)
CACCGCCCATAATCGAGAAGCGACT;

(SEQ ID NO: 198)
CACCGGAGAAGCGACTCGACATGGA;

(SEQ ID NO: 199)
CACCGGAAGCGACTCGACATGGAGG;

(SEQ ID NO: 200)
CACCGGCGACTCGACATGGAGGCGA;

(SEQ ID NO: 201)
AAACTGTCGAGTCGCTTCTCGATTC;

(SEQ ID NO: 202)
AAACGCAGGGCAACGCCCAGGGACC;

(SEQ ID NO: 203)
AAACCTGCAGGGCAACGCCCAGGGC;

(SEQ ID NO: 204)
AAACATTAGTTTATCTTCCCACGGC;

(SEQ ID NO: 205)
AAACGGGCGTTGCCCTGCAGGGGAC;

(SEQ ID NO: 206)
AAACTAATCGAGAAGCGACTCGACC;

(SEQ ID NO: 207)
AAACTACAAGACGGGAGGCAGCAGC;

(SEQ ID NO: 208)
AAACATAAAGGTATTGCGGCACTCC;

(SEQ ID NO: 209)
AAACTTGCTGCACCACCAAAGTGTC;

(SEQ ID NO: 210)
AAACGAGTTTTATACCATTTGAGAC;

-continued (SEQ ID NO: 211)
AAACTCTCGATTATGGGCGGGATTC;

(SEQ ID NO: 212)
AAACCTTCTCGATTATGGGCGGGAC;

(SEQ ID NO: 213)
AAACAGTCGCTTCTCGATTATGGGC;

(SEQ ID NO: 214)
AAACTCCATGTCGAGTCGCTTCTCC;

(SEQ ID NO: 215)
AAACCCTCCATGTCGAGTCGCTTCC;

(SEQ ID NO: 216)
AAACTCGCCTCCATGTCGAGTCGCC;

(SEQ ID NO: 217)
CACCGACAGGGTTAATGTGAAGTCC;

(SEQ ID NO: 218)
CACCGTCCCCCTCTACATTTAAAGT;

(SEQ ID NO: 219)
CACCGCATTTAAAGTTGGTTTAAGT;

(SEQ ID NO: 220)
CACCGTTAGAAAATATAAAGAATAA;

(SEQ ID NO: 221)
CACCGTAAATGCTTACTGGTTTGAA;

(SEQ ID NO: 222)
CACCGTCCTGGGTCCAGAAAAAGAT;

(SEQ ID NO: 223)
CACCGTTGGGTGGTGAGCATCTGTG;

(SEQ ID NO: 224)
CACCGCGGGGAGAGTGGAGAAAAAG;

(SEQ ID NO: 225)
CACCGGTTAAAACTCTTTAGACAAC;

(SEQ ID NO: 226)
CACCGGAAAATCCCCACTAAGATCC;

(SEQ ID NO: 227)
AAACGGACTTCACATTAACCCTGTC;

(SEQ ID NO: 228)
AAACACTTTAAATGTAGAGGGGGAC;

(SEQ ID NO: 229)
AAACACTTAAACCAACTTTAAATGC;

(SEQ ID NO: 230)
AAACTTATTCTTTATATTTTCTAAC;

(SEQ ID NO: 231)
AAACTTCAAACCAGTAAGCATTTAC;

(SEQ ID NO: 232)
AAACATCTTTTTCTGGACCCAGGAC;

(SEQ ID NO: 233)
AAACCACAGATGCTCACCACCCAAC;

(SEQ ID NO: 234)
AAACCTTTTTCTCCACTCTCCCCGC;

(SEQ ID NO: 235)
AAACGTTGTCTAAAGAGTTTTAACC;

(SEQ ID NO: 236)
AAACGGATCTTAGTGGGGATTTTCC;

(SEQ ID NO: 237)
AGTAGCAGTAATGAAGCTGG;

-continued (SEQ ID NO: 238)
ATACCCAGACGAGAAAGCTG;

(SEQ ID NO: 239)
TACCCAGACGAGAAAGCTGA;

(SEQ ID NO: 240)
GGTGGTGAGCATCTGTGTGG;

(SEQ ID NO: 241)
AAATGAGAAGAAGAGGCACA;

(SEQ ID NO: 242)
CTTGTGGCCTGGGAGAGCTG;

(SEQ ID NO: 243)
GCTGTAGAAGGAGACAGAGC;

(SEQ ID NO: 244)
GAGCTGGTTGGGAAGACATG;

(SEQ ID NO: 245)
CTGGTTGGGAAGACATGGGG;

(SEQ ID NO: 246)
CGTGAGGATGGGAAGGAGGG;

(SEQ ID NO: 247)
ATGCAGAGTCAGCAGAACTG;

(SEQ ID NO: 248)
AAGACATCAAGCACAGAAGG;

(SEQ ID NO: 249)
TCAAGCACAGAAGGAGGAGG;

(SEQ ID NO: 250)
AACCGTCAATAGGCAAAGGG;

(SEQ ID NO: 251)
CCGTATTTCAGACTGAATGG;

(SEQ ID NO: 252)
GAGAGGACAGGTGCTACAGG;

(SEQ ID NO: 253)
AACCAAGGAAGGGCAGGAGG;

(SEQ ID NO: 254)
GACCTCTGGGTGGAGACAGA;

(SEQ ID NO: 255)
CAGATGACCATGACAAGCAG;

(SEQ ID NO: 256)
AACACCAGTGAGTAGAGCGG;

(SEQ ID NO: 257)
AGGACCTTGAAGCACAGAGA;

(SEQ ID NO: 258)
TACAGAGGCAGACTAACCCA;

(SEQ ID NO: 259)
ACAGAGGCAGACTAACCCAG;

(SEQ ID NO: 260)
TAAATGACGTGCTAGACCTG;

(SEQ ID NO: 261)
AGTAACCACTCAGGACAGGG;

(SEQ ID NO: 262)
ACCACAAAACAGAAACACCA;

(SEQ ID NO: 263)
GTTTGAAGACAAGCCTGAGG;

(SEQ ID NO: 264)
GCTGAACCCCAAAAGACAGG;

-continued (SEQ ID NO: 265)
GCAGCTGAGACACACACCAG;

(SEQ ID NO: 266)
AGGACACCCCAAAGAAGCTG;

(SEQ ID NO: 267)
GGACACCCCAAAGAAGCTGA;

(SEQ ID NO: 268)
CCAGTGCAATGGACAGAAGA;

(SEQ ID NO: 269)
AGAAGAGGGAGCCTGCAAGT;

(SEQ ID NO: 270)
GTGTTTGGGCCCTAGAGCGA;

(SEQ ID NO: 271)
CATGTGCCTGGTGCAATGCA;

(SEQ ID NO: 272)
TACAAAGAGGAAGATAAGTG;

(SEQ ID NO: 273)
GTCACAGAATACACCACTAG;

(SEQ ID NO: 274)
GGGTTACCCTGGACATGGAA;

(SEQ ID NO: 275)
CATGGAAGGGTATTCACTCG;

(SEQ ID NO: 276)
AGAGTGGCCTAGACAGGCTG;

(SEQ ID NO: 277)
CATGCTGGACAGCTCGGCAG;

(SEQ ID NO: 278)
AGTGAAAGAAGAGAAAATTC;

(SEQ ID NO: 279)
TGGTAAGTCTAAGAAACCTA;

(SEQ ID NO: 280)
CCCACAGCCTAACCACCCTA;

(SEQ ID NO: 281)
AATATTTCAAAGCCCTAGGG;

(SEQ ID NO: 282)
GCACTCGGAACAGGGTCTGG;

(SEQ ID NO: 283)
AGATAGGAGCTCCAACAGTG;

(SEQ ID NO: 284)
AAGTTAGAGCAGCCAGGAAA;

(SEQ ID NO: 285)
TAGAGCAGCCAGGAAAGGGA;

(SEQ ID NO: 286)
TGAATACCCTTCCATGTCCA;

(SEQ ID NO: 287)
CCTGCATTGCACCAGGCACA;

(SEQ ID NO: 288)
TCTAGGGCCCAAACACACCT;

(SEQ ID NO: 289)
TCCCTCCATCTATCAAAAGG;

(SEQ ID NO: 290)
AGCCCTGAGACAGAAGCAGG;

(SEQ ID NO: 291)
GCCCTGAGACAGAAGCAGGT;

-continued (SEQ ID NO: 292)
AGGAGATGCAGTGATACGCA;

(SEQ ID NO: 293)
ACAATACCAAGGGTATCCGG;

(SEQ ID NO: 294)
TGATAAAGAAAACAAAGTGA;

(SEQ ID NO: 295)
AAAGAAAACAAAGTGAGGGA;

(SEQ ID NO: 296)
GTGGCAAGTGGAGAAATTGA;

(SEQ ID NO: 297)
CAAGTGGAGAAATTGAGGGA;

(SEQ ID NO: 298)
GTGGTGATGATTGCAGCTGG;

(SEQ ID NO: 299)
CTATGTGCCTGACACACAGG;

(SEQ ID NO: 300)
GGGTTGGACCAGGAAAGAGG;

(SEQ ID NO: 301)
GATGCCTGGAAAAGGAAAGA;

(SEQ ID NO: 302)
TAGTATGCACCTGCAAGAGG;

(SEQ ID NO: 303)
TATGCACCTGCAAGAGGCGG;

(SEQ ID NO: 304)
AGGGGAAGAAGAGAAGCAGA;

(SEQ ID NO: 305)
GCTGAATCAAGAGACAAGCG;

(SEQ ID NO: 306)
AAGCAAATAAATCTCCTGGG;

(SEQ ID NO: 307)
AGATGAGTGCTAGAGACTGG;
and (SEQ ID NO: 308)
CTGATGGTTGAGCACAGCAG.

See FIG. 4.

Embodiments of the present disclosure make use of the ability of TALE or dCas9/gRNA DBDs to target specific sites in a host genome. The DNA targeting ability of a TALE or dCas9/gRNA DBD is provided by TALE repeat sequences (e.g., modular arrays) or gRNA which are linked together to recognize flanking DNA sequences. Each TALE or gRNA can recognize certain base pair(s) or residue(s).

TALE nucleases (TALENs) are a known tool for genome editing and introducing targeted double-stranded breaks. TALENs comprise endonucleases, such as FokI nuclease domain, fused to a customizable DBD. This DBD is composed of highly conserved repeats derived from TALEs, which are proteins secreted by *Xanthomonas* bacteria to alter transcription of genes in host plant cells. The DBD includes a repeated highly conserved 33-34 amino acid sequence with divergent 12th and 13th amino acids. These two positions, referred to as the RVD, are highly variable and show a strong correlation with specific base pair or nucleotide recognition. This straightforward relationship between amino acid sequence and DNA recognition has allowed for the engineering of specific DBDs by selecting a combination of repeat segments containing the appropriate RVDs. Boch et al. Nature Biotechnology. 2011; 29 (2): 135-6.

Accordingly, TALENs can be readily designed using a "protein-DNA code" that relates modular DNA-binding TALE repeat domains to individual bases in a target-binding site. See Joung et al. *Nat Rev Mol Cell Biol.* 2013; 14(1): 49-55. doi:10.1038/nrm3486. FIG. 3, for example, shows such code.

It has been demonstrated that TALENs can be used to target essentially any DNA sequence of interest in human cell. Miller et al. *Nat Biotechnol.* 2011; 29:143-148. Guidelines for selection of potential target sites and for use of particular TALE repeat domains (harboring NH residues at the hypervariable positions) for recognition of G bases have been proposed. See Streubel et al. *Nat Biotechnol.* 2012; 30:593-595.

Accordingly, in some embodiments, the TALE DBD comprises one or more repeat sequences. In some embodiments, the TALE DBD comprises about 15, or about, 16, or about 17, or about 18, or about 18.5 repeat sequences. In some embodiments, the TALE DBD repeat sequences comprise 33 or 34 amino acids.

In some embodiments, the one or more of the TALE DBD repeat sequences comprise an RVD at residue 12 or 13 of the 33 or 34 amino acids. The RVD can recognize certain base pair(s) or residue(s). In some embodiments, the RVD recognizes one base pair in the nucleic acid molecule. In some embodiments, the RVD recognizes a "C" residue in the nucleic acid molecule and is selected from HD, N(gap), HA, ND, and HI. In some embodiments, the RVD recognizes a "G" residue in the nucleic acid molecule and is selected from NN, NH, NK, HN, and NA. In some embodiments, the RVD recognizes an "A" residue in the nucleic acid molecule and is selected from NI and NS. In some embodiments, the RVD recognizes a "T" residue in the nucleic acid molecule and is selected from NG, HG, H(gap), and IG.

In embodiments, the GSHS is in an open chromatin location in a chromosome. In some embodiments, the GSHS is selected from adeno-associated virus site 1 (AAVS1), chemokine (C-C motif) receptor 5 (CCR5) gene, HIV-1 coreceptor; and human Rosa26 locus. In some embodiments, the GSHS is located on human chromosome 2, 4, 6, 10, 11, or 17.

In some embodiments, the GSHS is selected from TALC1, TALC2, TALC3, TALC4, TALC5, TALC7, TALC8, AVS1, AVS2, AVS3, ROSA1, ROSA2, TALER1, TALER2, TALER3, TALER4, TALER5, SHCHR2-1, SHCHR2-2, SHCHR2-3, SHCHR2-4, SHCHR4-1, SHCHR4-2, SHCHR4-3, SHCHR6-1, SHCHR6-2, SHCHR6-3, SHCHR6-4, SHCHR10-1, SHCHR10-2, SHCHR10-3, SHCHR10-4, SHCHR10-5, SHCHR11-1, SHCHR11-2, SHCHR11-3, SHCHR17-1, SHCHR17-2, SHCHR17-3, and SHCHR17-4.

In some embodiments, the GSHS comprises one or more of TGGCCGGCCTGACCACTGG (SEQ ID NO: 23), TGAAGGCCTGGCCGGCCTG (SEQ ID NO: 24), TGAGCACTGAAGGCCTGGC (SEQ ID NO: 25), TCCACTGAGCACTGAAGGC (SEQ ID NO: 26), TGGTTTCCACTGAGCACTG (SEQ ID NO: 27), TGGGGAAAATGACCCAACA (SEQ ID NO: 28), TAGGACAGTGGGGAAAATG (SEQ ID NO: 29), TCCAGGGACACGGTGCTAG (SEQ ID NO: 30), TCAGAGCCAGGAGTCCTGG (SEQ ID NO: 31), TCCTTCAGAGCCAGGAGTC (SEQ ID NO: 32), TCCTCCTTCAGAGCCAGGA (SEQ ID NO: 33), TCCAGCCCCTCCTCCTTCA (SEQ ID NO: 34), TCCGAGCTTGACCCTTGGA (SEQ ID NO: 35), TGGTTTCCGAGCTTGACCC (SEQ ID NO: 36), TGGGGTGGTTTCCGAGCTT (SEQ ID NO: 37), TCTGCTGGGGTGGTTTCCG (SEQ ID NO: 38), TGCAGAGTATCTGCTGGGG (SEQ ID NO: 39), CCAATCCCCTCAGT (SEQ ID NO: 40), CAGTGCTCAGTGGAA (SEQ ID NO: 41), GAAACATCCGGCGACTCA (SEQ ID NO: 42), TCGCCCCTCAAATCTTACA (SEQ ID NO: 43), TCAAATCTTACAGCTGCTC (SEQ ID NO: 44), TCTTACAGCTGCTCACTCC (SEQ ID NO: 45), TACAGCTGCTCACTCCCCT (SEQ ID NO: 46), TGCTCACTCCCCTGCAGGG (SEQ ID NO: 47), TCCCCTGCAGGGCAACGCC (SEQ ID NO: 48), TGCAGGGCAACGCCCAGGG (SEQ ID NO: 49), TCTCGATTATGGGCGGGAT (SEQ ID NO: 50), TCGCTTCTCGATTATGGGC (SEQ ID NO: 51), TGTCGAGTCGCTTCTCGAT (SEQ ID NO: 52), TCCATGTCGAGTCGCTTCT (SEQ ID NO: 53), TCGCCTCCATGTCGAGTCG (SEQ ID NO: 54), TCGTCATCGCCTCCATGTC (SEQ ID NO: 55), TGATCTCGTCATCGCCTCC (SEQ ID NO: 56), GCTTCAGCTTCCTA (SEQ ID NO: 57), CTGTGATCATGCCA (SEQ ID NO: 58), ACAGTGGTACACACCT (SEQ ID NO: 59), CCACCCCCCACTAAG (SEQ ID NO: 60), CATTGGCCGGGCAC (SEQ ID NO: 61), GCTTGAACCCAGGAGA (SEQ ID NO: 62), ACACCCGATCCACTGGG (SEQ ID NO: 63), GCTGCATCAACCCC (SEQ ID NO: 64), GCCACAAACAGAAATA (SEQ ID NO: 65), GGTGGCTCATGCCTG (SEQ ID NO: 66), GATTTGCACAGCTCAT (SEQ ID NO: 67), AAGCTCTGAGGAGCA (SEQ ID NO: 68), CCCTAGCTGTCCC (SEQ ID NO: 69), GCCTAGCATGCTAG (SEQ ID NO: 70), ATGGGCTTCACGGAT (SEQ ID NO: 71), GAAACTATGCCTGC (SEQ ID NO: 72), GCACCATTGCTCCC (SEQ ID NO: 73), GACATGCAACTCAG (SEQ ID NO: 74), ACACCACTAGGGGT (SEQ ID NO: 75), GTCTGCTAGACAGG (SEQ ID NO: 76), GGCCTAGACAGGCTG (SEQ ID NO: 77), GAGGCATTCTTATCG (SEQ ID NO: 78), GCCTGGAAACGTTCC (SEQ ID NO: 79), GTGCTCTGACAATA (SEQ ID NO: 80), GTTTTGCAGCCTCC (SEQ ID NO: 81), ACAGCTGTGGAACGT (SEQ ID NO: 82), GGCTCTCTTCCTCCT (SEQ ID NO: 83), CTATCCCAAAACTCT (SEQ ID NO: 84), GAAAAACTATGTAT (SEQ ID NO: 85), AGGCAGGCTGGTTGA (SEQ ID NO: 86), CAATACAACCACGC (SEQ ID NO: 87), ATGACGGACTCAACT (SEQ ID NO: 88), CACAACATTTGTAA (SEQ ID NO: 89), and ATTTCCAGTGCACA (SEQ ID NO: 90).

In some embodiments, the TALE DBD binds to one of TGGCCGGCCTGACCACTGG (SEQ ID NO: 23), TGAAGGCCTGGCCGGCCTG (SEQ ID NO: 24), TGAGCACTGAAGGCCTGGC (SEQ ID NO: 25), TCCACTGAGCACTGAAGGC (SEQ ID NO: 26), TGGTTTCCACTGAGCACTG (SEQ ID NO: 27), TGGGGAAAATGACCCAACA (SEQ ID NO: 28), TAGGACAGTGGGGAAAATG (SEQ ID NO: 29), TCCAGGGACACGGTGCTAG (SEQ ID NO: 30), TCAGAGCCAGGAGTCCTGG (SEQ ID NO: 31), TCCTTCAGAGCCAGGAGTC (SEQ ID NO: 32), TCCTCCTTCAGAGCCAGGA (SEQ ID NO: 33), TCCAGCCCCTCCTCCTTCA (SEQ ID NO: 34), TCCGAGCTTGACCCTTGGA (SEQ ID NO: 35), TGGTTTCCGAGCTTGACCC (SEQ ID NO: 36), TGGGGTGGTTTCCGAGCTT (SEQ ID NO: 37), TCTGCTGGGGTGGTTTCCG (SEQ ID NO: 38), TGCAGAGTATCTGCTGGGG (SEQ ID NO: 39), CCAATCCCCTCAGT (SEQ ID NO: 40), CAGTGCTCAGTGGAA (SEQ ID NO: 41), GAAACATCCGGCGACTCA (SEQ ID NO: 42), TCGCCCCTCAAATCTTACA (SEQ ID NO: 43), TCAAATCTTACAGCTGCTC (SEQ ID NO: 44), TCTTACAGCTGCTCACTCC (SEQ ID NO: 45), TACAGCTGCTCACTCCCCT (SEQ ID NO: 46), TGCTCACTCCCCTGCAGGG (SEQ ID NO: 47), TCCCCTGCAGGGCAACGCC (SEQ ID NO: 48), TGCAGGGCAACGCCCAGGG (SEQ ID NO: 49), TCTCGATTATGGGCGGGAT (SEQ ID NO: 50), TCGCTTCTCGATTATGGGC (SEQ ID NO: 51), TGTCGAGTCGCTTCTCGAT (SEQ ID NO: 52), TCCATGTCGAGTCGCTTCT (SEQ ID NO: 53), TCGCCTCCATGTCGAGTCG (SEQ ID NO: 54), TCGTCATCGCCTCCATGTC (SEQ ID NO: 55), TGATCTCGTCATCGCCTCC (SEQ ID NO: 56), GCTTCAGCTTCCTA (SEQ ID NO: 57), CTGTGATCATGCCA (SEQ ID NO: 58), ACAGTGGTACACACCT (SEQ ID NO: 59), CCACCCCCCACTAAG (SEQ ID NO: 60), CATTGGCCGGGCAC (SEQ ID NO: 61), GCTTGAACCCAGGAGA (SEQ ID NO: 62), ACACCCGATCCACTGGG (SEQ ID NO: 63), GCTGCATCAACCCC (SEQ ID NO: 64), GCCACAAACAGAAATA (SEQ ID NO: 65), GGTGGCTCATGCCTG (SEQ ID NO: 66), GATTTGCACAGCTCAT (SEQ ID NO: 67), AAGCTCTGAGGAGCA (SEQ ID NO: 68), CCCTAGCTGTCCC (SEQ ID NO: 69), GCCTAGCATGCTAG (SEQ ID NO: 70), ATGGGCTTCACGGAT (SEQ ID NO: 71), GAAACTATGCCTGC (SEQ ID NO: 72), GCACCATTGCTCCC (SEQ ID NO: 73), GACATGCAACTCAG (SEQ ID NO: 74), ACACCACTAGGGGT (SEQ ID NO: 75), GTCTGCTAGACAGG (SEQ ID NO: 76), GGCCTAGACAGGCTG (SEQ ID NO: 77), GAGGCATTCTTATCG (SEQ ID NO: 78), GCCTGGAAACGTTCC (SEQ ID NO: 79), GTGCTCTGACAATA (SEQ ID NO: 80), GTTTTGCAGCCTCC (SEQ ID NO: 81), ACAGCTGTGGAACGT (SEQ ID NO: 82), GGCTCTCTTCCTCCT (SEQ ID NO: 83), CTATCCCAAAACTCT (SEQ ID NO: 84), GAAAAACTATGTAT (SEQ ID NO: 85), AGGCAGGCTGGTTGA (SEQ ID NO: 86), CAATACAACCACGC (SEQ ID NO: 87), ATGACGGACTCAACT (SEQ ID NO: 88), CACAACATTTGTAA (SEQ ID NO: 89), and ATTTCCAGTGCACA (SEQ ID NO: 90).

In some embodiments, the TALE DBD comprises one or more of

```
                                          (SEQ ID NO: 355)
NH NH HD HD NH NH HD HD NG NH NI HD HD NI HD NG NH
NH,

                                          (SEQ ID NO: 356)
NH NI NI NH NH HD HD NG NH NH HD HD NH NH HD HD NG
NH,

                                          (SEQ ID NO: 357)
NH NI NH HD NI HD NG NH NI NI NH NH HD HD NG NH NH
HD,

                                          (SEQ ID NO: 358)
HD HD NI HD NG NH NI NH HD NI HD NG NH NI NI NH NH
HD,

                                          (SEQ ID NO: 359)
NH NH NG NG NG HD HD NI HD NG NH NI NH HD NI HD NG
NH,
```

-continued (SEQ ID NO: 360)
NH NH NH NH NI NI NI NI NG NH NI HD HD HD NI NI HD NI, (SEQ ID NO: 361)
NI NH NH NI HD NI NH NG NH NH NH NH NI NI NI NI NG NH, (SEQ ID NO: 362)
HD HD NI NH NH NH NI HD NI HD NH NH NG NH HD NG NI NH, (SEQ ID NO: 363)
HD NI NH NI NH HD HD NI NH NH NI NH NG HD HD NG NH NH, (SEQ ID NO: 364)
HD HD NG NG HD NI NH NI NH HD HD NI NH NH NI NH NG HD, (SEQ ID NO: 365)
HD HD NG HD HD NG NG HD NI NH NI NH HD HD NI NH NH NI, (SEQ ID NO: 366)
HD HD NI NH HD HD HD HD NG HD HD NG HD HD NG NG HD NI, (SEQ ID NO: 367)
HD HD NH NI NH HD NG NG NH NI HD HD HD NG NG NH NH NI, (SEQ ID NO: 368)
NH NH NG NG NG HD HD NH NI NH HD NG NG NH NI HD HD HD, (SEQ ID NO: 369)
NH NH NH NH NG NH NH NG NG NG HD HD NH NI NH HD NG NG, (SEQ ID NO: 370)
HD NG NH HD NG NH NH NH NH NG NH NH NG NG NG HD HD NH, (SEQ ID NO: 371)
NH HD NI NH NI NH NG NI NG HD NG NH HD NG NH NH NH NH, (SEQ ID NO: 372)
HD HD NI NI NG HD HD HD HD NG HD NI NH NG, (SEQ ID NO: 373)
HD NI NH NG NH HD NG HD NI NH NG NH NH NI NI, (SEQ ID NO: 374)
NH NI NI NI HD NI NG HD HD NH NH HD NH NI HD NG HD NI, (SEQ ID NO: 375)
HD NH HD HD HD HD NG HD NI NI NI NG HD NG NG NI HD NI, (SEQ ID NO: 376)
HD NI NI NI NG HD NG NG NI HD NI NH HD NG NH HD NG HD, (SEQ ID NO: 377)
HD NG NG NI HD NI NH HD NG NH HD NG HD NI HD NG HD HD, (SEQ ID NO: 378)
NI HD NI NH HD NG NH HD NG HD NI HD NG HD HD HD HD NG, (SEQ ID NO: 379)
NH HD NG HD NI HD NG HD HD HD HD NG NH HD NI NH NH NH, (SEQ ID NO: 380)
HD HD HD HD NG NH HD NI NH NH NH HD NI NI HD NH HD HD, (SEQ ID NO: 381)
NH HD NI NH NH NH HD NI NI HD NH HD HD HD NI NH NH NH, (SEQ ID NO: 382)
HD NG HD NH NI NG NG NI NG NH NH NH HD NH NH NH NI NG, (SEQ ID NO: 383)
HD NH HD NG NG HD NG HD NH NI NG NG NI NG NH NH NH HD, (SEQ ID NO: 384)
NH NG HD NH NI NH NG HD NH HD NG NG HD NG HD NH NI NG, (SEQ ID NO: 385)
HD HD NI NG NH NG HD NH NI NH NG HD NH HD NG NG HD NG, (SEQ ID NO: 386)
HD NH HD HD NG HD HD NI NG NH NG HD NH NI NH NG HD NH, (SEQ ID NO: 387)
HD NH NG HD NI NG HD NH HD HD NG HD HD NI NG NH NG HD, (SEQ ID NO: 388)
NH NI NG HD NG HD NH NG HD NI NG HD NH HD HD NG HD HD, (SEQ ID NO: 389)
NH HD NG NG HD NI NH HD NG NG HD HD NG NI, (SEQ ID NO: 390)
HD NG NK NG NH NI NG HD NI NG NH HD HD NI, (SEQ ID NO: 391)
NI HD NI NN NG NN NN NG NI HD NI HD NI HD HD NG, (SEQ ID NO: 392)
HD HD NI HD HD HD HD HD HD NI HD NG NI NI NN, (SEQ ID NO: 393)
HD NI NG NG NN NN HD HD NN NN NN HD NI HD, (SEQ ID NO: 394)
NN HD NG NG NN NI NI HD HD HD NI NN NN NI NN NI, (SEQ ID NO: 395)
NI HD NI HD HD HD NN NI NG HD HD NI HD NG NN NN NN, -continued (SEQ ID NO: 396)
NN HD NG NN HD NI NG HD NI NI HD HD HD HD, (SEQ ID NO: 397)
NN NN HD NI HD NN NI NI NI HD NI HD HD HD NG HD HD, (SEQ ID NO: 398)
NN NN NG NN NN HD NG HD NI NG NN HD HD NG NN, (SEQ ID NO: 399)
NN NI NG NG NG NN HD NI HD NI NN HD NG HD NI NG, (SEQ ID NO: 400)
NI NI NH HD NG HD NG NH NI NH NH NI NH HD, (SEQ ID NO: 401)
HD HD HD NG NI NK HD NG NH NG HD HD HD HD, (SEQ ID NO: 402)
NH HD HD NG NI NH HD NI NG NH HD NG NI NH, (SEQ ID NO: 403)
NI NG NH NH NH HD NG NG HD NI HD NH NH NI NG, (SEQ ID NO: 404)
NH NI NI NI HD NG NI NG NH HD HD NG NH HD, (SEQ ID NO: 405)
NH HD NI HD HD NI NG NG NH HD NG HD HD HD, (SEQ ID NO: 406)
NH NI HD NI NG NH HD NI NI HD NG HD NI NH, (SEQ ID NO: 407)
NI HD NI HD HD NI HD NG NI NH NH NH NH NG, (SEQ ID NO: 408)
NH NG HD NG NH HD NG NI NH NI HD NI NH NH, (SEQ ID NO: 409)
NH NH HD HD NG NI NH NI HD NI NH NH HD NG NH, (SEQ ID NO: 410)
NH NI NH NH HD NI NG NG HD NG NG NI NG HD NH, (SEQ ID NO: 411)
NN HD HD NG NN NN NI NI NI HD NN NG NG HD HD, (SEQ ID NO: 412)
NN NG NN HD NG HD NG NN NI HD NI NI NG NI, (SEQ ID NO: 413)
NN NG NG NG NG NN HD NI NN HD HD NG HD HD, (SEQ ID NO: 414)
NI HD NI NN HD NG NN NG NN NN NI NI HD NN NG, (SEQ ID NO: 415)
HD NI NI NN NI HD HD NN NI NN HD NI HD NG NN HD NG NN, (SEQ ID NO: 416)
HD NG NI NG HD HD HD NI NI NI NI HD NG HD NG, (SEQ ID NO: 417)
NH NI NI NI NI NI HD NG NI NG NH NG NI NG, (SEQ ID NO: 418)
NI NH NH HD NI NH NH HD NG NH NH NG NG NH NI, (SEQ ID NO: 419)
HD NI NI NG NI HD NI NI HD HD NI HD NN HD, (SEQ ID NO: 420)
NI NG NN NI HD NN NN NI HD NG HD NI NI HD NG, (SEQ ID NO: 421)
HD NI HD NI NI HD NI NG NG NG NN NG NI NI,
and -continued (SEQ ID NO: 422)
NI NG NG NG HD HD NI NN NG NN HD NI HD NI.

In some embodiments, the GSHS is selected from sites listed in FIG. 3 and the TALE DBD comprises a sequence of FIG. 3.

In some embodiments, the TALE DBD comprises one or more of the sequences of FIG. 3 or a sequence having at least about 90%, or at least about 93%, or at least about 95%, or at least about 97%, or at least about 98%, or at least about 99% identity thereto.

In some embodiments, the GSHS and the TALE DBD sequences are selected from:

(SEQ ID NO: 23)
TGGCCGGCCTGACCACTGG
and (SEQ ID NO: 355)
NH NH HD HD NH NH HD HD NG NH NI HD HD NI HD NG NH NH;

(SEQ ID NO: 24)
TGAAGGCCTGGCCGGCCTG
and (SEQ ID NO: 356)
NH NI NI NH NH HD HD NG NH NH HD HD NH NH HD HD NG NH;

(SEQ ID NO: 25)
TGAGCACTGAAGGCCTGGC
and (SEQ ID NO: 357)
NH NI NH HD NI HD NG NH NI NI NH NH HD HD NG NH NH HD;

(SEQ ID NO: 26)
TCCACTGAGCACTGAAGGC
and (SEQ ID NO: 358)
HD HD NI HD NG NH NI NH HD NI HD NG NH NI NI NH NH HD;

(SEQ ID NO: 27)
TGGTTTCCACTGAGCACTG
and (SEQ ID NO: 359)
NH NH NG NG NG HD HD NI HD NG NH NI NH HD NI HD NG NH;

(SEQ ID NO: 28)
TGGGGAAAATGACCCAACA
and (SEQ ID NO: 360)
NH NH NH NH NI NI NI NI NG NH NI HD HD HD NI NI HD NI;

(SEQ ID NO: 29)
TAGGACAGTGGGGAAAATG
and (SEQ ID NO: 361)
NI NH NH NI HD NI NH NG NH NH NH NH NI NI NI NI NG NH;

-continued (SEQ ID NO: 30)
TCCAGGGACACGGTGCTAG
and (SEQ ID NO: 362)
HD HD NI NH NH NH NI HD NI HD NH NH NG NH HD NG NI NH;

(SEQ ID NO: 31)
TCAGAGCCAGGAGTCCTGG
and (SEQ ID NO: 363)
HD NI NH NI NH HD HD NI NH NH NI NH NG HD HD NG NH NH;

(SEQ ID NO: 32)
TCCTTCAGAGCCAGGAGTC
and (SEQ ID NO: 364)
HD HD NG NG HD NI NH NI NH HD HD NI NH NH NI NH NG HD;

(SEQ ID NO: 33)
TCCTCCTTCAGAGCCAGGA
and (SEQ ID NO: 365)
HD HD NG HD HD NG NG HD NI NH NI NH HD HD NI NH NH NI;

(SEQ ID NO: 34)
TCCAGCCCCTCCTCCTTCA
and (SEQ ID NO: 366)
HD HD NI NH HD HD HD HD NG HD HD NG HD HD NG NG HD NI;

(SEQ ID NO: 35)
TCCGAGCTTGACCCTTGGA
and (SEQ ID NO: 367)
HD HD NH NI NH HD NG NG NH NI HD HD HD NG NG NH NH NI;

(SEQ ID NO: 36)
TGGTTTCCGAGCTTGACCC
and (SEQ ID NO: 368)
NH NH NG NG NG HD HD NH NI NH HD NG NG NH NI HD HD HD;

(SEQ ID NO: 37)
TGGGGTGGTTTCCGAGCTT
and (SEQ ID NO: 369)
NH NH NH NH NG NH NH NG NG NG HD HD NH NI NH HD NG NG;

(SEQ ID NO: 38)
TCTGCTGGGGTGGTTTCCG
and (SEQ ID NO: 370)
HD NG NH HD NG NH NH NH NH NG NH NH NG NG NG HD HD NH;

-continued (SEQ ID NO: 39)
TGCAGAGTATCTGCTGGGG
and (SEQ ID NO: 371)
NH HD NI NH NI NH NG NI NG HD NG NH HD NG NH NH NH NH;

(SEQ ID NO: 40)
CCAATCCCCTCAGT
and (SEQ ID NO: 372)
HD HD NI NI NG HD HD HD HD NG HD NI NH NG;

(SEQ ID NO: 41)
CAGTGCTCAGTGGAA
and (SEQ ID NO: 373)
HD NI NH NG NH HD NG HD NI NH NG NH NH NI NI;

(SEQ ID NO: 42)
GAAACATCCGGCGACTCA
and (SEQ ID NO: 374)
NH NI NI NI HD NI NG HD HD NH NH HD NH NI HD NG HD NI;

(SEQ ID NO: 43)
TCGCCCCTCAAATCTTACA
and (SEQ ID NO: 375)
HD NH HD HD HD HD NG HD NI NI NI NG HD NG NG NI HD NI;

(SEQ ID NO: 44)
TCAAATCTTACAGCTGCTC
and (SEQ ID NO: 376)
HD NI NI NI NG HD NG NG NI HD NI NH HD NG NH HD NG HD;

(SEQ ID NO: 45)
TCTTACAGCTGCTCACTCC
and (SEQ ID NO: 377)
HD NG NG NI HD NI NH HD NG NH HD NG HD NI HD NG HD HD;

(SEQ ID NO: 46)
TACAGCTGCTCACTCCCCT
and (SEQ ID NO: 378)
NI HD NI NH HD NG NH HD NG HD NI HD NG HD HD HD HD NG;

(SEQ ID NO: 47)
TGCTCACTCCCCTGCAGGG
and (SEQ ID NO: 379)
NH HD NG HD NI HD NG HD HD HD HD NG NH HD NI NH NH NH;

(SEQ ID NO: 48)
TCCCCTGCAGGGCAACGCC
and

-continued (SEQ ID NO: 380)
HD HD HD HD NG NH HD NI NH NH NH HD NI NI HD NH HD HD;

(SEQ ID NO: 49)
TGCAGGGCAACGCCCAGGG
and (SEQ ID NO: 381)
NH HD NI NH NH NH HD NI NI HD NH HD HD HD NI NH NH NH;

(SEQ ID NO: 50)
TCTCGATTATGGGCGGGAT
and (SEQ ID NO: 382)
HD NG HD NH NI NG NG NI NG NH NH NH HD NH NH NH NI NG;

(SEQ ID NO: 51)
TCGCTTCTCGATTATGGGC
and (SEQ ID NO: 383)
HD NH HD NG NG HD NG HD NH NI NG NG NI NG NH NH NH HD;

(SEQ ID NO: 52)
TGTCGAGTCGCTTCTCGAT
and (SEQ ID NO: 384)
NH NG HD NH NI NH NG HD NH HD NG NG HD NG HD NH NI NG;

(SEQ ID NO: 53)
TCCATGTCGAGTCGCTTCT
and (SEQ ID NO: 385)
HD HD NI NG NH NG HD NH NI NH NG HD NH HD NG NG HD NG;

(SEQ ID NO: 54)
TCGCCTCCATGTCGAGTCG
and (SEQ ID NO: 386)
HD NH HD HD NG HD HD NI NG NH NG HD NH NI NH NG HD NH;

(SEQ ID NO: 55)
TCGTCATCGCCTCCATGTC
and (SEQ ID NO: 387)
HD NH NG HD NI NG HD NH HD HD NG HD HD NI NG NH NG HD;

(SEQ ID NO: 56)
TGATCTCGTCATCGCCTCC
and (SEQ ID NO: 388)
NH NI NG HD NG HD NH NG HD NI NG HD NH HD HD NG HD HD;

(SEQ ID NO: 57)
GCTTCAGCTTCCTA
and

-continued (SEQ ID NO: 389)
NH HD NG NG HD NI NH HD NG NG HD HD NG NI;

(SEQ ID NO: 58)
CTGTGATCATGCCA
and (SEQ ID NO: 390)
HD NG NK NG NH NI NG HD NI NG NH HD HD NI;

(SEQ ID NO: 59)
ACAGTGGTACACACCT
and (SEQ ID NO: 391)
NI HD NI NN NG NN NN NG NI HD NI HD NI HD HD NG;

(SEQ ID NO: 60)
CCACCCCCCACTAAG
and (SEQ ID NO: 392)
HD HD NI HD HD HD HD HD HD NI HD NG NI NI NN;

(SEQ ID NO: 61)
CATTGGCCGGGCAC
and (SEQ ID NO: 393)
HD NI NG NG NN NN HD HD NN NN NN HD NI HD;

(SEQ ID NO: 62)
GCTTGAACCCAGGAGA
and (SEQ ID NO: 394)
NN HD NG NG NN NI NI HD HD HD NI NN NN NI NN NI;

(SEQ ID NO: 63)
ACACCCGATCCACTGGG
and (SEQ ID NO: 395)
NI HD NI HD HD HD NN NI NG HD HD NI HD NG NN NN NN;

(SEQ ID NO: 64)
GCTGCATCAACCCC
and (SEQ ID NO: 396)
NN HD NG NN HD NI NG HD NI NI HD HD HD HD;

(SEQ ID NO: 65)
GCCACAAACAGAAATA
and (SEQ ID NO: 397)
NN NN HD NI HD NN NI NI NI HD NI HD HD HD NG HD HD;

(SEQ ID NO: 66)
GGTGGCTCATGCCTG
and (SEQ ID NO: 398)
NN NN NG NN NN HD NG HD NI NG NN HD HD NG NN;

(SEQ ID NO: 67)
GATTTGCACAGCTCAT
and (SEQ ID NO: 399)
NN NI NG NG NG NN HD NI HD NI NN HD NG HD NI NG;

(SEQ ID NO: 68)
AAGCTCTGAGGAGCA
and

-continued (SEQ ID NO: 400)
NI NI NH HD NG HD NG NH NI NH NH NI NH HD;

(SEQ ID NO: 69)
CCCTAGCTGTCCC
and (SEQ ID NO: 401)
HD HD HD NG NI NK HD NG NH NG HD HD HD HD;

(SEQ ID NO: 70)
GCCTAGCATGCTAG
and (SEQ ID NO: 402)
NH HD HD NG NI NH HD NI NG NH HD NG NI NH;

(SEQ ID NO: 71)
ATGGGCTTCACGGAT
and (SEQ ID NO: 403)
NI NG NH NH NH HD NG NG HD NI HD NH NH NI NG;

(SEQ ID NO: 72)
GAAACTATGCCTGC
and (SEQ ID NO: 404)
NH NI NI NI HD NG NI NG NH HD HD NG NH HD;

(SEQ ID NO: 73)
GCACCATTGCTCCC
and (SEQ ID NO: 405)
NH HD NI HD HD NI NG NG NH HD NG HD HD HD;

(SEQ ID NO: 74)
GACATGCAACTCAG
and (SEQ ID NO: 406)
NH NI HD NI NG NH HD NI NI HD NG HD NI NH;

(SEQ ID NO: 75)
ACACCACTAGGGGT
and (SEQ ID NO: 407)
NI HD NI HD HD NI HD NG NI NH NH NH NH NG;

(SEQ ID NO: 76)
GTCTGCTAGACAGG
and (SEQ ID NO: 408)
NH NG HD NG NH HD NG NI NH NI HD NI NH NH;

(SEQ ID NO: 77)
GGCCTAGACAGGCTG
and (SEQ ID NO: 409)
NH NH HD HD NG NI NH NI HD NI NH NH HD NG NH;

(SEQ ID NO: 78)
GAGGCATTCTTATCG
and (SEQ ID NO: 410)
NH NI NH NH HD NI NG NG HD NG NG NI NG HD NH;

(SEQ ID NO: 79)
GCCTGGAAACGTTCC
and (SEQ ID NO: 411)
NN HD HD NG NN NN NI NI NI HD NN NG NG HD HD;

-continued (SEQ ID NO: 80)
GTGCTCTGACAATA
and (SEQ ID NO: 412)
NN NG NN HD NG HD NG NN NI HD NI NI NG NI;

(SEQ ID NO: 81)
GTTTTGCAGCCTCC
and (SEQ ID NO: 413)
NN NG NG NG NG NN HD NI NN HD HD NG HD HD;

(SEQ ID NO: 82)
ACAGCTGTGGAACGT
and (SEQ ID NO: 414)
NI HD NI NN HD NG NN NG NN NN NI NI HD NN NG;

(SEQ ID NO: 83)
GGCTCTCTTCCTCCT
and (SEQ ID NO: 415)
HD NI NI NN NI HD HD NN NI NN HD NI HD NG NN HD NG NN;

(SEQ ID NO: 84)
CTATCCCAAAACTCT
and (SEQ ID NO: 416)
HD NG NI NG HD HD HD NI NI NI NI HD NG HD NG;

(SEQ ID NO: 85)
GAAAAACTATGTAT
and (SEQ ID NO: 417)
NH NI NI NI NI NI HD NG NI NG NH NG NI NG;

(SEQ ID NO: 86)
AGGCAGGCTGGTTGA
and (SEQ ID NO: 418)
NI NH NH HD NI NH NH HD NG NH NH NG NG NH NI;

(SEQ ID NO: 87)
CAATACAACCACGC
and (SEQ ID NO: 419)
HD NI NI NG NI HD NI NI HD HD NI HD NN HD;

(SEQ ID NO: 88)
ATGACGGACTCAACT
and (SEQ ID NO: 420)
NI NG NN NI HD NN NN NI HD NG HD NI NI HD NG;
and (SEQ ID NO: 89)
CACAACATTTGTAA
and (SEQ ID NO: 421)
HD NI HD NI NI HD NI NG NG NG NN NG NI NI.

In some embodiments, the GSHS is within about 25, or about 50, or about 100, or about 150, or about 200, or about 300, or about 500 nucleotides of the TA dinucleotide site or TTAA (SEQ ID NO: 1) tetranucleotide site.

In some embodiments, guide RNAs (gRNAs) for targeting human genomic safe harbor sites using dCas in areas of open chromatin are as shown in FIG. 4.

In embodiments, the enzyme (e.g., without limitation, a transposase enzyme) is capable of inserting a transposon at a TA dinucleotide site. In some embodiments, the enzyme (e.g., without limitation, a transposase enzyme) is capable of inserting a transposon at a TTAA (SEQ ID NO: 1) tetranucleotide site.

Figure 1A:
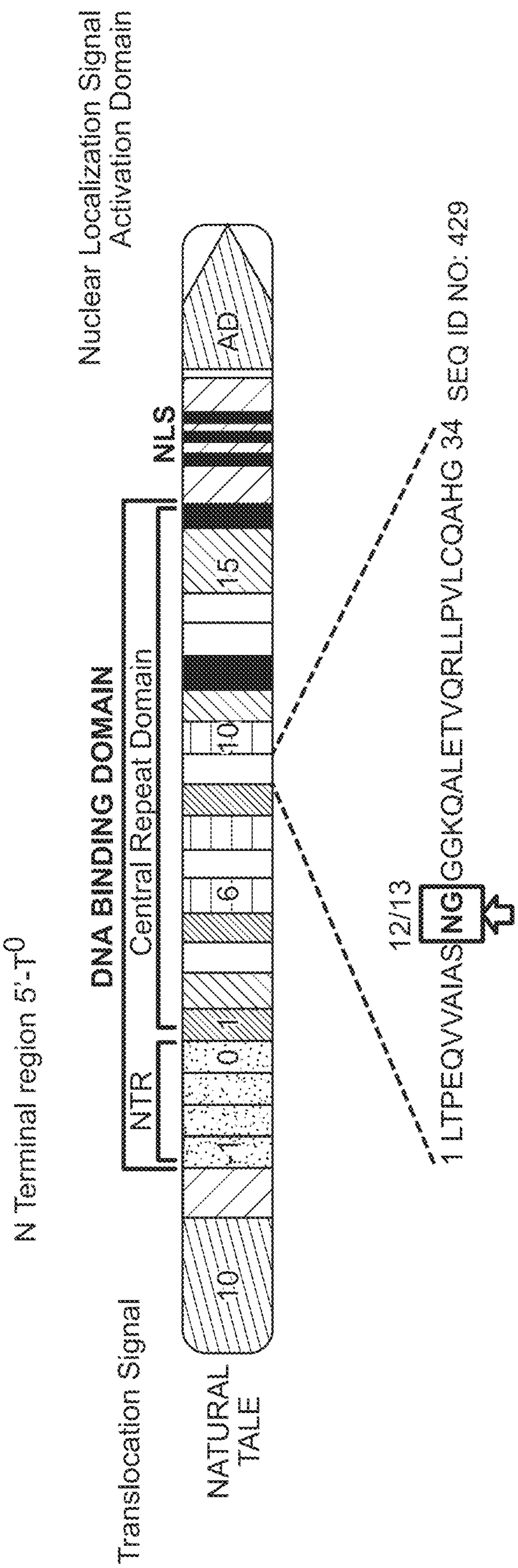
FIGS. 1A-D depict non-limiting representations of chimeric, monomer or head-to-tail dimer transposases that are designed to target human GSHS using TALE and Cas9/guide RNA DNA binders.
Figure 1B:
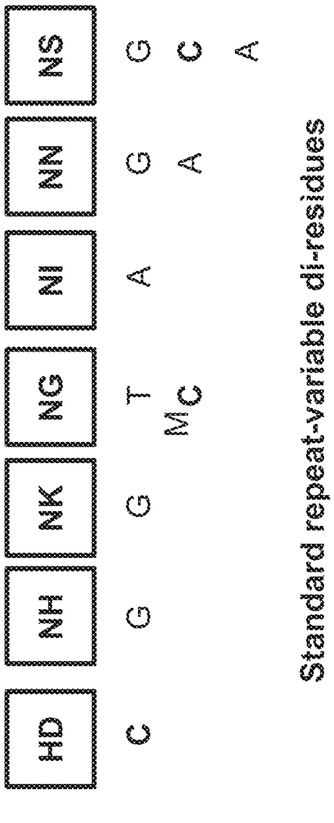
Figure 1C:
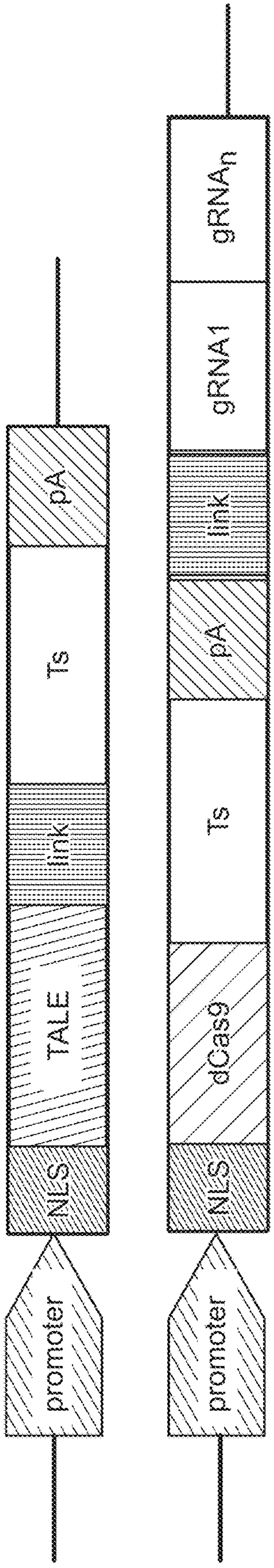
Figure 1D:
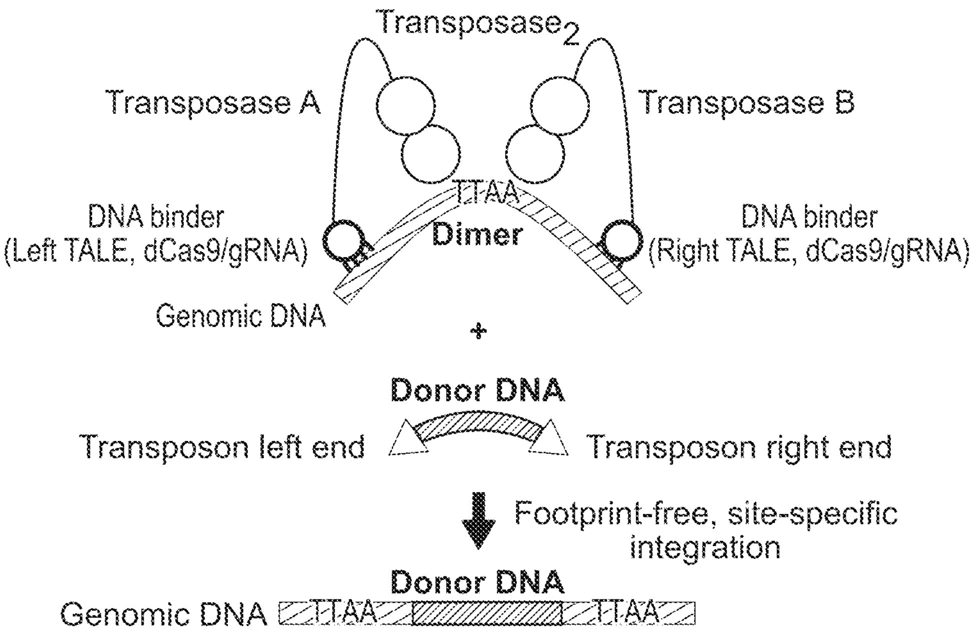
Figure 2:
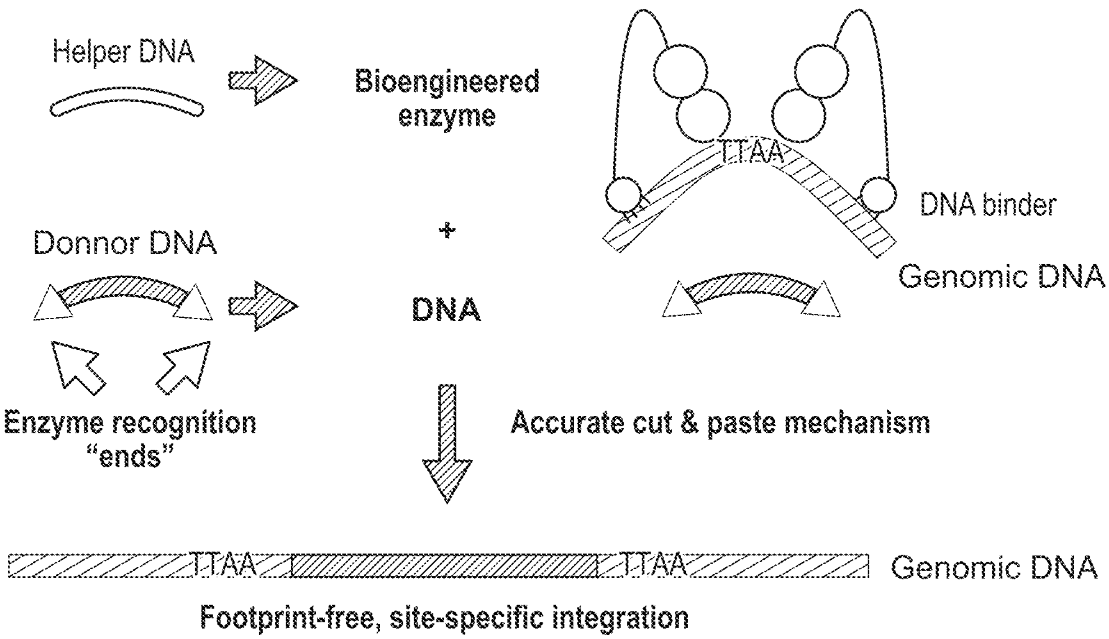
FIG. 2 is a non-limiting representation of a system in accordance with embodiments of the present disclosure comprising a nucleic acid (e.g., helper RNA) encoding an enzyme capable of targeted genomic integration by transposition and a nucleic acid encoding a transposase (donor DNA). The helper RNA is translated into a bioengineered enzyme (e.g., integrase, recombinase, or transposase) that recognizes specific ends and seamlessly inserts the donor DNA into the human genome in a site-specific manner without a footprint. The enzyme can form a dimer or a tetramer at open chromatin to insert donor DNA at TTAA (SEQ ID NO: 1) recognition sites near DNA binding regions targeted by dCas9/gRNA or TALEs. Binding of the dCas9/gRNA to TALE GSHS physically sequesters the enzyme to the same location and promotes transposition to the nearby TTAA (SEQ ID NO: 1) sequences (see FIG. 3 and FIG. 4).

In embodiments, the composition comprises a system having nucleic acids encoding the enzyme and the transposon, respectively. FIGS. 1A-1D show examples of a system in accordance with embodiments of the present disclosure. For example, as shown in FIG. 2, in some embodiments, the system comprises a nucleic acid (e.g., helper RNA) encoding an enzyme capable of targeted genomic integration by transposition, and a nucleic acid encoding a transposase (e.g., donor DNA). The helper RNA is translated into a bioengineered enzyme (e.g., integrase, recombinase, or transposase) that recognizes specific ends and seamlessly inserts the donor DNA into the human genome in a site-specific manner without a footprint.

In embodiments, an enzyme capable of targeted genomic integration by transposition is encoded by a first nucleic acid, and the transposon is encoded by a second, non-viral nucleic acid. The transposon comprises a transgene and is flanked by ends recognized by the enzyme, and the enzyme causes the transgene be inserted in a certain genomic locus and/or site (e.g., at a TA dinucleotide site or a TTAA (SEQ ID NO: 1) tetranucleotide site in a genomic safe harbor site (GSHS) of a nucleic acid molecule. In some embodiments, the first nucleic acid is RNA, for example, helper RNA; and the second, non-viral nucleic acid is DNA. In embodiments, inteins (also referred to as splicing domains) are used to synthesize a recombinant enzyme (e.g., without limitation, an MLT fusion protein) that includes desired internal DNA biding domains (DNA binders) that target specific sites within the human genome for integration of a donor transgene.

Inteins (INTervening protEINS) are mobile genetic elements that are protein domains, found in nature, with the capability to carry out the process of protein splicing. See Sarmiento & Camarero (2019) *Current protein & peptide science,* 20(5), 408-424, which is incorporated by reference herein in its entirety. Protein spicing is a post-translation biochemical modification which results in the cleavage and formation of peptide bonds between precursor polypeptide segments flanking the intein. Id. Inteins apply standard enzymatic strategies to excise themselves post-translationally from a precursor protein via protein splicing. Nanda et al., Microorganisms vol. 8, 12 2004. 16 Dec. 2020, doi: 10.3390/microorganisms8122004. An intein can splice its flanking N- and C-terminal domains to become a mature protein and excise itself from a sequence. For example, split inteins have been used to control the delivery of heterologous genes into transgenic organisms. See Wood & Camarero (2014) *J Biol Chem.* 289(21):14512-14519. This approach relies on splitting the target protein into two segments, which are then post-translationally reconstituted in vivo by protein trans-splicing (PTS). See Aboye & Camarero (2012) *J. Biol. Chem.* 287, 27026-27032. More recently, an intein-mediated split-Cas9 system has been developed to incorporate Cas9 into cells and reconstitute nuclease activity efficiently. Truong et al., *Nucleic Acids Res.* 2015, 43 (13), 6450-6458. The protein splicing excises the internal region of the precursor protein, which is then followed by the ligation of the N-extein and C-extein fragments, resulting in two polypeptides—the excised intein and the new polypeptide produced by joining the C- and N-exteins. Sarmiento & Camarero (2019).

In embodiments, intein-mediated incorporation of DNA binders such as, without limitation, dCas9, dCas12j, or TALEs, allows creation of a split-MLT transposase system that permits reconstitution of the full-length MLT transposase from two smaller fragments. This allows avoiding the need to express DNA binders at the N- or C-terminus of an MLT transposase. In this approach, the two portions of an MLT transposase are fused to the intein and, after co-expression, the intein allows producing a full-length MLT transposase by post-translation modification. Thus, in embodiments, a nucleic acid encoding the enzyme capable of targeted genomic integration by transposition comprises an intein. In embodiments, the nucleic acid encodes the enzyme in the form of first and second portions with the intein encoded between the first and second portions, such that the first and second portions are fused into a functional enzyme upon post-translational excision of the intein from the enzyme.

In embodiments, an intein can be a suitable ligand-dependent intein, for example, an intein selected from those described in U.S. Pat. No. 9,200,045; Mootz et al., J. Am. Chem. Soc. 2002; 124, 9044-9045; Mootz et al., *J. Am. Chem. Soc.* 2003; 125, 10561-10569; Buskirk et al., *Proc. Natl. Acad. Sci. USA.* 2004; 101, 10505-10510; Skretas & Wood. *Protein Sci.* 2005; 14, 523-532; Schwartz, et al., *Nat. Chem. Biol.* 2007; 3, 50-54; Peck et al., *Chem. Biol.* 2011; 18 (5), 619-630; the entire contents of each of which are hereby incorporated by reference herein.

In embodiments the intein is NpuN (Intein-N) (SEQ ID NO: 423) and/or NpuC (Intein-C) (SEQ ID NO: 424), or a variant thereof, e.g. a sequence having at least about 90%, or at least about 93%, or at least about 95%, or at least about 97%, or at least about 98%, or at least about 99% identity thereto.

In embodiments, an enzyme capable of targeted genomic integration by transposition is, without limitation, a transposase enzyme. In embodiments, the transposase enzyme is derived from *Bombyx mori, Xenopus tropicalis*, or *Trichoplusia ni*. In embodiments, the enzyme (e.g., without limitation, a transposase enzyme) is an engineered version of a transposase enzyme, including but not limited to monomers, dimers, tetramers, hyperactive, or Int-forms, derived from *Bombyx mori, Xenopus tropicalis*, or *Trichoplusia ni*.

In embodiments, the transposase enzyme is an engineered version, including but not limited to a transposase enzyme that is a monomer, dimer, tetramer, hyperactive, or has a reduced interaction with non-TTAA (SEQ ID NO: 1) recognitions sites (Int−), derived from any of *Bombyx mori, Xenopus tropicalis, Trichoplusia ni, Rhinolophus ferrumequinum, Rousettus aegyptiacus, Phyllostomus discolor, Myotis myotis, Myotis lucifugus, Pipistrellus kuhlii, Pteropus vampyrus*, and *Molossus molossus Bombyx mori, Xenopus tropicalis, Trichoplusia ni* or *Myotis lucifugus*. The transposase enzyme can be either the wild type, monomer, dimer, tetramer, hyperactive, or an Int-mutant.

In some embodiments, the linker that connects the TALE DBD or dCas9/gRNA and the transposase enzyme is a flexible linker. In some embodiments, the flexible linker is substantially comprised of glycine and serine residues, optionally wherein the flexible linker comprises $(Gly_4Ser)_n$ (SEQ ID NO: 435), where n is from about 1 to about 12. The flexible linker can be about 20, or about 30, or about 40, or about 50, or about 60 amino acid residues.

In some aspects, a nucleic acid encoding a chimeric transposase in accordance with embodiments of the present disclosure is provided. The nucleic acid can be DNA or RNA. In some embodiments, the chimeric transposase is incorporated into a vector. In some embodiments, the vector is a non-viral vector.

In some aspects, a host cell comprising the nucleic acid in accordance with embodiments of the present disclosure is provided.

In some embodiments, a composition or a nucleic acid in accordance with embodiments of the present disclosure is provided wherein the composition is in the form of a lipid nanoparticle (LNP). The composition can comprise one or more lipids selected from 1,2-dioleoyl-3-trimethylammonium propane (DOTAP), a cationic cholesterol derivative mixed with dimethylaminoethane-carbamoyl (DC-Chol), phosphatidylcholine (PC), triolein (glyceryl trioleate), and 1,2-distearoyl-sn-glycero-3-phosphoethanolamine-N-[carboxy(polyethylene glycol)-2000] (DSPE-PEG), 1,2-dimyristoyl-rac-glycero-3-methoxypolyethyleneglycol-2000 (DMG-PEG 2K), and 1,2 distearol-sn-glycerol-3phosphocholine (DSPC) and/or comprising of one or more molecules selected from polyethylenimine (PEI) and poly (lactic-co-glycolic acid) (PLGA), and N-Acetylgalactosamine (GalNAc).

In some aspects, a method for inserting a gene into the genome of a cell is provided that comprises contacting a cell with a chimeric transposase in accordance with embodiments of the present disclosure. The method can be an in vivo or ex vivo method.

In some embodiments, the cell is contacted with a nucleic acid encoding the chimeric transposase in accordance with embodiments of the present disclosure. In some embodiments, the cell is contacted with an RNA encoding the chimeric transposase. In some embodiments, the cell is contacted with a construct comprising a transposon. In some embodiments, the cell is contacted with a DNA encoding the chimeric transposase.

In embodiments, the present method for inserting a gene into the genome of a cell utilizes the present MLT transposase, e.g. with an amino acid sequence of SEQ ID NO: 2, or a variant thereof (and optionally one or more hyperactive mutations), or the described chimera thereof, at a ratio of about 0.5:1, or a ratio of about 1:1 or a ratio of about 2:1, or a ratio of about 1:0.5, or a ratio of about 1:2, the ratio being the amount of transposon (or payload/transgene) to amount of MLT transposase or the described chimera thereof (e.g. weight:weight, concentration:concentration).

In embodiments, the present method for inserting a gene into the genome of a cell utilizes an immortalized cell line. In embodiments, the present method for inserting a gene into the genome of a cell utilizes a cell derived from a human subject (e.g. the method is performed ex vivo or invitro). In embodiments, the present method for inserting a gene into the genome of a cell utilizes a kidney cell, or a ovary cell, or an immune cell, e.g. a T cell).

In embodiments, the present method for inserting a gene into the genome allows for expression of the inserted gene. In embodiments, the present method for inserting a gene into the genome provides expression of the inserted gene for at least 7 days, or at least 8 days, or at least 9 days, or at least 10 days, or at least 14 days, or at least 21 days, or at least about 7-21 days, or at least about 7-14 days, or at least about 7-10 days, or at least about 10-14 days.

In embodiments, the present method for inserting a gene into the genome does not substantially effect recipient cell viability (e.g. at least about 95%, or at least about 90%, or at least about 85%, or at least about 80%, or at least about 75%, or at least about 50% of cells remain viable after insertion).

As would be appreciated in the art, a transposon often includes an open reading frame that encodes a transgene at the middle of transposon and terminal repeat sequences at the 5' and 3' end of the transposon. The translated transposase binds to the 5' and 3' sequence of the transposon and carries out the transposition function.

In embodiments, a transposon is used interchangeably with transposable elements, which are used to refer to polynucleotides capable of inserting copies of themselves into other polynucleotides. The term transposon is well known to those skilled in the art and includes classes of transposons that can be distinguished on the basis of sequence organization, for example inverted terminal sequences at each end, and/or directly repeated long terminal repeats (LTRs) at the ends. In some embodiments, the transposon as described herein may be described as a piggyBac like element, e.g. a transposon element that is characterized by its traceless excision, which recognizes TTAA (SEQ ID NO: 1) sequence and restores the sequence at the insert site back to the original TTAA (SEQ ID NO: 1) sequence after removal of the transposon.

In embodiments, the transposon includes a MLT transposase. In embodiments, the MLT transposase is a transposase having an amino acid sequence of SEQ ID NO: 2, or an amino acid sequence having at least about 90%, or at least about 93%, or at least about 95%, or at least about 97%, or at least about 98%, or at least about 99% identity thereto. In embodiments, the MLT transposase is a transposase having an amino acid sequence of SEQ ID NO: 4, or an amino acid sequence having at least about 90%, or at least about 93%, or at least about 95%, or at least about 97%, or at least about 98%, or at least about 99% identity thereto.

In embodiments, the transposase can act on an MLT left terminal end, or a sequence having at least about 90%, or at least about 93%, or at least about 95%, or at least about 97%, or at least about 98%, or at least about 99% identity thereto, wherein the nucleotide sequence of the MLT left terminal end (5' to 3') is as follows:

(SEQ ID NO: 21)
TTAACACTTGGATTGCGGGAAACGAGTTAAGTCGGCTCGCGTGAATTGCG
CGTACTCCGCGGGAGCCGTCTTAACTCGGTTCATATAGATTTGCGGTGGA
GTGCGGGAAACGTGTAAACTCGGGCCGATTGTAACTGCGTATTACCAAAT
ATTTGTT.

In embodiments, the transposase can act on an MLT right terminal end, or a sequence having at least about 90%, or at least about 93%, or at least about 95%, or at least about 97%, or at least about 98%, or at least about 99% identity thereto, wherein the nucleotide sequence of the MLT right terminal end (5' to 3') is as follows:

(SEQ ID NO: 22)
AATTATTTATGTACTGAATAGATAAAAAAATGTCTGTGATTGAATAAA
TTTTCATTTTTTACACAAGAAACCGAAAATTTCATTTCAATCGAACCC
ATACTTCAAAAGATATAGGCATTTTAAACTAACTCTGATTTTGCGCGG
GAAACCTAAATAATTGCCCGCGCCATCTTATATTTTGGCGGGAAATTC
ACCCGACACCGTAGTGTTAA.

In some embodiments, the transposon is flanked by one or more terminal ends. In some embodiments, the transposon is or comprises a gene encoding a compete polypeptide. In some embodiments, the transposon is or comprises a gene which is defective or substantially absent in a disease state.

In embodiments, the transposon can encode various genes. For example, in some embodiments, the transposon is an ATP Binding Cassette Subfamily A Member 4 gene (ABC) transporter gene (ABCA4), or functional fragment thereof. As another example, in some embodiments, the transposon is a very low-density lipoprotein receptor gene (VLDLR) or a low-density lipoprotein receptor gene (LDLR) or a functional fragment thereof.

In some embodiments, a therapeutic gene is inserted into a GSHS location in a host genome. GSHSs can be defined as loci well-suited for gene transfer, as integrations within these sites are not associated with adverse effects such as proto-oncogene activation, tumor suppressor inactivation, or insertional mutagenesis. GSHSs can defined by the following criteria: 1) distance of at least 50 kb from the 5' end of any gene, (2) distance of at least 300 kb from any cancer-related gene, (3) distance of at least 300 kb from any microRNA (miRNA), (4) location outside a transcription unit, and (5) location outside ultra-conserved regions (UCRs) of the human genome. See Papapetrou et al. *Nat Biotechnol* 2011; 29:73-8; Bejerano et al. *Science* 2004; 304:1321-5.

Furthermore, the use of GSHS locations can allow stable transgene expression across multiple cell types. One such site, chemokine C-C motif receptor 5 (CCR5) has been identified and used for integrative gene transfer. CCR5 is a member of the beta chemokine receptor family and is required for the entry of R5 tropic viral strains involved in primary infections. A homozygous 32 bp deletion in the CCR5 gene confers resistance to HIV-1 virus infections in humans. Disrupted CCR5 expression, naturally occurring in about 1% of the Caucasian population, does not appear to result in any reduction in immunity. Lobritz at al., *Viruses* 2010; 2:1069-105. A clinical trial has demonstrated safety and efficacy of disrupting CCR5 via targetable nucleases. Tebas at al., *HIV. N Engl J Med* 2014; 370:901-10.

The transposon can be under control of a tissue-specific promoter. The tissue-specific promoter can be, e.g., a liver-specific promoter. In some embodiments, the liver-specific promoter is an LP1 promoter that, in some embodiments, is a human LP1 promoter. The LP1 promoter is described, e.g., in Nathwani et al. *Blood* vol. 2006; 107(7):2653-61, and it can be constructed as described in Nathawani et al. In some embodiments, the tissue-specific promoter is retina-specific promoter, such as, e.g. a retinal pigment epithelium (RPE) promoter, which can be RPE65, IRBP, or VMD2 promoter. The RPE65, IRBP, and VMD2 promoters are described in, e.g., Aguirre. *Invest Ophthalmol Vis Sci.* 2017; 58(12):5399-5411. doi:10.1167/iovs.17-22978. In some embodiments, the retina-specific promoter is a photoreceptor promoter, optionally selected from β-phosphodiesterase (PDE) (see, e.g. Di Polo et al., *Nucleic Acids Res.* 1997; 25(19):3863-3867), rhodopsin kinase (GRK1) (see, e.g. Khani et al., 2007; McDougald et al., *Mol Ther Methods Clin Dev.* 2019; 13:380-389. Published 2019 Mar. 28), CAR (cone arrestin) (see, e.g. McDougald et al., *Mol Ther Methods Clin Dev.* 2019; 13:380-389. Published 2019 Mar. 28), retinitis pigmentosa 1 (RP1), and L-opsin (see, e.g. Kan et al., *Molecular Therapy*, vol. 15, Suppl. 1, S258, May 1, 2007; Lee et al., *Vision Res.* 2008 February; 48(3):332-8).

It should be appreciated however that a variety of promoters can be used, including other tissue-specific promoters, inducible promoters, constitutive promoters, etc.

The chimeric transposase can be incorporated into a vector such as a non-viral vector. The chimeric transposase can be encoded on the same vector as a vector encoding a transposon, or it can be encoded on a separate vector plasmid or RNA.

Furthermore, various transposase enzymes can be used to construct a chimeric transposase.

In some embodiments, the transposase is from a Tcl/mariner transposon system. See, e.g. Plasterk et al. *Trends in Genetics.* 1999; 15(8):326-32.

In some embodiments, the promoter is a cytomegalovirus (CMV) enhancer fused to the chicken β-actin (CAG) promoter. See Alexopoulou et al., *BMC Cell Biol.* 2008; 9:2, published online Jan. 11, 2008.

In some embodiments, the transposase is from a Sleeping Beauty transposon system (see, e.g., *Cell.* 1997; 91:501-510), e.g. a hyperactive form of Sleeping Beauty (hypSB), e.g. SB100X (see *Gene Therapy* volume 18, pages 849-856 (2011), or a piggyBac (PB) transposon system (see, e.g. Trends Biotechnol. 2015 September; 33(9):525-33, which is incorporated herein by reference in its entirety), e.g. a hyperactive form of PB transposase (hypPB), e.g. with seven amino acid substitutions (e.g. I30V, S103P, G165S, M282V, S509G, N570S, N538K on mPB, or functional equivalents in non-mPB, see *Mol Ther Nucleic Acids.* 2012 October; 1(10): e50, which is incorporated herein by reference in its entirety); see also Yusa et al., *PNAS* Jan. 25, 2011 108 (4) 1531-1536; Voigt et al., *Nature Communications* volume 7, Article number: 11126 (2016).

The piggyBac transposases belong to the IS4 transposase family. De Palmenaer et al., *BMC Evolutionary Biology.* 2008; 8:18. doi: 10.1186/1471-2148-8-18. The piggyBac family includes a large diversity of transposons, and any of these transposons can be used in embodiments of the present disclosure. See, e.g., Bouallègue et al., *Genome Biol Evol.* 2017; 9(2):323-339. The founding member of the piggyBac (super)family, insect piggyBac, was originally identified in the cabbage looper moth (*Trichoplusiani ni*) and studied both in vivo and in vitro. Insect piggyBac is known to transpose by a canonical cut-and-paste mechanism promoted by an element-encoded transposase with a catalytic site resembling the RNase H fold shared by many recombinases. The insect piggyBac transposon system has been shown to be highly active in a wide range of animals, including *Drosophila* and mice, where it has been developed as a powerful tool for gene tagging and genome engineering. Other transposons affiliated to the piggyBac superfamily are common in arthropods and vertebrates including *Xenopus* and *Bombyx*. Mammalian piggyBac transposons and transposases, including hyperactive mammalian piggyBac variants, which can be used in embodiments of the present disclosure, are described, e.g., in International Application WO2010085699, which is incorporated herein by reference in its entirety.

In some embodiments, the transposase is from a MLT transposon system that is based on a cut-and-paste MLT element obtained from the little brown bat (*Myotis lucifugus*) or other bat transposases, such as *Rhinolophus ferrumequinum, Rousettus aegyptiacus, Phyllostomus discolor, Myotis myotis, Pipistrellus kuhlii* and *Molossus molossus*. See Mitra et al., *Proc Natl Acad Sci USA.* 2013 Jan. 2; 110(1):234-9; Jebb et al., *Nature*, volume 583, pages 578-584 (2020), which is incorporated by reference herein in its entirety. In some embodiments, hyperactive forms of a bat transposase is used. The MLT transposase has been shown to be capable of transposition in bat, human, and yeast cells. The hyperactive forms of the MLT transposase enhance the transposition process. In addition, chimeric MLT transposases are capable of site-specific excision without genomic integration.

Furthermore, in embodiments, the engineered and/or corrected MLT transposase is used that has certain mutations relative to the wild-type MLT transposase. In embodiments, hyperactive forms of the corrected MLT transposase are used.

In embodiments, the transposase enzyme is derived from any of *Bombyx mori, Xenopus tropicalis, Trichoplusia ni, Rhinolophus ferrumequinum, Rousettus aegyptiacus, Phyllostomus discolor, Myotis myotis, Myotis lucifugus, Pipistrellus kuhlii, Pteropus vampyrus*, and *Molossus molossus*. In embodiments, the transposase enzyme is derived from any of *Trichoplusia ni, Myotis lucifugus, Myotis myotis*, or *Pteropus vampyrus* (see FIG. 7). The transposases can have one or more hyperactive and/or integration deficient mutations selected from FIGS. 5A and 5B, or equivalents thereof. One skilled in the art can correspond such mutants to transposases from any of *Trichoplusia ni, Myotis lucifugus, Myotis myotis*, or *Pteropus vampyrus*, with reference to FIG. 7.

Figure 7:
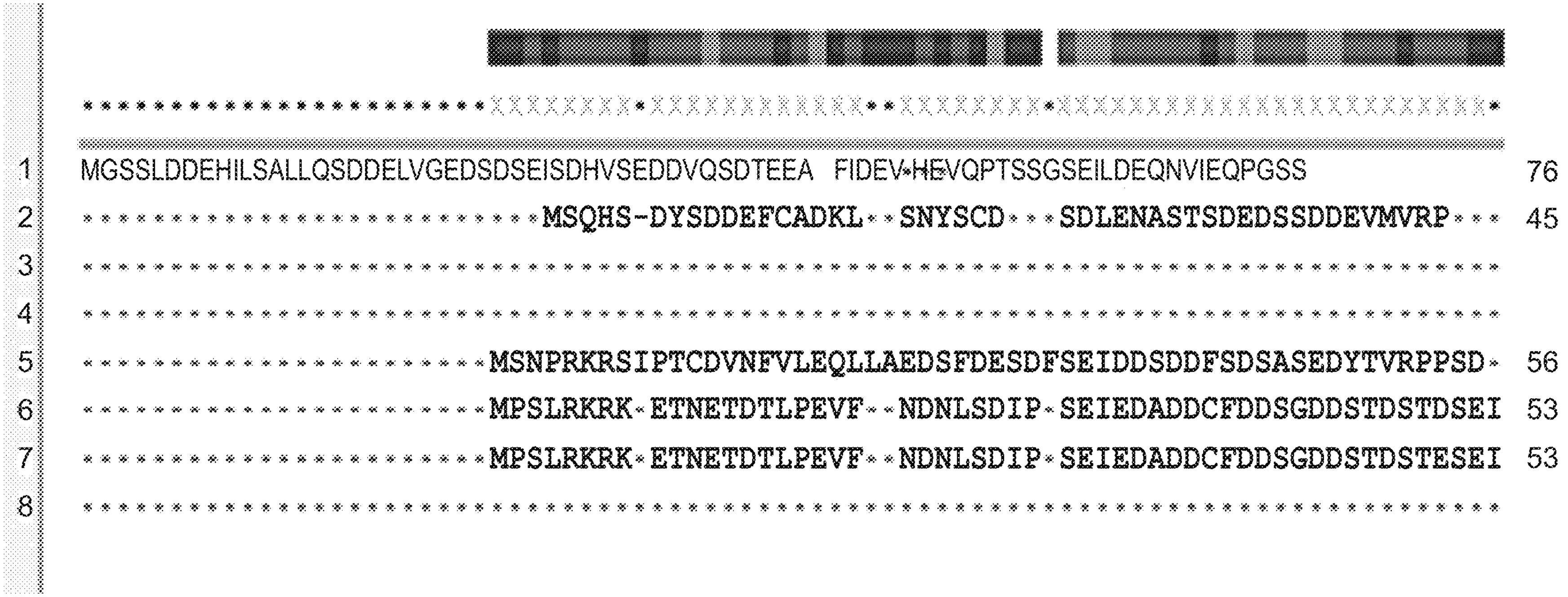
FIG. 7 depicts an amino acid sequence alignment of piggyBac ("Tni") transposase to MLT ("bat") transposase and other bat transposases (*Trichoplusia ni, Myotis lucifugus, Myotis myotis*, and *Pteropus vampyrus*). Amino acid sequence alignment of piggyBac (SEQ ID NO: 10) versus MLT and other mammalian transposases (SEQ ID NO: 14 (*Myotis lucifugus*), SEQ ID NO: 12 (*Myotis myotis* 2a), SEQ ID NO: 13 (*Myotis myotis* 1), SEQ ID NO: 11 (*Pteropus vampyrus*), SEQ ID NO: 14 (*Myotis lucifugus* 2), SEQ ID NO: 15 (*Myotis myotis* 2), and SEQ ID NO: 16 (*Myotis myotis* 2b), appear in the order listed below under "Consensus").
Figure 7:
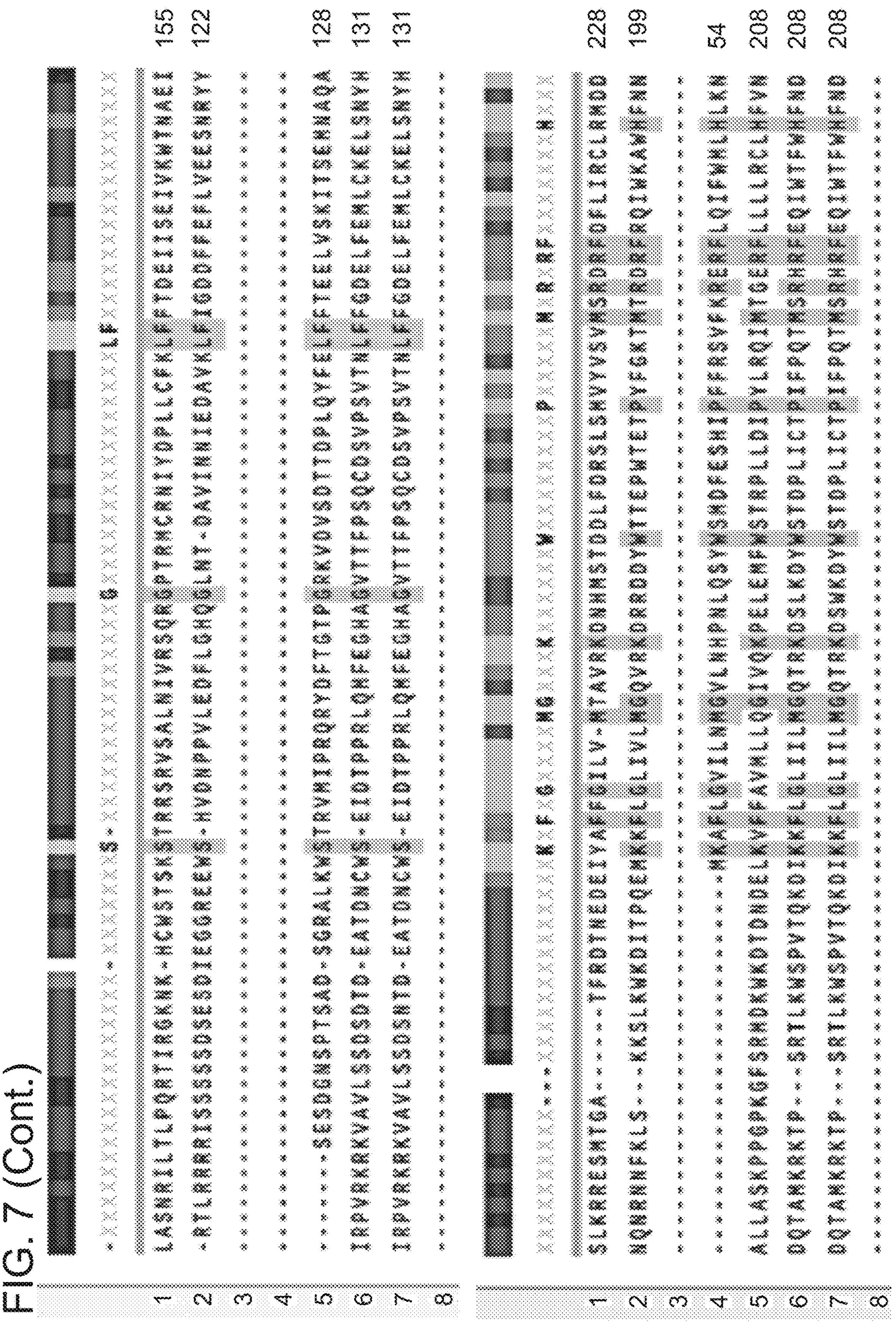
Figure 7:
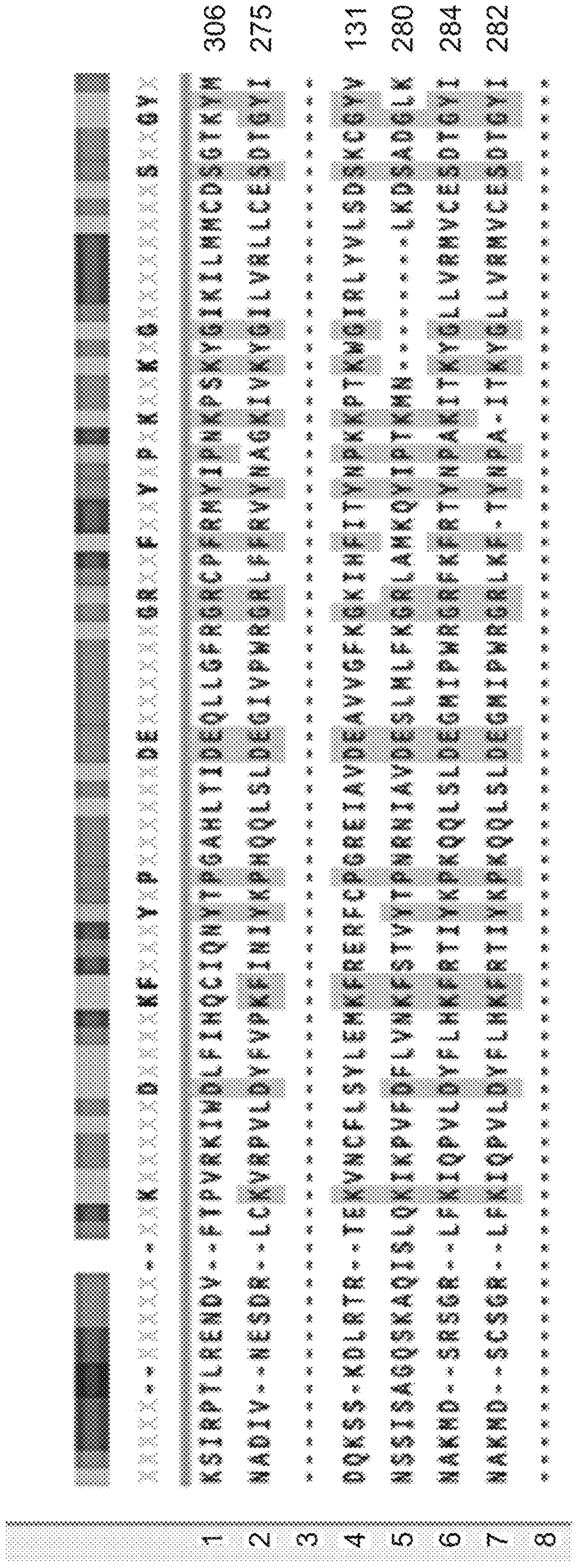
Figure 7:
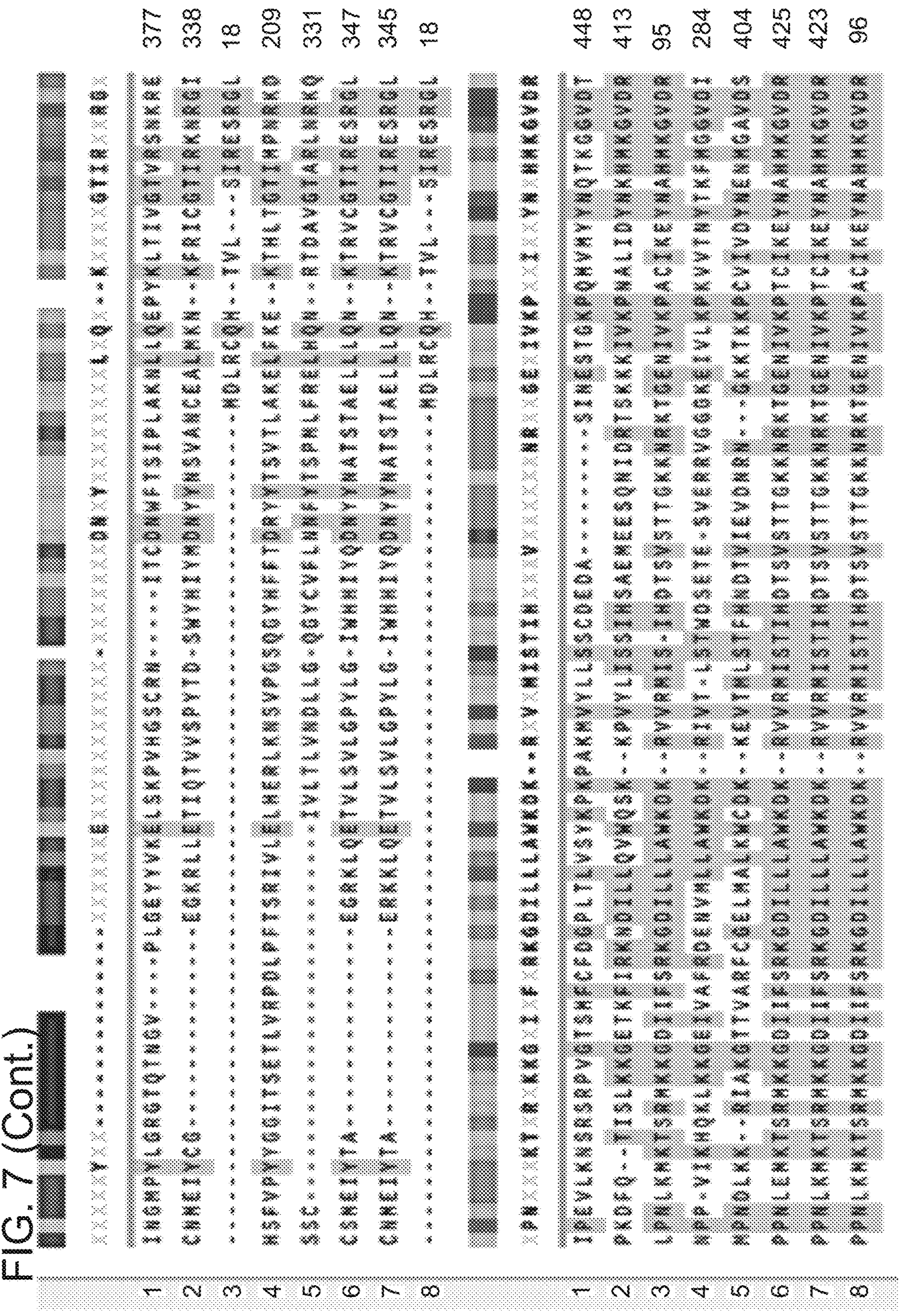
Figure 7:
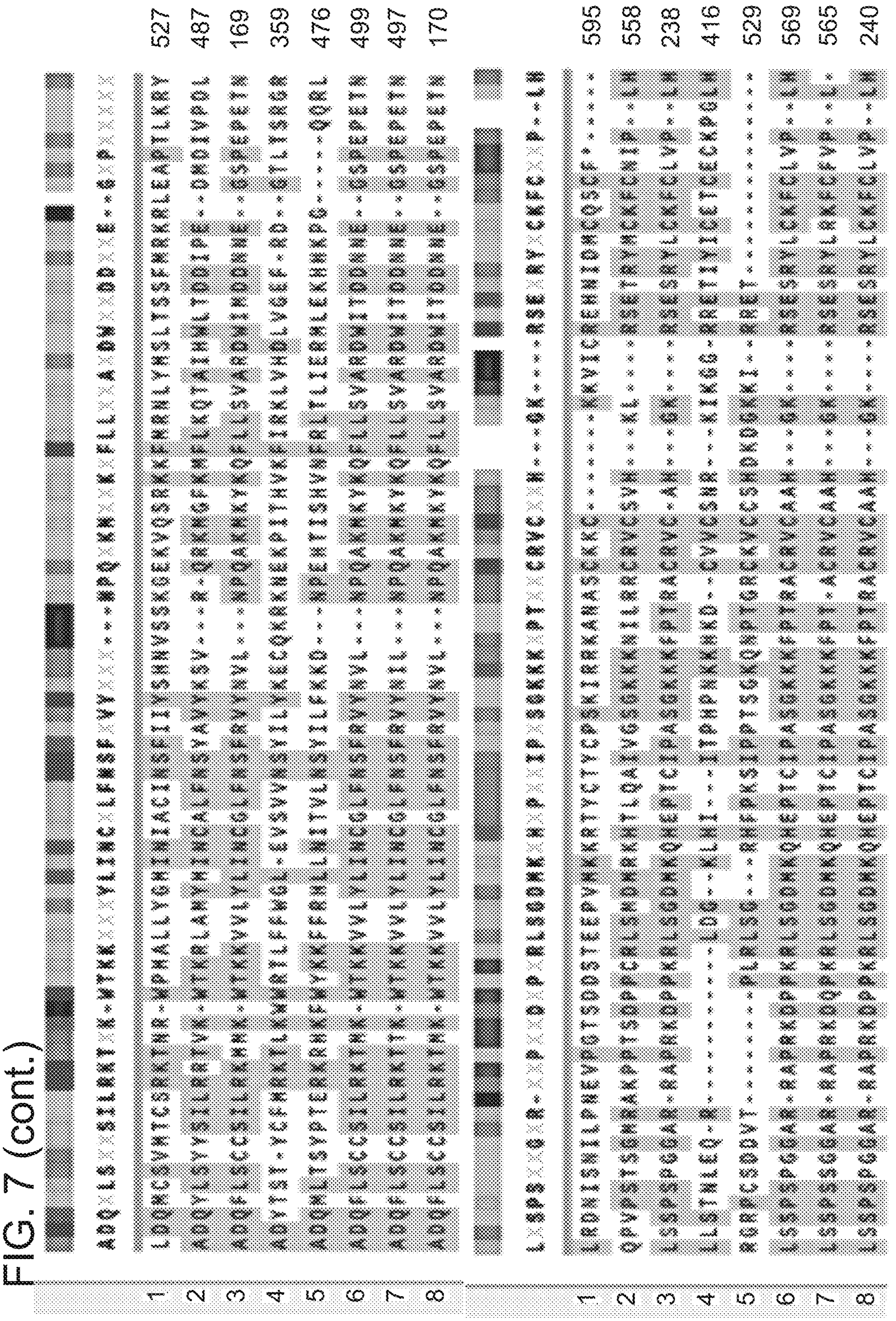
Figure 7:
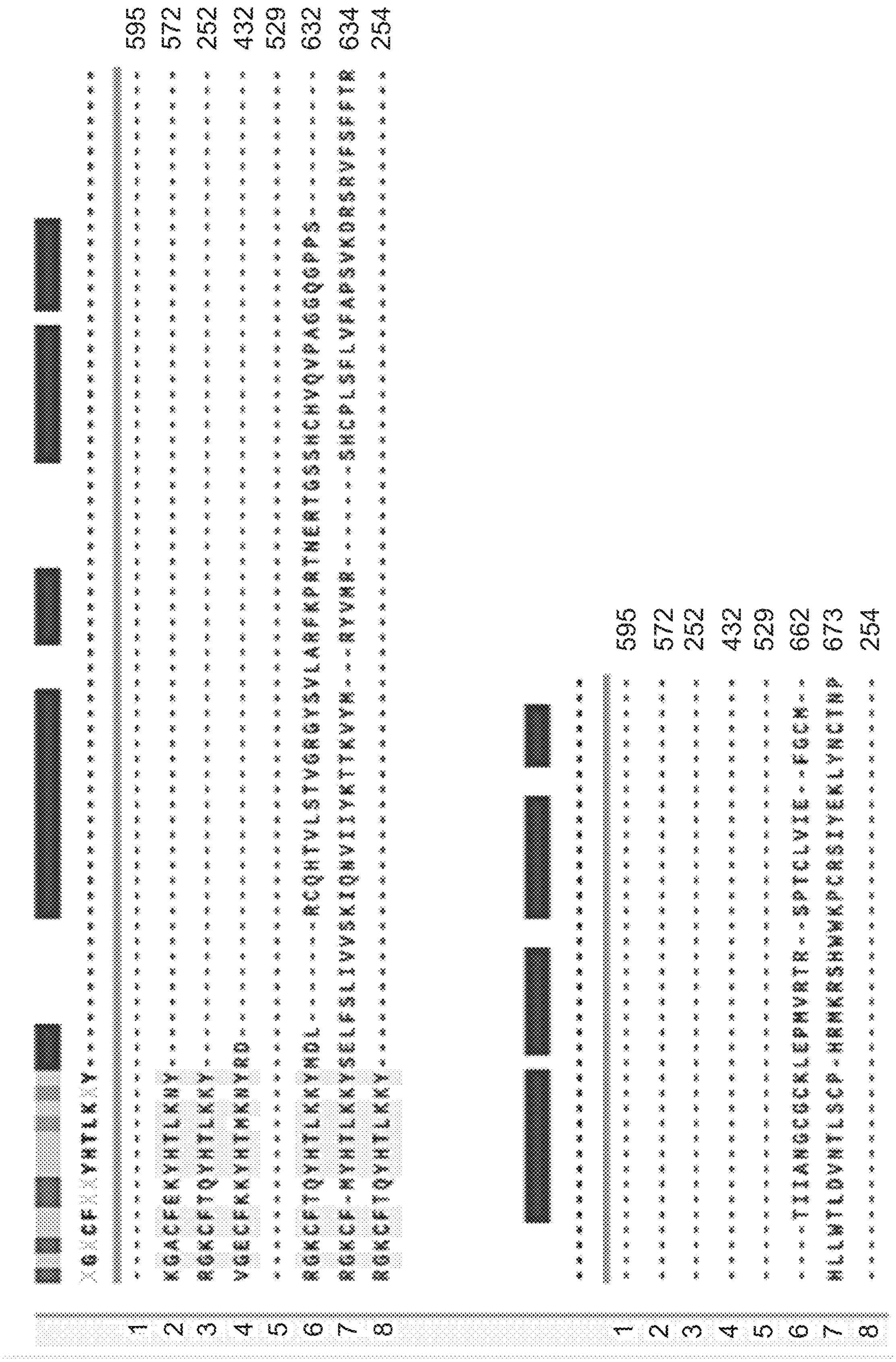

The amino acid sequences shown in the alignment of FIG. 7 are as follows (where notations in parentheses are for distinguishing between different types of sequences only):

```
Trichnoplusia ni
                                                    (SEQ ID NO: 10)
  1   MGSSLDDEHI LSALLQSDDE LVGEDSDSEI SDHVSEDDVQ SDTEEAFIDE VHEVQPTSSG

 61   SEILDEQNVI EQPGSSLASN KILTLPQRTI RGKNKHCWST SKSTRRSRVS ALNIVRSQRG

121   PTRMCRNIYD PLLCFKLFFT DEIISEIVKW TNAEISLKRR ESMTGATFRD TNEDEIYAFF

181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RMYIPNKPSK YGIKILMMCD

301   SGTKYMINGM PYLGRGTQTN GVPLGEYYVK ELSKPVRGSC RNITCDNWFT SIPLAKNLLQ

361   EPYKLTIVGT VRSNKREIPE VLKNSRSRPV GTSMFCFDGP LTLVSYKPKP AKMVYLLSSC

421   DEDASINEST GKPQMVMYYN QTKGGVDTLD QMCSVMTCSR KTNRWPMALL YGMINIACIN

481   SFIIYSHNVS SKGEKVQSRK KFMRNLYMSL TSSFMRKRLE APTLKRYLRD NISNILPNEV

541   PGTSDDSTEE PVTKKRTYCT YCPSKIRRKA NASCKKCKKV ICREHNIDMC QSCF

Pteropus vampyrus
                                                    (SEQ ID NO: 11)
  1   MSNPRKRSIP TCDVNFVLEQ LLAEDSFDES DFSEIDDSDD FSDSASEDYT VRPPSDSESD

 61   GNSPTSADSG RALKWSTRVM IPRQRYDFTG TPGRKVDVSD TTDPLQYFEL FFTEELVSKI

121   TSEMNAQAAL LASKPPGPKG FSRMDKWKDT DNDELKVFFA VMLLQGIVQK PELEMFWSTR

181   PLLDIPYLRQ IMTGERFLLL LRCLHFVNNS SISAGQSKAQ ISLQKIKPVF DFLVNKFSTV

241   YTPNRNIAVD ESLMLFKGRL AMKQYIPTKM NLKDSADGLK

Myotis myotis ("2a")
                                                    (SEQ ID NO: 12)
  1   MDLRCQHTVL SIRESRGLLP NLKMKTSRMK KGDIIFSRKG DILLLAWKDK RVVRMISIHD

 61   TSVSTTGKKN RKTGENIVKP ACIKEYNAHM KGVDRADQFL SCCSILRKMM KWTKKVVLYL

121   INCGLFNSFR VYNVLNPQAK MKYKQFLLSV ARDWIMDDNN EGSPEPETNL SSPSPGGARR

181   APRKDPPKRL SGDMKQHEPT CIPASGKKKF PTRACRVCAH GKRSESRYLC KFCLVPLHRG

241   KCFTQYHTLK KY

Myotis myotis ("1")
                                                    (SEQ ID NO: 13)
  1   MKAFLGVILN MGVLNHPNLQ SYWSMDFESH IPFFRSVFKR ERFLQIFWML HLKNDQKSSK

 61   DLRTRTEKVN CFLSYLEMKF RERFCPGREI AVDEAVVGFK GKIHFITYNP KKPTKWGIRL

121   YVLSDSKCGY VHSFVPYYGG ITSETLVRPD LPFTSRIVLE LHERLKNSVP GSQGYHFFTD

181   RYYTSVTLAK ELFKEKTHLT GTIMPNRKDN PPVIKHQKLK KGEIVAFRDE NVMLLAWKDK

241   RIVTLSTWDS ETESVERRVG GGKEIVLKPK VVTNYTKFMG GVDIADYTST YCFMRKTLKW
```

-continued

```
301   WRTLFFWGLE VSVVNSYILY KECQKRKNEK PITHVKFIRK LVHDLVGEFR DGTLTSRGRL

361   LSTNLEQRLD GKLHIITPHP NKKHKDCVVC SNRKIKGGRR ETIYICETCE CKPGLHVGEC

421   FKKYHTMKNY RD
```

*Myotis lucifugus* ("2")

(SEQ ID NO: 14)

```
  1   MPSLRKRKET NETDTLPEVF NDNLSDIPSE IEDADDCFDD SGDDSTDSTD SEIIRPVRKR

 61   KVAVLSSDSD TDEATDNCWS EIDTPPRLQM FEGHAGVTTF PSQCDSVPSV TNLFFGDELF

121   EMLCKELSNY HDQTAMKRKT PSRTLKWSPV TQKDIKKFLG LIILMGQTRK DSLKDYWSTD

181   PLICTPIFPQ TMSRHRFEQI WTFWHFNDNA KMDSRSGRLF KIQPVLDYFL HKFRTIYKPK

241   QQLSLDEGMI PWRGRFKFRT YNPAKITKYG LLVRMVCESD TGYICSMEIY TAEGRKLQET

301   VLSVLGPYLG IWHHIYQDNY YNATSTAELL LQNKTRVCGT IRESRGLPPN LEMKTSRMKK

361   GDIIFSRKGD ILLLAWKDKR VVRMISTIHD TSVSTTGKKN RKTGENIVKP TCIKEYNAHM

421   KGVDRADQFL SCCSILRKTM KWTKKVVLYL INCGLFNSFR VYNVLNPQAK MKYKQFLLSV

481   ARDWITDDNN EGSPEPETNL SSPSPGGARR APRKDPPKRL SGDMKQHEPT CIPASGKKKF

541   PTRACRVCAA HGKRSESRYL CKFCLVPLHR GKCFTQYHTL KKYMDLRCQH TVLSTVGRGY

601   SVLARFKPRT NERTGSSHCH VQVPAGGQGP PSTIIANGCG CKLEPMVRTR SPTCLVIEFG

661   CM
```

*Myotis myotis* ("2")

(SEQ ID NO: 15)

```
  1   MPSLRKRKET NETDTLPEVF NDNLSDIPSE IEDADDCFDD SGDDSTDSTE SEIIRPVRKR

 61   KVAVLSSDSN TDEATDNCWS EIDTPPRLQM FEGHAGVTTF PSQCDSVPSV TNLFFGDELF

121   EMLCKELSNY HDQTAMKRKT PSRTLKWSPV TQKDIKKFLG LIILMGQTRK DSWKDYWSTD

181   PLICTPIFPQ TMSRHRFEQI WTFWHFNDNA KMDSCSGRLF KIQPVLDYFL HKFRTIYKPK

241   QQLSLDEGMI PWRGRLKFTY NPAITKYGLL VRMVCESDTG YICNMEIYTA ERKKLQETVL

301   SVLGPYLGIW HHIYQDNYYN ATSTAELLLQ NKTRVCGTIR ESRGLPPNLK MKTSRMKKGD

361   IIFSRKGDIL LLAWKDKRVV RMISTIHDTS VSTTGKKNRK TGENIVKPTC IKEYNAHMKG

421   VDRADQFLSC CSILRKTTKW TKKVVLYLIN CGLFNSFRVY NILNPQAKMK YKQFLLSVAR

481   DWITDDNNEG SPEPETNLSS PSSGGARRAP RKDQPKRLSG DMKQHEPTCI PASGKKKFPT

541   ACRVCAAHGK RSESRYLRKF CFVPLRGKCF MYHTLKKYSE LFSLIVVSKI QNVIIYKTTK

601   VYMRYVMRSH CPLSFLVFAP SVKDRSRVFS FFTRHLLWTL DVNTLSCPHR MKRSHWWKPC

661   RSIYEKLYNC TNP
```

*Myotis myotis* ("2b")

(SEQ ID NO: 16)

```
  1   MDLRCQHTVL SIRESRGLPP NLKMKTSRMK KGDIIFSRKG DILLLAWKDK RVVRMISTIH

 61   DTSVSTTGKK NRKTGENIVK PACIKEYNAH MKGVDRADQF LSCCSILRKT MKWTKKVVLY

121   LINCGLFNSF RVYNVLNPQA KMKYKQFLLS VARDWITDDN NEGSPEPETN LSSPSPGGAR

181   RAPRKDPPKR LSGDMKQHEP TCIPASGKKK FPTRACRVCA AHGKRSESRY LCKFCLVPLH

241   RGKCFTQYHT LKKY
```

In embodiments, one skilled in the art can correspond such mutants to transposases from any of *Bombyx mori, Xenopus tropicalis, Trichoplusia ni, Rhinolophus ferrumequinum, Rousettus aegyptiacus, Phyllostomus discolor, Myotis myotis, Myotis lucifugus, Pipistrellus kuhlii, Pteropus vampyrus*, and *Molossus molossus*.

In some embodiments, the transposase enzyme can have a nucleotide sequence having at least about 90%, or at least about 93%, or at least about 95%, or at least about 97%, or at least about 98%, or at least about 99% identity to a nucleotide sequence of any of *Rhinolophus ferrumequinum, Rousettus aegyptiacus, Phyllostomus discolor, Myotis myotis, Myotis lucifugus, Pteropus vampyrus, Pipistrellus kuhlii*, Pan *troglodytes, Molossus molossus*, or *Homo sapiens*. In some embodiments, the transposase enzyme can have an amino acid sequence having at least about 90%, or at least about 93%, or at least about 95%, or at least about 97%, or at least about 98%, or at least about 99% identity to an amino acid sequence of any of *Rhinolophus ferrumequinum, Rousettus aegyptiacus, Phyllostomus discolor, Myotis myotis, Myotis lucifugus, Pteropus vampyrus, Pipistrellus kuhlii, Pan troglodytes, Molossus molossus*, or *Homo sapiens*. See Jebb, et al. (2020).

In some embodiments, a wild type MLT transposase is encoded by the following nucleotide sequence:

```
                                          (SEQ ID NO: 5)
ATGTCGCAGCATTCAGACTATTCTCATGATGAGTTTTGTGCAGACAAG
TTGTCCAATTATTCTTGTGATAGCGATCTTGAAAATGCGAGTACAAGT
GATGAAGATTCTAGTGATGATGAAGTAATGGTGCGTCCCAGGACATTG
AGGCGACGAAGAATTTCGAGCTCCAGCTCTGACTCAGAGTCAGATATA
GAAGGCGGGAGAGAAGAATGGTCGCATGTTGATAATCCACCGGTCTTA
GAAGATTTTTTAGGGCATCAAGGATTAAACACAGATGCTGTTATAAAT
AATATAGAAGATGCCGTGAAATTATTTATCGGAGATGATTTTTTTGAA
TTTCTTGTAGAGGAGTCAAACAGGTATTATAATCAAAATAGGAATAAT
TTCAAACTTTCAAAAAAAAAGCCTAAAGTGGAAAGATATAACCCCTCAA
GAGATGAAGAAGTTTTTAGGGTTAATTGTTCTCATGGGACAGGTGCGC
AAAGATAGAAGAGATGACTATTGGACCACGGAGCCATGGACGGAGACG
CCATATTTTGGTAAAACGATGACGAGAGACAGGTTCCGACAGATATGG
AAAGCTTGGCACTTCAATAATAATGCGGATATCGTAAATGAATCAGAT
AGACTTTGCAAAGTGAGACCAGTACTAGATTATTTTGTGCCTAAATTT
ATAAATATTTACAAACCTCATCAGCAATTATCACTAGATGAAGGGATC
GTACCTTGGAGGGGAAGATTATTCTTTAGGGTATATAATGCTGGCAAG
ATCGTTAAATATGGAATATTGGTTCGTTTGTTGTGCGAAAGTGATACA
GGATATATCTGTAACATGGAAATTTATTGCGGCGAAGGAAAGCGATTA
TTGGAAACGATACAAACAGTAGTGTCTCCATACACTGATTCGTGGTAC
CATATATATATGGACAATTATTATAATAGCGTCGCAAATTGTGAAGCA
CTTATGAAAAACAAATTCAGAATATGTGGAACAATCCGGAAAAATCGA
GGTATACCTAAAGATTTTCAAACAATTTCTTTGAAAAAAGGTGAAACA
AAATTTATAAGGAAAAATGATATATTGTTACAAGTGTGGCAATCAAAA
AAGCCTGTATACCTGATTTCTTCGATTCATTCTGCGGAGATGGAAGAA
AGTCAGAATATTGACAGAACATCAAAAAAGAAAATTGTCAAACCGAAT
GCACTCATTGACTACAATAAACATATGAAAGGTGTTGACCGGGCCGAC
CAATACCTTTCATATTATTCGATATTGCGGAGGACGGTCAAATGGACA
AAAAGGTTGGCAATGTATATGATAAATTGCGCATTATTTAATTCTTAT
GCAGTTTACAAATCAGTGAGGCAAAGAAAAATGGGTTTTAAAATGTTT
TTGAAACAAACAGCTATCCACTGGTTGACGGATGATATTCCAGAGGAC
ATGGACATTGTTCCAGACCTTCAACCAGTACCGTCTACTTCTGGAATG
CGGGCTAAACCACCTACATCTGATCCACCATGCAGGCTATCGATGGAC
ATGAGAAAGCATACGTTACAGGCAATTGTCGGAAGTGGAAAAAAGAAA
AACATTTTGAGAAGGTGTCGCGTATGTTCCGTTCATAAATTGCGCAGT
```

-continued

```
GAGACACGCTACATGTGCAAATTTTGCAATATACCTCTACATAAAGGG
GCGTGTTTTGAAAAATATCATACGCTAAAAAACTAT,
```

or a nucleotide sequence having at least about 90%, or at least about 93%, or at least about 95%, or at least about 97%, or at least about 98%, or at least about 99% identity thereto.

In some embodiments, a wild type MLT transposase, encoded by the nucleotide sequence of SEQ ID NO: 5 (above), has the following amino acid sequence:

```
                                          (SEQ ID NO: 4)
MSQHSDYSDDEFCADKLSNYSCDSDLENASTSDEDSSDDEVMVRPRTL
RRRRISSSSSDSESDIEGGREEWSHVDNPPVLEDFLGHQGLNTDAVIN
NIEDAVKLFIGDDFFEFLVEESNRYYNQNRNNFKLSKKSLKWKDITPQ
EMKKFLGLIVLMGQVRKDRRDDYWITEPWTETPYFGKTMTRDRFRQIW
KAWHENNNADIVNESDRLCKVRPVLDYFVPKFINIYKPHQQLSLDEGI
VPWRGRLFFRVYNAGKIVKYGILVRLLCESDTGYICNMEIYCGEGKRL
LETIQTWSPYTDSWYHIYMDNYYNSVANCEALMKNKFRICGTIRKNRG
IPKDFQTISLKKGETKFIRKNDILLQVWQSKKPVYLISS1HSAEMEES
QNIDRTSKKKIVKPNALIDYNKHMKGVDRADQYLSYYSILRRWKWTKR
LAMYMINCALFNSYAVYKSVRQRKMGFKMELKQTA1HWLTDDIPEDMD
IVPDLQPVPSTSGMRAKPPTSDPPCRLSMDMRKHTLQAIVGSGKKKNI
LRRCRVCSVHKLRSETRYMCKFCNIPLHKGACFEKYHTLKNY,
```

or an amino acid sequence having at least about 90%, or at least about 93%, or at least about 95%, or at least about 97%, or at least about 98%, or at least about 99% identity thereto.

In some embodiments, an MLT transposase has the immediately above amino acid sequence (SEQ ID NO: 4) and includes a hyperactive mutation selected from FIG. 5A or FIG. 5B. For example, a MLT transposase can include about 1, or about 2, or about 3, or about 4, or about 5 hyperactive mutations selected from FIG. 5A or FIG. 5B, or combinations thereof.

In embodiments, an MLT transposase comprises one or more mutations selected from L573X, E574X, and S2X, wherein X is any amino acid or no amino acid, optionally X is A, G, or a deletion, optionally the mutations are L573del, E574del, and S2A.

In embodiments, an MLT transposase comprises L573del, E574del, and S2A mutations, and comprises an amino acid sequence of SEQ ID NO: 2:

```
                                          (SEQ ID NO: 2)
MAQHSDYSDDEFCADKLSNYSCDSDLENASTSDEDSSDDEVMVRPRTL
RRRRISSSSSDSESDIEGGREEWSHVDNPPVLEDFLGHQGLNTDAVIN
NIEDAVKLFIGDDFFEFLVEESNRYYNQNRNNFKLSKKSLKWKDITPQ
EMKKFLGLIVLMGQVRKDRRDDYWITEPWTETPYFGKTMTRDRFRQIW
KAWHENNNADIVNESDRLCKVRPVLDYFVPKFINIYKPHQQLSLDEGI
VPWRGRLFFRVYNAGKIVKYGILVRLLCESDTGYICNMEIYCGEGKRL
LETIQTVVSPYTDSWYHIYMDNYYNSVANCEALMKNKFRICGTIRKNR
GIPKDFQTISLKKGETKFIRKNDILLQVWQSKKPVYLISSIHSAEMEE
```

-continued

SQNIDRTSKKKIVKPNALIDYNKHMKGVDRADQYLSYYSILRRTVKWT

KRLAMYMINCALENSYAVYKSVRQRKMGFKMFLKQTAIHWLTDDIPED

MDIVPDLQPVPSTSGMRAKPPTSDPPCRLSMDMRKHTLQAIVGSGKKK

NILRRCRVCSVHKLRSETRYMCKFCNIPLHKGACFEKYHTLKNY, or an amino acid sequence having at least about 90%, or at least about 93%, or at least about 95%, or at least about 97%, or at least about 98%, or at least about 99% identity thereto.

The MLT transposase comprising the amino acid sequence of SEQ ID NO: 2, or a variant thereof, was engineered to improve upon the enzymes of Mitra et al. (*Proc Natl Acad Sci USA.* 2013 Jan. 2; 110(1):234-9) and WO2010085699, which are both incorporated by reference herein in their entireties. The MLT transposase comprising the amino acid sequence of SEQ ID NO: 2, or a variant thereof (with mutations L573del, E574del, and S2A), is referred to herein as an "engineered" and/or "corrected" MLT transposase.

In some embodiments, an MLT transposase comprising the amino acid sequence of SEQ ID NO: 2 is encoded by the following nucleotide sequence:

(SEQ ID NO: 3)

ATGGCCCAGCACAGCGACTACAGCGACGACGAGTTCTGTGCCGATAAG

CTGAGTAACTACAGCTGCGACAGCGACCTGGAAAACGCCAGCACATCC

GACGAGGACAGCTCTGACGACGAGGTGATGGTGCGGCCCAGAACCCTG

AGACGGAGAAGAATCAGCAGCTCTAGCAGCGACTCTGAATCCGACATC

GAGGGCGGCCGGGAAGAGTGGAGCCACGTGGACAACCCTCCTGTTCTG

GAAGATTTTCTGGGCCATCAGGGCCTGAACACCGACGCCGTGATCAAC

AACATCGAGGATGCCGTGAAGCTGTTCATAGGAGATGATTTCTTTGAG

TTCCTGGTCGAGGAATCCAACCGCTATTACAACCAGAATAGAAACAAC

TTCAAGCTGAGCAAGAAAAGCCTGAAGTGGAAGGACATCACCCCTCAG

GAGATGAAAAAGTTCCTGGGACTGATCGTTCTGATGGGACAGGTGCGG

AAGGACAGAAGGGATGATTACTGGACAACCGAACCTTGGACCGAGACC

CCTTACTTTGGCAAGACCATGACCAGAGACAGATTCAGACAGATCTGG

AAAGCCTGGCACTTCAACAACAATGCTGATATCGTGAACGAGTCTGAT

AGACTGTGTAAAGTGCGGCCAGTGTTGGATTACTTCGTGCCTAAGTTC

ATCAACATCTATAAGCCTCACCAGCAGCTGAGCCTGGATGAAGGCATC

GTGCCCTGGCGGGGCAGACTGTTCTTCAGAGTGTACAATGCTGGCAAG

ATCGTCAAATACGGCATCCTGGTGCGCCTTCTGTGCGAGAGCGATACA

GGCTACATCTGTAATATGGAAATCTACTGCGGCGAGGGCAAAAGACTG

CTGGAAACCATCCAGACCGTCGTTTCCCCTTATACCGACAGCTGGTAC

CACATCTACATGGACAACTACTACAATTCTGTGGCCAACTGCGAGGCC

CTGATGAAGAACAAGTTTAGAATCTGCGGCACAATCAGAAAAAACAGA

GGCATCCCTAAGGACTTCCAGACCATCTCTCTGAAGAAGGGCGAAACC

AAGTTCATCAGAAAGAACGACATCCTGCTCCAAGTGTGGCAGTCCAAG

AAACCCGTGTACCTGATCAGCAGCATCCATAGCGCCGAGATGGAAGAA

AGCCAGAACATCGACAGAACAAGCAAGAAGAAGATCGTGAAGCCCAAT

-continued

GCTCTGATCGACTACAACAAGCACATGAAAGGCGTGGACCGGGCCGAC

CAGTACCTGTCTTATTACTCTATCCTGAGAAGAACAGTGAAATGGACC

AAGAGACTGGCCATGTACATGATCAATTGCGCCCTGTTCAACAGCTAC

GCCGTGTACAAGTCCGTGCGACAAAGAAAAATGGGATTCAAGATGTTC

CTGAAGCAGACAGCCATCCACTGGCTGACAGACGACATTCCTGAGGAC

ATGGACATTGTGCCAGATCTGCAACCTGTGCCCAGCACCTCTGGTATG

AGAGCTAAGCCTCCCACCAGCGATCCTCCATGTAGACTGAGCATGGAC

ATGCGGAAGCACACCCTGCAGGCCATCGTCGGCAGCGGCAAGAAGAAG

AACATCCTTAGACGGTGCAGGGTGTGCAGCGTGCACAAGCTGCGGAGC

GAGACTCGGTACATGTGCAAGTTTTGCAACATTCCCCTGCACAAGGGA

GCCTGCTTCGAGAAGTACCACACCCTGAAGAATTACTAG, or a nucleotide sequence having at least about 90%, or at least about 93%, or at least about 95%, or at least about 97%, or at least about 98%, or at least about 99% identity thereto.

In some embodiments, a MLT transposase comprising the amino acid sequence of SEQ ID NO: 2 includes one or more hyperactive mutations selected from FIG. 5A or FIG. 5B. For example, a MLT transposase can include about 1, or about 2, or about 3, or about 4, or about 5 hyperactive mutations selected from FIG. 5A or FIG. 5B, or combinations thereof.

In some embodiments, a MLT transposase comprising the amino acid sequence of SEQ ID NO: 2 includes one or more hyperactive mutations selected from a substitution or deletion at one or more of positions S5, S8, D9, D10, E11, C13, A14, S36, S54, N125, K130, G239, T294, T300, I345, R427, D475, M481, P491, A520, and A561.

In some embodiments, a MLT transposase comprising the amino acid sequence of SEQ ID NO: 2 includes one or more hyperactive mutations selected from S5P, S8P, S8P/C13R, D9G, D10G, E11G, C13R, A14V, S36G, S54N, N125K, K130T, G239S, T294A, T300A, I345V, R427H, D475G, M481V, P491Q, A520T, and A561T.

In embodiments, the MLT transposase comprises one or more of hyperactive mutants selected from $S8X_1$, $C13X_2$ and/or $N125X_3$ (e.g., all of $S8X_1$, $C13X_2$ and $N125X_3$, $S8X_1$ and $C13X_2$, $S8X_1$ and $N125X_3$, and $C13X_2$ and $N125X_3$), where $X_1$, $X_2$, and $X_3$ is each independently any amino acid, or $X_1$ is a non-polar aliphatic amino acid, selected from G, A, V, L, I and P, $X_2$ is a positively charged amino acid selected from K, R, and H, and/or $X_3$ is a positively charged amino acid selected from K, R, and H. In embodiments, $X_1$ is P, $X_2$ is R, and/or $X_3$ is K.

In some embodiments, an MLT transposase is encoded by a nucleotide sequence (SEQ ID NO: 6) that corresponds to an amino acid (SEQ ID NO: 7) having the N125K mutation relative to the amino acid sequence of SEQ ID NO: 2 or a functional equivalent thereof:

```
                                                          (SEQ ID NO: 6)
   1  atggcccagc acagcgacta cagcgacgac gagttctgtg ccgataagct gagtaactac
  61  agctgcgaca gcgacctgga aaacgccagc acatccgacg aggacagctc tgacgacgag
 121  gtgatggtgc ggcccagaac cctgagacgg agaagaatca gcagctctag cagcgactct
 181  gaatccgaca tcgagggcgg ccgggaagag tggagccacg tggacaaccc tcctgttctg
 241  gaagattttc tgggccatca gggcctgaac accgacgccg tgatcaacaa catcgaggat
 301  gccgtgaagc tgttcatagg agatgatttc tttgagttcc tggtcgagga atccaaccgc
 361  tattacaacc agaagagaaa caacttcaag ctgagcaaga aaagcctgaa gtggaaggac
 421  atcacccctc aggagatgaa aaagttcctg ggactgatcg ttctgatggg acaggtgcgg
 481  aaggacagaa gggatgatta ctggacaacc gaaccttgga ccgagacccc ttactttggc
 541  aagaccatga ccagagacag attcagacag atctggaaag cctggcactt caacaacaat
 601  gctgatatcg tgaacgagtc tgatagactg tgtaaagtgc ggccagtgtt ggattacttc
 661  gtgcctaagt tcatcaacat ctataagcct caccagcagc tgagcctgga tgaaggcatc
 721  gtgccctggc ggggcagact gttcttcaga gtgtacaatg ctggcaagat cgtcaaatac
 781  ggcatcctgg tgcgccttct gtgcgagagc gatacaggct acatctgtaa tatggaaatc
 841  tactgcggcg agggcaaaag actgctggaa accatccaga ccgtcgtttc cccttatacc
 901  gacagctggt accacatcta catggacaac tactacaatt ctgtggccaa ctgcgaggcc
 961  ctgatgaaga acaagtttag aatctgcggc acaatcagaa aaacagagg catccctaag
1021  gacttccaga ccatctctct gaagaagggc gaaaccaagt tcatcagaaa gaacgacatc
1081  ctgctccaag tgtggcagtc caagaaaccc gtgtacctga tcagcagcat ccatagcgcc
1141  gagatggaag aaagccagaa catcgacaga acaagcaaga gaaagatcgt gaagcccaat
1201  gctctgatcg actacaacaa gcacatgaaa ggcgtggacc gggccgacca gtacctgtct
1261  tattactcta tcctgagaag aacagtgaaa tggaccaaga gactggccat gtacatgatc
1321  aattgcgccc tgttcaacag ctacgccgtg tacaagtccg tgcgacaaag aaaaatggga
1381  ttcaagatgt tcctgaagca gacagccatc cactggctga cagacgacat tcctgaggac
1441  atggacattg tgccagatct gcaacctgtg cccagcacct ctggtatgag agctaagcct
1501  cccaccagcg atcctccatg tagactgagc atggacatgc ggaagcacac cctgcaggcc
1561  atcgtcggca gcggcaagaa gaagaacatc cttagacggt gcagggtgtg cagcgtgcac
1621  aagctgcgga gcgagactcg gtacatgtgc aagttttgca acattcccct gcacaaggga
1681  gcctgcttcg agaagtacca caccctgaag aattactag,
```

or a nucleotide sequence having at least about 90%, or at least about 93%, or at least about 95%, or at least about 97%, or at least about 98%, or at least about 99% identity thereto (the codon corresponding to the N125K mutation is underlined and bolded).

```
                                                          (SEQ ID NO: 7)
   1  MAQHSDYSDD EFCADKLSNY SCDSDLENAS TSDEDSSDDE VMVRPRTLRR RRISSSSSDS
  61  ESDIEGGREE WSHVDNPPVL EDFLGHQGLN TDAVINNIED AVKLFIGDDF FEFLVEESNR
 121  YYNQKRNNFK LSKKSLKWKD ITPQEMKKFL GLIVLMGQVR KDRRDDYWTT EPWTETPYEG
 181  KTMTRDRFRQ IWKAWHFNNN ADIVNESDRL CKVRPVLDYF VPKFINIYKP HQQLSLDEGI
 241  VPWRGRLFFR VYNAGKIVKY GILVRLLCES DTGYICNMEI YCGEGKRLLE TIQTVVSPYT
 301  DSWYHIYMDN YYNSVANCEA LMKNKFRICG TIRKNRGIPK DFQTISLKKG ETKFIRKNDI
```

-continued

```
361 LLQVWQSKKP VYLISSIHSA EMEESQNIDR TSKKKIVKPN ALIDYNKHMK GVDRADQYLS

421 YYSILRRTVR WTKRLAMYMI NCALFNSYAV YKSVRQRKMG FKMFLKQTAI HWLTDDIPED

481 MDIVPDLQPV PSTSGMRAKP PTSDPPCRLS MDMRKHTLQA IVGSGKKHNI LRRCRVSVH

541 KLRSETRYMC KFCNIPLHKG ACFEKYHTLK NY,
```

or an amino acid sequence having at least about 90%, or at least about 93%, or at least about 95%, or at least about 97%, or at least about 98%, or at least about 99% identity thereto (the amino acid corresponding to the N125K mutation is underlined and bolded).

In some embodiments, the MLT transposase encoded by the nucleotide sequence of SEQ ID NO: 7 and having the amino acid sequence of SEQ ID NO: 7 is referred to as an MLT transposase 1 (or MLT1).

In some embodiments, an MLT transposase is encoded by a nucleotide sequence (SEQ ID NO: 8) that corresponds to an amino acid (SEQ ID NO: 9) having the S8P and C13R mutations relative to the amino acid sequence of SEQ ID NO: 2 or a functional equivalent thereof:

```
                                                          (SEQ ID NO: 8)
   1 atggcccagc acagcgacta ccccgacgac gagttcagag ccgataagct gagtaactac

  61 agctgcgaca gcgacctgga aaacgccagc acatccgacg aggacagctc tgacgacgag

 121 gtgatggtgc ggcccagaac cctgagacgg agaagaatca gcagctctag cagcgactct

 181 gaatccgaca tcgagggcgg ccgggaagag tggagccacg tggacaaccc tcctgttctg

 241 gaagattttc tgggccatca gggcctgaac accgacgccg tgatcaacaa catcgaggat

 301 gccgtgaagc tgttcatagg agatgatttc tttgagttcc tggtcgagga atccaaccgc

 361 tattacaacc agaatagaaa caacttcaag ctgagcaaga aaagcctgaa gtggaaggac

 421 atcacccctc aggagatgaa aaagttcctg ggactgatcg ttctgatggg acaggtgcgg

 481 aaggacagaa gggatgatta ctggacaacc gaaccttgga ccgagacccc ttactttggc

 541 aagaccatga ccagagacag attcagacag atctggaaag cctggcactt caacaacaat

 601 gctgatatcg tgaacgagtc tgatagactg tgtaaagtgc ggccagtgtt ggattacttc

 661 gtgcctaagt tcatcaacat ctataagcct caccagcagc tgagcctgga tgaaggcatc

 721 gtgccctggc ggggcagact gttcttcaga gtgtacaatg ctggcaagat cgtcaaatac

 781 ggcatcctgg tgcgccttct gtgcgagagc gatacaggct acatctgtaa tatggaaatc

 841 tactgcggcg agggcaaaag actgctggaa accatccaga ccgtcgtttc cccttatacc

 901 gacagctggt accacatcta catggacaac tactacaatt ctgtggccaa ctgcgaggcc

 961 ctgatgaaga acaagtttag aatctgcggc acaatcagaa aaaacagagg catccctaag

1021 gacttccaga ccatctctct gaagaagggc gaaaccaagt tcatcagaaa gaacgacatc

1081 ctgctccaag tgtggcagtc caagaaaccc gtgtacctga tcagcagcat ccatagcgcc

1141 gagatggaag aaagccagaa catcgacaga acaagcaaga agaagatcgt gaagcccaat

1201 gctctgatcg actacaacaa gcacatgaaa ggcgtggacc gggccgacca gtacctgtct

1261 tattactcta tcctgagaag aacagtgaaa tggaccaaga gactggccat gtacatgatc

1321 aattgcgccc tgttcaacag ctacgccgtg tacaagtccg tgcgacaaag aaaaatggga

1381 ttcaagatgt tcctgaagca gacagccatc cactggctga cagacgacat tcctgaggac

1441 atggacattg tgccagatct gcaacctgtg cccagcacct ctggtatgag agctaagcct

1501 cccaccagcg atcctccatg tagactgagc atggacatgc ggaagcacac cctgcaggcc

1561 atcgtcggca gcggcaagaa gaagaacatc cttagacggt gcagggtgtg cagcgtgcac

1621 aagctgcgga gcgagactcg gtacatgtgc aagttttgca acattcccct gcacaaggga

1681 gcctgcttcg agaagtacca caccctgaag aattactag,
```

or a nucleotide sequence having at least about 90%, or at least about 93%, or at least about 95%, or at least about 97%, or at least about 98%, or at least about 99% identity thereto (the codons corresponding to the S8P and C13R mutations are underlined and bolded).

(SEQ ID NO: 9)

1 MAQHSDYPDD EFRADKLSNY SCDSDLENAS TSDEDSSDDE VMVRPRTLRR RRISSSSSDS

61 ESDIEGGREE WSHVDNPPVL EDFLGHQGLN TDAVINNIED AVKLFIGDDF FEFLVEESNR

121 YYNQNRNNFK LSKKSLKWKD ITPQEMKKFL GLIVLMGQVR KDRRDDYWTT EPWTETPYFG

181 KTMTRDRFRQ IWKAWHFNNN ADIVNESDRL CKVRPVLDYF VPKFINIYKP HQQLSLDEGI

241 VPWRGRLFFR VYNAGKIVKY GILVRLLCES DTGYICNMEI YCGEGKRLLE TIQTVVSPYT

301 DSWYHIYMDN YYNSVANCEA LMKNKFRICG TIRKNRGIPK DFQTISLKKG ETKFIRKNDI

361 LLQVWQSKKP VYLISSIHSA EMEESQNIDR TSKKKIVKPN ALIDYNKHMK GVDRADQYLS

421 YYSILRRTVK WTKRLAMYMI NCALFNSYAV YKSVRQRKMG FKMFLKQTAI HWLTDDIPED

481 MDIVPDLQPV PSTSGMRAKP PTSDPPCRLS MDMRKHTLQA IVGSGKKKNI LRRCRVCSVH

541 KLRSETRYMC KFCNIPLHKG ACFEKYHTLK NY, or an amino acid sequence having at least about 90%, or at least about 93%, or at least about 95%, or at least about 97%, or at least about 98%, or at least about 99% identity thereto (the amino acids corresponding to the S8P and C13R mutations are underlined and bolded).

In some embodiments, the MLT transposase encoded by the nucleotide sequence of SEQ ID NO: 8 and having the amino acid sequence of SEQ ID NO: 9 is referred to as an MLT transposase 2 (or MLT2).

In aspects, there is provided a composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto. In embodiments, the substitution is a non-polar aliphatic amino acid, optionally one of G, A, V, L, I and P, optionally S2A. In embodiments, the enzyme does not have additional residues at the C terminus. In embodiments, the enzyme has one or more mutations which confer hyperactivity, e.g. selected from $S8X_1$, $C13X_2$ and/or $N125X_3$, e.g. and where $X_1$ is selected from G, A, V, L, I and P, $X_2$ is selected from K, R, and H, and $X_3$ is selected from K, R, and H, e.g. $X_1$ is P, $X_2$ is R, and/or $X_3$ is K. In embodiments, there is provided a composition comprising a nucleic acid encoding the transposase enzyme (e.g. an MLT transposase) described here, e.g. having a nucleotide sequence of SEQ ID NO: 3, or a nucleotide sequence having at least about 80%, at least about 90%, or at least about 93%, or at least about 95%, or at least about 98% identity thereto. In embodiments, the transposase or nucleic acid is in the form of a lipid nanoparticle (LNP). In embodiments, the enzyme is co-formulated with a nucleic acid encoding a transposon, e.g. in the same lipid nanoparticle (LNP). In embodiments, the co-formulation comprises the nucleic acid encoding the enzyme and the nucleic acid encoding the transposon.

In embodiments, there is provided a method for inserting a gene into the genome of a cell, comprising contacting a cell with the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto, or the nucleotide sequence having at least about 80%, at least about 90%, or at least about 93%, or at least about 95%, or at least about 98% identity thereto. In embodiments, the substitution is a non-polar aliphatic amino acid, optionally one of G, A, V, L, I and P, optionally S2A. In embodiments, the enzyme does not have additional residues at the C terminus. In embodiments, the enzyme has one or more mutations which confer hyperactivity, e.g. selected from $S8X_1$, $C13X_2$ and/or $N125X_3$, e.g. and where $X_1$ is selected from G, A, V, L, I and P, $X_2$ is selected from K, R, and H, and $X_3$ is selected from K, R, and H, e.g. $X_1$ is P, $X_2$ is R, and/or $X_3$ is K. In embodiments, the method further comprises contacting the cell with a construct comprising a transposon and/or the enzyme is co-formulated with a nucleic acid encoding a transposon (e.g. in an LNP). In embodiments, the co-formulation comprises the nucleic acid encoding the enzyme and the nucleic acid encoding the transposon.

In some embodiments, a MLT transposase comprising the amino acid sequence of SEQ ID NO: 2 includes one or more mutations selected from S8P and/or C13R and one of R164N, W168V, M278A, K286A, R287A, R333A, K334A, N335A, K349A, K350A, K368A, K369A, and D416N.

In some embodiments, a MLT transposase comprising the amino acid sequence of SEQ ID NO: 2 includes one or more mutations selected from S8P and/or C13R and one of R164N, W168V, M278A, K286A, R287A, R333A, K334A, N335A, K349A, K350A, K368A, K369A, and D416N and/or one or more of E284A, K286A, R287A, N310A, R333A, K334A, R336A, K349A, K350A, K368A, and K369A.

In some embodiments, a MLT transposase comprising the amino acid sequence of SEQ ID NO: 2 includes one or more mutations selected from S8P and/or C13R and one of R164N, W168V, M278A, K286A, R287A, R333A, K334A, N335A, K349A, K350A, K368A, K369A, and D416N and/or one or more of E284A, K286A, R287A, N310A, R333A, K334A, R336A, K349A, K350A, K368A, and K369A and/or one R336A.

In embodiments, there is provided a method for treating a disease or disorder ex vivo, comprising contacting a cell with the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto or comprising a transposase enzyme (e.g. an MLT transposase) having a nucleotide sequence having a nucleotide sequence of SEQ ID NO: 3, or the nucleotide sequence having at least about 80%, at least about 90%, or at least about 93%, or at least about 95%, or at least about 98% identity thereto.

In embodiments, there is provided a method for treating a disease or disorder in vivo, comprising administering the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto, or comprising a transposase enzyme (e.g. an MLT transposase) having a nucleotide sequence having a nucleotide sequence of SEQ ID NO: 3, or the nucleotide sequence having at least about 80%, at least about 90%, or at least about 93%, or at least about 95%, or at least about 98% identity thereto, or a cell comprising the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto, or comprising a transposase enzyme (e.g. an MLT transposase) having a nucleotide sequence having a nucleotide sequence of SEQ ID NO: 2, or the nucleotide sequence having at least about 80%, at least about 90%, or at least about 93%, or at least about 95%, or at least about 98% identity thereto.

In embodiments, the present MLT transposase, e.g. with an amino acid sequence of SEQ ID NO: 2, or a variant thereof (and optionally one or more hyperactive mutations) demonstrates improved integration efficiency relative to piggyBac. In embodiments, the present MLT transposase of an amino acid sequence of SEQ ID NO: 2, and S8P, C13R and/or N125K, demonstrates improved integration efficiency relative to piggyBac.

In embodiments, the present MLT transposase, e.g. with an amino acid sequence of SEQ ID NO: 2, or a variant thereof (and optionally one or more hyperactive mutations) can be in the form or an RNA or DNA and have one or two N-terminus nuclear localization signal (NLS) to shuttle the protein more efficiently into the nucleus. For example, in embodiments, the present MLT transposase further comprises one, two, three, four, five, or more NLSs. Examples of NLS are provided in Kosugi et al. (J. Biol. Chem. (2009) 284:478-485; incorporated by reference herein). In a particular embodiment, the NLS comprises the consensus sequence K(K/R)X(K/R) (SEQ ID NO: 348). In an embodiment, the NLS comprises the consensus sequence (K/R)(K/R)$X_{10-12}$(K/R)$_{3/5}$(SEQ ID NO: 349), where (K/R)$_{3/5}$ represents at least three of the five amino acids is either lysine or arginine. In an embodiment, the NLS comprises the c-myc NLS. In a particular embodiment, the c-myc NLS comprises the sequence PAAKRVKLD (SEQ ID NO: 350). In a particular embodiment, the NLS is the nucleoplasmin NLS. In a particular embodiment, the nucleoplasmin NLS comprises the sequence KRPAATKKAGQAKKKK (SEQ ID NO: 351). In a particular embodiment, the NLS comprises the SV40 Large T-antigen NLS. In a particular embodiment, the SV40 Large T-antigen NLS comprises the sequence PKKKRKV (SEQ ID NO: 352). In a particular embodiment, the NLS comprises three SV40 Large T-antigen NLSs (e.g., DPKKKRKVDPKKKRKVDPKKKRKV (SEQ ID NO: 353). In various embodiment, the NLS may comprise mutations/variations in the above sequences such that they contain 1 or more substitutions, additions or deletions (e.g. about 1, or about 2, or about 3, or about 4, or about 5, or about 10 substitutions, additions, or deletions).

In some embodiments, the transposase is from a LEAP-IN 1 type or LEAP-IN transposon system (Biotechnol J. 2018 October; 13(10):e1700748. doi: 10.1002/biot.201700748. Epub 2018 Jun. 11).

In some embodiments, a non-viral vector includes a LEAP-IN 1 type of LEAPIN Transposase (ATUM, Newark, Calif.). The LEAPIN Transposase system includes a transposase (e.g., a transposase mRNA) and a vector containing one or more genes of interest (transposons), selection markers, regulatory elements, insulators, etc., flanked by the transposon cognate inverted terminal ends and the transposition recognition motif (TTAT). Upon co-transfection of vector DNA and transposase mRNA, the transiently expressed enzyme catalyzes high-efficiency and precise integration of a single copy of the transposon cassette (all sequences between the terminal ends) at one or more sites across the genome of the host cell. Hottentot et al. *In Genotyping: Methods and Protocols*. White S J, Cantsilieris S, eds: 185-196. (New York, N.Y.: Springer): 2017. pp. 185-196. The LEAPIN Transposase generates stable transgene integrants with various advantageous characteristics, including single copy integrations at multiple genomic loci, primarily in open chromatin segments; no payload limit, so multiple independent transcriptional units may be expressed from a single construct; the integrated transgenes maintain their structural and functional integrity; and maintenance of transgene integrity ensures the desired chain ratio in every recombinant cell.

Furthermore, the LEAPIN Transposase has a self-inactivating mechanism. The 3-TRE, located within an intron of the transposase construct, spatially separates the promoter regions. Therefore, enzymatic excision of the transposon located between TTAA (SEQ ID NO: 1) sites, from the plasmid during transposition, results in the separation of the promoter from the 5' end of the LEAPIN Transposase construct. The now promoterless transposase residing in the remaining plasmid backbone is inactivated if inserted non-transpositionally into the genome, thereby reducing genotoxic effects in a host cell. This can stop any protein synthesis from the mRNA constructs that may be erroneously synthesized. Urschitz et al., *Proc Natl Acad Sci USA* 2010; 107:8117-22.

In some embodiments, the present dual system comprises a DNA plasmid encoding a transgene, and RNA encoding a transposase (e.g., the LEAPIN Transposase). In some embodiments, the use of mRNA that encodes a transposase can have a number of advantages over delivery of a transposase-encoding DNA molecule. See, e.g. Wilber et al. *Mol Ther* 2006; 13:625-30. The advantages include improved control with respect to the duration of transposase expression, minimizing persistence in the tissue, and the potential for transgene re-mobilization and re-insertion following the initial transposition event. Furthermore, the transposase-encoding RNA sequence is likely incapable of integrating into the host genome, thereby eliminating concerns about long-term transposase expression and destabilizing effects with respect to the gene of interest. Furthermore, in some embodiments, the dual plasmid DNA transposon/RNA transposase system is in the form of a lipid nanoparticle (LNP), to protect from extracellular RNA degradation, which improves the in vivo use.

In some embodiments, a transgene can be associated with various regulatory elements that are selected to ensure stable expression of a construct with the transgene. Thus, in some embodiments, a transgene can be encoded by a non-viral vector (e.g., a DNA plasmid) that can comprise one or more insulator sequences that prevent or mitigate activation or inactivation of nearby genes. The insulators flank the transposon (transgene cassette) to reduce transcriptional silencing and position effects imparted by chromosomal sequences. As an additional effect, the insulators can eliminate functional interactions of the transgene enhancer and promoter sequences with neighboring chromosomal sequences. In some embodiments, the one or more insulator sequences comprise an HS4 insulator (1.2-kb 5'-HS4 chicken β-globin (cHS4) insulator element) and an D4Z4 insulator (tandem macrosatellite repeats linked to Facio-Scapulo-Humeral Dystrophy (FSHD). In some embodiments, the sequences of the HS4 insulator and the D4Z4 insulator are as described in Rival-Gervier et al. *Mol Ther.* 2013 August; 21(8):1536-50, which is incorporated herein by reference in its entirety.

The described method enhances enzymes capable of targeted genomic integration by transposition (e.g., without limitation, transposases) by fusing them to DNA binding TALEs or dCas9/gRNA to target integrations to GSHS, which can be in areas that have open chromatin. In embodiments, a nucleic acid encoding the enzyme (e.g., DNA) encodes the enzyme in the form of first and second portions with an intein encoded between the first and second portions, such that the first and second portions are fused into a functional enzyme upon post-translational excision of the intein from the enzyme. The described method provides reduced insertional mutagenesis or oncogenesis as compared to a method with a non-chimeric transposase. Also, in some embodiments, the method is used to treat an inherited or acquired disease in a patient in need thereof.

In embodiments, there is provided a transgenic organism that may comprise cells which have been transformed by the methods of the present disclosure. In embodiments, the organism may be a mammal or an insect. When the organism is a mammal, the organism may include, but is not limited to, a mouse, a rat, a monkey, a dog, a rabbit and the like. When the organism is an insect, the organism may include, but is not limited to, a fruit fly, a mosquito, a bollworm and the like.

The compositions can be included in a container, kit, pack, or dispenser together with instructions for administration.

Also provided herein are kits comprising: i) any of the aforementioned gene transfer constructs of this invention, and/or any of the aforementioned cells of this invention and ii) a container. In certain embodiments, the kits further comprise instructions for the use thereof. In certain embodiments, any of the aforementioned kits can further comprise a recombinant DNA construct comprising a nucleic acid sequence that encodes a transposase.

In embodiments, a composition in accordance with embodiments of the present disclosure is in the form of a pharmaceutical composition, in combination with a pharmaceutically acceptable carrier. A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject (e.g., a mammal, such as a human, non-human primate, dog, cat, sheep, pig, horse, cow, mouse, rat, or rabbit), which is nontoxic to the cell or subject being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick, *Regul Toxicol Pharmacol* 32:210-218, 2000; Wang, *Int J Pharm* 203:1-60, 2000; Charman *J Pharm Sci* 89:967-978, 2000; and Powell et al. *PDA J Pharm Sci Technol* 52:238-311, 1998), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can contain sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a pharmaceutical composition including a composition as provided herein can be, at least in part, in the form of a solution or powder with or without a diluent to make an injectable suspension. The composition may include additional ingredients including, without limitation, pharmaceutically acceptable vehicles, such as saline, water, lactic acid, mannitol, or combinations thereof, for example.

Any appropriate method can be used to administer a composition as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing a composition as described herein can be administered prior to, after, or in lieu of surgical resection of a tumor.

This invention is further illustrated by the following non-limiting examples.

EXAMPLES

Example 1—Design of Chimeric Transposases with Transcription Activator-Like Effector (TALE) DNA Binding Domains (DBDs) or dCas9/gRNA that Target Human Genomic Safe Harbor Sites (GSHS)

In this example, chimeric transposases were designed using human GSHS TALE or dCas9/gRNA DBD. FIGS. 1A-1D and FIG. 2 depict representations of chimeric transposase designed using human GSHS TALE or dCas9/gRNA DBD. FIG. 1A. TALEs includes nuclear localization signals (NLS) and an activation domain (AD) to function as transcriptional activators. A central tandem repeat domain confers specific DNA-binding and host specificity. Translocation signal (TD) and four cryptic repeats required for initiation of DNA binding and for the recognition of 5'-$T^0$ are located at the N-terminus (checkered rectangles). Each 34 amino acid (aa) long repeat in the CRD binds to one nucleotide with specificity determined mainly by aa at position 13. One sample repeat is shown below the protein scheme. Numbers 12/13 refer to aa positions within the repeat. See Jankele et al., *Brief Funct Genomics* 2014; 13:409-19. FIG. 1B. Repeat types are shown that have specificity for one or several nucleotides. Only bases of the DNA leading strand are shown. FIG. 1C. A chimeric transposase having a TALE DNA-binding protein fused thereto by a linker that is greater than 23 amino acids in length (top). See Hew et al., *Synth Biol*(Oxf) 2019; 4:ysz018. FIG. 1D. Binding of the TALE to GSHS physically sequesters the transposase to the same location and promotes transposition to the nearby TTAA (SEQ ID NO: 1) sequences near repeat variable di-residues (RVD) nucleotide sequences. All RVD are preceded by a thymine (T) to bind to the NTR shown in FIG. 1A. All of these GSHS regions are in open chromatin and are susceptible to transposase activity).

FIG. 2 is a non-limiting representation of a system in accordance with embodiments of the present disclosure comprising a nucleic acid (e.g., helper RNA) encoding an enzyme capable of targeted genomic integration by transposition and a nucleic acid encoding a transposase (donor DNA). The helper RNA is translated into a bioengineered enzyme (e.g., integrase, recombinase, or transposase) that recognizes specific ends and seamlessly inserts the donor DNA into the human genome in a site-specific manner without a footprint. The enzyme can form a dimer or a tetramer at open chromatin to insert donor DNA at TTAA (SEQ ID NO: 1) recognition sites near DNA binding regions targeted by dCas9/gRNA or TALEs. Binding of the dCas9/gRNA to TALE GSHS physically sequesters the enzyme to the same location and promotes transposition to the nearby TTAA (SEQ ID NO: 1) sequences (See FIG. 3 and FIG. 4).

FIG. 1C also illustrates (bottom) a chimeric transposase construct comprising dCas9 linked to one or more guide RNAs. An engineered chimeric transposase may include: a guide RNA (gRNA) and an inactivated Cas protein. The gRNA is a short synthetic RNA composed of a scaffold sequence necessary for Cas-binding and a user-defined ~20 nucleotide spacer that defines the genomic target to be modified. Thus, the genomic target of the Cas protein is based upon the sequence present in the gRNA. FIG. 4 shows gRNA sequences that physically sequester the transposase to GSHS and promotes transposition to the nearby TTAA (SEQ ID NO: 1) sequences.

Figure 8A:
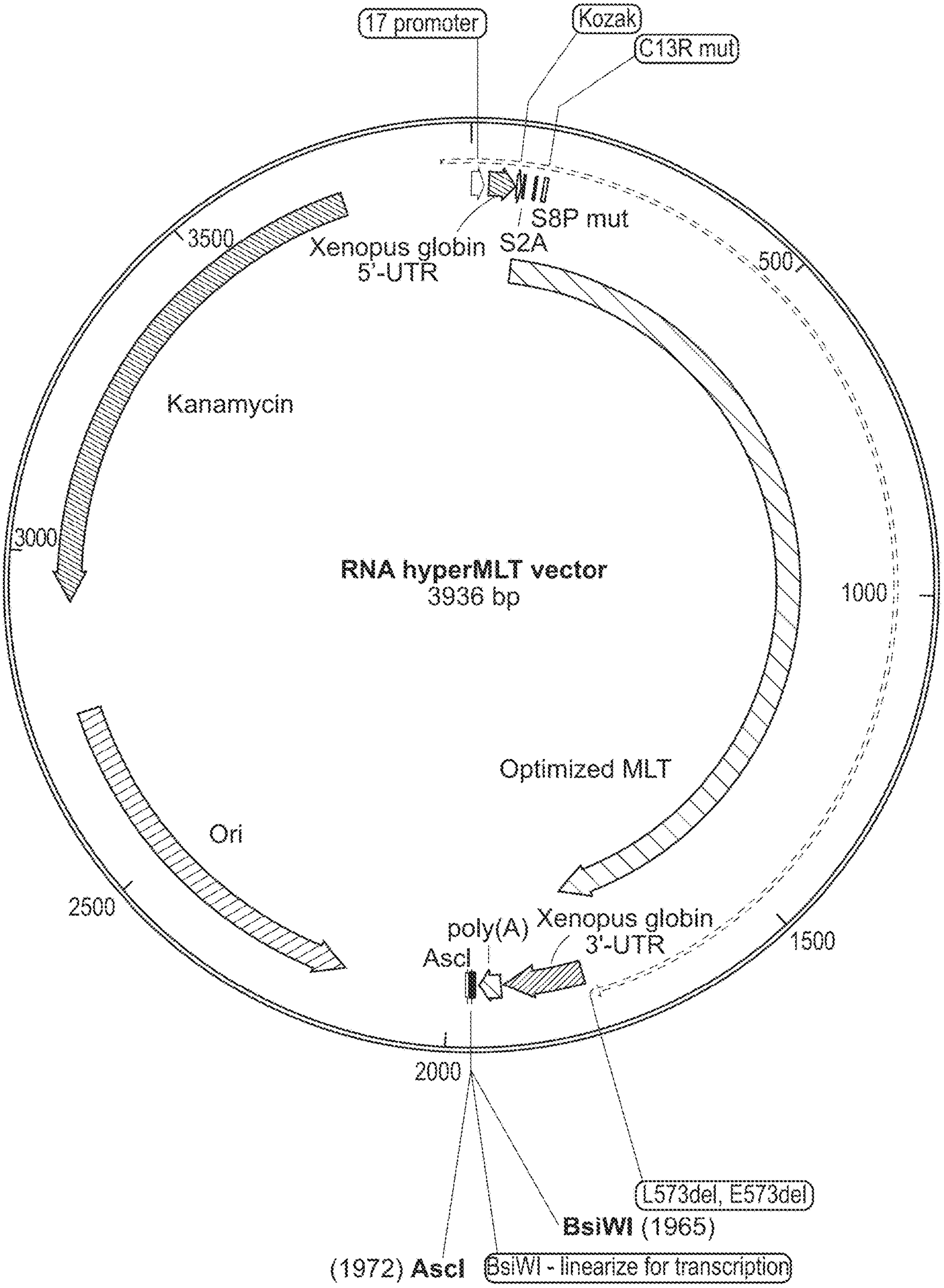
FIGS. 8A and 8B depict non-limiting examples of construct templates.
Figure 8B:
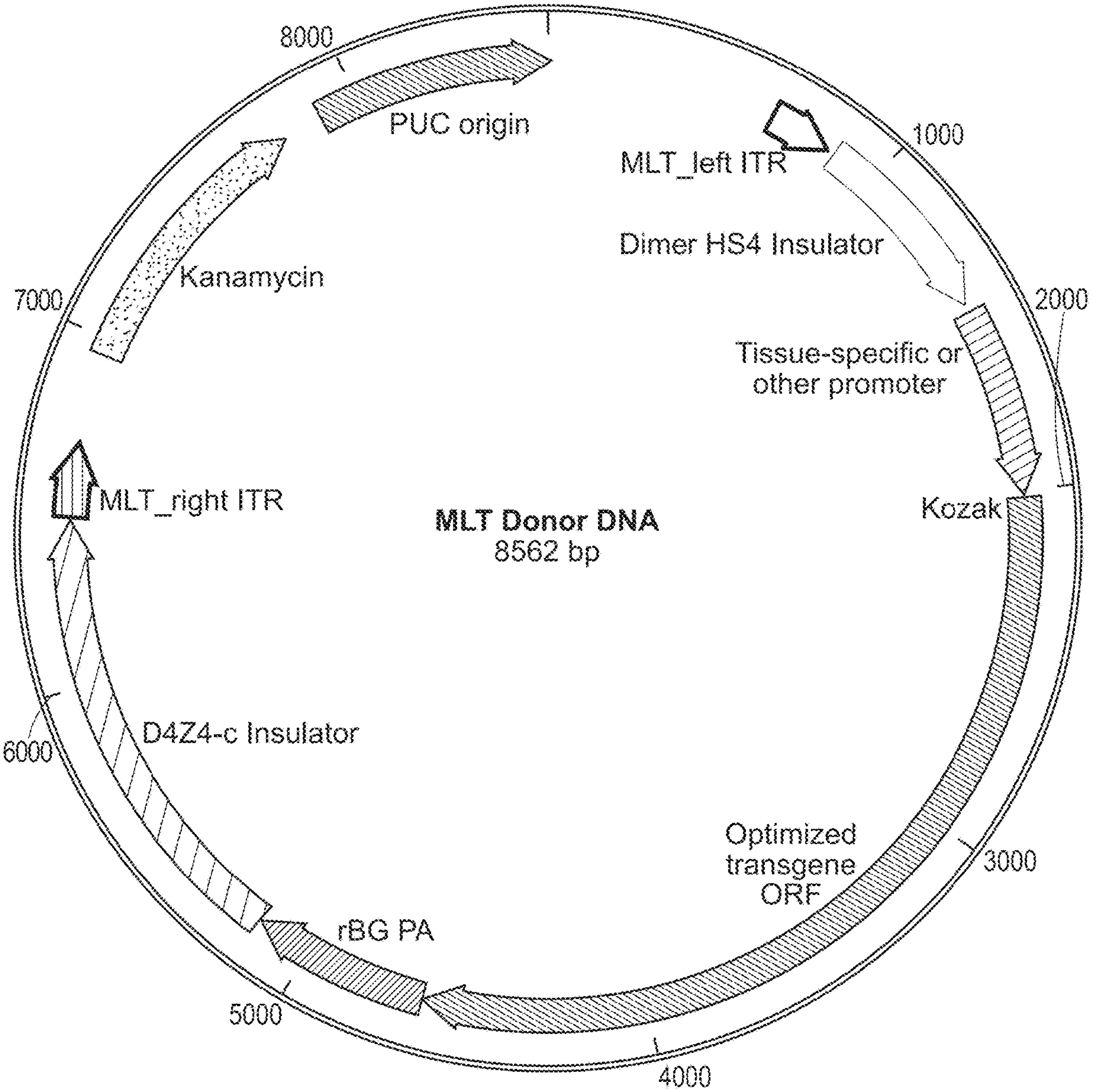

FIGS. 8A-8D depict examples of construct templates. FIG. 8A depicts a plasmid construct template that transcribes transposase RNA that is later processed with a 5'-m7G cap1 and pseudouridine substitution. Other transposases can be substituted. FIG. 8B depicts a (generic) MLT donor DNA construct template that can be used for transfer of any transgene. Other dCas9/gRNAs and transposases can be substituted.

Example 2—Characterizing Transposition Activity of *M. lucifugus* MLT Transposase and its Hyperactive Forms This study, in part, aims at functionally characterizing the transposition activity of *M. lucifugus* (MLT) transposase, including monomer, dimer, tetramer, hyperactive, and Int-forms of MLT transposase. The MLT transposase protein with the L573del, E574del, and S2A mutations, discovered in the present disclosure, can be referred to as an engineered, corrected MLT transposase in accordance with the present disclosure.

FIGS. 5A and 5B depict hyperactive, excision positive, and integration deficient (Int−) MLT mutants from the MLT transposase DNA and MLT transposase protein. For each mutant, FIG. 5A shows nucleotide changes and corresponding amino acid changes relative to a non-mutated wild type MLT transposase, having the amino acid sequence of SEQ ID NO: 4 and that is encoded by the nucleotide sequence of SEQ ID NO: 5. FIG. 5B shows mutations in the MLT transposase backbone and various MLT mutants (1, 2, and 3).

Figure 6A:
FIG. 6A depicts the three dimensional MLT protein structure with 100% confidence that shows DNA binding domains.
Figure 6B:
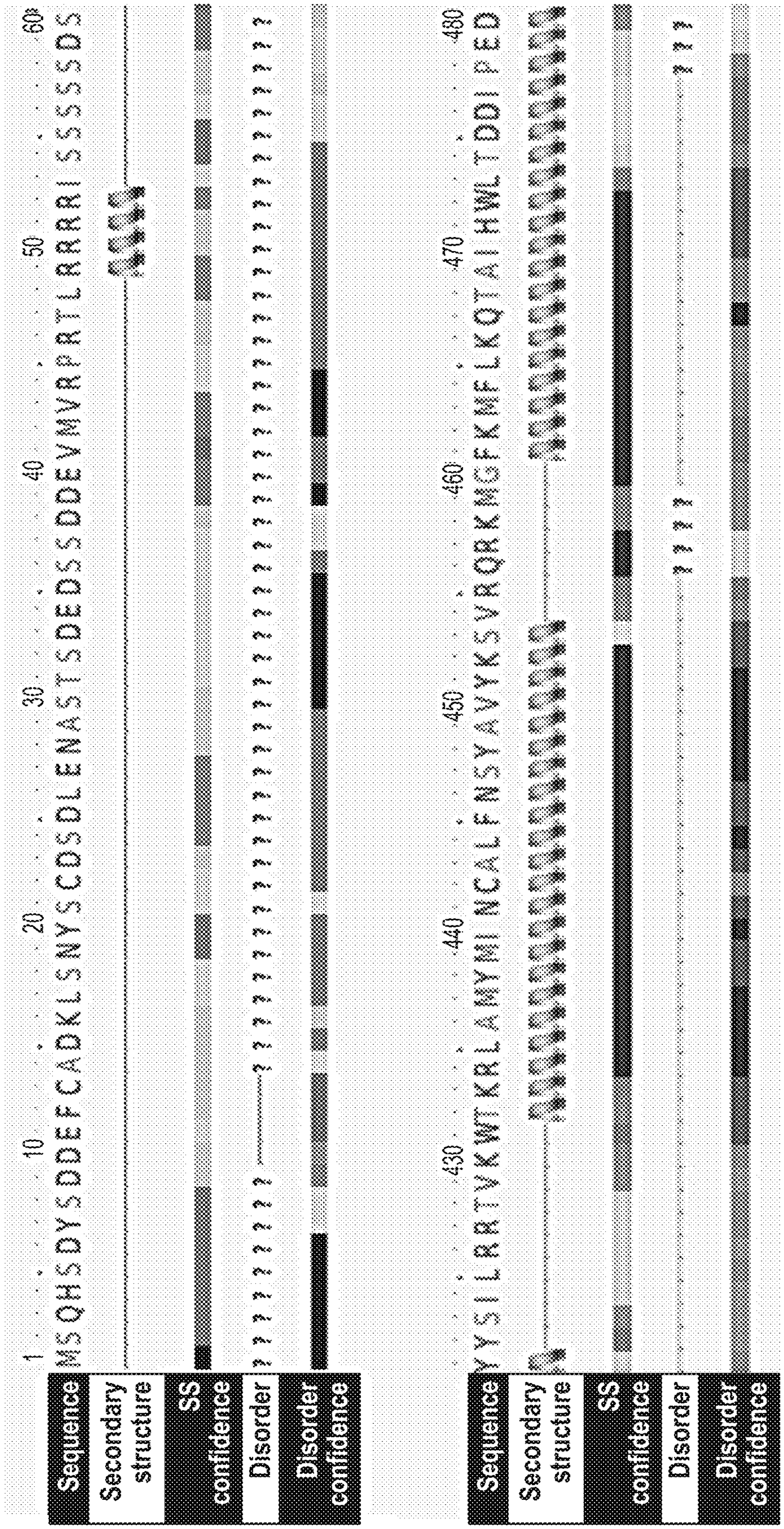
FIG. 6B depicts secondary structure prediction for an MLT transposase comprising the amino acid sequence of SEQ ID NO: 4 encoded by a nucleotide sequence of SEQ ID NO: 5
Figure 6B:
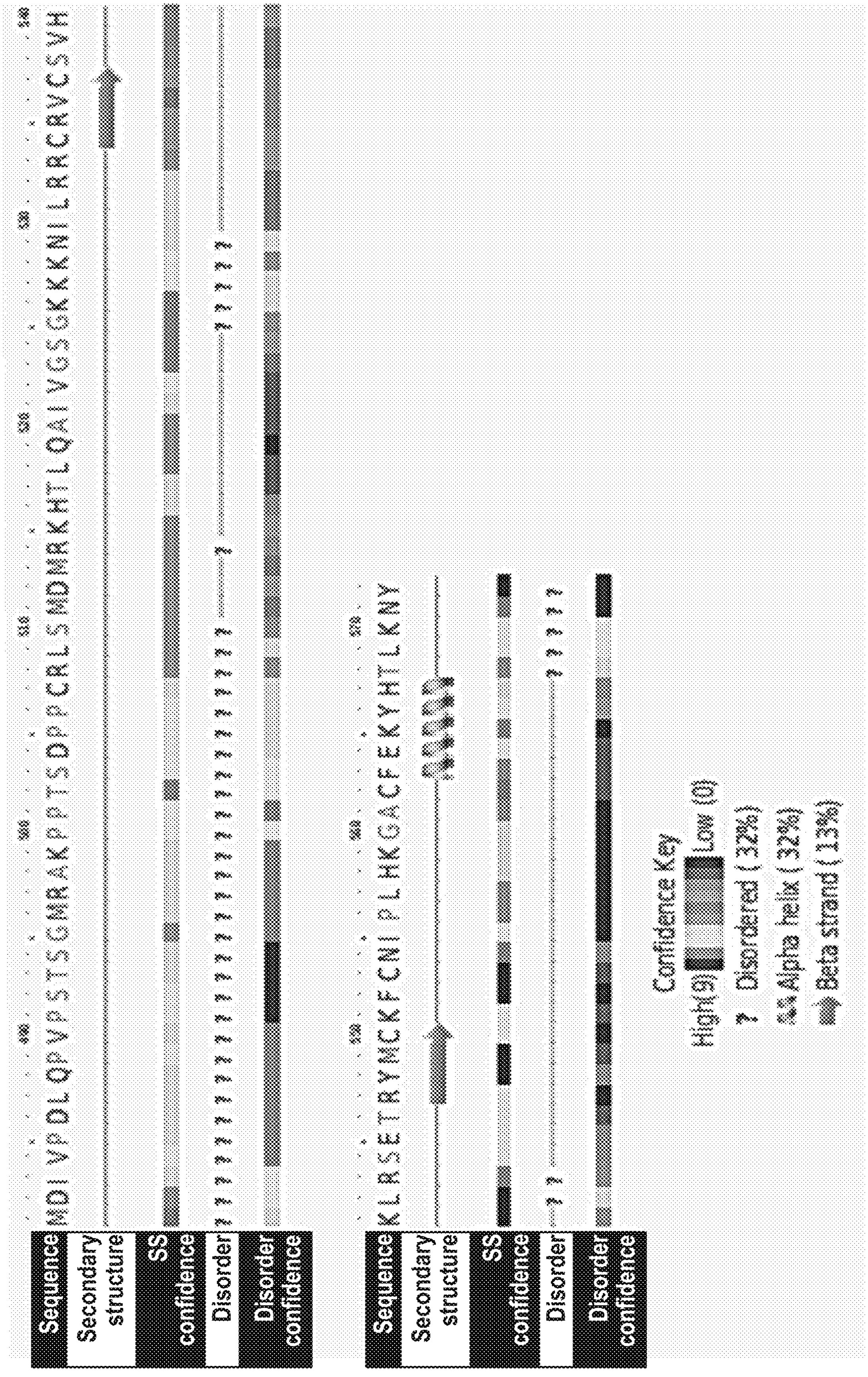

FIG. 6A depicts the three-dimensional MLT protein structure with 100% confidence that shows DNA binding domains (in red). The three dimensional MLT protein structure is generated using Phyre$^2$ (Protein Homology/AnalogY Recognition Engine), Kelley L A et al. *Nature Protocols* 10, 845-858 (2015). FIG. 6B depicts secondary structure prediction for MLT, using Phyre$^2$.

FIG. 7 depicts an amino acid sequence alignment of piggyBac ("*Trichoplusia ni*") transposase to MLT ("*Myotis lucifugus*") transposase (two different sequences), and bat transposases *Myotis myotis* (four different sequences) and *Pteropus vampyrus*. The sequences were obtained from Jebb, et al., *Nature*, volume 583, pages 578-584 (2020), which is incorporated herein by reference in its entirety. In FIG. 7, the alignment, generated using SnapGene® software (from GSL Biotech), is to the consensus sequence. Amino acids that match the reference (consensus), i.e. highly conserved mammalian transposase sequences, are marked with yellow highlighting. Consensus threshold is greater than 50%.

In this example, the sequences shown in FIGS. 3, 4, and 7, or any other sequences, are used in testing varying combinations of MLT mutants, to identify candidates for targeting genomic safe harbor sites with site-specific TALEs or dCas9/gRNA. Hyperactive, excision positive, or Int-MLT mutants can be generated by synthetic DNA synthesis by substituting the mutations in FIGS. 5A and 5B in a MLT transposase described herein, e.g. a nucleotide and amino acid sequence.

In this example, a genetic assay as described, for example, in Example 8 of International Application WO2010085699, which is incorporated herein by reference in its entirety, can be used for screening for an increased frequency of Ura+ reversion. The genetic assay uses a modified version of the yeast URA3 gene as a transposon donor, for the excision of MLT in yeast (*Saccharomyces cerevisiae*).

Example 3—Characterizing Integration Efficiency of Piggybac, Wild-Type MLT Transposase, and Engineered MLT Transposase of the Disclosure A goal of this study was to assess integration efficiency of known hyperactive piggyBac transposases, including those from published sources, and of an engineered MLT transposase in accordance with the present disclosure. The wild type *Myotis Lucifugus* transposase (MLT) sequence was described in a WO2010/085699 publication (of PCT/US2010/021871) and in Mitra et al., PNAS 2013; 110:234. The nucleotide sequence of a transposase from Mitra et al. (2013) has 77% sequence identity to the MLT transposase of the present disclosure (referred to as "MLT") that has the nucleotide sequence of SEQ ID NO: 3. See FIG. 10, which depicts a nucleotide sequence alignment of hyperactive MLT (human codon-optimized for RNA) and published sequence from Mitra et al. (2013) (Identity 77.67%, gaps 1.44%). The nucleotide sequence of MLT and the nucleotide sequence from WO2010085699 have 73.68%, identity (gaps 1.16%), as shown in FIG. 11 containing their alignment.

Furthermore, the end sequences of the engineered MLT transposase of the present disclosure are different than those referenced by Mitra et al. (2013) (see Ray et al., *Genome Res* 2008; 18:717). FIG. 14 and FIG. 15 show left and right terminal ends of the engineered MLT transposase, compared to left and right terminal ends of the published sequence from Ray et al., 2018.

FIG. 12 illustrates an amino acid alignment of the engineered hyperactive MLT transposase (L573del/E574del/S2A, with S8P, C13R, and N125K mutations, "MLT") and a published sequence by Mitra et al. (the differences between the amino acid sequences are underlined and bolded). As shown in FIG. 12, the amino acid sequence from Mitra et al. contained two extra C-terminal amino acids relative to the MLT transposase of the present disclosure.

FIG. 13 illustrates an amino acid alignment of the engineered, hyperactive MLT transposase (L573del/E574del/S2A, with S8P and C13R mutations, "MLT") and a published sequence from WO2010085699 (the differences between the amino acid sequences are underlined and bolded). The sequence from the WO2010085699 publication had multiple amino acid residue changes compared to the amino acid sequence of the MLT transposase of the present disclosure. WO2010085699 described hyperactive transposase enzymes comprising amino acid changes in the sequence as shown in FIG. 13, the amino acid changes selected from A14V, D475G, P491Q, A561T, T546T, T300A, T294A, A520T, G239S, S5P, S8F, S54N, D9N, D9G, I345V, M481V, E11G, K130T, G9G, R427H, S8P, S36G, D10G, S36G and silent.

Figure 9A:
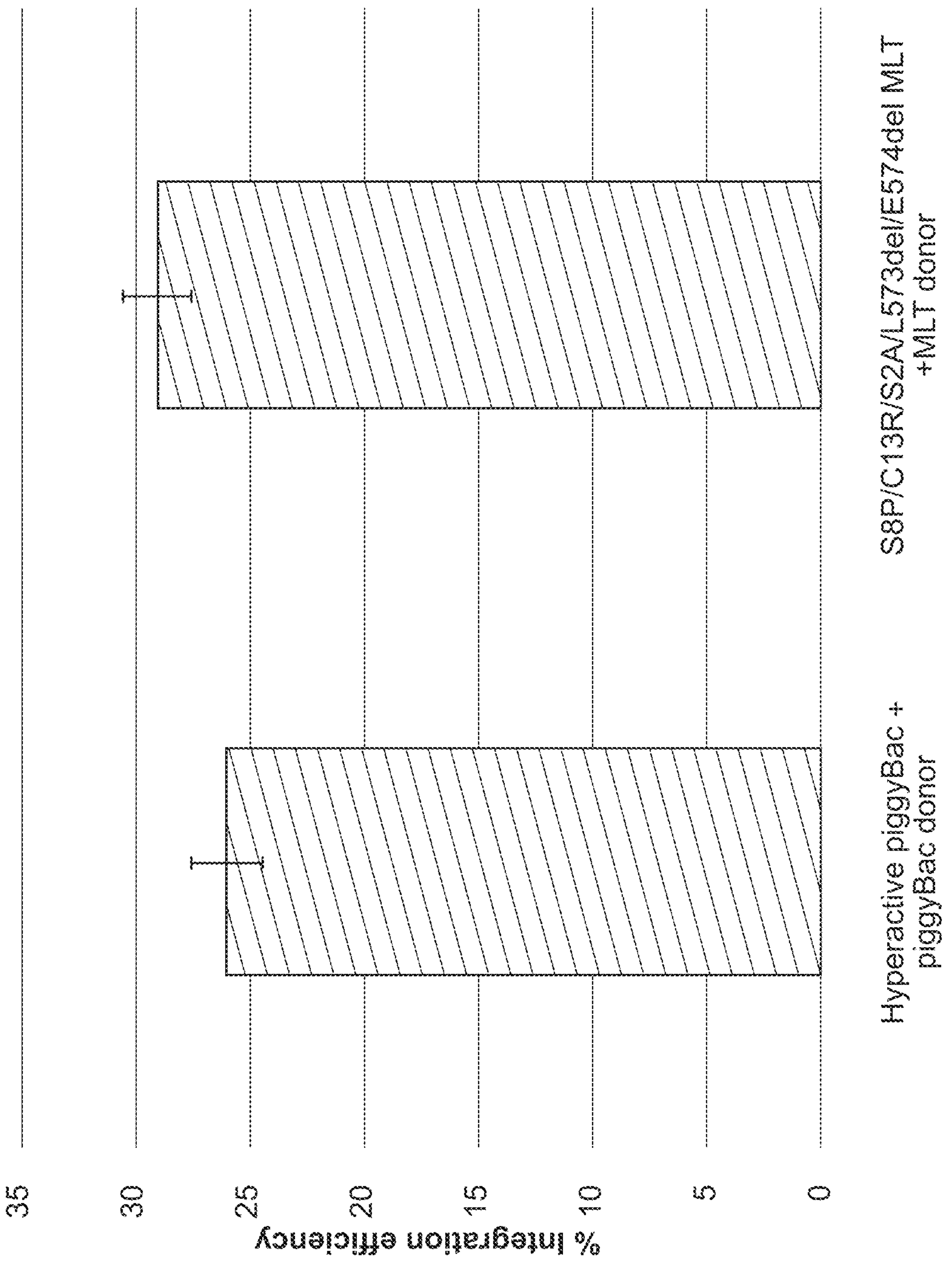
FIG. 9A is a bar chart illustrating integration efficiency of hyperactive piggyBac transposase versus hyperactive MLT variants (S8P/C13R double mutant; L573del E574del) using sequences from Yusa et al. (2010).
Figure 9B:
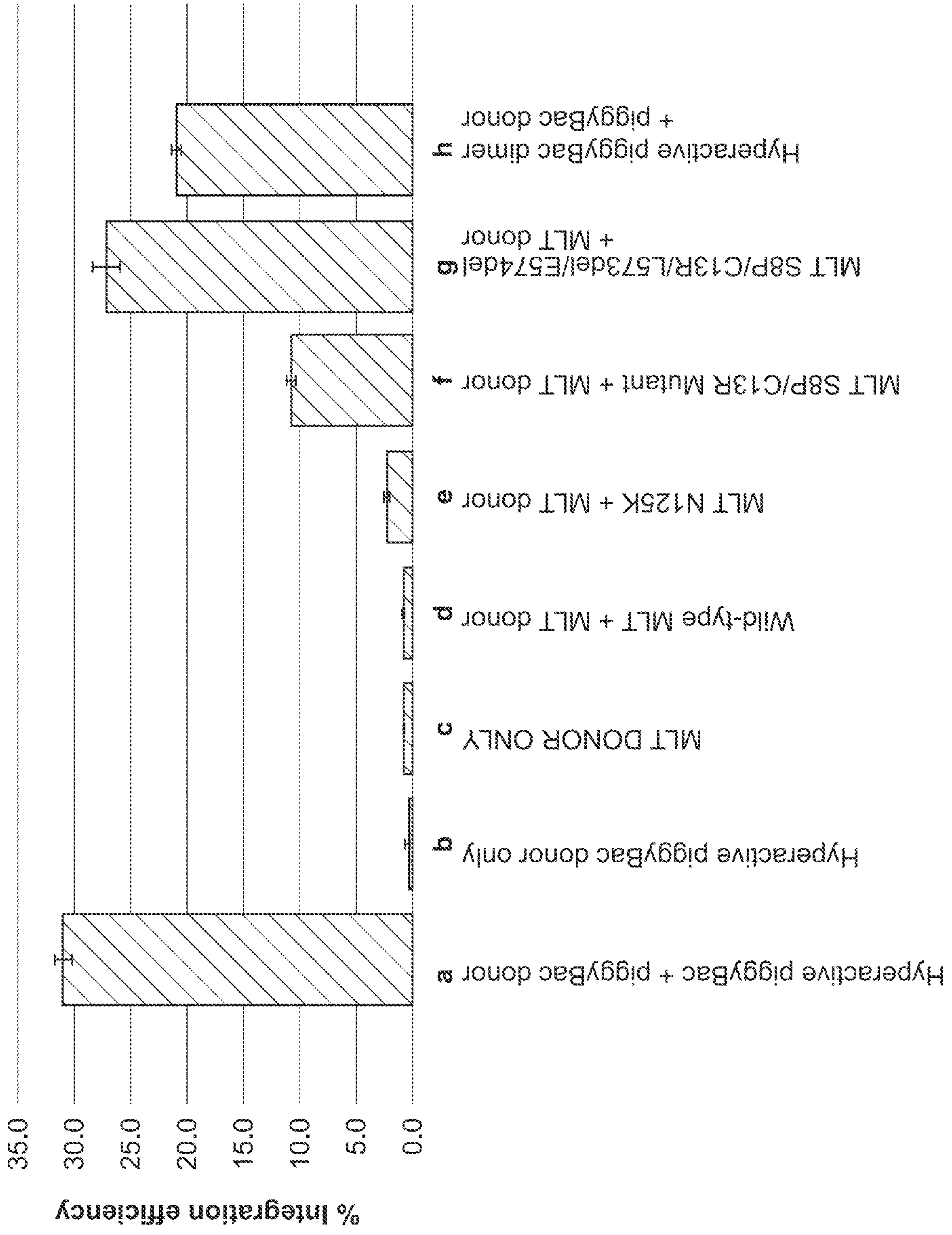
FIG. 9B is a bar chart illustrating integration efficiency of engineered MLT (S8P/C13R double mutant; L573del E574del, S2A) compared to hyperactive piggyBac, using sequences from Yusa et al. (2010).
Figure 16:
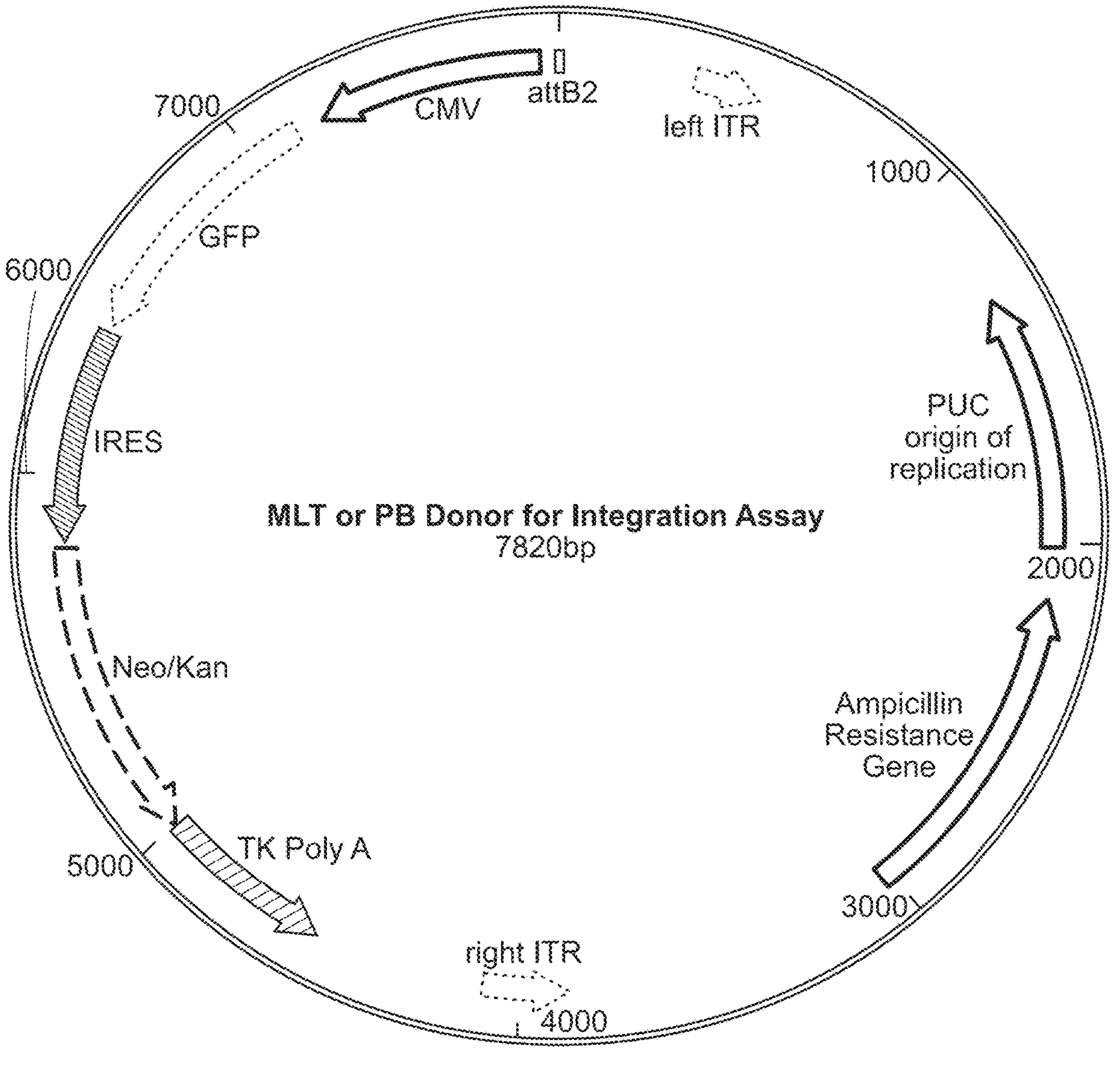
FIG. 16 depicts a DNA donor construct template used with either *Myotis lucifugus* transposase (MLT) or piggyBac (PB) transposase, for an integration assay. The DNA donor construct template has a cytomegalovirus (CMV) promoter that drives expression of green fluorescent protein (GFP).

FIGS. 9A and 9B are bar charts illustrating results of assessment of integration efficiency of the engineered MLT transposase of the present disclosure and other (known) transposases. FIG. 9A illustrates integration efficiency of a hyperactive piggyBac transposase from Yusa et al. *PNAS* 2010; 108:1531-1536 (see FIGS. 16A, 16B, 16C, and 16D), used with a piggyBac donor (CMV-GFP, see FIG. 15), versus the engineered MLT transposase of the present disclosure (S8P/C13R/S2A/L573del/E574del MLT) used with an MLT donor (CMV-GFP, see FIG. 16 that shows an example of a DNA donor construct template).

The hyperactive piggyBac amino acid sequence used in the study show in FIG. 9A and FIG. 9B (from Yusa et al. (2010), with I30V, S103P, G165S, M282V, S509G, N538K, and N571S mutations, shown bolded and underlined) is as follows:

(SEQ ID NO: 17)

```
1    MGSSLDDEHI LSALLQSDDE LVGEDSDSEV SDHVSEDDVQ SDTEEAFIDE VHEVQPTSSG

61   SEILDEQNVI EQPGSSLASN RILTLPQRTI RGKNKHCWST SKPTRRSRVS ALNIVRSQRG

121  PTRMCRNIYD PLLCFKLFFT DEIISEIVKW TNAEISLKRR ESMTSATFRD TNEDEIYAFF
```

-continued

```
181   GILVMTAVRK DNHMSTDDLF DRSLSMVYVS VMSRDRFDFL IRCLRMDDKS IRPTLRENDV

241   FTPVRKIWDL FIHQCIQNYT PGAHLTIDEQ LLGFRGRCPF RVYIPNKPSK YGIKILMMCD

301   SGTKYMINGM PYLGRGTQTN GVPLGEYYVK ELSKPVHGSC RNITCDNWFT SIPLAKNLLQ

361   EPYKLTIVGT VRSNKREIPE VLKNSRSRPV GTSMFCFDGP LTLVSYKPKP AKMVYLLSSC

421   DEDASINEST GKPQMVMYYN QTKGGVDTLD QMCSVMTCSR KTNRWPMALL YGMINIACIN

481   SFIIYSHNVS SKGEKVQSRK KFMRNLYMGL TSSFMRKRLE APTLKRYLRD NISNILPKEV

541   PGTSDDSTEE PVMKKRTYCT YCPSKIRRKA SASCKKCKKV ICREHNIDMC QSCF
```

The hyperactive piggyBac nucleotide sequence used in the study show in FIG. 9A and FIG. 9B (mutated codons underlined and bolded) is as follows:

```
                                                           (SEQ ID NO: 18)
   1   ATGGGCAGCA GCCTGGACGA CGAGCACATC CTGAGCGCCC TGCTGCAGAG CGACGACGAG

  61   CTGGTCGGCG AGGACAGCGA CAGCGAGGTG AGCGACCACG TGAGCGAGGA CGACGTGCAG

 121   TCCGACACCG AGGAGGCCTT CATCGACGAG GTGCACGAGG TGCAGCCTAC CAGCAGCGGC

 181   TCCGAGATCC TGGACGAGCA GAACGTGATC GAGCAGCCCG GCAGCTCCCT GGCCAGCAAC

 241   AGGATCCTGA CCCTGCCCCA GAGGACCATC AGGGGCAAGA ACAAGCACTG CTGGTCCACC

 301   TCCAAGCCCA CCAGGCGGAG CAGGGTGTCC GCCCTGAACA TCGTGAGAAG CCAGAGGGGC

 361   CCCACCAGGA TGTGCAGGAA CATCTACGAC CCCCTGCTGT GCTTCAAGCT GTTCTTCACC

 421   GACGAGATCA TCAGCGAGAT CGTGAAGTGG ACCAACGCCG AGATCAGCCT GAAGAGGCGG

 481   GAGAGCATGA CCTCCGCCAC CTTCAGGGAC ACCAACGAGG ACGAGATCTA CGCCTTCTTC

 541   GGCATCCTGG TGATGACCGC CGTGAGGAAG GACAACCACA TGAGCACCGA CGACCTGTTC

 601   GACAGATCCC TGAGCATGGT GTACGTGAGC GTGATGAGCA GGGACAGATT CGACTTCCTG

 661   ATCAGATGCC TGAGGATGGA CGACAAGAGC ATCAGGCCCA CCCTGCGGGA GAACGACGTG

 721   TTCACCCCCG TGAGAAAGAT CTGGGACCTG TTCATCCACC AGTGCATCCA GAACTACACC

 781   CCTGGCGCCC ACCTGACCAT CGACGAGCAG CTGCTGGGCT TCAGGGGCAG GTGCCCCTTC

 841   AGGGTCTATA TCCCCAACAA GCCCAGCAAG TACGGCATCA AGATCCTGAT GATGTGCGAC

 901   AGCGGCACCA AGTACATGAT CAACGGCATG CCCTACCTGG GCAGGGGCAC CCAGACCAAC

 961   GGCGTGCCCC TGGGCGAGTA CTACGTGAAG GAGCTGTCCA AGCCCGTCCA CGGCAGCTGC

1021   AGAAACATCA CCTGCGACAA CTGGTTCACC AGCATCCCCC TGGCCAAGAA CCTGCTGCAG

1081   GAGCCCTACA AGCTGACCAT CGTGGGCACC GTGAGAAGCA ACAAGAGAGA GATCCCCGAG

1141   GTCCTGAAGA ACAGCAGGTC CAGGCCCGTG GGCACCAGCA TGTTCTGCTT CGACGGCCCC

1201   CTGACCCTGG TGTCCTACAA GCCCAAGCCC GCCAAGATGG TGTACCTGCT GTCCAGCTGC

1261   GACGAGGACG CCAGCATCAA CGAGAGCACC GGCAAGCCCC AGATGGTGAT GTACTACAAC

1321   CAGACCAAGG GCGGCGTGGA CACCCTGGAC CAGATGTGCA GCGTGATGAC CTGCAGCAGA

1381   AAGACCAACA GGTGGCCCAT GGCCCTGCTG TACGGCATGA TCAACATCGC CTGCATCAAC

1441   AGCTTCATCA TCTACAGCCA CAACGTGAGC AGCAAGGGCG AGAAGGTGCA GAGCCGGAAA

1501   AAGTTCATGC GGAACCTGTA CATGGGCCTG ACCTCCAGCT TCATGAGGAA GAGGCTGGAG

1561   GCCCCCACCC TGAAGAGATA CCTGAGGGAC AACATCAGCA ACATCCTGCC CAAAGAGGTG

1621   CCCGGCACCA GCGACGACAG CACCGAGGAG CCCGTGATGA AGAAGAGGAC CTACTGCACC
```

-continued

```
1681    TACTGTCCCA GCAAGATCAG AAGAAAGGCC AGCGCCAGCT GCAAGAAGTG TAAGAAGGTC

1741    ATCTGCCGGG AGCACAACAT CGACATGTGC CAGAGCTGTT TC
```

The hyperactive piggyBac left ITR nucleotide sequence used in the study show in FIG. 9A and FIG. 9B (205 bp) is as follows:

```
                                                    (SEQ ID NO: 19)
  1  TTAACCCTAG AAAGATAATC ATATTGTGAC GTACGTTAAA GATAATCATG CGTAAAATTG

 61  ACGCATGTGT TTTATCGGTC TGTATATCGA GGTTTATTTA TTAATTTGAA TAGATATTAA

121  GTTTTATTAT ATTTACACTT ACATACTAAT AATAAATTCA ACAAACAATT TATTTATGTT

181  TATTTATTTA TTAAAAAAAA ACAAA
```

The hyperactive piggyBac right ITR nucleotide sequence used in the study show in FIG. 9A and FIG. 9B (310 bp) is as follows:

```
                                                    (SEQ ID NO: 20)
  1  ATCTATAACA AGAAAATATA TATATAATAA GTTATCACGT AAGTAGAACA TGAAATAACA

 61  ATATAATTAT CGTATGAGTT AAATCTTAAA AGTCACGTAA AAGATAATCA TGCGTCATTT

121  TGACTCACGC GGTCGTTATA GTTCAAAATC AGTGACACTT ACCGCATTGA CAAGCACGCC

181  TCACGGGAGC TCCAAGCGGC GACTGAGATG TCCTAAATGC ACAGCGACGG ATTCGCGCTA

241  TTTAGAAAGA GAGAGCAATA TTTCAAGAAT GCATGCGTCA ATTTTACGCA GACTATCTTT

301  CTAGGGTTAA
```

As shown in FIG. 9A, the MLT transposase of the present disclosure had a greater integration efficiency that the transposase from Yusa et al. (2010). The inventors have discovered that a transposase sequence without the last two amino acids (L573del, E574del) has a greater efficiency than a transposase with those terminal amino acids present.

FIG. 9B illustrates an integration efficiency of the engineered MLT of the present disclosure, compared to integration efficiencies of piggyBac mutants. FIG. 9B shows percent of integration efficiency for a) hyperactive piggyBac (from Yusa et al. (2010), see SEQ ID NOs: 17, 18, 19, and 20)+piggyBac donor (see FIG. 16); b) hyperactive piggyBac donor only (see FIG. 16); c) MLT donor only (see FIG. 16); d) wild-type MLT+MLT donor; e) MLT N125K+MLT donor; f) MLT S8P/C13R+MLT donor; g) engineered MLT of the present disclosure (MLT S8P/C13R/L573del/E574del)+MLT donor; and h) hyperactive piggyBac dimer+piggyBac donor. The hyperactive piggyBac donor (b) and the MLT donor (c) were used as controls. As shown in FIG. 9A and FIG. 9B, the engineered MLT of the present disclosure has an integration efficiency comparable to the hyperactive piggyBac+piggyBac donor system.

Example 4—In Vitro Analysis of Hyperactive MLT Transposase Variants in HeLa and HEK293 Cells This study showed a discovery of novel mutations in a mammalian transposase in accordance with the present disclosure (an MLT transposase), to improve its excision capabilities (Exc+) by evaluating hyperactive mutants for their relative integration efficiency. This study details the analysis of hyperactive MLT transposase mutants in HeLa and HEK293 cells.

DNAs for the Mammalian Cell Integration Assays.

A two-plasmid transposition assay, using a donor plasmid including a transposon carrying a GFP gene and blasticidin resistance (BsdR) cassette and a helper plasmid expressing the transposase under a cytomegalovirus (CMV) promoter to measure transposition. The insect piggyBac donor plasmid contained GFP and BsdR cassettes driven by a CMV promoter, flanked by end sequences in a ZeoCassette™ Vector (pCMV/Zeo) (Thermo Fisher Scientific) backbone. The insect piggyBac helper plasmid contained the piggyBac ORF cloned into pcDNA3.1 myc His A-His (Invitrogen). For the MLT donor plasmid, the GFP-Bsd cassette from the insect piggyBac mammalian donor pCMV/miniPB-GFP-Bsd was PCR amplified using specific primers. The fragment was digested and cloned into the MLT donor plasmid. In the MLT mammalian helper plasmid, the enzyme was tagged with a HA tag. The MLT ORF was PCR amplified from plasmid—with a primer from the 5' end of the gene and a primer from the 3' end of the gene. The PCR product was digested and cloned into the plasmid. Various mutations in the putative catalytic domains were synthesized and evaluated.

Mammalian Cell Integration Assay.

HeLa cells were grown in DMEM+10% FBS+penicillin-streptomycin. HeLa cells ($2\times10^5$) were transfected with donor (294 nM) and helper (42 nM) plasmids with FuGENE-HD (Roche) in OPTI-MEM media (Life Technologies) according to the manufacturer's protocol. Cells transfected with donor plasmid and empty pCDNA3.1/myc-His A were the non-transposase control. After 46 h of transfection, cells were trypsinized and serially diluted in the appropriate DMEM as described above+blasticidin (3.5 μg/mL). Fresh media with antibiotics were administered every 24 h and continued for 21 d. After 21 days, cells were fixed with 4% paraformaldehyde and stained with 0.2% methylene blue, and blue colonies were counted.

Results

Figure 17A:
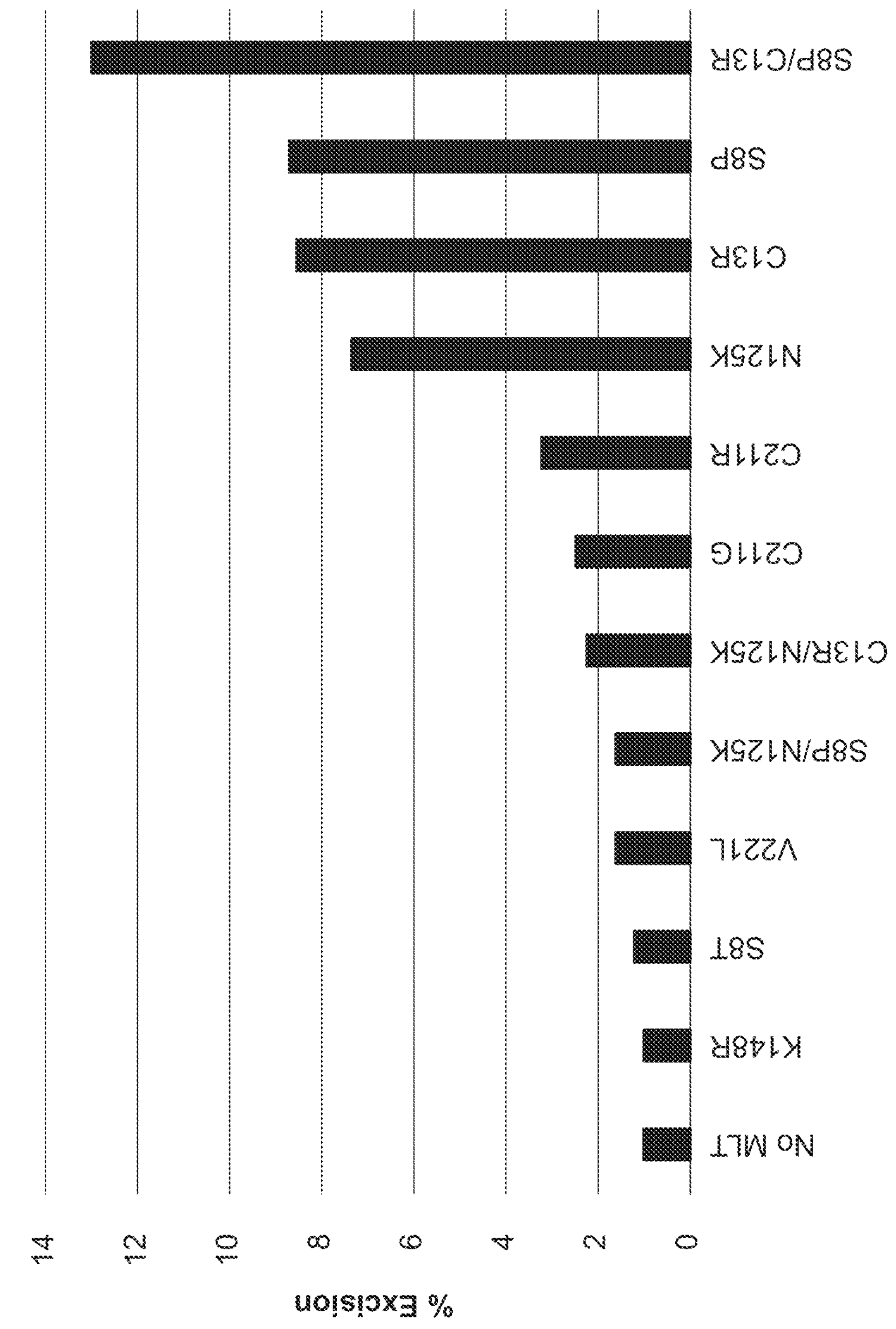
FIGS. 17A and 17B show results of functional assessment of the hyperactive MLT transposase mutants in HeLa cell.
Figure 17B:
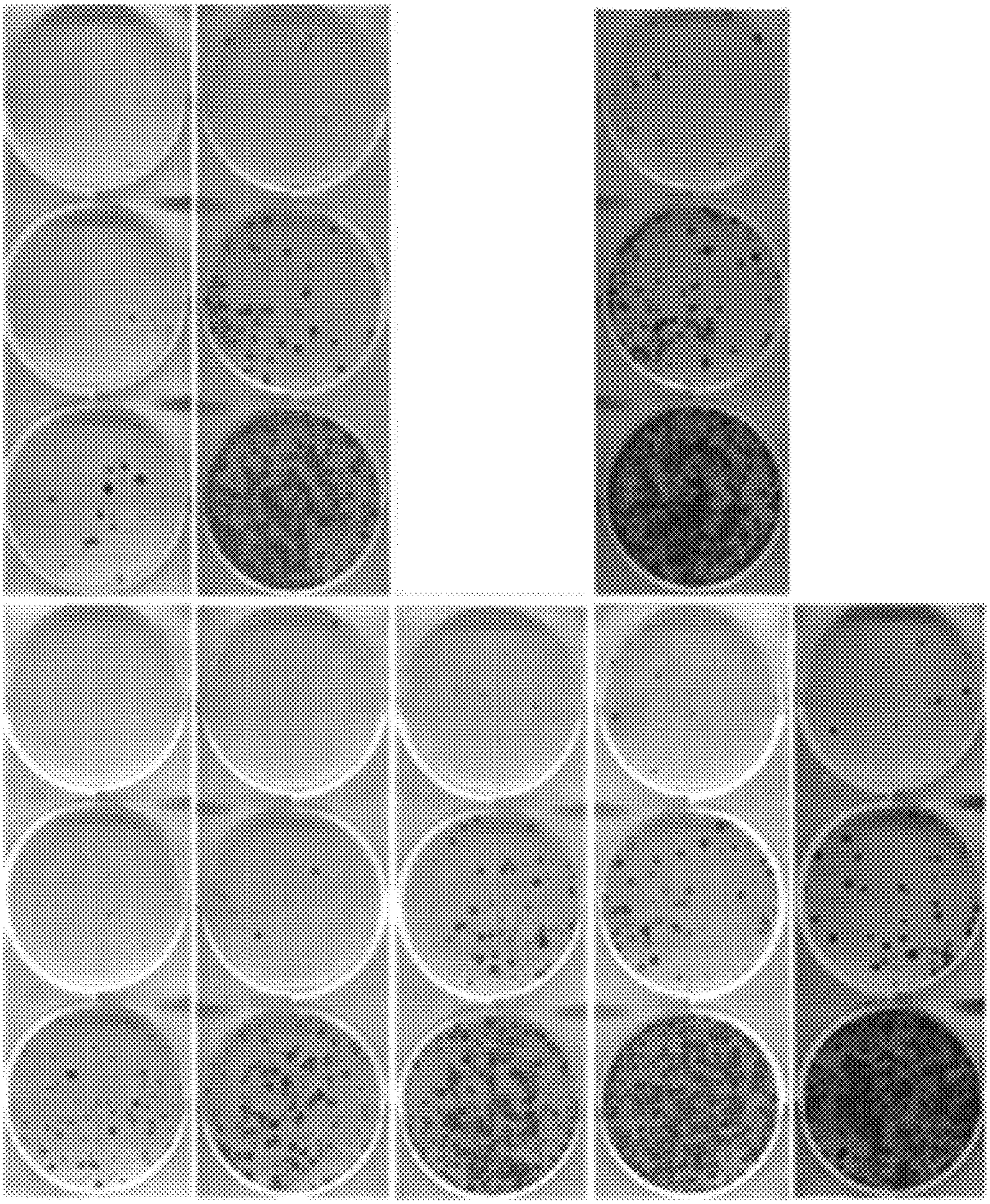

FIGS. 17A and 17B show results of functional assessment of the hyperactive MLT transposase mutants in HeLa cell.

FIG. 17A shows that mammalian transposase (Ts) variants S8P, C13R, N125K and S8P/C13R have higher excision and integration frequency than the native enzyme. FIG. 17B shows functional transgene expression in HeLa cells transfected with a donor neomycin transgene, 1:20 serial dilutions. The mammalian MLT transposase variant S8P/C13R showed comparable relative integration to the insect piggyBac in HeLa cells.

Figure 18:
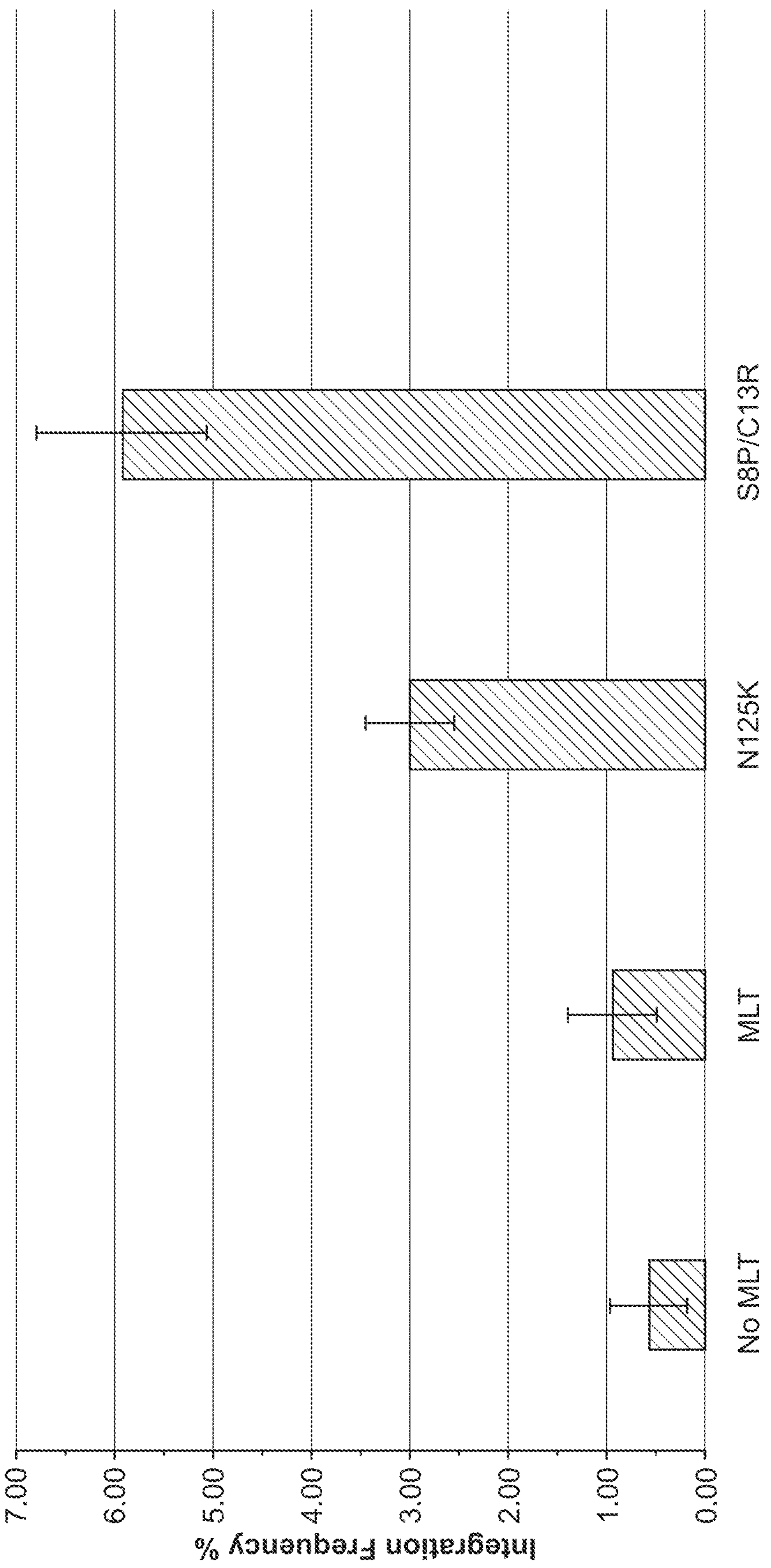
FIG. 18 are bar charts illustrating percent (%) of integration efficiency of MLT transposase hyperactive mutants in HEK293 cells, for no MLT, MLT, N125K mutant, and S8P/C13R mutant. The double mutant S8P/C13R shows that highest integration efficiency was observed in HEK293 cells. The MLT transposase is an MLT transposase comprising the amino acid sequence of SEQ ID NO: 4 and encoded by a nucleotide sequence of SEQ ID NO: 5.

FIG. 18 shows relative integration frequency of MLT transposase hyperactive mutants in HEK293 cells. The double mutant A/C shows that highest integration efficiency was observed in HEK293 cells.

The MLT transposase transposed successfully in human cultured HeLa and HEK293. A two-plasmid co-transfection assay was used in which a donor plasmid carried a transposon comprising an antibiotic resistance marker and a helper plasmid expressing the transposase, measuring the transposase-dependent chromosomal integration of the transposon antibiotic marker. It was found that the relative frequency of integration using the hyperactive MLT transposase was comparable to the insect wild type and hyperactive piggyBac in HeLa cells (FIGS. 17A and 17B) but about 50% in HEK293 cells (FIG. 18).

In the present study, the relative integration efficiencies of mammalian MLT transposase hyperactive variants D and A/C were comparable to insect piggyBac in HeLa cells. These variants also showed integration hyperactivity in HEK293 cells.

Example 5—MLT Transposase Protein Isolation and Purification

A goal of this study was to isolate an MLT transposase protein.

Protein Expression and Purification

The gene for a full-length MLT transposase of the present disclosure was codon-optimized for mammalian expression and cloned into the pD2610 expression vector between BamHI and KpnI restriction sites, downstream of an N-terminal maltose-binding protein (MBP) tag followed by a TEV protease cleavage site. The plasmid pD2610-MPB-MLT transposase was transfected into 500 ml EXPI293F cells (Thermo Fisher Scientific) for transient protein expression using a standard PEI transfection protocol. The transfected cells were supplied with 1 L Expi293 expression medium after 24 h. Cells were harvested 3 days after transfection at 300×g and stored at −80° C. Cells expressing MBP-tagged MLT transposase were resuspended in lysis buffer containing 25 mM Tris-CI, pH 7.5, 500 mM NaCl, 1 mM TCEP, and protease inhibitor cocktail (Roche). The cells were lysed by three cycles of sonication. Cell lysates were centrifuged at ~95,000×g for 30 min at 4° C. (Beckman Coulter Optima L-100 XP Ultracentrifuge, Type 45 Ti rotor). The supernatant was filtered and mixed with 10 ml amylose resin (New England BioLabs) equilibrated with lysis buffer. After one hour of continual rotation, the mixture was loaded onto a gravity flow column and washed with 100 ml lysis buffer. The protein was eluted with 50 ml elution buffer (25 mM Tris-CI, pH 7.5, 500 mM NaCl, 10 mM maltose, 1 mM TCEP, and protease inhibitor cocktail). The eluate was incubated with TEV protease and dialyzed against dialysis buffer (50 mM Tris-CI, pH 7.5, 500 mM NaCl, and 1 mM TCEP) for 16-20 h at 4° C. The cleaved MBP tag and the MLT transposase were separated heparin elution. A sample volume onto the Superdex 200 column connected to an AKTA system equipped with an autosampler and installed with the UNICORN system control software. Eluted protein was monitored at 260 nm and 280 nm. For data analysis, the QtiPlot software was used. Purified MLT transposase was stored at −80° C. The yield was 0.45 mL at 2.2 mg/mL or about 1 mg/L cell culture.

Results

Figure 19A:
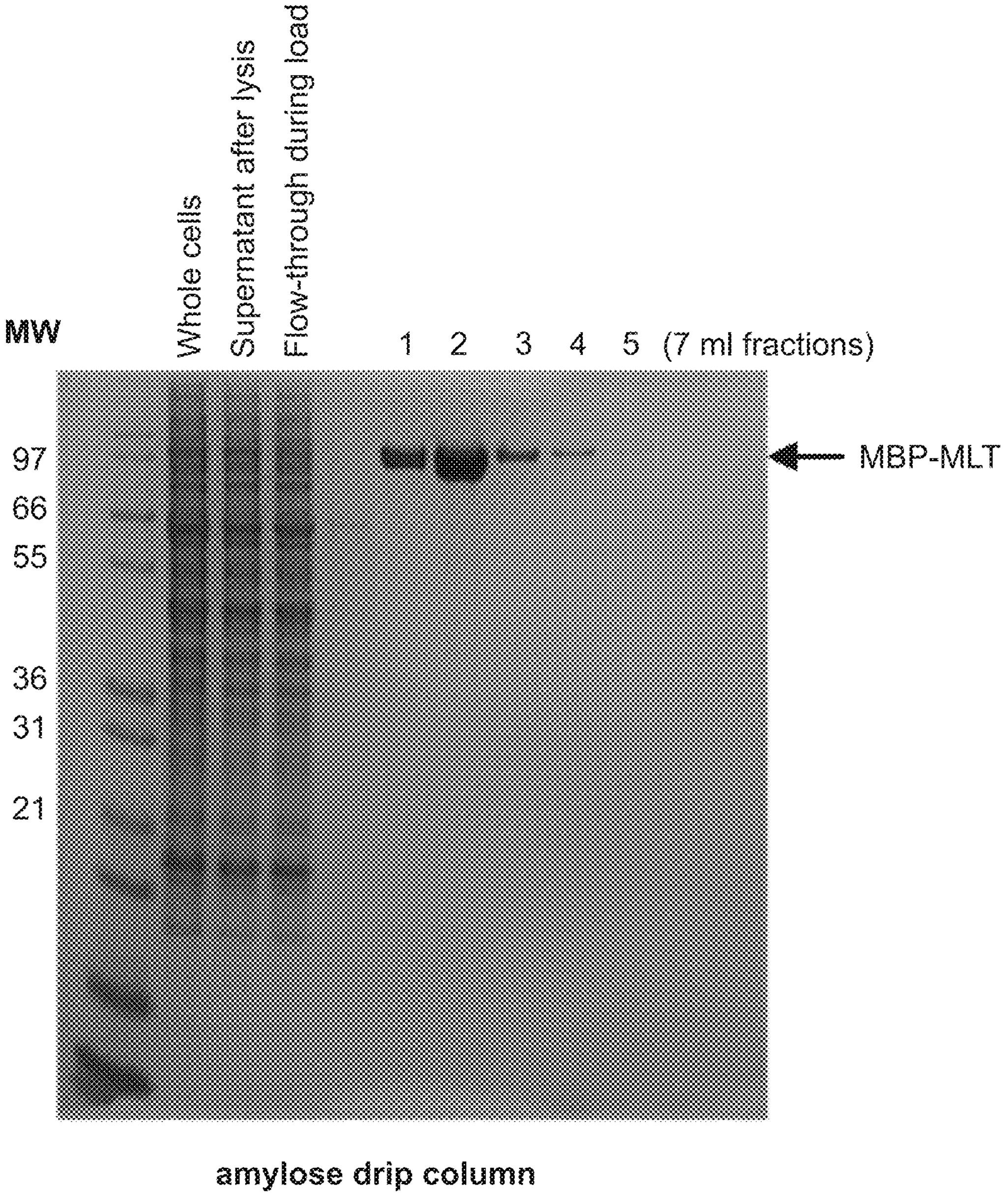
FIGS. 19A and 19B show images of sodium dodecyl sulfate-polyacrylamide gel electrophoresis.
Figure 19B:
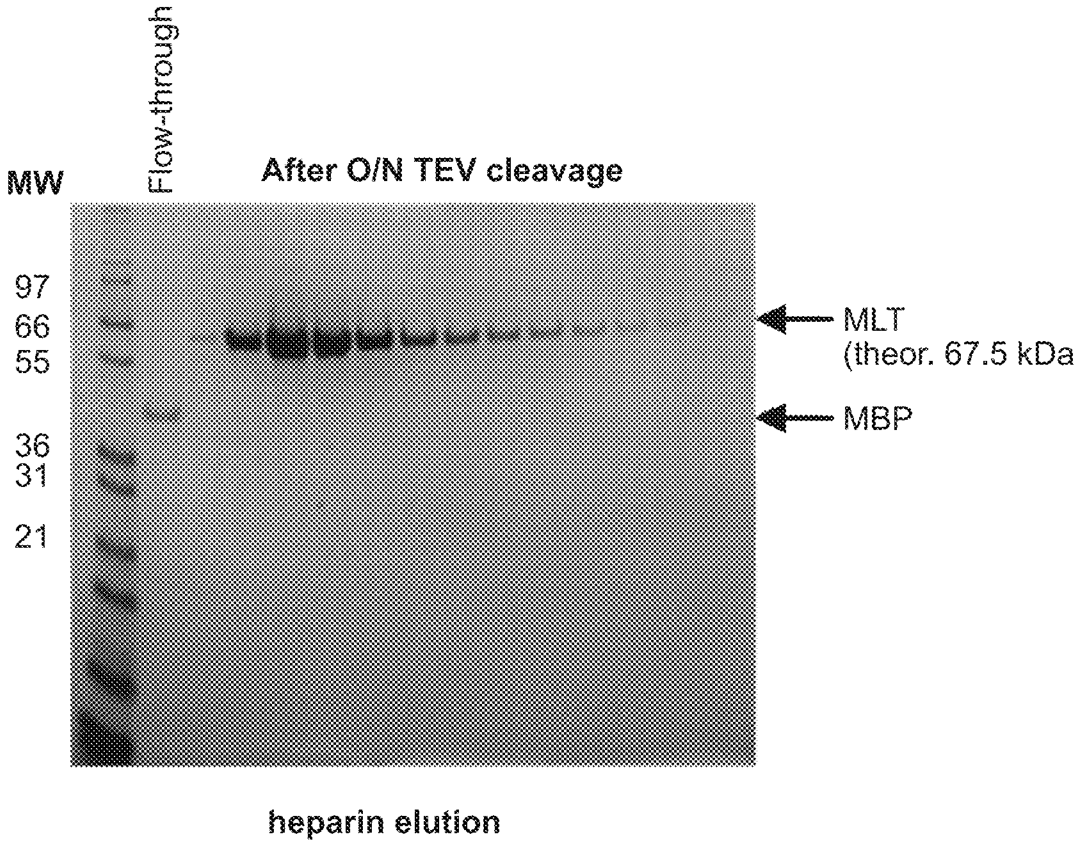

FIGS. 19A and 19B show images of sodium dodecyl sulfate-polyacrylamide gel electrophoresis. FIG. 19A shows analysis of purified MBP-MLT transposase fusion protein by an amylose-resin column. A major protein band of 100+ kDa was identified by SDS-PAGE after purification of the expressed protein (MBP-MLT transposase) from the supernatant of the sonicated bacteria on a column of amylose resin. In FIG. 19B, shows a 67.5 kDa MLT transposase-specific band was shown after overnight cleavage of the MBP tag by TEV protease and heparin elution.

Affinity chromatography of the MBP MLT transposase fusion protein was performed with amylose agarose resin, followed by a step elution. The loaded samples, flow through, washes, and eluted proteins were analyzed by SDS-PAGE to show the pool peak fractions containing the MBP-MLT transposase purified protein (FIG. 19A). The MLT transposase was separated from the MBP tag by heparin elution with a size of 66-68 kD by SDS PAGE (FIG. 19B).

Figure 20:
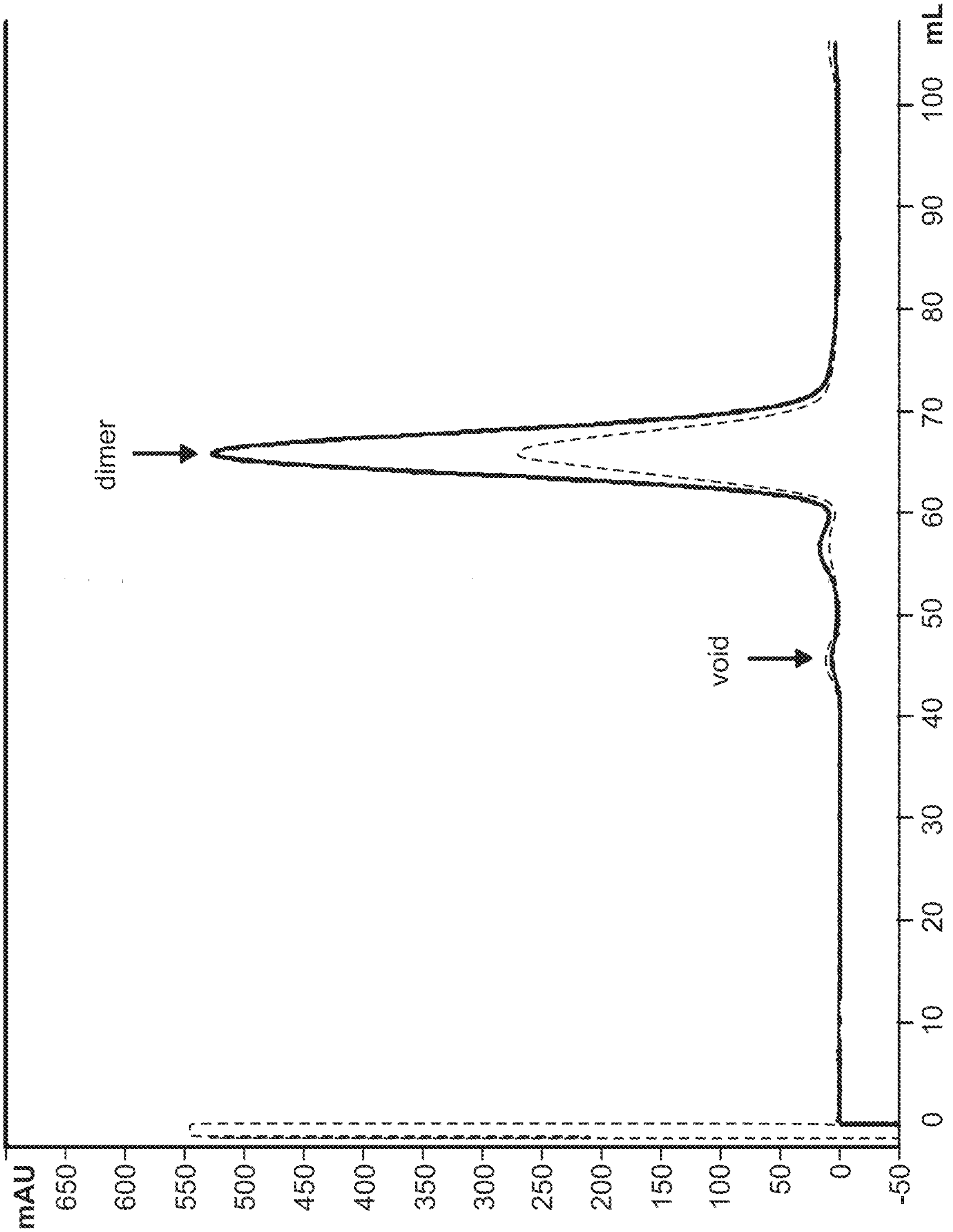
FIG. 20 shows Superdex size exclusion chromatography of maltose-binding protein (MBP)-MLT transposase fusion protein.

FIG. 20 shows Superdex size exclusion chromatography. A sample volume of purified MLT transposase was loaded onto the Superdex 200 column. The eluted protein peaks at 260 nm and 280 nm suggest a dimer formation. Thus, the chromatographic profile indicates that the MLT transposase exists as a dimer (FIG. 20).

This study demonstrated that DNA binding proteins can be produced as fusion proteins to enable more specific purification, but their ability to bind DNA also enable affinity purification using heparin as a ligand. This study also showed that the MLT transposase of the present disclosure is a DNA binding protein with a molecular weight of approximately 67.5 kD that exists as a dimer.

Figure 21:
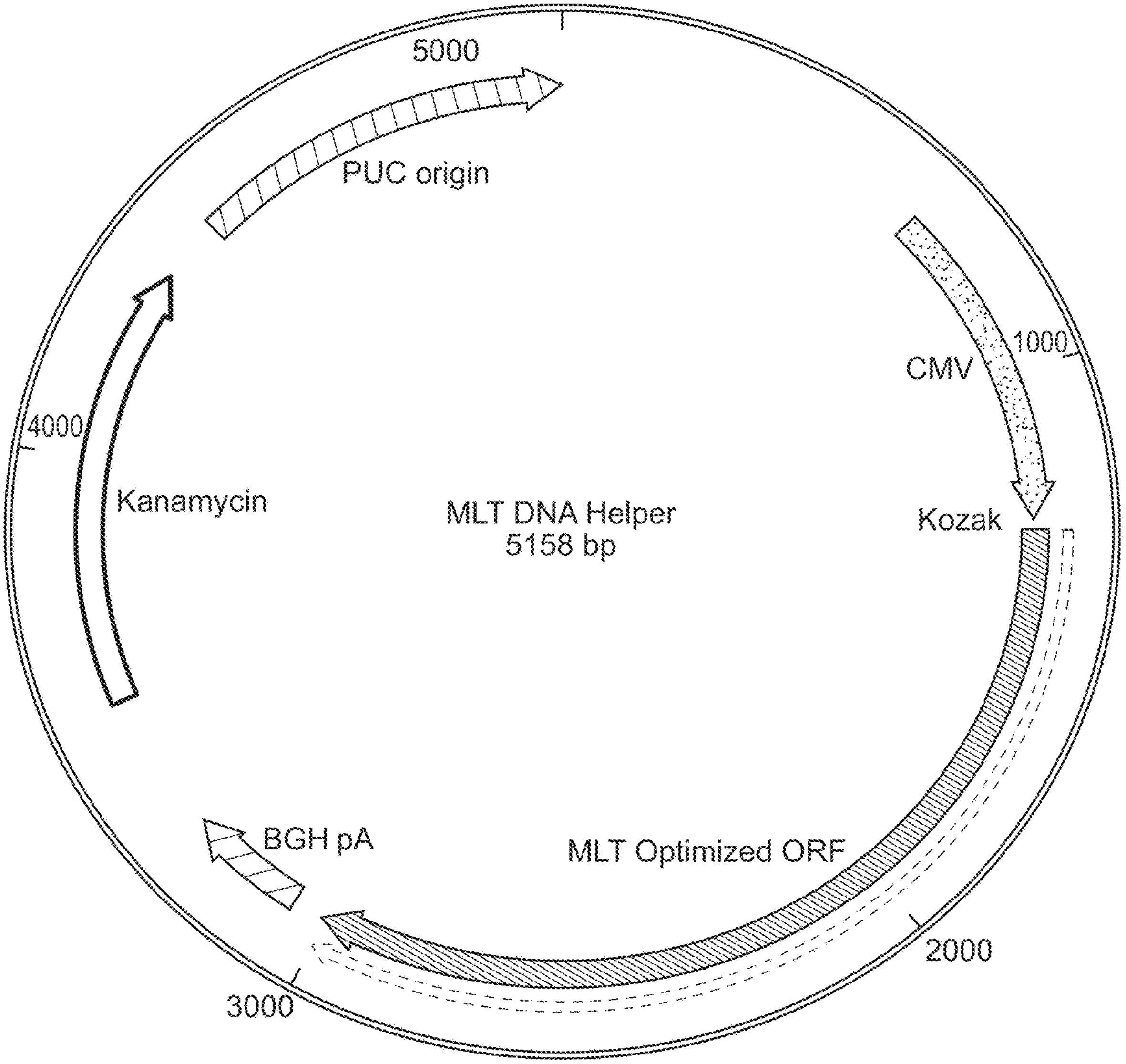
FIG. 21 depicts an example of a donor plasmid comprising an MLT transposon.

Example 6—Assessing Integration Profile Differences Between MLT Transposase and PiggyBac Transposase An objective of this study was to assess the integration pattern differences between the insect derived PiggyBac (PB) transposase and the non-specific, mammal-derived MLT transposase of the present disclosure. The comparison involved comparison of molecular sizes, protein lengths, recognition ends, integration in RefSeq genes, ±5 kb transcription start site, 5 kb from CpG islands, and immunogenicity. An example of a DNA MLT Helper construct is shown in FIG. 21.

In general, the MLT transposase and the PiggyBac transposase when delivered as DNA are similar in the integration and molecular characteristics, as shown in Table 1.

TABLE 1

Comparison of certain properties of piggyBac and MLT DNA transposases.

| Characteristics | piggyBac | MLT |
|---|---|---|
| Species of origin | Cabbage looper moth | Mammalian |
| Molecular size | ~2.5 kb in length | 1.9 kb in length |
| Protein length | 594 amino acids | 571 amino acids |
| Recognition Ends | ITRs: 35 bp, 63 bp | Ends: 157 bp; 212 bp |
| Integration in RefSeq genes (random 34%) | ~55% | ~40% |

TABLE 1-continued

Comparison of certain properties of piggyBac and MLT DNA transposases.

| Characteristics | piggyBac | MLT |
|---|---|---|
| ±5 kb transcription start site (random 0.04%) | ~20% | ~10% |
| ±5 kb from CpG islands | ~20% | ~10% |
| immunogenicity | Unknown (insect protein) | Likely low (mammal protein) |

The comparisons made herein showed that the MLT and piggyBac when delivered as DNA have similar characterics. The comparisons in Table 1 also show that the MLT transposase is safer than the piggyBac transposase and is thus less likely to cause undesired disruption or activation of genes during integration.

Example 7—Comparison of Integration Efficiency of Hyperactive Mlt Transposase and Hyperactive Piggybac An objective of this study was to assess the integration efficiency differences of the most hyperactive form of insect derived transposase PiggyBac (PB) (I30V/G165S, S103P, M282V, S509G/N570S, N538K) and the hyperactive, non-specific mammal-derived transposase, MLT transposase in accordance with the present disclosure (with S8P/C13R mutations) (referred to as hypMLT herein).

Hyperactive piggyBac (hypPB) transposase enzyme [containing seven mutations—I30V/G165S, S103P, M282V, S509G/N570S, N538K—(7pB)] is used for gene transfer in human cells in vitro and to somatic cells in mice in vivo. Despite a protein level expression similar to that of a native PB, hypPB significantly increased the gene transfer efficiency of a neomycin resistance cassette transposon in both HEK293 and HeLa cultured human cells. Native PB and SB100X, the most active transposase of the Sleeping Beauty transposon system, exhibited similar transposition efficiency in cultured human cell lines. When delivered to primary human T cells ex vivo, hypPB increased gene delivery two- to threefold compared with piggyBac and SB100X. hypPB was compared with native PB and SB100X in vivo in mice using hydrodynamic tail-vein injection of a limiting dose of transposase DNA combined with luciferase reporter transposons. Transgene expression was monitored for up to 6 months and observed approximately 10-fold greater long-term gene expression in mice injected with a hypPB, compared with mice injected with native PB or SB100X.

Methodology

- HEK293 cells were plated in 12-well size plates the day before transfection.
- The day of the transfection, the media was exchanged 1 hour and 30 min before the transfection was performed.
- The X-tremeGENE™ 9 DNA Transfection Reagent was used, in accordance with manufacturer's protocol (Sigma-Aldrich).
- In duplicate, a donor plasmid containing GFP and a helper plasmid (600 ng each), were co-transfected. The donor DNA was mixed for each duplicate transfection, and 1200 ng of helper RNA (transposase) was mixed with 1200 ng of donor DNA for 2400 ng total. A 3:1 ratio of X-tremeGENE™ 9 DNA Transfection Reagent was used; therefore, each duplicate had 2400 ng of DNA and used 7.2 ul of the X-tremeGENE™ 9 DNA Transfection Reagent.
- Two different donor plasmids, one for hypPB and one for hypMLT, were used. All PB transposases were mixed with the PB donor but not with an MLT donor.
- 48 hours after the transfection, the cells were analyzed by flow cytometry, and percent (%) of GFP expressing cells was counted, to measure transient transfection efficiency. The cells were gated to distinguish them from the debris, and 20,000 cells were counted each. GFP gating was liberal, such that even GFP-dim cells were counted as GFP-positive (GFP+) cells.
- The cells were cultured for 15-20 days without an antibiotic. The cells were passaged 2/3 times per week.
- Flow cytometry was used to percent (%) of GFP-expressing cells, to measure integration efficiency at 2 weeks (80,000 cells were counted). Gating was conservative, such that a gate was drawn around the obvious bright population and excluded very dim cells.
- The final integration efficiency was calculated by dividing 2-week % GFP cells by 48 hours.

Results

Figure 22A:
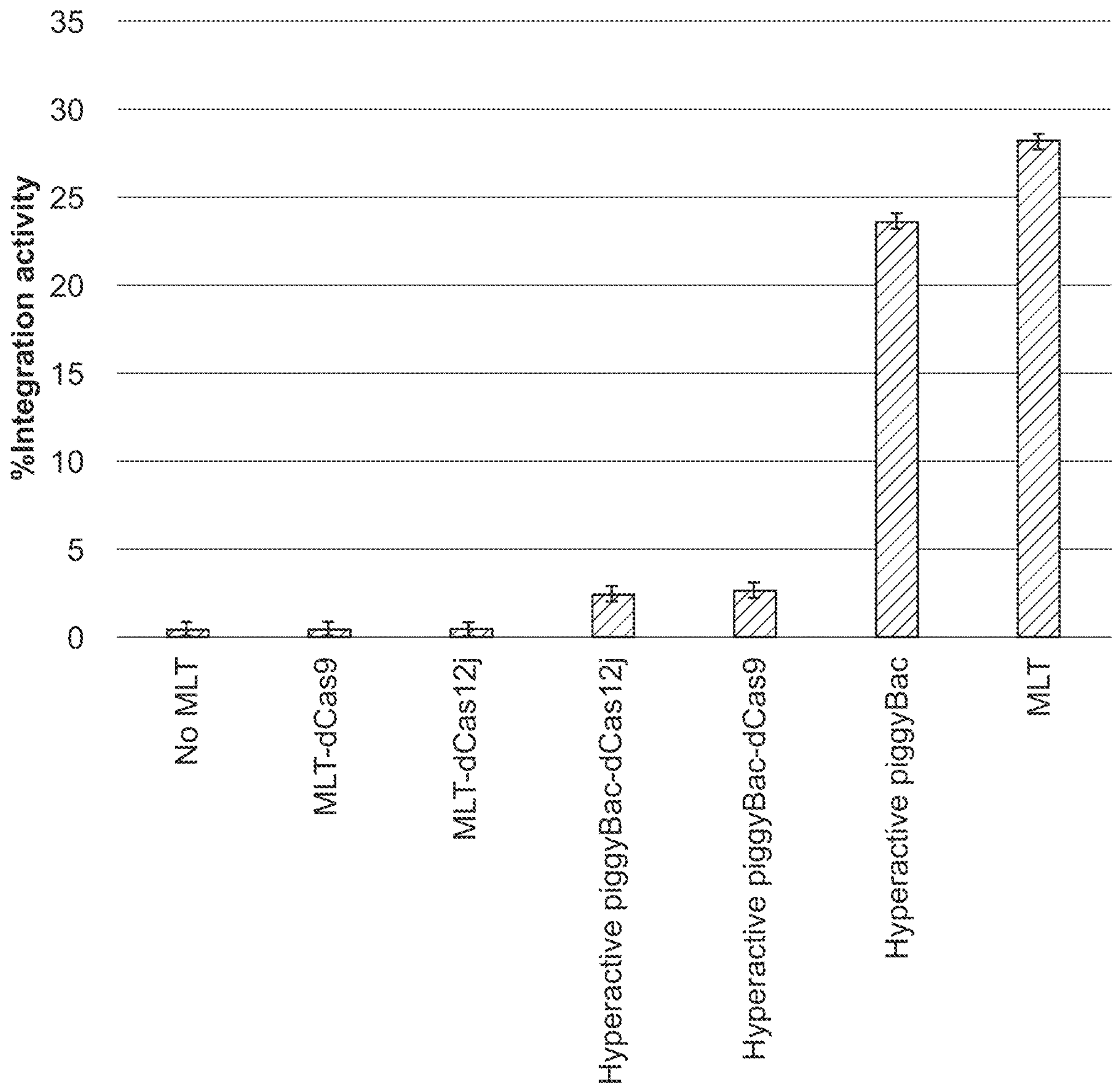
FIGS. 22A, 22B, 22C, 22B, and 22D are bar charts illustrating integration efficiency and excision activity of variants of a hyperactive form of piggyBac (hypPB) compared to a hyperactive MLT transposase (hypMLT) that comprises L573del/E574del/S2A and has the S8P/C13R mutations (the MLT transposase encoded by the nucleotide sequence of SEQ ID NO: 8 and having the amino acid sequence of SEQ ID NO: 9).
Figure 22B:
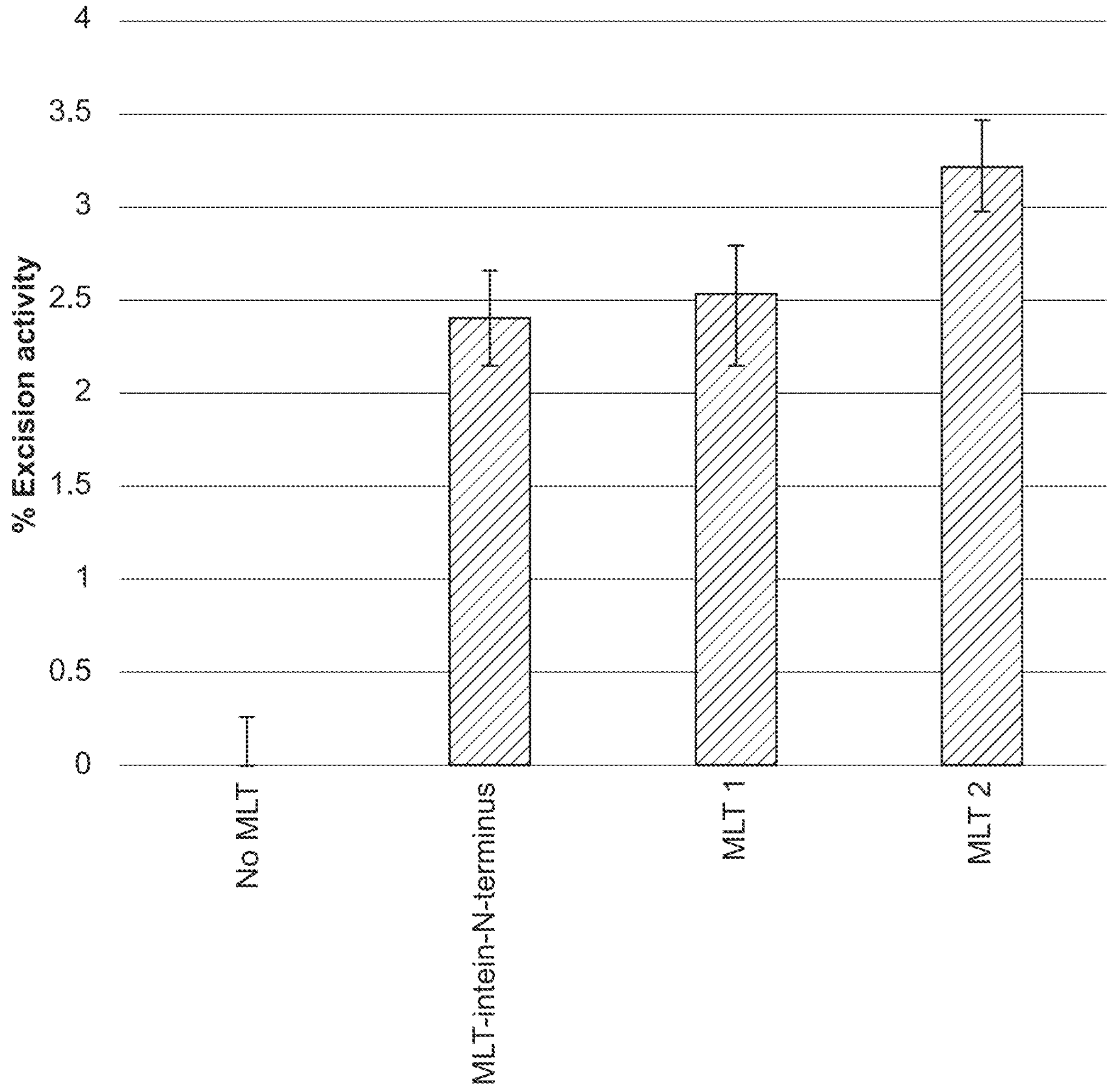
Figure 22C:
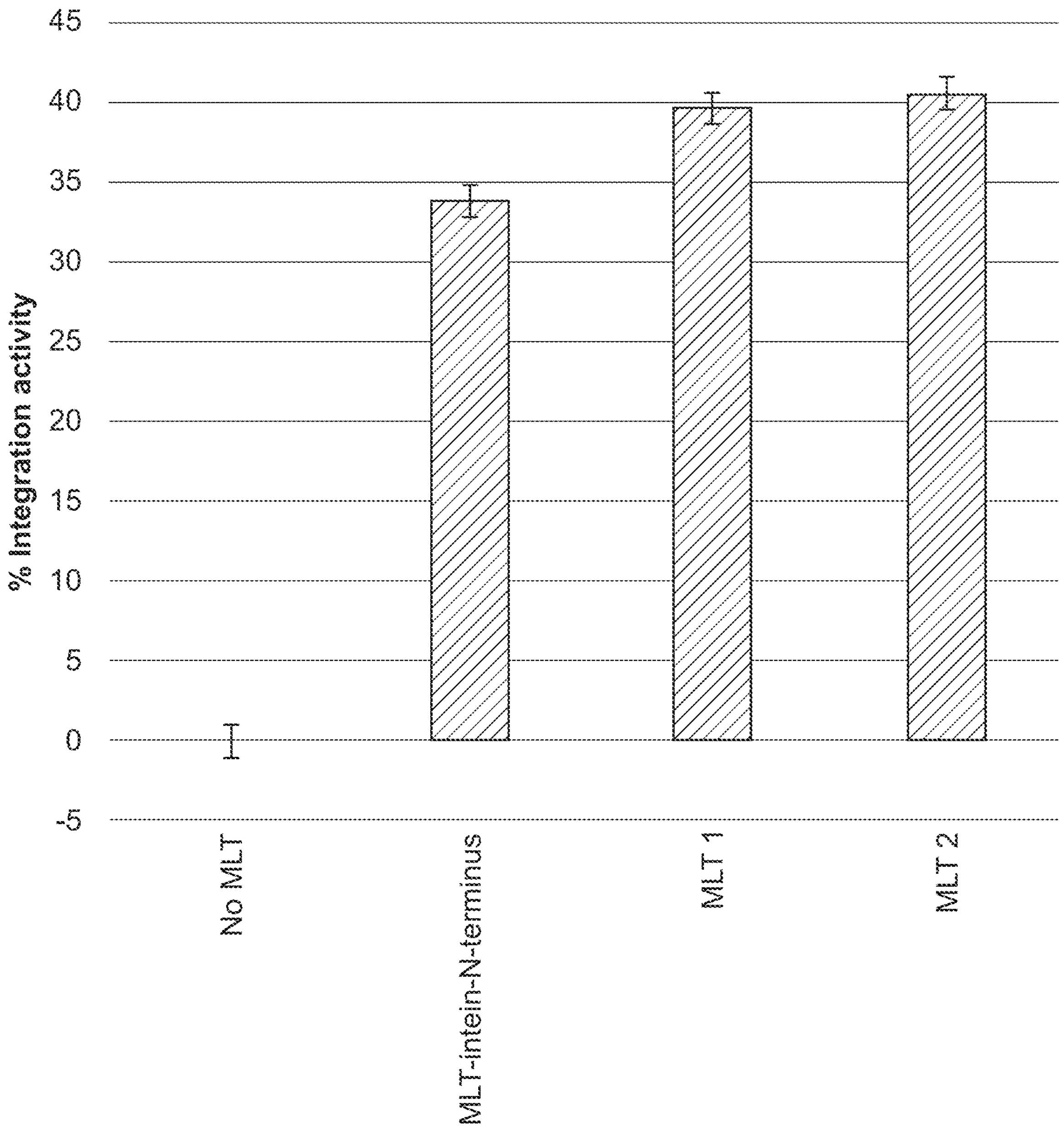
Figure 22D:
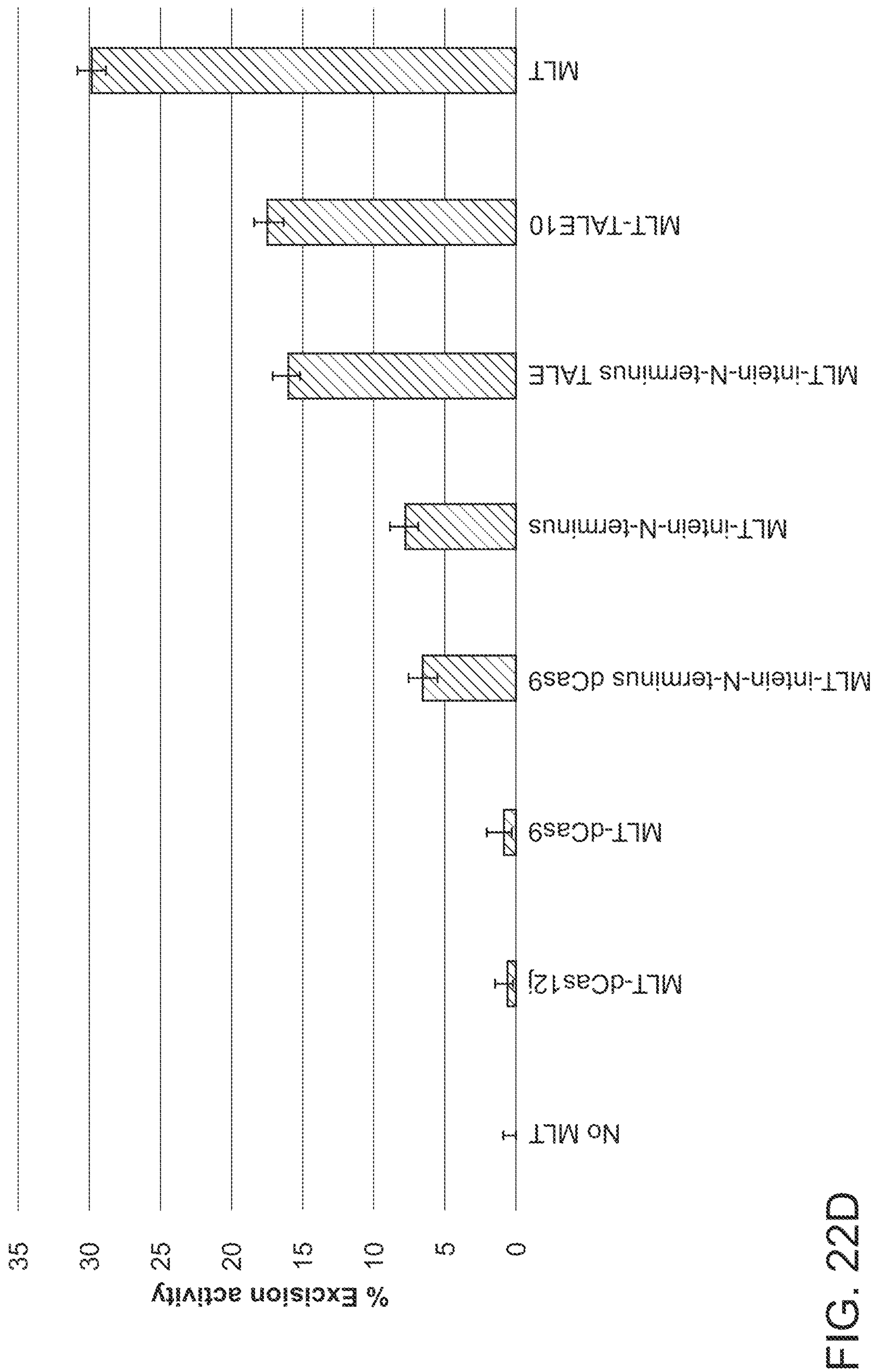

FIG. 22A shows % of integration activity for no MLT, MLT-dCas9, MLT-dCas12j, hyperacive piggyBac-dCas12j, hyperacive piggyBac-dCas9, hyperacive piggyBac, and MLT. FIG. 22B shows % of excision activity for no MLT, MLT-Intein-N-terminus, MLT1, and MLT2. FIG. 22C shows % of integration activity for no MLT, MLT-Intein-N-terminus, MLT1, and MLT2. FIG. 22D shows % of excision activity for no MLT, MLT-Cas12j, MLT-Cas9, MLT-Intein-N-terminus Cas9, MLT-Intein-N-terminus, MLT-Intein-N-terminus TALE, MLT-TALE10, and MLT.

FIG. 22A shows integration efficiency of a hyperactive form of piggyBac (hypPB) compared to MLT transposase (MLT2). The integration efficiency for the hyperactive MLT transposase (about 28%) was greater than the integration efficiency for the hyperactive form of piggyBac (about 24%) that is typically used for cell and gene therapy. Integration efficiency was reduced by the addition of dead Cas (dCas) binders. The addition of reduced excision activity from 30% to 18% (FIG. 22D). The addition of dCas to MLT reduced excision activity to 8% (FIG. 22D).

Example 8—In Vitro Analysis of Human ROSA26 Genomic Safe Harbor Site Targeting A goal of this study was to assess efficacy of RNA-guided transposition to direct a transposase to the human safe harbor site, ROSA26.

In the present study, a panel of RNA-guided transposase vectors containing mutations in the native piggyBac DBD was studied for their ability to target the human ROSA26 safe harbor site.

Plasmid Development

Figures 23A, 23B, 23C:
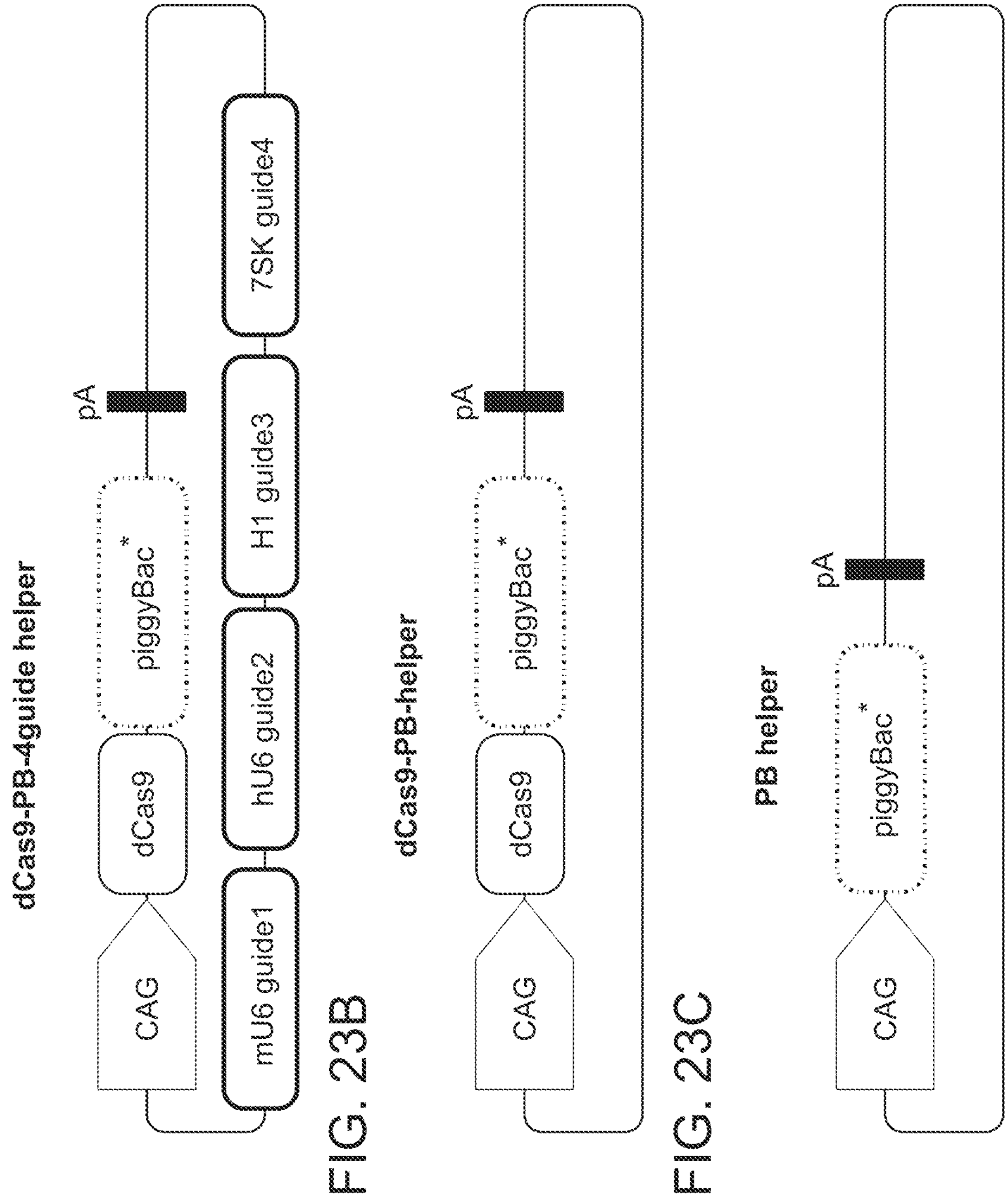
FIGS. 23A, 23B, 23C, 23D, and 23E depict examples of a structure of targeting piggyBac plasmids used in the present study.
Figure 23D:
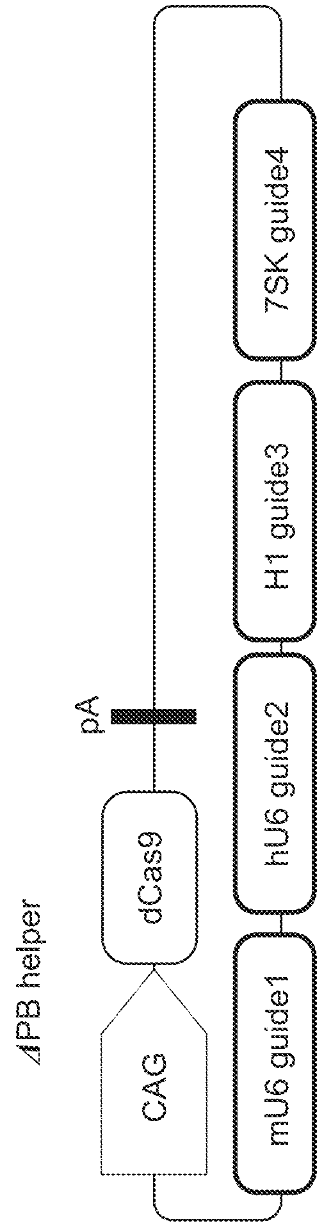
Figure 23E:
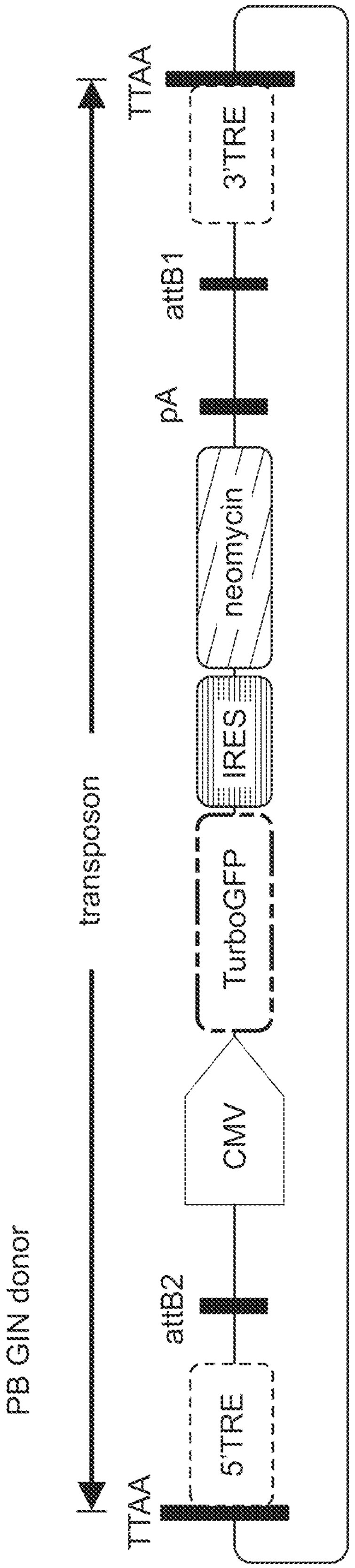

Representations of targeting piggyBac plasmids are shown in FIGS. 23A, 23B, 23C, 23D, and 23E. FIG. 23A shows a dCas9-PB-4 guide helper—catalytically inactive dCas9 fused to the transposase (piggyBac) via a flexible linker and placed under control the CAG promoter, with guide RNA. FIG. 23B shows the shows a dCas9-PB-4 guide helper, devoid of guide RNA. FIG. 23C shows a control PB (piggyBac) helper, devoid of the dCas9 DNA-binding protein. FIG. 23D shows a non-insertional control helper (dCas9 under control the CAG promoter) devoid of the transposase (DPB). FIG. 23E shows a donor plasmid including the TurboGFP internal ribosomal entry site (IRES) neomycin transgene under the CMV promoter and flanked by the transposon terminal repeat elements (TREs).

Figure 23F:
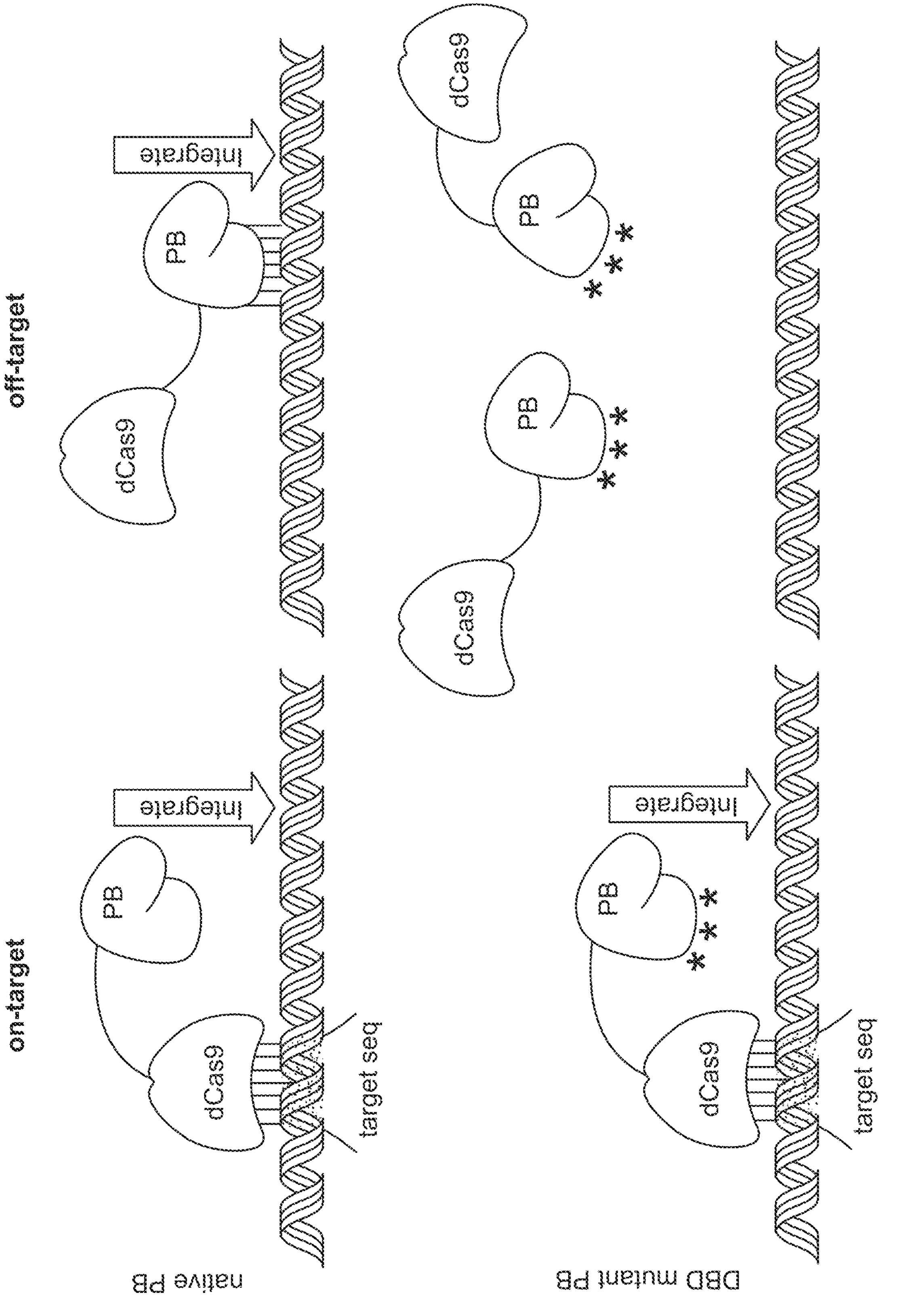
FIG. 23F is a non-limiting schematic of a model for improvement of specificity by disruption of the piggyBac transposase DNA binding domain DBD, in accordance with embodiments of the present invention.

FIG. 23F is a non-limiting schematic of a model for improvement of specificity by disruption of a piggyBac transposase DNA binding domain DBD. The native PB transposase retains full DNA-binding capability and can either integrate following dCas9 targeting (on-target), or integrate following binding to off-target sequences without dCas9 targeting (off-target). Similar to PB, the H2 and H3 mutant transposase integration deficient variants (Int−) can integrate following dCas9 targeting (on-target). However, off-target binding of the transposase is inhibited due to mutations in the DNA binding domain. FIG. 23F illustrates a rationale for using Int-transposase mutants.

Figure 23G:
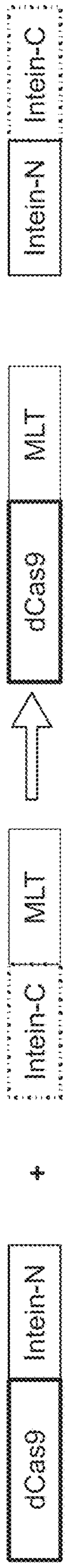
FIG. 23G depicts an MLT transposase attached to dCas by using e.g. NpuN (Intein-N) (SEQ ID NO: 423) and NpuC (Intein-C) (SEQ ID NO: 424) intein protein splicing. Other dCas can be substituted to target specific genomic sites.
Figure 23H:
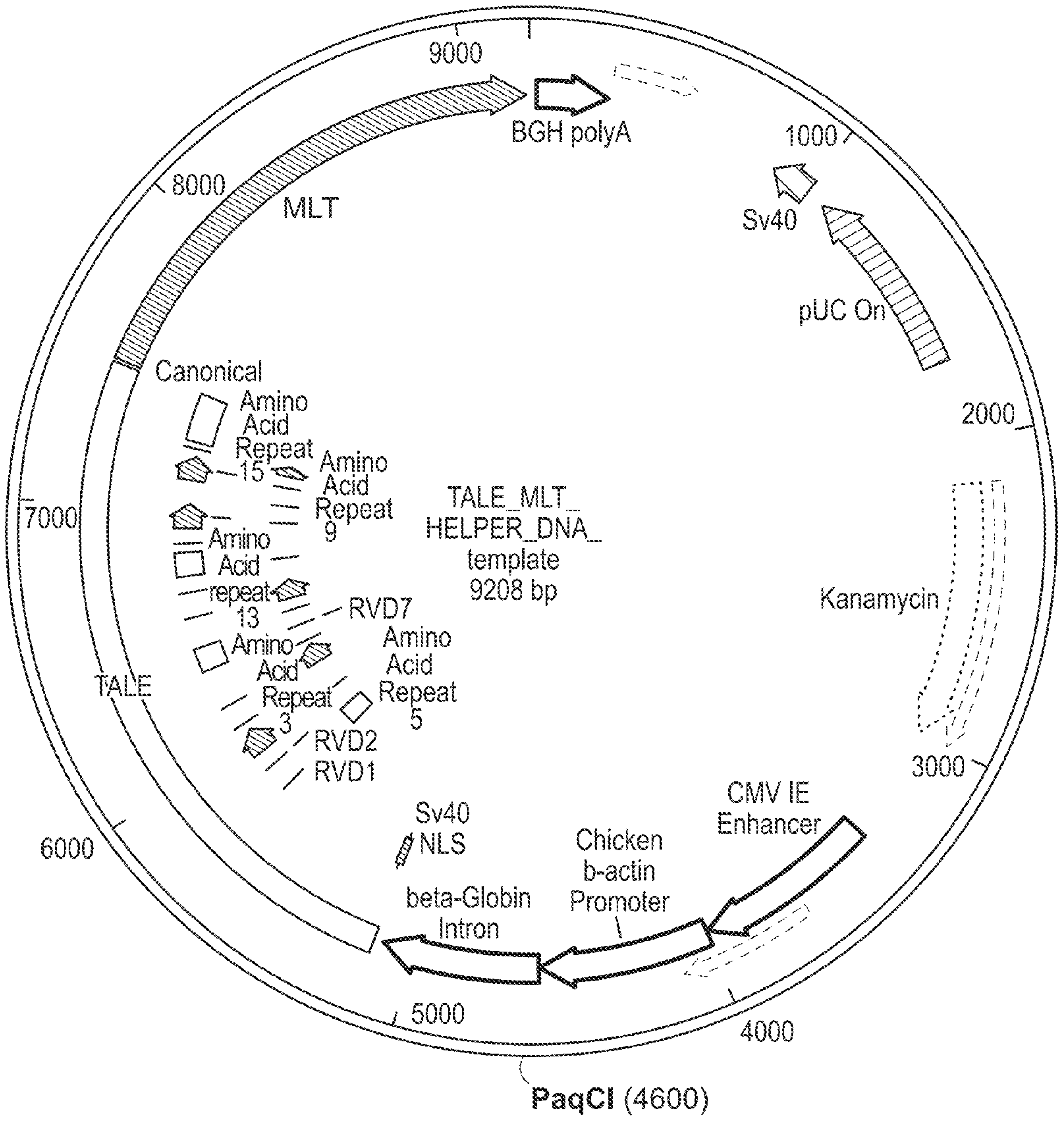
FIG. 23H depicts a chimeric MLT transposase construct attached to a TALE DNA binder. Other TALEs and transposases can be substituted to target specific genomic sites.

FIG. 23H depicts a chimeric MLT transposase construct attached to a TALE DNA binder. Other TALEs and transposases can be substituted to target specific genomic sites.

FIG. 23G depicts a MLT transposase attached to dCas by using NpuN:

(SEQ ID NO: 423)
ggcggatctggcggtagtgctgagtattgtctgagttacgaaacgga
aatactcacggttgagtatgggcttcttccaattggcaaaatcgttg
aaaagcgcatagagtgtacggtgtattccgtcgataacaacggtaat
atctacacccagccggtagctcagtggcacgaccgaggcgaacagga
agtgttcgagtattgcttggaagatggctcccttatccgcgccacta
aagaccataagtttatgacggttgacgggcagatgctgcctatagac
gaaatatttgagagagagctggacttgatgagagtcgataatctgcc
aaat and NpuC:

(SEQ ID NO: 424)
ggcggatctggcggtagtgggggttccggatccataaagatagcta
ctaggaaatatcttggcaaacaaaacgtctatgacataggagttga
gcgagatcacaattttgctttgaagaatgggttcatcgcgtctaat
tgcttcaacgctagcggcgggtcaggaggctctggtggaagc intein protein splicing. Other dCas can be substituted to target specific genomic sites.

The SpCas9-HF1 gene was mutated at the D10A and H840A residues to inactivate the catalytic domain and generate dCas9. The dCas9-PB helper plasmid was generated using Gibson assembly by fusing the a transposase gene (PB) to the dCas9 DNA-binding protein using a flexible linker described previously. The fusion protein was placed under the CAG (cytomegalovirus (CMV) immediate early enhancer, chicken b-actin promoter and b-globin intron) promoter. Two mutant transposase helper plasmids containing codon changes in the DBD were generated using Gibson assembly. First, the transposase was human codon-optimized and synthesized by Genscript. Next, mutations R372A and D450N were introduced to generate the dCas9-H2 helper plasmid and a third K375A mutation was introduced to generate the dCas9-H3 helper plasmid. Four gRNAs were appended to the helper plasmid backbone using Golden Gate. Briefly, single stranded oligos containing the guide sequence were annealed and ligated into Bbsl linearized expression plasmids containing either the hU6, mU6, H1 or 7SK promoter. One of each of the four resulting guide expression plasmids were first digested with BsmBI and then assembled into a single BsmBI-linearized helper plasmid in a single step. For experiments requiring eight guides, two plasmids each containing four guides were co-transfected in equal amounts. Negative control helper plasmids lacked gRNAs. Control helper plasmids that contained either the PB, H2 or H3 transposase but lacking a DBD were also generated using Gibson assembly. To generate the non-integrating DPB control, the entire piggyBac coding sequence was removed from the dCas9-PB helper plasmid using Gibson assembly. To generate the donor plasmid, Gateway cloning (Thermo Fisher) was used to recombine a pENTR plasmid featuring the CMV promoter driving TurboGFP, internal ribosome entry site (IRES) and neomycin (GIN) gene with a pDONR plasmid containing piggyBac terminal repeat elements (TREs) flanking the transgene.

Cell Transfections

Human embryonic kidney (HEK293) cells were maintained incomplete Dulbecco's modified Eagle's medium (DMEM) supplemented with 10% heat inactivated fetal bovine serum. Prior to transfection, $4\times10^5$ cells per well were seeded in 6-well plates. Cells at ~80% confluency were transfected with 2 ug of plasmid DNA using X-tremeGENE 9 (Sigma-Aldrich). Twenty-four hours after transfection, cells were resuspended and 10% of cells were removed for flow cytometry analysis to measure transfection efficiency. Forty-eight hours after transfection, 90% of the cells were transferred to a T75 flask and cultured for 3 weeks under 200 mg/ml G418 at which point the cells were pelleted for lysis and genomic polymerase chain reaction (PCR) analysis. The remaining 10% of cells in the 6-well dish were cultured without antibiotic for 3 weeks and analyzed by flow cytometry to measure stable insertion efficiency. For single-cell isolation, two dCas9-H2-8 guide transfections were repeated. The G418-selected polyclonal populations were each plated into a 96-well poly-D-lysine coated plate (BD Biosciences) resulting in an average of 50 colonies per well. After wells became greater than 40% confluent, media was aspirated, and the cells were manually resuspended in 30 ml of phosphate-buffered saline. A volume of 20 ml of the resuspension was removed and mixed with 30 ml of the DirectPCR Lysis Reagent (Viagen Biotech) for analysis. The remaining cells were cultured further. Two wells identified to contain targeted clones by genomic PCR were expanded and single-cell sorted using serial dilution. Wells were visually monitored until 157 single-cell expansions were obtained. Clonally expanded cells were subsequently resuspended by manual pipetting and lysed for analysis. Positive clonal lines, containing targeted insertions to human ROSA26 (FIG. 24A) were expanded for flow cytometry analysis to detect potential silencing of the transgene.

Flow Cytometry

Green fluorescent protein (GFP) expression of 20,000 live cells from ROSA26-targeted single-cell expansions was analyzed using a FACSAria III cytometer (BD Biosciences) after 13 weeks of culture, following transfection with dCas9-H2-8guide.

Colony Count Assay

In order to determine the number of transposons present in human ROSA26-targeted single clones, a copy number assay was performed by TaqMan quantitative PCR to estimate the number of neomycin genes present in the genome. The human RNase P gene was used to normalize the total genomes per sample. Templates included: genomic DNA from clonal lines, negative control untransfected human genomic DNA and reference control genomic DNA from a clonal cell line with a single neomycin gene insertion. Quantitative PCR using the QuantStudio 12K Flex thermocycler (Applied Biosystems) was performed using the TaqPath ProAmp Master Mix reagent (Thermo Fisher) according to the manufacturer's instructions. Primers and probes were included in the TaqMan Copy Number Reference Assay for human RNase P and the TaqMan NeoR Assay ID:Mr00299300_cn (Thermo Fisher). CopyCaller Software v2.1 was used to predict the number of insertions for each sample.

T7 Endonuclease I Assay

In 12-well plates, HEK293 cells at 80% confluency in DMEM supplemented with 10% heat inactivated fetal bovine serum, were co-transfected with 500 ng of SpCas9-HF1 expression plasmid and 500 ng of one of eight ROSA26 directed gRNA or negative control gRNA expression plasmids, using X-tremeGENE 9 (Sigma-Aldrich). Seventy-two hours later, cells were pelleted and lysed using DirectPCR Cell lysis buffer (Viagen Biotech). Genomic PCR using the KOD Xtreme Hot Start DNA Polymerase (Novagen) was performed using primers designed to flank all eight guide binding sites. Products were purified with the PureLink PCR Micro Kit (Invitrogen) and melted and reannealed to form heteroduplexes. For each sample, identical incubations with or without T7 endonuclease I (T7E1) (New England Biolabs) were performed to cut DNA containing mismatched sequences. Products were separated on a 2% gel for gel imaging. A 2100 Bioanalyzer (Agilent) was used to measure the concentration of products obtained by the T7E1 assay. The fraction of cleaved products was calculated by dividing the total pg/II of the two expected cleavage products by the total pg/II of the two expected cleavage products and uncleaved product. Percent of indel occurrence was calculated.

Nested PCR

HEK293 cells were plated in 12-well size plates the day before transfection. The day of the transfection the media is exchanged 1.5 hr before the transfection is performed. The present experiments used X-tremeGENE™ 9 DNA Transfection Reagent and manufacturer's protocol (Sigma-Aldrich).

In triplicate transfections, a donor plasmid containing GFP and neomycin, a helper plasmid with a DBD fused to either pB or MLT transposase, and a guide RNA expression plasmid or combination of plasmids were co-transfected. The DNA was mixed for each triplicate transfection, i.e. 1500 ng of helper plasmid was mixed with 1500 ng of donor plasmid and 600 ng of guide RNA, with a total of 3600 ng. A 3:1 ratio of XtremeGene9 reagent was used, such that each triplicate transfection had 3600 ng of DNA and used 10.8 ul of reagent. 48 hours after transfection, the cells are resuspended and plated into a T75 flask. 72 hours after transfection, the media was changed from a normal media to a G418-containing media. The cells in the G418-containing media were cultured for 3 weeks, and the cells were then pelleted.

Cell lysis and Proteinase K treatment was then performed (DirectPCR Lysis Reagent, Viagen Biotech), to prepare genomic DNA for template for PCR.

Figure 24A:
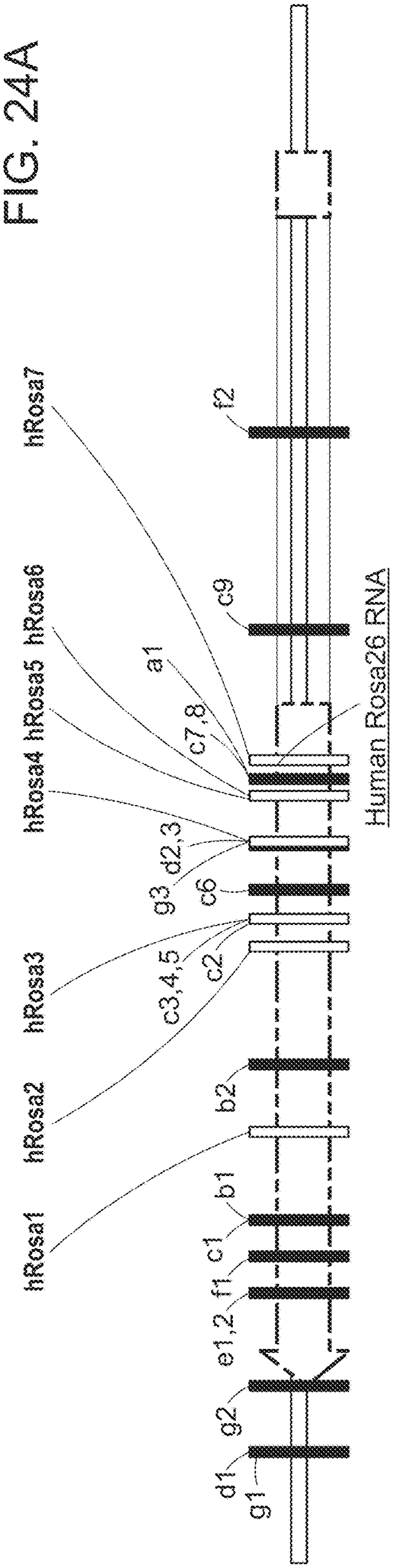
FIG. 24A depicts positive clonal lines containing targeted insertions to human ROSA26 using hyperactive piggyBac transposase donor and helper with Cas9/gRNA, identified in the present disclosure.
Figure 24B:
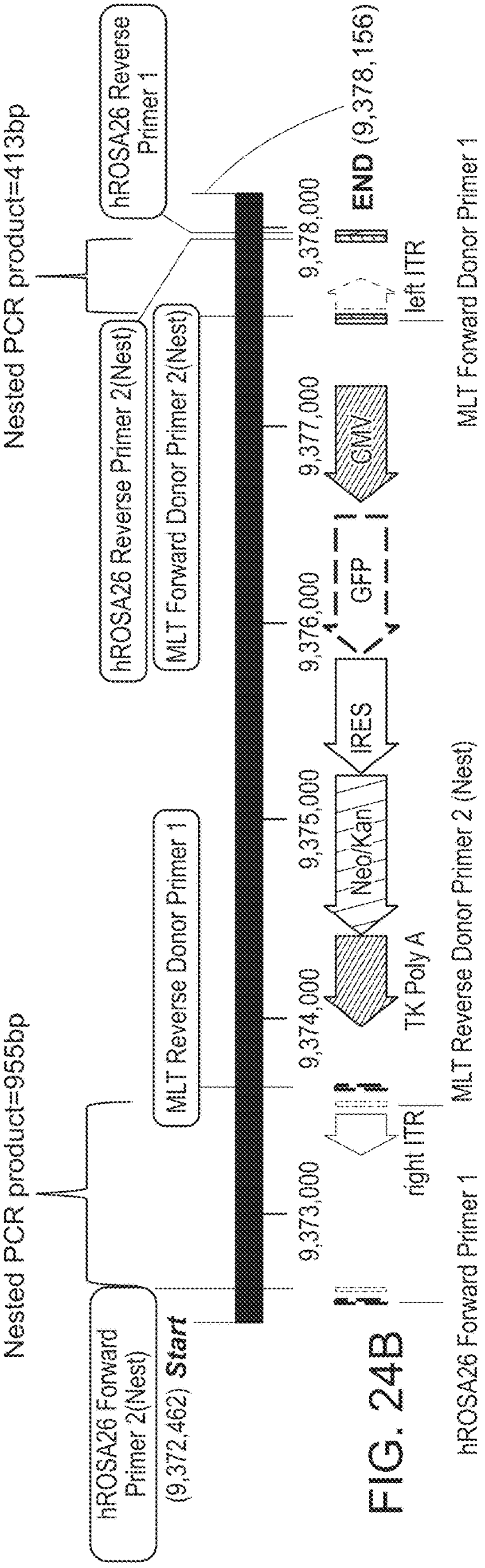
FIG. 24B depicts a nested PCR strategy to detect the insertion of a donor MLT at a specific TTAA (SEQ ID NO: 1) site in human ROSA26 locus using MLT helper with Cas9 and two different sets of gRNA (Set 1: AATCGAGAAGCGACTCGACA (SEQ ID NO: 425), TGCCCTGCAGGGGAGTGAGC (SEQ ID NO: 426); Set 2: GAAGCGACTCGACATGGAGG (SEQ ID NO: 427), CCTGCAGGGGAGTGAGCAGC (SEQ ID NO: 428)) that were 61 bp and 62 bp respectively, from the TTAA (SEQ ID NO: 1) targeted site.

Primary PCR was performed using half the primers extending from the genome and half the primers extending from the transposon insert (FIG. 24B). FIG. 24B depicts a nested PCR strategy to detect the insertion of a donor MLT at a specific TTAA (SEQ ID NO: 1) site in human ROSA26 locus using MLT helper with Cas9 and two different sets of gRNA (Set 1: AATCGAGAAGCGACTCGACA (SEQ ID NO: 425), TGCCCTGCAGGGGAGTGAGC (SEQ ID NO: 426); Set 2: GAAGCGACTCGACATGGAGG (SEQ ID NO: 427), CCTGCAGGGGAGTGAGCAGC (SEQ ID NO: 428)) that were 61 bp and 62 bp respectively, from the TTAA (SEQ ID NO: 1) targeted site.

Figure 24C:
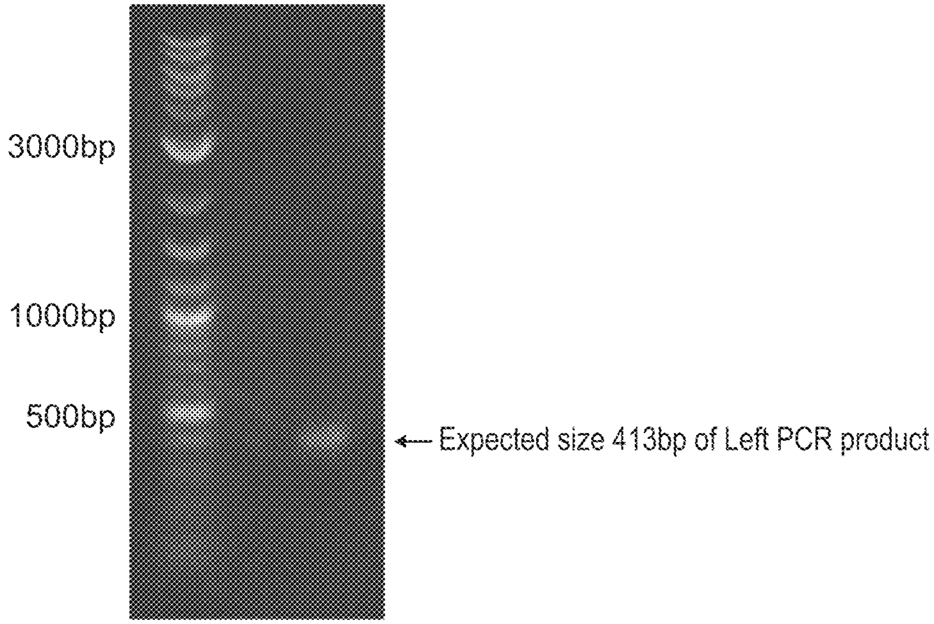
FIG. 24C depicts a 1.0% agarose gel showing the expected nester PCR fragment when an MLT donor is inserted at hROSA26 after transfection with MLT helper with Cas9/gRNA, identified in the present disclosure.
Figure 24D:
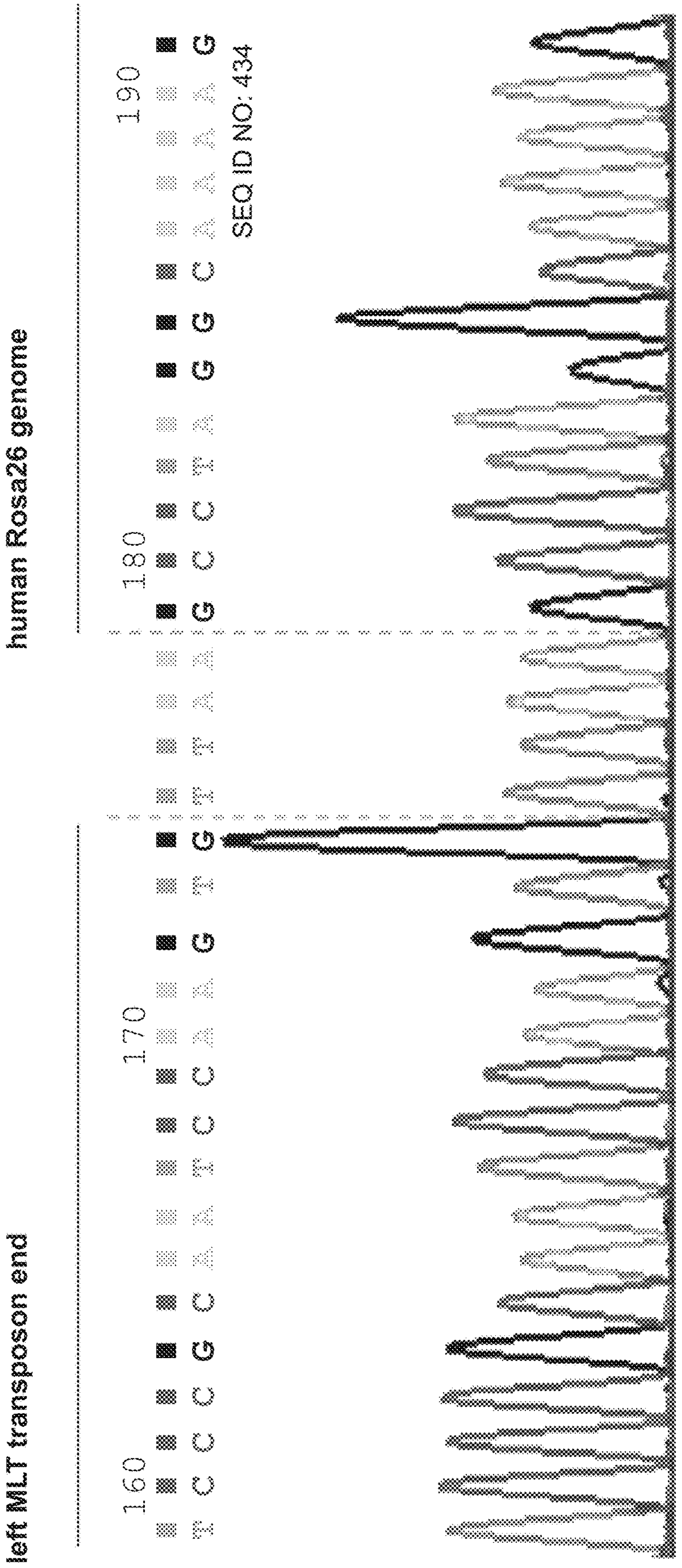
FIG. 24D depicts a DNA sequencing chromatogram that shows the correct junction DNA sequence when a MLT donor is inserted at hROSA26 after transfection with an MLT helper with Cas9/gRNA, identified in the present disclosure.

KOD One polymerase was used: 10 ul reaction, and 1 ul of direct lysis as template. The primary PCR product was diluted 1:50 in water. Then, 1 ul of the 1:50 dilution was used as a template for Nested PCR, using primers that are nested within the Primary products. PrimeStar GXL polymerase was used (20 ul reaction). The nested PCR products were run on a 1% agarose gel (FIG. 24C), a band of the expected size was sequenced. The sequences were aligned and positive insertions were identified—those that include genomic sequence with the TTAA (SEQ ID NO: 1) insertions site and the edge of the transposon insert (FIG. 24D).

Targeted Genomic Integration Site Recovery

Pellets from stable transfections of HEK293 cells were lysed using the DirectPCR Cell lysis buffer (Viagen Biotech) for use as template for nested PCR to identify targeted transposon insertions. In order to optimize the PCR, the lysate template was used at three dilutions, 1:1, 1:4 and 1:8. Forward primers were designed to extend outward from the transposon whereas reverse primers were designed to extend from the ROSA26 target sequence (FIG. 24B). A 10 uL primary PCR was performed using the KOD Xtreme Hot Start DNA Polymerase (Novagen) that was diluted 1:50 in $H_2O$ and used as template for a 20 uL nested PCR using PrimeSTAR GXL DNA Polymerase (Clontech). Amplification products were gel purified with the Zymoclean Gel DNA Recovery Kit (Zymo Research) and sequenced directly or cloned into pJet1.2 (Thermo Fisher) for sequencing. Sequences were aligned against the transposon sequence using BLAST and against the human reference genome (hg38) using BLAT to identify insertion site locations.

RNA-Guided Transposition to the Genome

We tested the ability of our dCas9-piggyBac fusion constructs to deliver a transgene to the human ROSA26 safe harbor locus. The donor plasmid was cotransfected with dCas9-PB, dCas9-H2 or dCas9 H3 each with 0, 4 or 8 guides, in duplicate. Following 3 weeks of antibiotic selection, the cultures were lysed for use as template for genomic PCR. To improve the chances of recovering insertions, three dilutions of the lysate template were used. Primary PCR primers were designed to extend out from each side of the transposon. Four additional primary PCR primers were designed to extend towards the target site in ROSA26 (two on each side). Individual PCR reactions were performed using all pair-wise primer combinations (eight total). Products arising from the primary PCR reactions were used as template for nested PCR. Sequenced products included the flanking TRE of the transposon, the canonical TTAA (SEQ ID NO: 1) sequence at the junction and the genomic sequence flanking the insertion site.

Results

In the present study, a total of 22 insert junctions were recovered, which are shown in FIG. 24A. The present study demonstrated RNA-guided transposition to ROSA26 in human cells and provided a proof-of-concept for directing integration deficient (Int−) PB transposase mutants to human ROSA26, for gene therapy use.

The present study also demonstrates that the inventors were able to target one specific TTAA (SEQ ID NO: 1) site at ROSA26 using MLT fused to dCas9 by intein splicing and gRNA.

It was observed that helper MLT-TALE and MLT-Cas9/gRNA transposases expression targets hROSA26 at a specific TTAA (SEQ ID NO: 1) site (FIG. 24B, FIG. 24C, and FIG. 24D) used genomic PCR to recover targeted insertions to human ROSA26. Despite millions of potential TTAA (SEQ ID NO: 1) sequences available for insertion throughout the genome, a number of inserted transposons adjacent to the gRNA target sequence were uncovered. Control transfections without gRNA did not result in any targeted insertions. The results shown in FIG. 24B, FIG. 24C, and FIG. 24D demonstrate that a transgene was successfully integrated into the genomic safe harbor site, hROSA26, without a footprint (as shown by DNA sequencing). This indicates that any gene can be placed in that TTAA (SEQ ID NO: 1) location.

Example 9—Study of Integration in Various Cell Lines (FACs) Using MLT Transposase (RNA Helper)

An objective of this study was to use the MLT transposase of the present disclosure and CMV-GFP to integrate into four different cell lines (HEK293, Huh7, CHO-K1, and T-cells), to compare the efficiency of integration for various cell lines. A further objective was to integrate CMV-GFP only, to determine whether the MLT transposase had an effect on cell viability. This was quantified by using FACs to measure GFP expression in each cell line, once it was integrated.

The following protocol was used:

CHO-K1, HEK293, HUH7, and-T-cells were seeded at three different cell densities.

Nucleofection efficiency of the three cell lines was tested using the Cell Line 4D-Nucleofector™ Kit and program (Lonza Bioscience) using 0.4 μg of pmaxGFP™ Vector (following the provider's recommendation for each specific cell line) as a positive control.

Measurement of GFP expression was assessed using high-content analysis (visual) and flowcytometry (quantitative) at two timepoints (24 h and 72 h). Nuclei were stained and quantified with Hoechst33342 vital dye. Percentage of GFP positive cells was calculated. As T-cells are suspension cells, only flow cytometry read-out was performed.

Results

All of the studied cell lines (CHO-K1, HEK293, HUH7, and-T-cells) were more than 80% nucleofected. All of the cell lines showed 85-95% GFP expression in presence or absence of the MLT transposase after three days of nucleofection, as shown in FIGS. 25 to 28.

Figure 25:
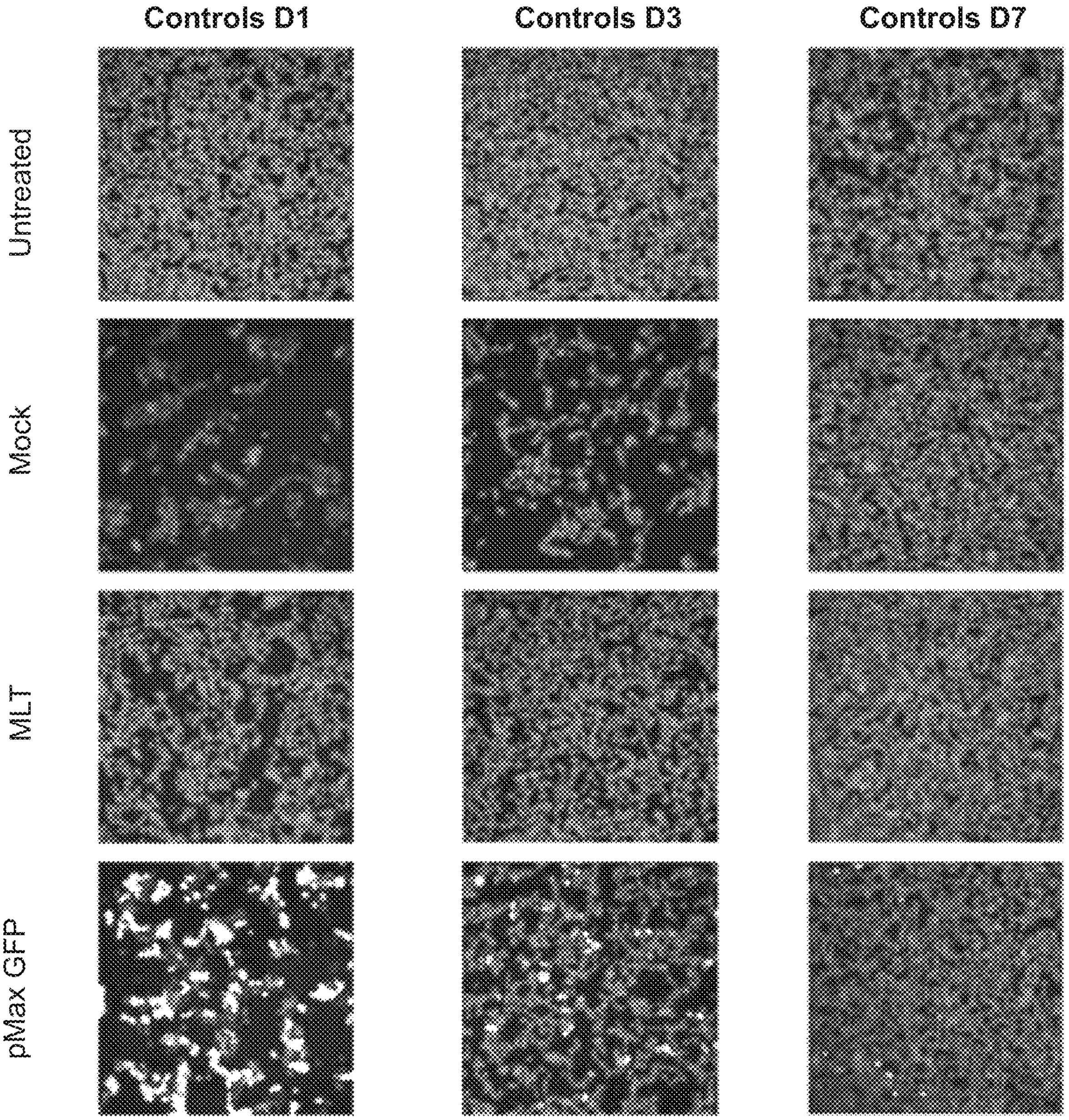
FIG. 25 shows initial Huh7 cell lines transfected under different conditions to show that Huh7 express GFP. The rows show (from the top) untreated cells, mock, cells treated with MLT, and cells treated with pmaxGFP; the columns show controls at day 1 (D1), day 3 (D3), and day 7 (D7).

FIG. 25 shows initial Huh7 cell lines transfected under different conditions to show that Huh7 express GFP. The rows show (from the top) untreated cells, mock transfections (without a nucleic acid), cells treated with MLT, and cells treated with pmaxGFP; the columns show controls at day 1 (D1), day 3 (D3), and day 7 (D7).

Figure 26:
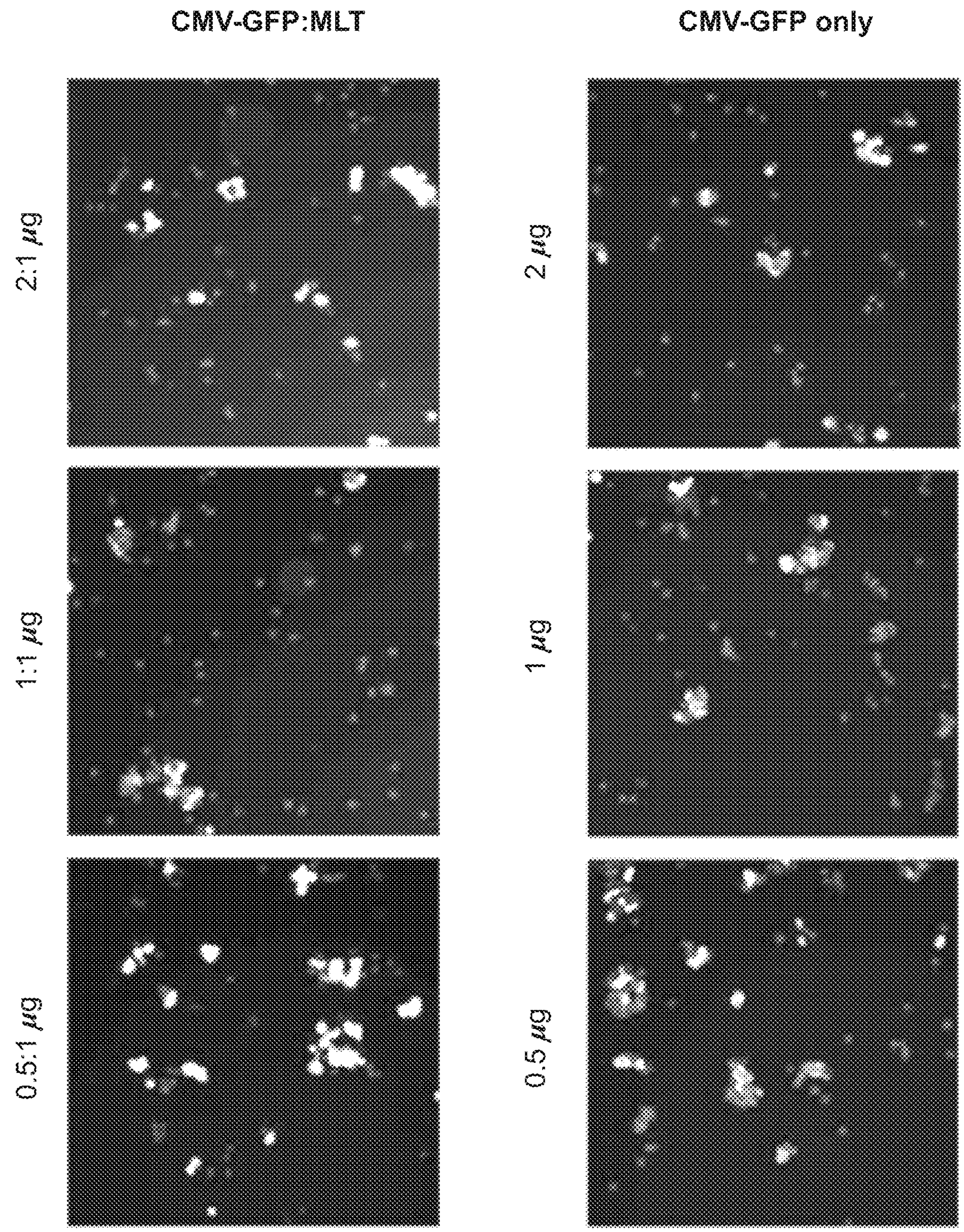
FIG. 26 shows Huh7 cells transfected with CMV-GFP+MLT, compared to cells transfected with CMV-GFP only, at different ratios, 24 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

FIG. 26 shows Huh7 cells transfected with CMV-GFP+MLT, compared to cells transfected with CMV-GFP only, at different ratios, 24 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

Figure 27:
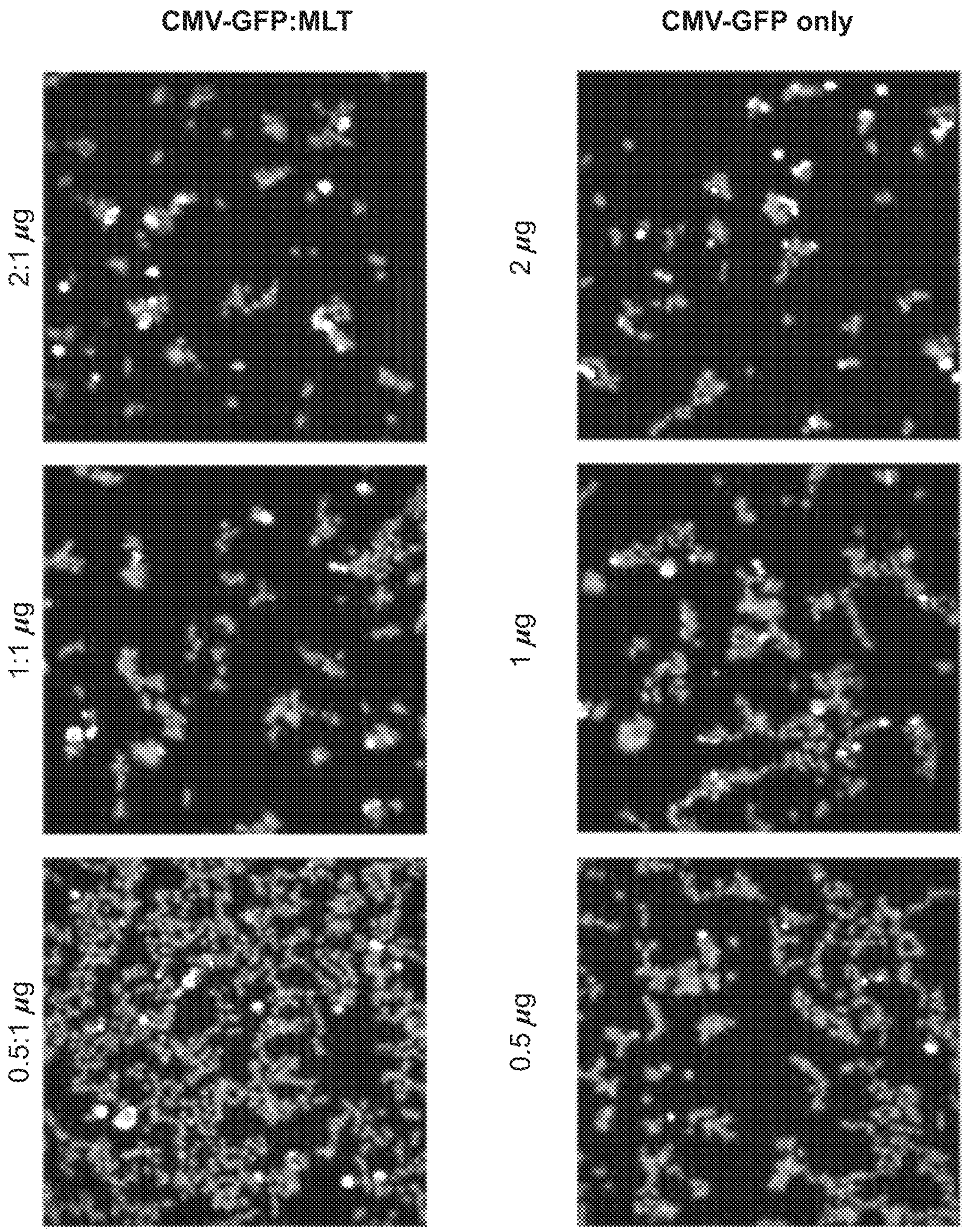
FIG. 27 shows Huh7 cells transfected with CMV-GFP+MLT, compared to cells transfected with CMV-GFP only at different ratios, 72 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

FIG. 27 shows Huh7 cells transfected with CMV-GFP+MLT, compared to cells transfected with CMV-GFP only at different ratios, 72 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

Figure 28:
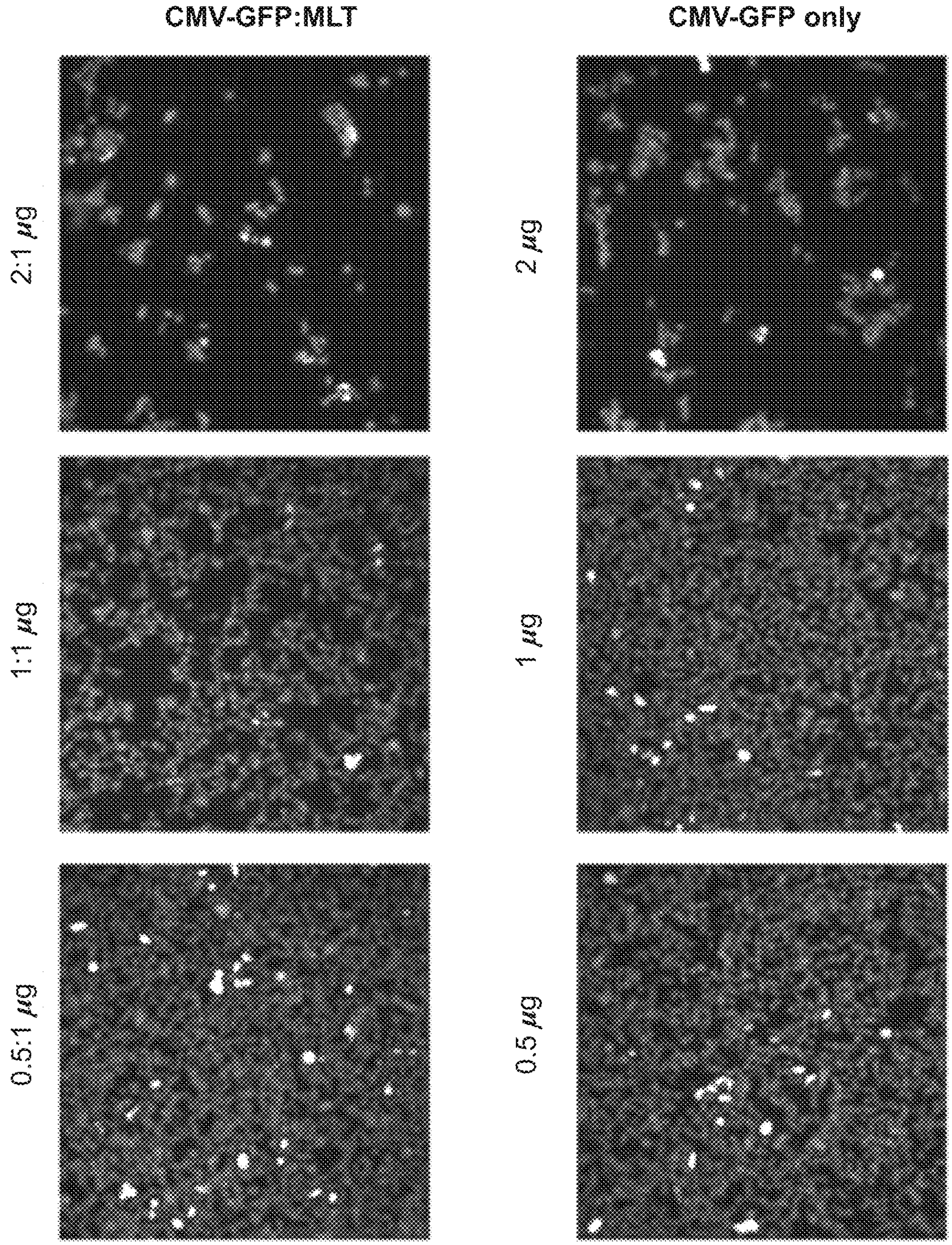
FIG. 28 shows Huh7 cells transfected with CMV-GFP+MLT, compared to cells transfected with CMV-GFP only at different ratios, 1 week post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

FIG. 28 shows Huh7 cells transfected with CMV-GFP+MLT, compared to cells transfected with CMV-GFP only at different ratios, 1 week post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

FIG. 29A shows the viability of HEK293 cells at 14 and 21 days after transfection using CMV-GFP MLT DNA donor and a MLT RNA helper. There was no apparent toxicity due to lipofectamine, DNA or RNA. Robust GFP expression was found in over 40% of the cells after 14 and 21 days (FIG. 29B). Integration efficiency was analyzed FACs and showed that 37% of cells were stably integrated with the MLT donor DNA (FIG. 29C and FIG. 29D). FIG. 29E shows the percentage of GFP positive HEK293 cells after nucleofection lipofection in T25 flasks. The % GFP positive cells was the same in CMV-GFP MLT Donor alone compared to CMV-GFP MLT Donor plus MLT Helper RNA. The % GFP positivity declined rapidly in HEK293 cells transfected with CMV-GFP MLT Donor alone and reached 5% at Day 21. The % GFP positivity stabilized in HEK293 cells transfected with CMV-GFP MLT Donor plus MLT Helper RNA and reached 42% at Day 21. The integration efficiency was calculated at 37%. Gated FACs was able to select GFP positive and mnCHerry positive cell populations in order to evaluate the effects of RNA expression (mCherry) (FIG. 30A-D).

Example 10—Transposition of HT1080 Cells Using CMV-GFP/MLT Transposase

An objective of this study was to transfect HT1080 cells with CMV-GFP MLT DNA Donor and MLT DNA Helper transposase 1 or MLT DNA Helper transposase 2, and quantify their transposition efficiency by comparing their GFP expression. HT1080 is a human fibrosarcoma cell line.

FIG. 31 shows CMV-GFP MLT DNA Donor expression 24 hours post transfection of HT1080 cells, and FIG. 32 shows CMV-GFP MLT DNA Donor expression 2 weeks post transfection of HT1080 cells.

As shown in FIG. 31, both MLT DNA Helper transposase 1 and MLT DNA Helper transposase 2 effectively transfected the HT1080 cells when combined with CMV-GFP MLT Donor DNA. Both of these transposases expressed very similar levels of GFP, while the donor DNA-only (CMV-GFP only) demonstrated that GFP can be expressed in these cells. The untransfected cell line had no GFP expression, since none is present in this cell line.

After 2 weeks, as shown in FIG. 32, less GFP expression was observed from MLT DNA Helper transposase 1 and MLT DNA Helper transposase 2, while the MLT DNA Helper transposase 2 expressed GFP slightly stronger when compared to the MLT DNA Helper transposase 1. The CMV-GFP only (donor DNA only) and the untransfected cells had no GFP expression, because the donor DNA did not integrate into the cell line while the untransfected cell never expressed GFP to begin with.

In this study, when comparing the transfection efficiency of the MLT DNA Helper transposase 1 and MLT DNA Helper transposase 2 in HT1080 cells, the MLT DNA Helper transposase 2 with CMV-GFP MLT DNA Donor was shown to more effectively transfect the HT1080 cells (FIG. 32, 2 weeks post-transfection). Although the integration efficiency is comparable between The MLT RNA Helper transposase 2 and MLT DNA Helper transposase 2, the MLT DNA Helper transposase 2 is more suitable for transfection of cell lines, including for ex-vivo experiments.

Definitions

The following definitions are used in connection with the invention disclosed herein. Unless defined otherwise, all technical and scientific terms used herein have the same meaning as commonly understood to one of skill in the art to which this invention belongs.

The term "in vivo" refers to an event that takes place in a subject's body.

The term "ex vivo" refers to an event which involves treating or performing a procedure on a cell, tissue and/or organ which has been removed from a subject's body. Aptly, the cell, tissue and/or organ may be returned to the subject's body in a method of treatment or surgery.

As used herein, the term "variant" encompasses but is not limited to nucleic acids or proteins which comprise a nucleic acid or amino acid sequence which differs from the nucleic acid or amino acid sequence of a reference by way of one or more substitutions, deletions and/or additions at certain positions. The variant may comprise one or more conservative substitutions. Conservative substitutions may involve, e.g., the substitution of similarly charged or uncharged amino acids.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, lipid or the like, which is nontoxic and which does not interact with other components of the composition in a deleterious manner.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A composition comprising a nucleic acid encoding a transposase enzyme, wherein the transposase enzyme comprises an amino acid sequence having at least 95% sequence identity to SEQ ID NO: 2 and has a non-polar aliphatic amino acid at position 2 of SEQ ID NO: 2, wherein the transposase enzyme further comprises a substitution $C13X_2$, wherein $X_2$ is selected from lysine (K), arginine (R), and histidine (H).

2. The composition of claim 1, wherein the non-polar aliphatic amino acid is selected from alanine (A), glycine (G), valine (V), leucine (L), isoleucine (I), and proline (P).

3. The composition of claim 2, wherein the non-polar aliphatic amino acid is alanine (A).

4. The composition of claim 1, wherein the transposase enzyme further comprises a substitution $S8X_1$, wherein $X_1$ is selected from alanine (A), glycine (G), valine (V), leucine (L), isoleucine (I), and proline (P).

5. The composition of claim 4, wherein $X_1$ is proline (P).

6. The composition of claim 1, wherein $X_2$ is arginine (R).

7. The composition of claim 1, wherein the transposase enzyme does not have additional amino acid residues at the C terminus relative to SEQ ID NO: 2.

8. The composition of claim 1, wherein the transposase enzyme comprises an amino acid sequence having at least 98% identity to SEQ ID NO: 2.

9. The composition of claim 1, wherein the nucleic acid further encodes a transcription activator-like effector (TALE) DNA binding domain (DBD), or a nuclease-deficient Cas9 (dCas9) connected to the transposase enzyme.

10. The composition of claim 9, wherein the transposase enzyme is capable of inserting a transposon at a TA dinucleotide site or a TTAA (SEQ ID NO: 1) tetranucleotide site in a genomic safe harbor site (GSHS) of a nucleic acid molecule.

11. The composition of claim 10, wherein the TALE DBD or dCas9 is suitable for directing the transposase enzyme to the GSHS sequence.

12. The composition of claim 10, wherein the GSHS is selected from adeno-associated virus site 1 (AAVS1), chemokine (C-C motif) receptor 5 (CCR5) gene, HIV-1 coreceptor, and human Rosa26 locus.

13. The composition of claim 1, wherein the nucleic acid is co-formulated with a nucleic acid encoding a transposon.

14. The composition of claim 13, wherein the composition is in the form of a lipid nanoparticle (LNP).

15. A composition comprising a nucleic acid encoding a transposase enzyme, wherein the transposase enzyme comprises an amino acid sequence having at least 95% sequence identity to SEQ ID NO: 2 and has a non-polar aliphatic amino acid at position 2 of SEQ ID NO: 2, wherein the transposase enzyme further comprises a substitution $N125X_3$, wherein $X_3$ is selected from is selected from lysine (K), arginine (R), and histidine (H).

16. The composition of claim 15, wherein $X_3$ is lysine (K).

17. The composition of claim 15, wherein the non-polar aliphatic amino acid is selected from alanine (A), glycine (G), valine (V), leucine (L), isoleucine (I), and proline (P).

18. The composition of claim 15, wherein the nucleic acid further encodes a transcription activator-like effector (TALE) DNA binding domain (DBD), or a nuclease-deficient Cas9 (dCas9) connected to the transposase enzyme.

19. A composition comprising a nucleic acid encoding a transposase enzyme, wherein the transposase enzyme comprises an amino acid sequence having at least 95% sequence identity to SEQ ID NO: 2 and has a non-polar aliphatic amino acid at position 2 of SEQ ID NO: 2, wherein the transposase enzyme further comprises two or more of substitutions S8P, C13R, and N125K.

20. The composition of claim 19, wherein the non-polar aliphatic amino acid is selected from alanine (A), glycine (G), valine (V), leucine (L), isoleucine (I), and proline (P).

21. The composition of claim 19, wherein the nucleic acid further encodes a transcription activator-like effector (TALE) DNA binding domain (DBD), or a nuclease-deficient Cas9 (dCas9) connected to the transposase enzyme.

22. A composition comprising a first nucleic acid encoding a transposase enzyme and a DNA binding domain and a second nucleic acid encoding a transposon, wherein the transposase enzyme comprises an amino acid sequence having at least 97% sequence identity to SEQ ID NO: 2 and comprises two or more of substitutions of S8P, C13R, and N125K, wherein the transposase enzyme is operatively linked to the DNA binding domain, and wherein the first nucleic acid and second nucleic acid are contained in a LNP.

23. The composition of claim 22, wherein the DNA binding domain is a TALE DBD.

24. The composition of claim 22, wherein the DNA binding domain is a dCas9.

25. The composition of claim 22, wherein the transposase enzyme does not have additional amino acid residues at the C terminus relative to SEQ ID NO: 2.

26. The composition of claim 25, wherein the substitutions are S8P and C13R.

27. The composition of claim 23, wherein the transposase enzyme does not have additional amino acid residues at the C terminus relative to SEQ ID NO: 2.

28. The composition of claim 27, wherein the substitutions are S8P and C13R.

* * * * *